United States Patent [19]
Or et al.

[11] Patent Number: 6,075,011
[45] Date of Patent: Jun. 13, 2000

[54] 6-O-SUBSTITUTED ERYTHROMYCIN COMPOUNDS AND METHOD FOR MAKING SAME

[75] Inventors: Yat Sun Or, Libertyville; Richard F. Clark, Mundelein; Zhenkun Ma, Gurnee; George Griesgraber, Libertyville; Leping Li, Gurnee, all of Ill.; Daniel T. Chu, Santa Clara, Calif.

[73] Assignee: Abbott Laboratories, Abbott Park, Ill.

[21] Appl. No.: 08/841,038

[22] Filed: Apr. 29, 1997

Related U.S. Application Data

[63] Continuation-in-part of application No. 08/646,477, May 7, 1996, abandoned.

[51] Int. Cl.$^7$ .......................... A61K 31/70; C07H 17/08
[52] U.S. Cl. .................. 514/29; 536/7.2; 536/7.4
[58] Field of Search .......................... 536/7.2, 7.4; 514/29

[56] References Cited

U.S. PATENT DOCUMENTS 5,444,051   8/1995   Agouridas et al. .................. 514/29

FOREIGN PATENT DOCUMENTS

| | | |
|---|---|---|
| 0194833 | 9/1986 | European Pat. Off. . |
| 0215355 | 3/1987 | European Pat. Off. . |
| 0272110 | 6/1988 | European Pat. Off. . |
| 0487411 | 5/1992 | European Pat. Off. . |

OTHER PUBLICATIONS

*Chemical Abstracts*, vol. 118, No. 11 (Mar. 1993), p 18, col. 1, S. Omura et al., "Preparation of Erythromycin A Derivatives as Intermediates for 6–O–Alkylerythromycin".

*Chemical Abstracts*, vol. 113, No. 15 (Oct. 1990), p. 706, col. 1, S. Morimoto, et al "Preparation of Erythromycin A Derivatives as Intermediates for 6–O–Alkylerythromycin".

*Journal of Pharmaceutical Sciences*, vol. 79, No. 9 (1989), pp. 783–784, T.Suwa et al., "Uptake of O–Alkyl Erythromycin Derivatives in the Lung Tissue and Cells of Rats".

*Canadian Journal of Chemistry*, vol. 63, No. 10 (1985), pp. 2814–2818, B. Bernet et al., "Formal Total Synthesis of Erythromycin A. Part II. Preparation of a 1,7–Dioxaspiro (5.5)undecane Derivative of Erythromycin A Seco Acid Methyl Ester from Erythromycin A".

*Journal of Antibiotics*, vol. 37, No. 2 (1984), pp. 187–189, S. Morimoto et al., "Chemical Modification of Erythromycins. I. Synthesis and Antibacterial Activity of 6–O–Methylerythromycins A".

*Journal of Antibiotics*, vol. 43, No. 3 (1990), pp. 286–294, S. Morimoto et al., "Chemical Modification of Erythromycins. II. Synthesis and Antibacterial Activity of O–Alkyl of Erythromycin A".

*Primary Examiner*—Elli Peselev
*Attorney, Agent, or Firm*—Mona Anand

[57] ABSTRACT

Antimicrobial compounds having the formula

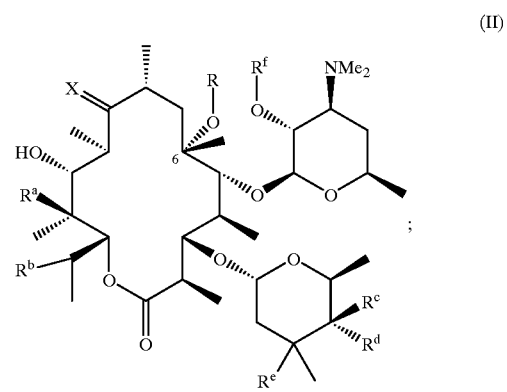

(II)

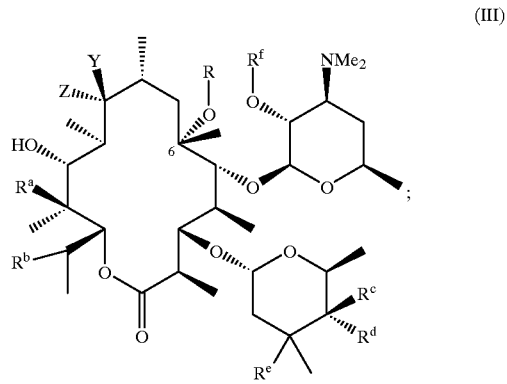

(III)

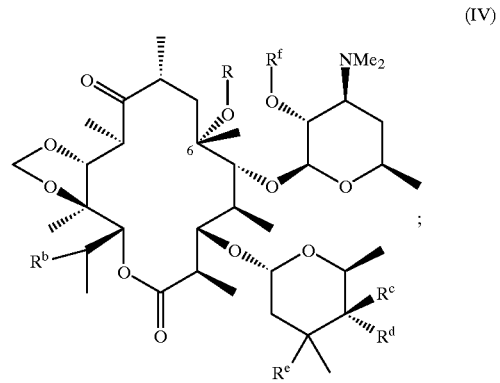

(IV)

-continued
(V)
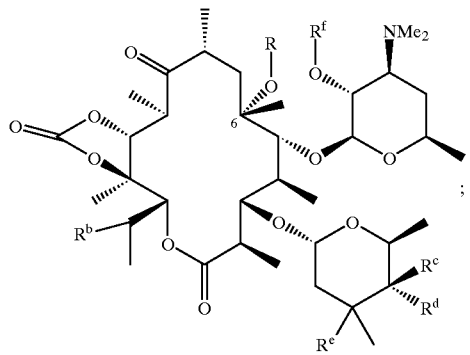
(VI)
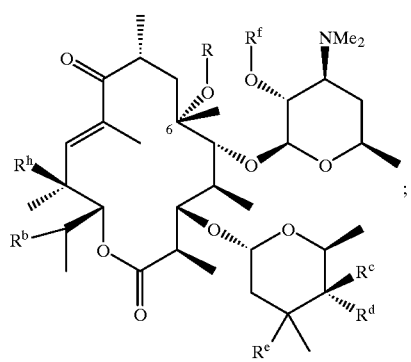
(VII)
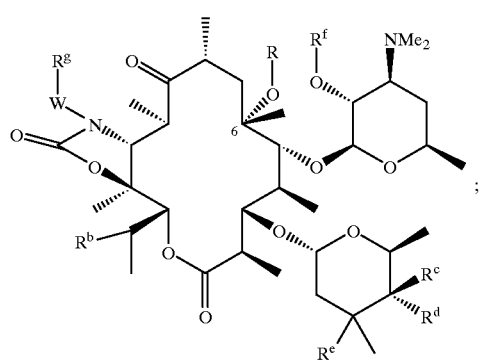
-continued
(VIII)
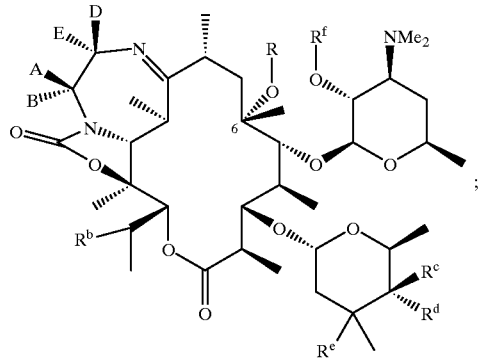
and
(IX)
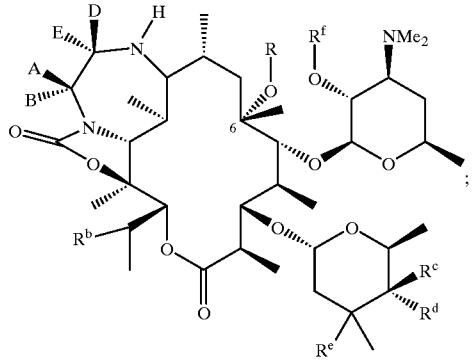
as well as the pharmaceutically acceptable salts, esters and prodrugs thereof; pharmaceutical compositions comprising such compounds; methods of treating bacterial infections by the administration of such compounds; and processes for the preparation of the compounds.
29 Claims, No Drawings

6-O-SUBSTITUTED ERYTHROMYCIN COMPOUNDS AND METHOD FOR MAKING SAME

This application is a continuation-in-part of U.S. application Ser. No. 08/646,477, filed May 7, 1996, now abandoned.

TECHNICAL FIELD

The present invention relates to novel semisynthetic macrolides having antibacterial activity and useful in the treatment and prevention of bacterial infections. More particularly, the invention relates to 6-O-substituted erythromycin derivatives, compositions containing such compounds and methods for using the same, as well as processes for making such compounds.

BACKGROUND OF THE INVENTION

Erythromycins A through D, represented by formula (I),

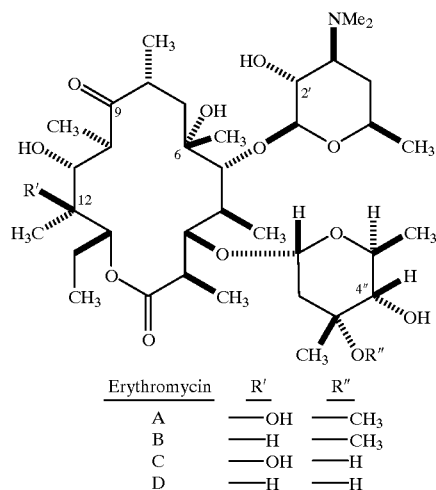

| Erythromycin | R' | R" |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Morimoto et al. described the preparation of 6-O-methyl erythromycin A in J. Antibiotics 37:187 (1984). Morimoto et al. further disclosed a series of O-alkyl erythromycin A derivatives in J. Antibiotics 43: 286 (1990). In their experience, "O-alkylation, other than methylation, took place at the C-11 hydroxyl group exclusively." However, in European Patent Application 272,110, published Jun. 22, 1988, Morimoto et al. disclose 6-O-C$_1$–C$_3$-alkyl erythromycin A compounds.

In European Patent Application 215,355, published Mar. 28, 1987, Omura and Itoh disclose 6-O-loweralkyl erythromycins as stimulants of gastrointestinal contractile motion.

SUMMARY OF THE INVENTION

The present invention provides a novel class of 6-O-substituted erythromycin compounds which possess antibacterial activity.

In one aspect of the present invention is disclosed a novel 6-O-substituted erythromycin compound selected from the formulae:

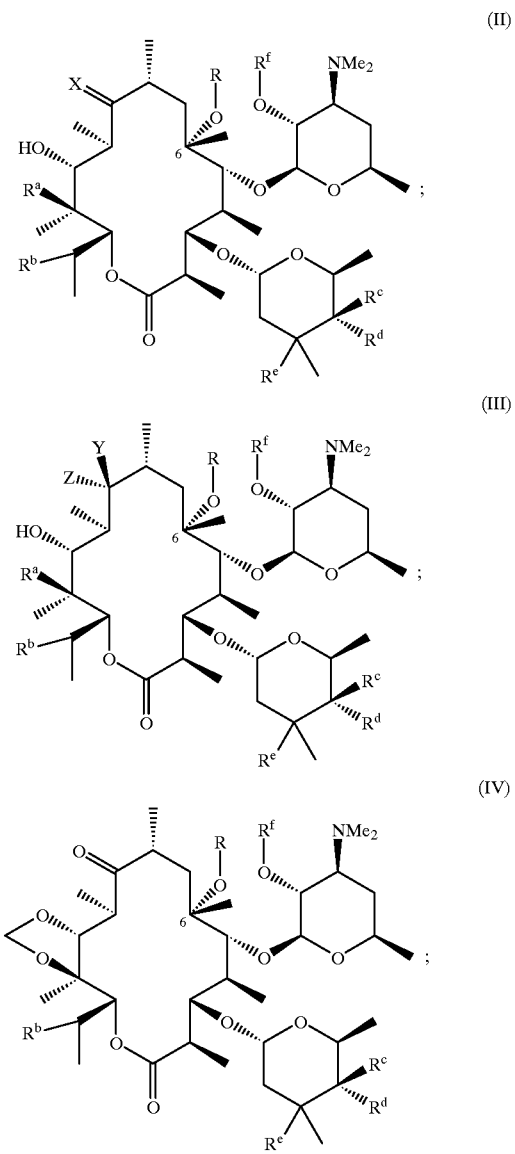

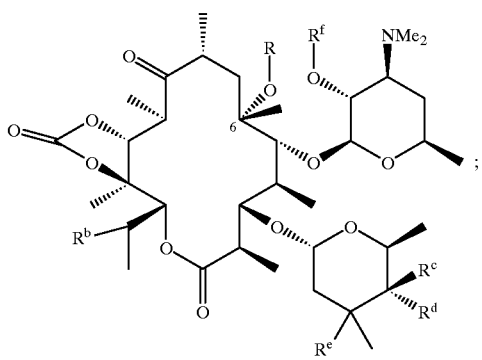
(V)

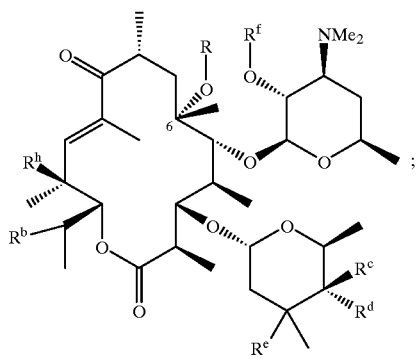
(VI)

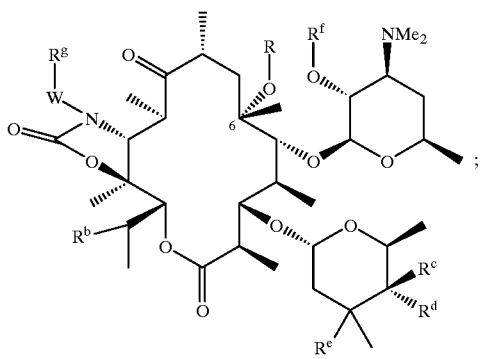
(VII)

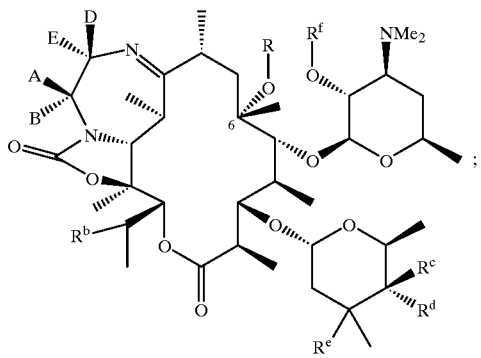
(VIII)

and

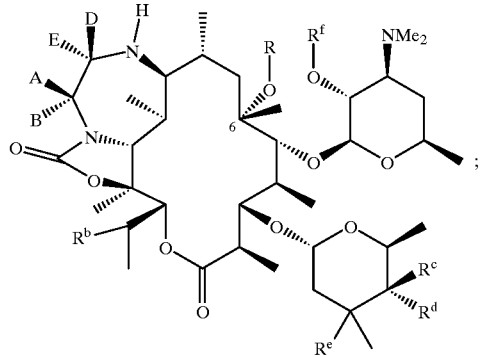
(IX)

as well as the pharmaceutically acceptable salts, esters and prodrugs thereof. In formulae (II)–(IX) above, X is selected from the group consisting of
(1) =O,
(2) =N—OH,
(3) =N—O—$R^1$ where $R^1$ is selected from the group consisting of
  (a) unsubstituted $C_1$–$C_{12}$-alkyl,
  (b) $C_1$–$C_{12}$-alkyl substituted with aryl,
  (c) $C_1$–$C_{12}$-alkyl substituted with substituted aryl,
  (d) $C_1$–$C_{12}$-alkyl substituted with heteroaryl,
  (e) $C_1$–$C_{12}$-alkyl substituted with substituted heteroaryl,
  (f) $C_3$–$C_{12}$-cycloalkyl,
  (g) —Si—$(R^2)(R^3)(R^4)$ wherein $R^2$, $R^3$ and $R^4$ are each independently selected from $C_1$–$C_{12}$-alkyl, and
  (h) —Si—$(Aryl)_3$;
and
(4) =N—O—$C(R^5)(R^6)$—O—$R^1$ where $R^1$ is as defined above and $R^5$ and $R^6$ are each independently selected from the group consisting of
  (a) hydrogen,
  (b) unsubstituted $C_1$–$C_{12}$-alkyl,
  (c) $C_1$–$C_{12}$-alkyl substituted with aryl,
  (d) $C_1$–$C_{12}$-alkyl substituted with substituted aryl,
  (e) $C_1$–$C_{12}$-alkyl substituted with heteroaryl, and
  (f) $C_1$–$C_{12}$-alkyl substituted with substituted heteroaryl,
or
  $R^5$ and $R^6$ taken together with the atom to which they are attached form a $C_3$–$C_{12}$-cycloalkyl ring;

$R^a$ is hydrogen or hydroxy;
$R^b$ is hydrogen or hydroxy;
one of $R^c$ and $R^d$ is hydrogen and the other of $R^c$ and $R^d$ is selected from the group consisting of
(1) hydroxy,
(2) protected hydroxy,
(3) halogen,
(4) $NR^7R^8$ where $R^7$ and $R^8$ are independently selected from the group consisting of
  (a) hydrogen,
  (b) $C_1$–$C_{12}$-alkyl,
  (c) substituted $C_1$–$C_{12}$-alkyl,
  (d) $C_1$–$C_8$-cycloalkyl, (e) substituted $C_1$–$C_8$-cycloalkyl,
(f) $C_1$–$C_{12}$-alkyl substituted with aryl,
(g) $C_1$–$C_{12}$-alkyl substituted with substituted aryl,
(h) $C_1$–$C_{12}$-alkyl substituted with heterocycloalkyl,
(i) $C_1$–$C_{12}$-alkyl substituted with substituted heterocycloalkyl,
(j) $C_1$–$C_{12}$-alkyl substituted with $C_1$–$C_8$-cycloalkyl,
(k) $C_1$–$C_{12}$-alkyl substituted with substituted $C_1$–$C_8$-cycloalkyl,
(l) $C_1$–$C_{12}$-alkyl substituted with heteroaryl, and
(m) $C_1$–$C_{12}$-alkyl substituted with substituted heteroaryl,
or
$R^7$ and $R^8$ taken together with the atom to which they are attached form a 3–10 membered heterocycloalkyl ring,
(5) O—CO—NH-aryl,
(6) O—CO—NH-heteroaryl,
(7) O—CO—$NR^7R^8$, where $R^7$ and $R^8$ are as defined above,
(8) O—$SO_2$—$C_1$–$C_6$-alkyl,
(9) O—$SO_2$-(substituted $C_1$–$C_6$-alkyl), and
(10) O—$SO_2$—$CH_2$—$CH_2$—$NR^7R^8$, where $R^7$ and $R^8$ are as defined above, or
$R^c$ and $R^d$ taken together form the grouping selected from the group consisting of
(1) =O,
(2) =N—OH, and
(3) =N—$OR^1$ wherein $R^1$ is as defned above;
$R^e$ is methoxy, fluorine or hydroxy;
$R^f$ is hydrogen or a hydroxy protecting group;
W is absent or selected from the group consisting of —O—, —NH—CO—, —N=CH— and —NH—;
$R^g$ is selected from the group consisting of
(1) hydrogen,
(2) $C_1$–$C_6$-alkyl optionally substituted with one or more substituents selected from the group consisting of
(a) aryl,
(b) substituted-aryl,
(c) heteroaryl,
(d) substituted-heteroaryl,
(e) hydroxy,
(f) $C_1$–$C_6$-alkoxy,
(g) $NR^9R^{10}$, where $R^9$ and $R^{10}$ are independently selected from hydrogen and $C_1$–$C_6$-alkyl, or $R^9$ and $R^{10}$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$–$C_6$-alkyl—)—, —N(aryl)—, —N(aryl-$C_1$–$C_6$-alkyl—)—, —N(substituted-aryl-$C_1$–$C_6$-alkyl—)—, —N(heteroaryl)—, —N(heteroaryl-$C_1$–$C_6$-alkyl—)—, —N(substituted-heteroaryl-$C_1$–$C_6$-alkyl—)—, and —S— or —S(O)$_n$—, wherein n is 1 or 2, and
(h) —$CH_2$—M—$R^{11}$
wherein M is selected from the group consisting of:

(i) —C(O)—NH—,
(ii) —NH—C(O)—,
(iii) —NH—,
(iv) —N=,
(v) —N($CH_3$)—,
(vi) —NH—C(O)—O—
(vii) —NH—C(O)—NH—
(viii) —O—C(O)—NH—
(ix) —O—C(O)—O—
(x) —O—,
(xi) —S(O)$_n$—, wherein n is 0, 1 or 2,
(xii) —C(O)—O—,
(xiii) —O—C(O)—, and
(xiv) —C(O)—, and
$R^{11}$ is selected from the group consisting of:
(i) $C_1$–$C_6$-alkyl, optionally substituted with a substituent selected from the group consisting of
(aa) aryl,
(bb) substituted-aryl,
(cc) heteroaryl, and
(dd) substituted-heteroaryl,
(ii) aryl,
(iii) substituted-aryl,
(iv) heteroaryl,
(v) substituted-heteroaryl, and
(vi) heterocycloalkyl,
(3) $C_3$–$C_7$-cycloalkyl,
(4) aryl,
(5) substituted-aryl,
(6) heteroaryl, and
(7) substituted-heteroaryl;
$R^h$ is selected from the group consisting of
(1) hydrogen,
(2) hydroxy,
(3) —O—C(O)-imidazolyl,
(4) —O—C(O)—O—$C_1$–$C_6$-alkyl,
(5) —O—C(O)—O-aryl,
(6) —O—C(O)—O-(substituted aryl),
(7) —O—C(O)—Cl, and
(8) —O—C(O)—$NH_2$;
R is selected from the group consisting of
(1) methyl substituted with a moiety selected from the group consisting of
(a) CN,
(b) F,
(c) —$CO_2R^{12}$ wherein $R^{12}$ is $C_1$–$C_3$-alkyl or aryl substituted $C_1$–$C_3$-alkyl, or heteroaryl substituted $C_1$–$C_3$-alkyl,
(d) $S(O)_nR^{12}$ where n is 0, 1 or 2 and $R^{12}$ is as defined above,
(e) $NHC(O)R^{12}$ where $R^{12}$ is as defined above,
(f) $NHC(O)NR^{13}R^{14}$ wherein $R^{13}$ and $R^{14}$ are independently selected from hydrogen and $C_1$–$C_3$-alkyl,
(g) aryl,
(h) substituted aryl,
(i) heteroaryl, and
(j) substituted heteroaryl,
(2) $C_2$–$C_{10}$-alkyl,
(3) $C_2$–$C_{10}$-alkyl substituted with one or more substituents selected from the group consisting of (a) halogen,
(b) hydroxy,
(c) $C_1$–$C_3$-alkoxy,
(d) $C_1$–$C_3$-alkoxy-$C_1$–$C_3$-alkoxy,
(e) oxo,
(f) —$N_3$,
(g) —CHO,
(h) O—$SO_2$-(substituted $C_1$–$C_6$-alkyl),
(i) —$NR^{15}R^{16}$ wherein $R^{15}$ and $R^{16}$ are selected from the group consisting of
  (i) hydrogen,
  (ii) $C_1$–$C_{12}$-alkyl,
  (iii) substituted $C_1$–$C_{12}$-alkyl,
  (iv) $C_1$–$C_{12}$-alkenyl,
  (v) substituted $C_1$–$C_{12}$-alkenyl,
  (vi) $C_1$–$C_{12}$-alkynyl,
  (vii) substituted $C_1$–$C_{12}$-alkynyl,
  (viii) aryl,
  (ix) $C_3$–$C_8$-cycloalkyl,
  (x) substituted $C_3$–$C_8$-cycloalkyl,
  (xi) substituted aryl,
  (xii) heterocycloalkyl,
  (xiii) substituted heterocycloalkyl,
  (xiv) $C_1$–$C_{12}$-alkyl substituted with aryl,
  (xv) $C_1$–$C_{12}$-alkyl substituted with substituted aryl,
  (xvi) $C_1$–$C_{12}$-alkyl substituted with heterocycloalkyl,
  (xvii) $C_1$–$C_{12}$-alkyl substituted with substituted heterocycloalkyl,
  (xviii) $C_1$–$C_{12}$-alkyl substituted with $C_3$–$C_8$-cycloalkyl,
  (xix) $C_1$–$C_{12}$-alkyl substituted with substituted $C_3$–$C_8$-cycloalkyl,
  (xx) heteroaryl,
  (xxi) substituted heteroaryl,
  (xxii) $C_1$–$C_{12}$-alkyl substituted with heteroaryl, and
  (xxiii) $C_1$–$C_{12}$-alkyl substituted with substituted heteroaryl,
or
$R^{15}$ and $R^{16}$ are taken together with the atom to which they are attached form a 3–10 membered heterocycloalkyl ring which may be substituted with one or more substituents independently selected from the group consisting of
  (i) halogen,
  (ii) hydroxy,
  (iii) $C_1$–$C_3$-alkoxy,
  (iv) $C_1$–$C_3$-alkoxy-$C_1$–$C_3$-alkoxy,
  (v) oxo,
  (vi) $C_1$–$C_3$-alkyl,
  (vii) halo-$C_1$–$C_3$-alkyl, and
  (vii) $C_1$–$C_3$-alkoxy-$C_1$–$C_3$-alkyl,
(j) —$CO_2R^{12}$ wherein $R^{12}$ is as defined above,
(k) —$C(O)NR^{13}R^{14}$ wherein $R^{13}$ and $R^{14}$ are defined above,
(l) =N—O—$R^{12}$ wherein $R^{13}$ is as previously defined,
(m) —C≡N,
(n) O—$S(O)_nR^{12}$ wherein n is 0, 1 or 2 and $R^{12}$ is as defined above,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) heterocycloalkyl,
(w) substituted heterocycloalkyl,
(x) $NHC(O)R^{12}$ where $R^{12}$ is as previously defined,
(y) $NHC(O)NR^{13}R^{14}$ wherein $R^{13}$ and $R^{14}$ are as previously defined,
(z) =N—$NR^{15}R^{16}$ wherein $R^{15}$ and $R^{16}$ are as previously defined,
(aa) =N—$R^{11}$ wherein $R^{11}$ is as previously defined,
(bb) =N—$NHC(O)R^{12}$ wherein $R^{12}$ is as previously defined, and
(cc) =N—$NHC(O)NR^{13}R^{14}$ wherein $R^{13}$ and $R^{14}$ are as previously defined;
(4) $C_3$-alkenyl substituted with a moiety selected from the group consisting of
(a) halogen,
(b) —CHO,
(c) —$CO_2R^{12}$ where $R^{12}$ is as defined above,
(d) —C(O)—$R^{11}$ where $R^{11}$ is as defined above,
(e) —$C(O)NR^{13}R^{14}$ wherein $R^{13}$ and $R^{14}$ are as previously defined,
(f) —C≡N,
(g) aryl,
(h) substituted aryl,
(i) heteroaryl,
(j) substituted heteroaryl,
(k) $C_3$–$C_7$-cycloalkyl, and
(l) $C_1$–$C_{12}$-alkyl substituted with heteroaryl,
(5) $C_4$–$C_{10}$-alkenyl;
(6) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^{12}$ where $R^{12}$ is as defined above,
(f) —$C(O)NR^{13}R^{14}$ wherein $R^{13}$ and $R^{14}$ are as previously defined,
(g) —$NR^{15}R^{16}$ wherein $R^{15}$ and $R^{16}$ are as previously defined,
(h) =N—O—$R^{12}$ where $R^{12}$ is as previously defined,
(i) —C≡N,
(j) O—$S(O)_nR^{12}$ where n is 0, 1 or 2 and $R^{12}$ is as previously defined,
(k) aryl,
(l) substituted aryl,
(m) heteroaryl,
(n) substituted heteroaryl,
(o) $C_3$–$C_7$-cycloalkyl,
(p) $C_1$–$C_{12}$-alkyl substituted with heteroaryl,
(q) $NHC(O)R^{12}$ where $R^{12}$ is as previously defined,
(r) $NHC(O)NR^{13}R^{14}$ wherein $R^{13}$ and $R^{14}$ are as previously defined,
(s) =N—$NR^{15}R^{16}$ wherein $R^{15}$ and $R^{16}$ are as previously defined,
(t) =N—$R^{11}$ wherein $R^{11}$ is as previously defined,
(u) =N—$NHC(O)R^{12}$ where $R^{12}$ is as previously defined, and
(v) =N—$NHC(O)NR^{13}R^{14}$ wherein $R^{13}$ and $R^{14}$ are as previously defined;
(7) $C_3$–$C_{10}$-alkynyl; and (8) $C_3$–$C_{10}$-alkynyl substituted with one or more substituents selected from the group consisting of
   (a) trialkylsilyl,
   (b) aryl,
   (c) substituted aryl,
   (d) heteroaryl,
   and
   (e) substituted heteroaryl;
one of Y and Z is hydrogen and the other is selected from a group consisting of
   (1) hydrogen,
   (2) hydroxy,
   (3) protected hydroxy,
   and
   (4) $NR^7R^8$ wherein $R^7$ and $R^8$ are as defined above;
and
A, B, D and E, with the provision that at least two of A, B, D and E are hydrogen, are independently selected from the group consisting of:
   (a) hydrogen;
   (b) $C_1$–$C_6$-alkyl, optionally substituted with one or more substituents selected from the group consisting of:
      (i) aryl;
      (ii) substituted-aryl;
      (iii) heteroaryl;
      (iv) substituted-heteroaryl;
      (v) heterocycloalkyl;
      (vi) hydroxy;
      (vii) $C_1$–$C_6$-alkoxy;
      (viii) halogen consisting of Br, Cl, F or I; and
      (ix) $NR^9R^{10}$, wherein $R^9$ and $R^{10}$ are as defined above;
   (c) $C_3$–$C_7$-cycloalkyl;
   (d) aryl;
      (e) substituted-aryl;
      (f) heteroaryl;
      (g) substituted-heteroaryl;
      (h) heterocycloalkyl; and
      (i) a group selected from option (b) above further substituted with —M—$R^{11}$, wherein M and $R^{11}$ are as defined above;
or
   any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$-alkyl—)—, —N(aryl-$C_1$–$C_6$-alkyl—)—, —N(substituted-aryl-$C_1$–$C_6$-alkyl—)—, —N(heteroaryl-$C_1$–$C_6$-alkyl—)—, —N(substituted-heteroaryl-$C_1$–$C_6$-alkyl—)—, —S— or —S(O)$_n$—, wherein n is 1 or 2, —C(O)—NH—, —C(O)—$NR^{12}$—, wherein $R^{12}$ is as defined above, —NH—C(O)—, —$NR^{12}$—C(O)—, wherein $R^{12}$ is as defined above, and —C(=NH)—NH—.

In another aspect of the present invention are disclosed pharmaceutical compositions comprising a therapeutically effective amount of a compound of the invention in combination with a pharmaceutically acceptable carrier and treatment of antibacterial infections with such compositions. Suitable carriers and methods of formulation are also disclosed. The compounds and compositions of the present invention have antibacterial activity.

In a further aspect of the present invention are provided processes for the preparation of 6-O-substituted macrolide derivatives of Formula (II), (III), (IV), (V), (VI), (VII), (VIII) and (IX) above.

DETAILED DESCRIPTION OF THE INVENTION

One embodiment of the present invention comprises a compound of formula (II) above, wherein X, R, $R^a$, $R^b$, $R^c$, $R^d$, $R^e$ and $R^f$ are as defined above.

Another embodiment of the present invention comprises a compound of formula (III) above, wherein Y, Z, R, $R^a$, $R^b$, $R^c$, $R^d$, $R^e$ and $R^f$ are as defined above.

Another embodiment of the present invention comprises a compound of formula (IV) above, wherein R, $R^b$, $R^c$, $R^d$, $R^e$ and $R^f$ are as defined above.

Another embodiment of the present invention comprises a compound of formula (V) above, wherein R, $R^b$, $R^c$, $R^d$, $R^e$ and $R^f$ are as defined above.

Another embodiment of the present invention comprises a compound of formula (VI) above, R, $R^b$, $R^c$, $R^d$, $R^e$, $R^f$ and $R^h$, are as defined above.

Another embodiment of the present invention comprises a compound of formula (VII) above, wherein W, R, $R^b$, $R^c$, $R^d$, $R^e$, $R^f$ and $R^g$ are as defined above.

Another embodiment of the present invention comprises a compound of formula (VIII) above, wherein A, B, D, E, R, $R^b$, $R^c$, $R^d$, $R^e$ and $R^f$ are as defined above.

Another embodiment of the present invention comprises a compound of formula (IX) above, wherein A, B, D, E, R, $R^b$, $R^c$, $R^d$, $R^e$ and $R^f$ are as defined above.

A preferred embodiment of the present invention is the compound of formula (X):

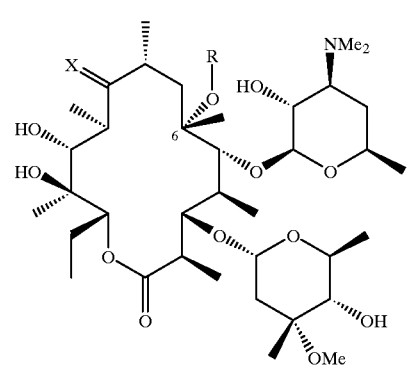

(X)

where X and R are as defined above.

Another preferred embodiment of the present invention is the compound of formula (XI):

(XI)

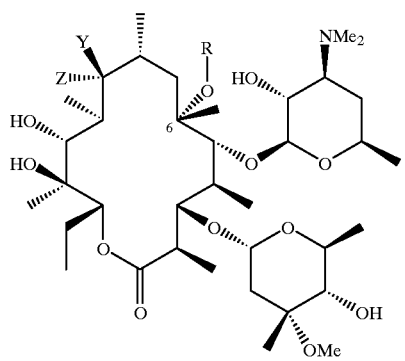

where Y, Z and R are as defined above.

A preferred intermediate in the preparation of the compound of formula (X) is the compound of formula (XII)

(XII)

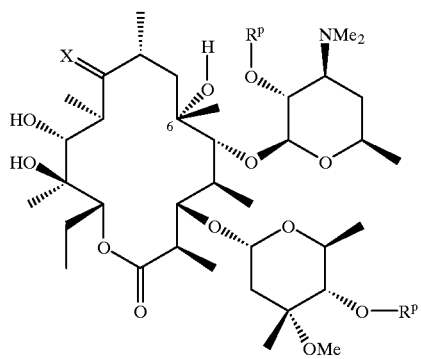

where X is as defined above and R^P is a hydroxy protecting group.

A compound according to claim 1 which is selected from the group consisting of:

(A) compounds wherein A, B, D, E, W, X, Y, Z, R, $R^a$, $R^b$, $R^c$, $R^d$, $R^e$, $R^f$, $R^g$ and $R^h$ are as previously defined, and R is selected from the group consisting of:

(1) 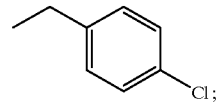

(2) 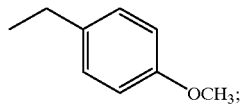

(3) 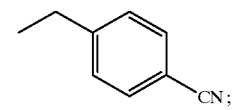

(4) 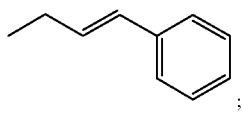

(5) 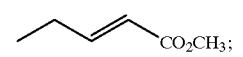

(6) 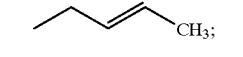

(7) 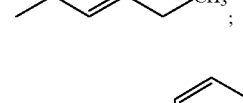

(8) 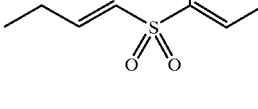

(9)

(10)

(11)

(12)

(13) 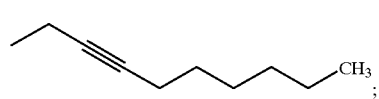

(14) 

(15)

(16) 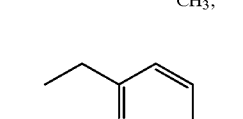

(17)

(18) 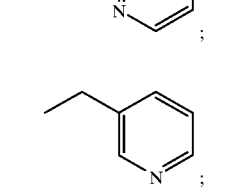

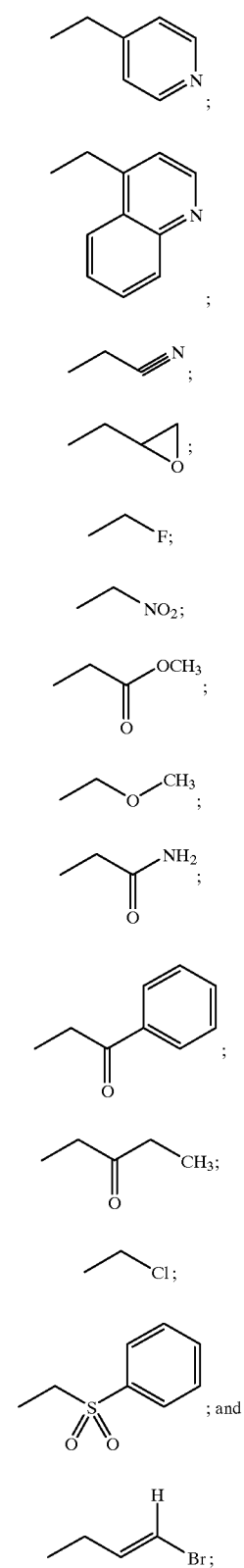

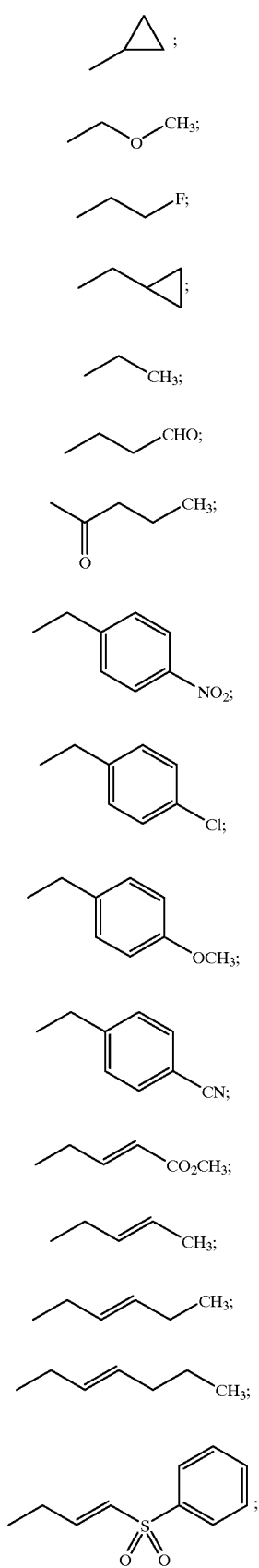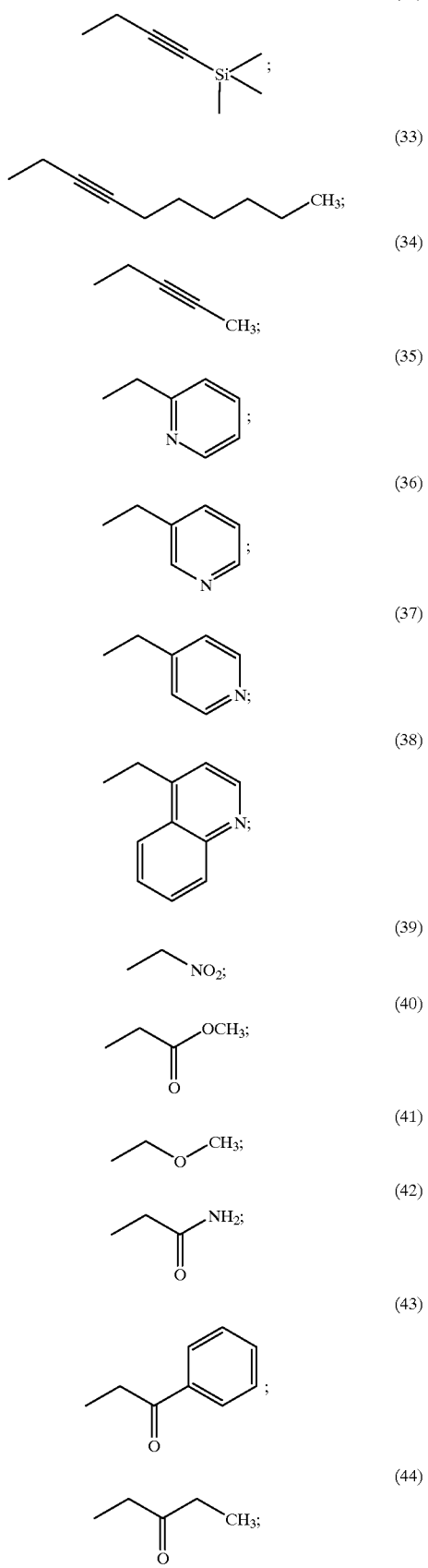

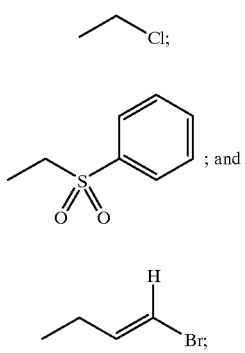

(C) a compound of Formula (II) therein wherein X is =O, $R^b$ is H; $R^c$ is H; $R^d$ is acetyl; $R^e$ is methoxy; $R^f$ is acetyl; R is —CH$_2$—CH=CH$_2$;

(D) a compound of Formula (V) therein which is selected from the group wherein
(1) $R^b$ is H; $R^c$ is H; $R^d$ is phenylmethyloxycarbonyl; $R^e$ is methoxy; $R^f$ is H; R is —CH$_2$—CH=CH$_2$; and
(2) $R^b$ is H; $R^c$ is H; $R^d$ is hydroxy; $R^e$ is methoxy; $R^f$ is H; R is —CH$_2$—CH=CH$_2$;

(E) a compound of Formula (VI) therein which is selected from the group wherein
(1) $R^b$ is H; $R^c$ is H; $R^d$ is phenylmethyloxycarbonyl; $R^e$ is methoxy; $R^f$ is acetyl; R is —CH$_2$—CH=CH$_2$; and
(2) $R^a$ is hydroxy; $R^b$ is H; $R^c$ is H; $R^d$ is H; $R^e$ is methoxy; $R^f$ is H; R is —CH$_2$—CH=CH$_2$;

(F) a compound of Formula (VII) therein which is selected from the group wherein
(1) W is —NH—; $R^b$ is H; $R^c$ is H; $R^d$ is phenylmethyloxycarbonyl; $R^e$ is methoxy; $R^f$ is H; $R^g$ is H; R is propyl;
(2) W is —NH—; $R^b$ is H; $R^c$ is H; $R^d$ is H; $R^e$ is methoxy; $R^f$ is H; $R^g$ is H; R is propyl;
(3) W is —NH—; $R^b$ is H; $R^c$ is H; $R^d$ is phenylmethyloxycarbonyl; $R^e$ is methoxy; $R^f$ is H; $R^g$ is H; R is —CH$_2$—CH=CH$_2$;
(4) W is absent; $R^b$ is H; $R^c$ is H; $R^d$ is phenylmethyloxycarbonyl; $R^e$ is methoxy; $R^f$ is acetyl; $R^g$ is 4-phenylbutyl; R is —CH$_2$—CH=CH$_2$;
(5) W is absent; $R^b$ is H; $R^c$ is H; $R^d$ is phenylmethyloxycarbonyl; $R^e$ is methoxy; $R^f$ is H; $R^g$ is 4-phenylbutyl; R is —CH$_2$—CH=CH$_2$;
(6) W is absent; $R^b$ is H; $R^c$ is H; $R^d$ is H; $R^e$ is methoxy; $R^f$ is H; $R^g$ is 4-phenylbutyl; R is propyl;
(7) W is absent; $R^b$ is H; $R^c$ is H; $R^d$ is phenylmethyloxycarbonyl; $R^e$ is methoxy; $R^f$ is acetyl; $R^g$ is 4-phenylbutyl; R is —CH$_2$—CH=CH$_2$-(3-quinolinyl);
(8) W is absent; $R^b$ is H; $R^c$ is H; $R^d$ is phenylmethyloxycarbonyl; $R^e$ is methoxy; $R^f$ is H; $R^g$ is 4-phenylbutyl; R is —CH$_2$—CH=CH$_2$-(3-quinolinyl);
(9) W is absent; $R^b$ is H; $R^c$ is H; $R^d$ is H; $R^e$ is methoxy; $R^f$ is H; $R^g$ is 4-phenylbutyl; R is —CH$_2$—CH$_2$—CH$_2$-(3-quinolinyl);
(10) W is absent; $R^b$ is H; $R^c$ is H; $R^d$ is H; $R^e$ is methoxy; $R^f$ is H; $R^g$ is H; R is —CH$_2$—CH=CH$_2$;
(11) W is absent; $R^b$ is H; $R^c$ is H; $R^d$ is H; $R^e$ is methoxy; $R^f$ is H; $R^g$ is H; R is propyl;
(12) W is absent; $R^b$ is H; $R^c$ is H; $R^d$ is H; $R^e$ is methoxy; $R^f$ is H; $R^g$ is H; R is —CH$_2$—C(O)—H;
(13) W is absent; $R^b$ is H; $R^c$ is H; $R^d$ is H; $R^e$ is methoxy; $R^f$ is H; $R^g$ is H; R is —CH$_2$—C=N—O—CH$_2$-phenyl;
(14) W is absent; $R^b$ is H; $R^c$ is H; $R^d$ is H; $R^e$ is methoxy; $R^f$ is H; $R^g$ is H; R is —CH$_2$—CH$_2$—NH—CH$_2$-phenyl;
(15) W is absent; $R^b$ is H; $R^c$ is H; $R^d$ is H; $R^e$ is methoxy; $R^f$ is H; $R^g$ is H; R is —CH$_2$—C=N—O—H (anti-isomer);
(16) W is absent; $R^b$ is H; $R^c$ is H; $R^d$ is H; $R^e$ is methoxy; $R^f$ is H; $R^g$ is H; R is —CH$_2$—C=N—O—H (syn-isomer);
(17) W is absent; $R^b$ is H; $R^c$ is H; $R^d$ is H; $R^e$ is methoxy; $R^f$ is H; $R^g$ is H; R is —CH$_2$—C=N—O-phenyl;
(18) W is absent; $R^b$ is H; $R^c$ is H; $R^d$ is H; $R^e$ is methoxy; $R^f$ is H; $R^g$ is H; R is —CH$_2$—C=N—O—CH$_2$-(4-nitrophenyl);
(19) W is absent; $R^b$ is H; $R^c$ is H; $R^d$ is H; $R^e$ is methoxy; $R^f$ is H; $R^g$ is H; R is —CH$_2$—C=N—O—CH$_2$-(4-quinolinyl);
(20) W is absent; $R^b$ is H; $R^c$ is H; $R^d$ is H; $R^e$ is methoxy; $R^f$ is H; $R^g$ is H; R is —CH$_2$—C=N—O—C(phenyl)$_3$;
(21) W is absent; $R^b$ is H; $R^c$ is H; $R^d$ is H; $R^e$ is methoxy; $R^f$ is H; $R^g$ is H; R is —CH$_2$—CH$_2$—NH$_2$;
(22) W is absent; $R^b$ is H; $R^c$ is H; $R^d$ is H; $R^e$ is methoxy; $R^f$ is H; $R^g$ is H; R is —CH$_2$—CH$_2$—NH—CH$_2$-phenyl;
(23) W is absent; $R^b$ is H; $R^c$ is H; $R^d$ is H; $R^e$ is methoxy; $R^f$ is H; $R^g$ is H; R is —CH$_2$—CH$_2$—NH—CH$_2$—CH$_2$-phenyl;
(24) W is absent; $R^b$ is H; $R^c$ is H; $R^d$ is H; $R^e$ is methoxy; $R^f$ is H; $R^g$ is H; R is —CH$_2$—CH$_2$—NH—CH$_2$—CH$_2$-CH$_2$-phenyl;
(25) W is absent; $R^b$ is H; $R^c$ is H; $R^d$ is acetyl; $R^e$ is methoxy; $R^f$ is acetyl; $R^g$ is H; R is —CH$_2$—CH=CH$_2$;
(26) W is absent; $R^b$ is H; $R^c$ is H; $R^d$ is acetyl; $R^e$ is methoxy; $R^f$ is acetyl; $R^g$ is H; R is —CH$_2$—CH=CH$_2$-(3-quinolinyl);
(27) W is absent; $R^b$ is H; $R^c$ is H; $R^d$ is acetyl; $R^e$ is methoxy; $R^f$ is H; $R^g$ is H; R is —CH$_2$CH=CH$_2$-(3-quinolinyl);
(28) W is absent; $R^b$ is H; $R^c$ is H; $R^d$ is H; $R^e$ is methoxy; $R^f$ is H; $R^g$ is H; R is —CH$_2$CH=CH$_2$-(3-quinolinyl);
(29) W is absent; $R^b$ is H; $R^c$ is H; $R^d$ is H; $R^e$ is methoxy; $R^f$ is acetyl; $R^g$ is H; R is —CH$_2$CH=CH$_2$-(3-quinolinyl);
(30) W is absent; $R^b$ is H; $R^c$ is H; $R^d$ is methoxy; $R^e$ is methoxy; $R^f$ is H; $R^g$ is H; R is —CH$_2$CH=CH$_2$-(3-quinolinyl);
(31) W is absent; $R^b$ is H; $R^c$ is H; $R^e$ is methoxy; $R^d$ is ethenesulfonyloxy; $R^f$ is acetyl; $R^g$ is H; R is —CH$_2$CH=CH$_2$-(3-quinolinyl);
(32) W is absent; $R^b$ is H; $R^c$ is H; $R^e$ is methoxy; $R^d$ is 2-(dimethylamino)ethylsulfonyloxy; $R^f$ is acetyl; $R^g$ is H; R is —CH$_2$CH=CH$_2$-(3-quinolinyl);
(33) W is absent; $R^b$ is H; $R^c$ is H; $R^d$ is methoxy; $R^e$ is 2-(phenylthio)ethoxy; $R^f$ is acetyl; $R^g$ is H; R is —CH$_2$CH=CH$_2$-(3-quinolinyl);
(34) W is absent; $R^b$ is H; $R^c$ is H; $R^d$ is methoxy; $R^e$ is (2-nitrophenyl)aminocarbonyloxy; $R^f$ is H; $R^g$ is H; R is —CH$_2$CH=CH$_2$-(3-quinolinyl); and
(35) W is absent; $R^b$ is H; $R^c$ is H; $R^d$ is methoxy; $R^e$ is (2-nitrophenyl)aminocarbonyloxy; $R^f$ is H; $R^g$ is H; R is —CH$_2$CH=CH$_2$-(3-quinolinyl);

(G) a compound wherein $R^a$ is OH; $R^b$ is H; $R^c$ is H; $R^d$ is H; $R^e$ is methoxy; $R^f$ is H; selected from the group consisting of compounds wherein
(1) X is =O, R is —CH$_2$—CH=CH$_2$-(3-quinolinyl);
(2) X is =O, R is allyl;
(3) X is =N—OH, R is allyl;
(4) X is =O, R is propyl;
(5) X is =O, R is 2,3-dihydroxypropyl;
(6) X is =O, R is 2,3-epoxypropyl;
(7) X is =O, R is 2-hydroxy-3-(imidazol-1-yl)propyl;
(8) X is =O, R is 2-hydroxy-3-(morpholin-4-yl)propyl;
(9) X is =O, R is 2-hydroxy-3-(benzylamino)propyl;
(10) X is =O, R is 2-oxoethyl;
(11) X is =O, R is 2-oxopropyl;
(12) X is =N—O-(1-isopropoxycyclohexyl), R is —CH$_2$—C∫CH;
(13) R is —CH$_2$—C∫CH, X is =N—O—H;
(14) X is =O, R is —CH$_2$—C∫CH;
(15) X is =O, R is —CH$_2$—CHOH—CH$_2$—N$_3$;
(16) X is =O, R is —CH$_2$—CH=N—OH;
(17) X is =O, R is —CH$_2$—CH$_2$OH;
(18) X is =O, R is —CH$_2$—CH$_2$NH$_2$;
(19) X is =O, R is —CH$_2$—CN;
(20) X is =O, R is —CH$_2$-Phenyl;
(21) X is =O, R is —CH$_2$—CH=CH—Phenyl—;
(22) X is =O, R is —CH$_2$—CH=N—O—CH$_3$;
(23) X is =O, R is —CH$_2$—CH=N—O—CH$_2$-Phenyl;
(24) X is =O, R is —CH$_2$—CH=N—N(CH$_3$)$_2$;
(25) X is =O, R is —CH$_2$—CH=N—NH(CH$_3$);
(26) X is =O, R is —CH$_2$—CH=N-(4-Morpholinyl);
(27) X is =O, R is —CH$_2$—CH=N—NH(Phenyl); and
(28) X is =O, R is —CH$_2$—CH=N—N(Phenyl)$_2$;
(29) X=O, R=Phenylpropyl;
(30) X=O, R is —CH$_2$CH=CH-(4-methylphenyl);
(31) X=O, R is —CH$_2$—CH(OH)-Phenyl;
(32) X=O, R is —CH$_2$—CH(Br)-CH$_2$Br;
(33) X=O, R is —CH$_2$CH$_2$NHCH$_2$CH$_2$-Phenyl;
(34) X=O, R is —CH$_2$CH$_2$NHCH(CH$_2$Phenyl)CO$_2$Me;
(35) X=O, R is —CH$_2$CH$_2$NHCH$_2$CH$_2$CH$_3$;
(36) X=O, R is —CH$_2$CH$_2$NHCH$_2$CO$_2$CH$_2$CH$_2$;
(37) X=O, R is —CH$_2$CH$_2$NHCH$_2$CH$_2$-Phenyl;
(38) X=O, R is —CH$_2$CH$_2$NHCH$_2$CH$_2$-(4-hydroxyphenyl);
(39) X=O, R is —CH$_2$CH$_2$NHCH$_2$CH$_2$-(3-hydroxyphenyl);
(40) X=O, R is —CH$_2$CH$_2$NHCH$_2$CH$_2$-(3-methoxyphenyl);
(41) X=O, R is —CH$_2$CH$_2$NHCH$_2$CH$_2$-(2-methoxyphenyl);
(42) X=O, R is —CH$_2$CH$_2$NHCH$_2$CH$_2$-(4-methoxyphenyl);
(43) X=O, R is —CH$_2$CH$_2$NHCH$_2$-phenyl;
(44) X is =N—O-(1-isopropoxycyclohexyl), R is fluoromethyl;
(45) X=O, R is —CH$_2$CH$_2$NHCH$_2$CH$_2$-(3-chlorophenyl);
(46) X=O, R is —CH$_2$CH$_2$NHCH$_2$CH$_2$-(2-chlorophenyl);
(47) X=O, R is —CH$_2$CH$_2$NHCH$_2$CH$_2$-(4-chlorophenyl);
(48) X=O, R is —CH$_2$CH$_2$NHCH$_2$CH$_2$—O-phenyl);
(49) X=O, R is —CH$_2$CH$_2$NHCH$_2$CH$_2$-(4-quinolinyl);
(50) X=O, R is —CH$_2$CH$_2$NHCH$_2$CH$_2$CH$_2$-(3-quinolinyl);
(51) X=O, R is —CH$_2$CH$_2$NHCH$_2$CH$_2$CH$_2$-phenyl;
(52) X=O, R is —CH$_2$—CH=N—NH—C(O)—NH$_2$;
(53) X=O, R is —CH$_2$—CH=N—NH-(2-pyridinyl);
(54) X=O, R is —CH$_2$—CH=N-(4-methylpiperazinyl);
(55) X=O, R is —CH$_2$—CH=N—O-phenyl;
(56) X=O, R is —CH$_2$CH(OH)CH$_2$NHCH$_2$CH$_2$-phenyl;
(57) X=O, R is —CH$_2$CH(OH)CH$_2$NHCH$_2$-(4-pyridinyl);
(58) X is =O, R is (3-iodophenyl)methyl; and
(59) X is =O, R is (4-fluorophenyl)methyl;
(H) a compound wherein $R^a$ is OH; $R^b$ is H; $R^c$ is H; $R^d$ is H; $R^e$ is methoxy; $R^f$ is H; X is O; R is CH$_2$—CH(OH)—CH$_2$—$R^V$; and $R^V$ is selected from the group consisting of:

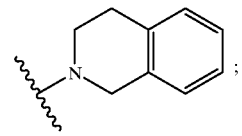
(1)

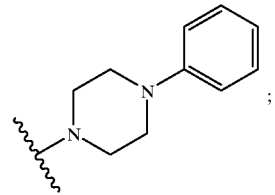
(2)

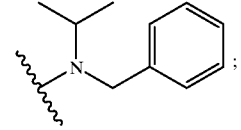
(3)

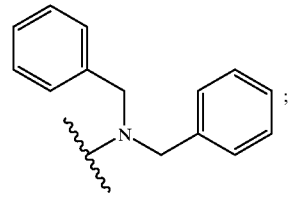
(4)

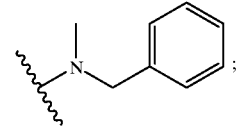
(5)

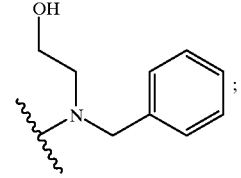
(6)

-continued (7) (8) (9) (10) (11) (12) (13) (14) (15) (16) (17) (18) (19) (20) (21) (22)

(23) 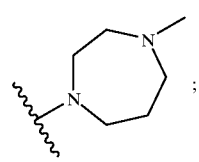
(24) 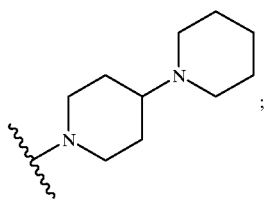
(25) 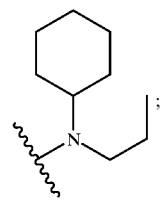
(26) 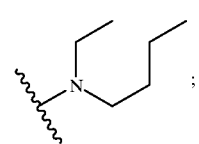
(27) 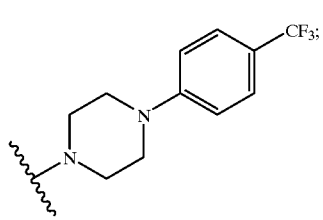
(28) 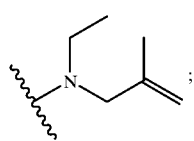
(29) 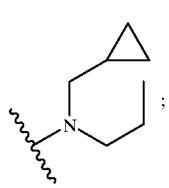
(30) 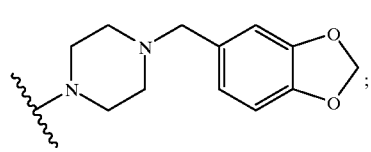
(31) 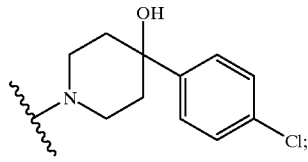
(32) 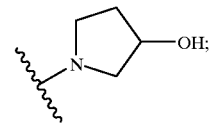
(33) 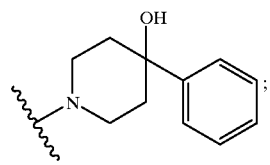
(34) 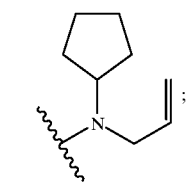
(35) 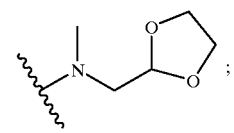
(36) 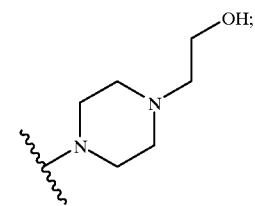
(37) 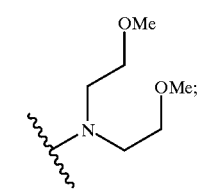
(38) 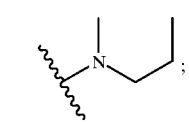

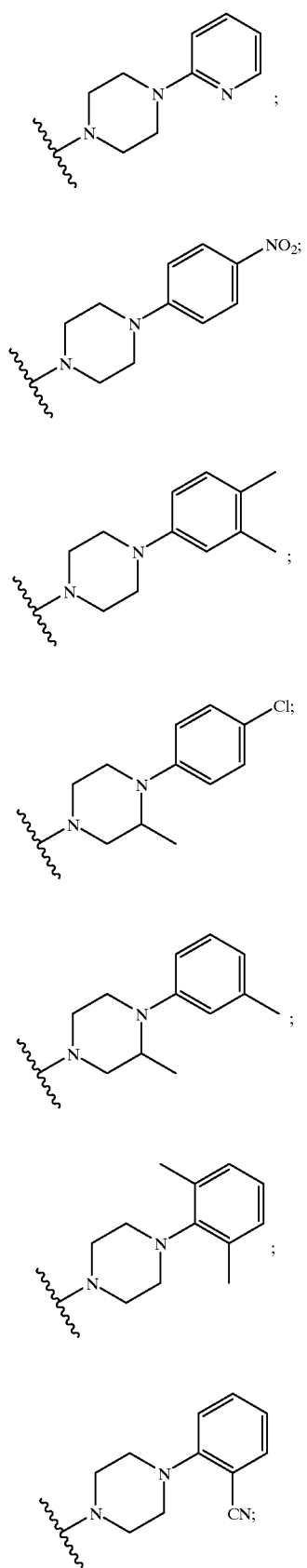
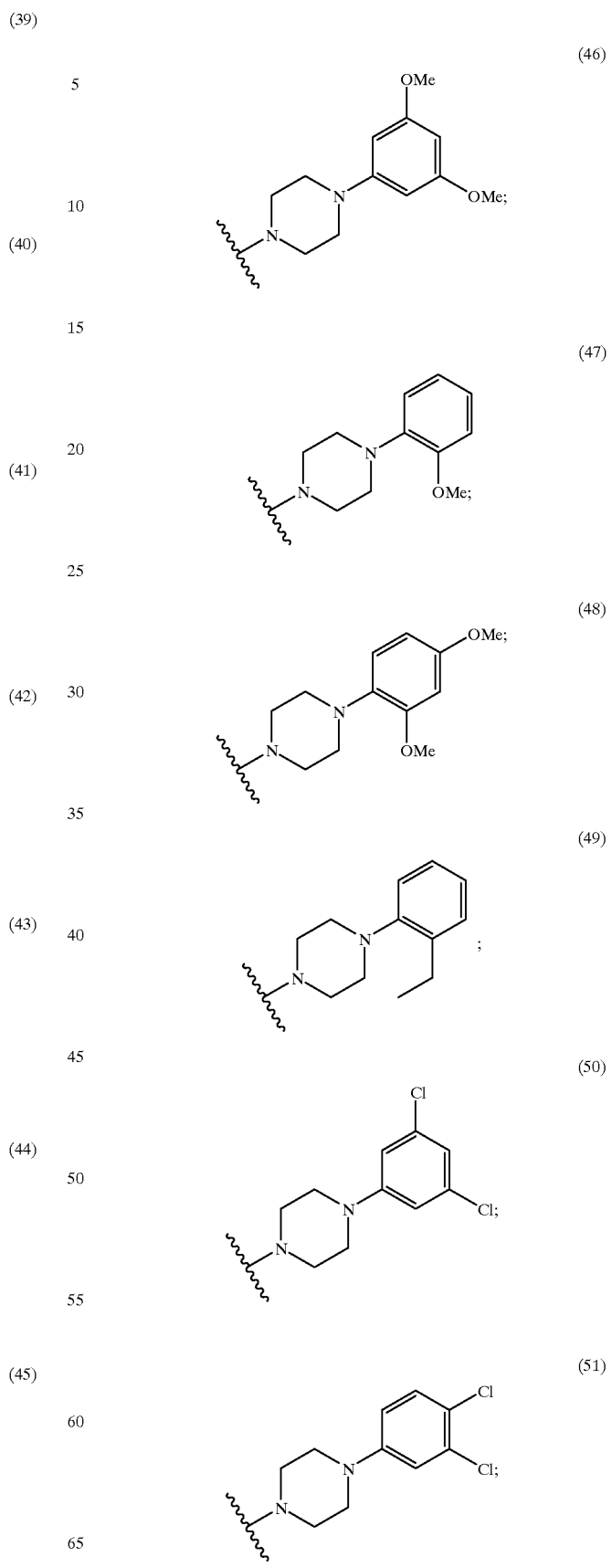

-continued
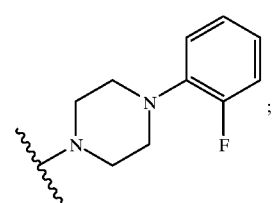 (52)
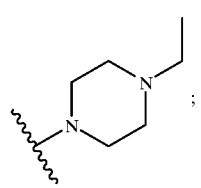 (53)
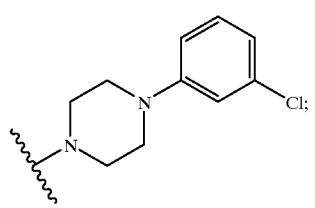 (54)
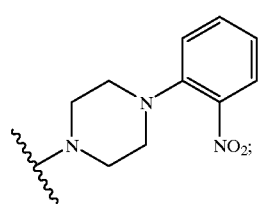 (55)
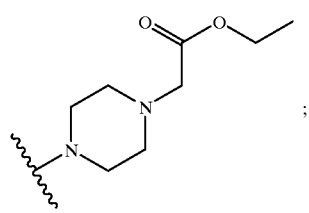 (56)
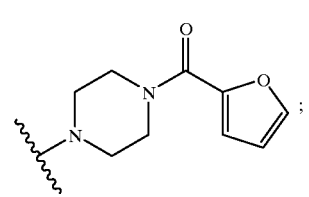 (57)
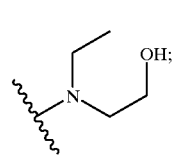 (58)
-continued
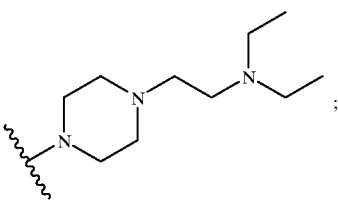 (59)
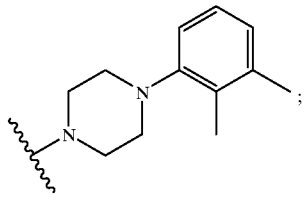 (60)
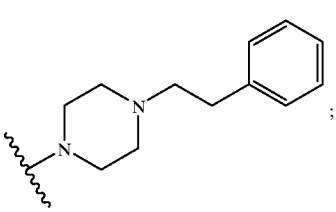 (61)
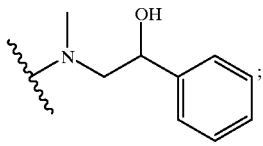 (62)
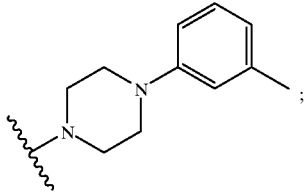 (63)
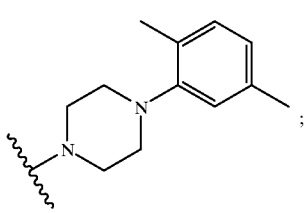 (64)
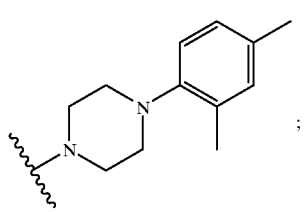 (65)

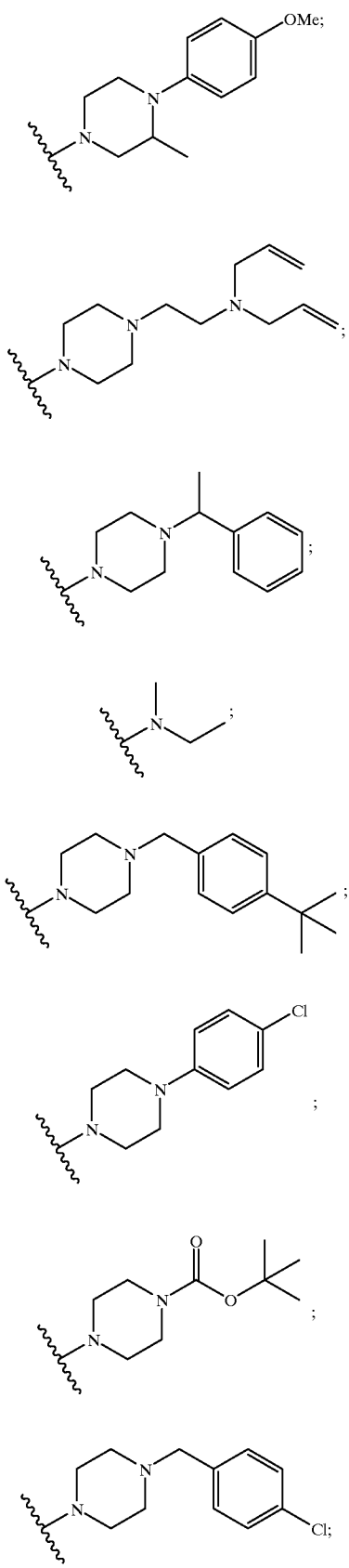
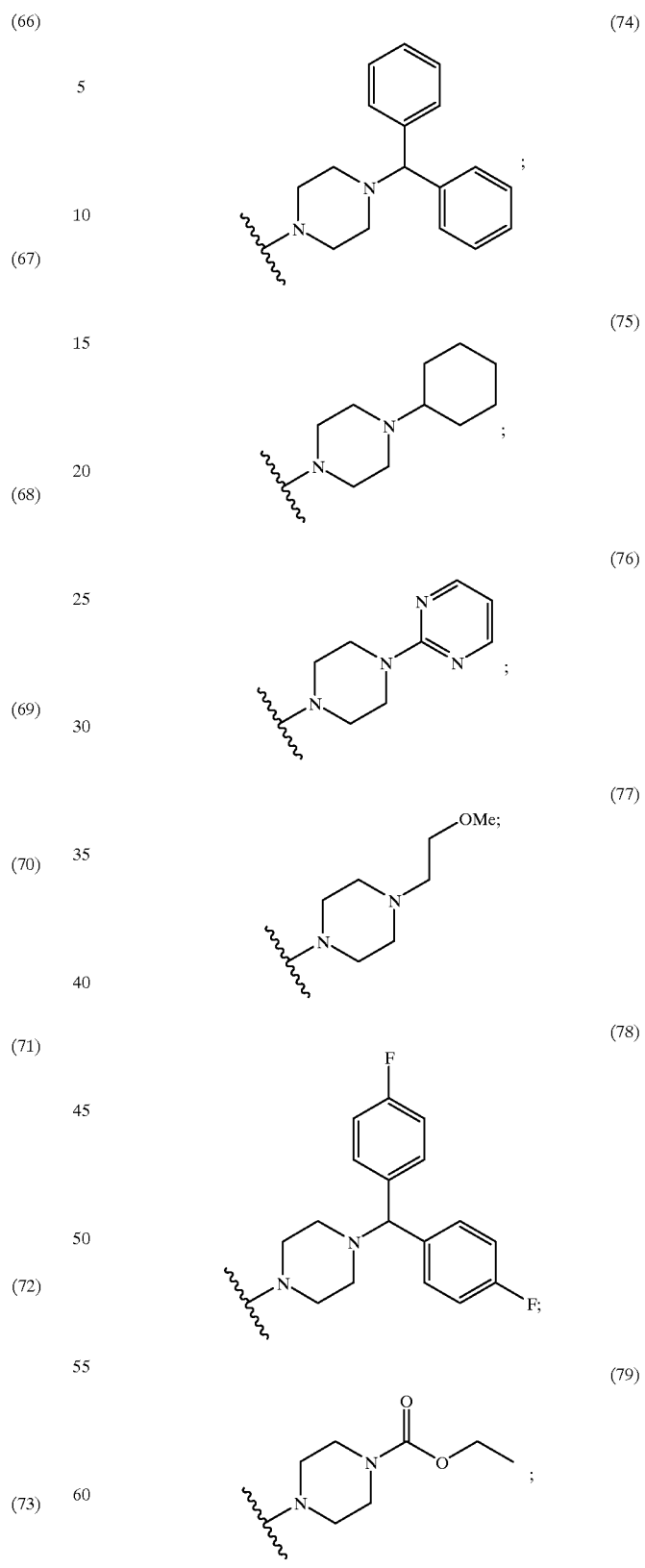
(I) a compound wherein X is O, R is $CH_2$—$CH_2$—$R^W$, and $R^W$ is selected from the group consisting of:

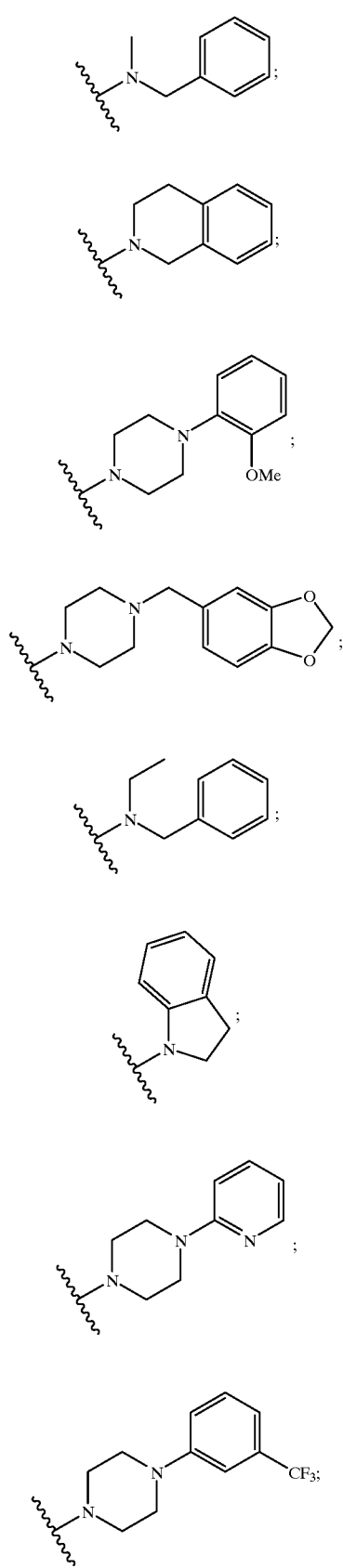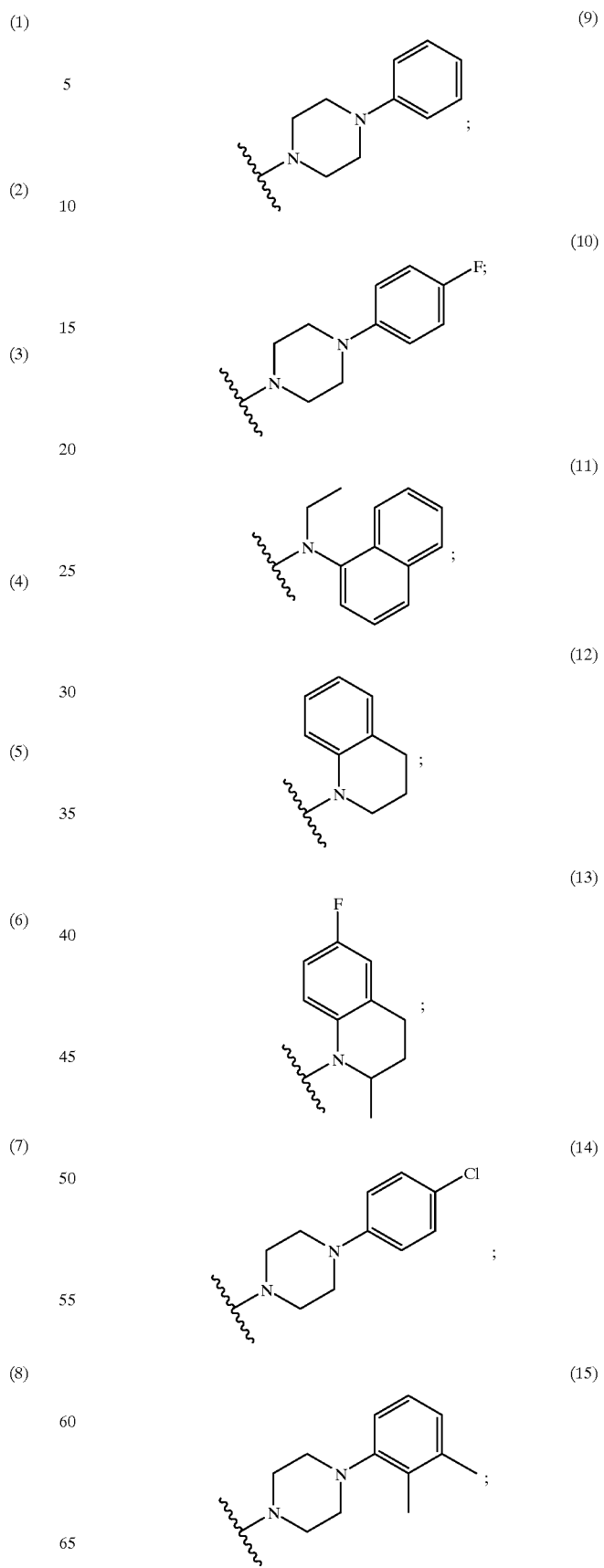

-continued
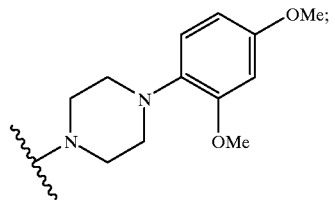 (16)
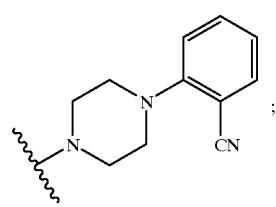 (17)
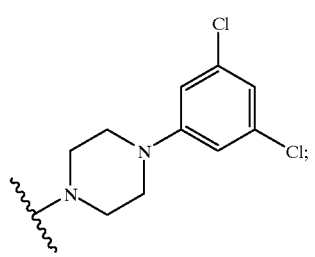 (18)
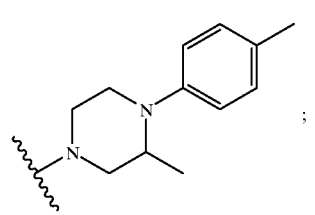 (19)
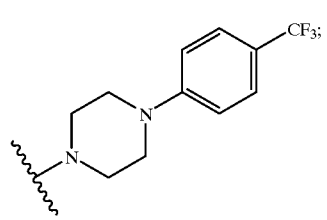 (20)
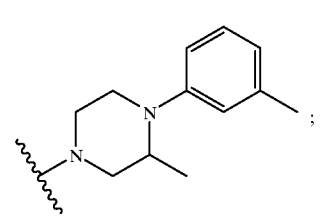 (21)
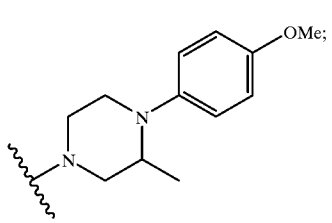 (22)
-continued
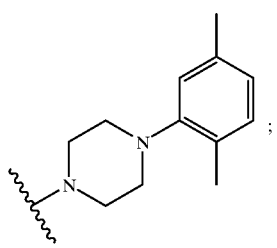 (23)
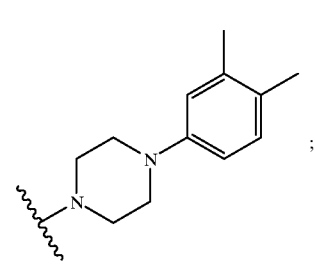 (24)
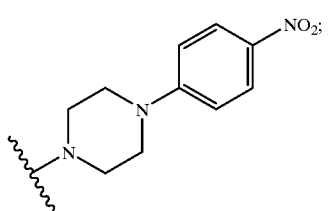 (25)
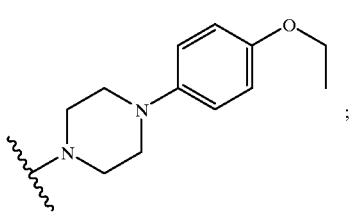 (26)
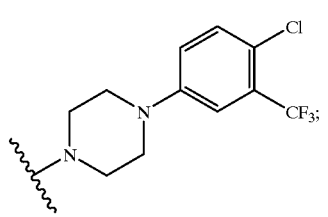 (27)
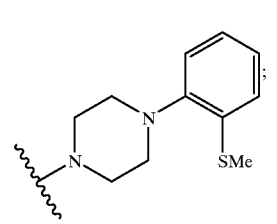 (28)

(29) 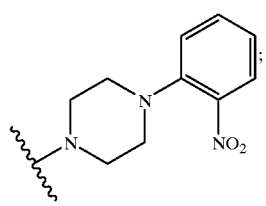
(30) 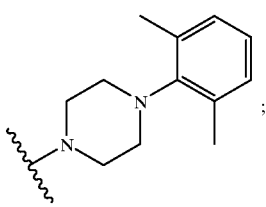
(31) 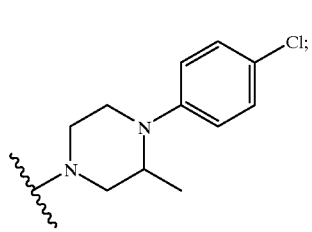
(32) 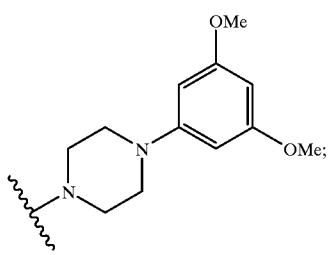
(33) 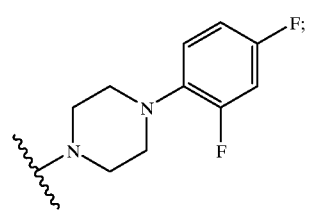
(34) 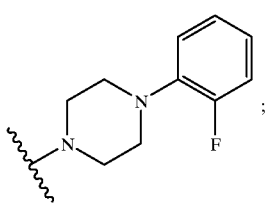
(35) 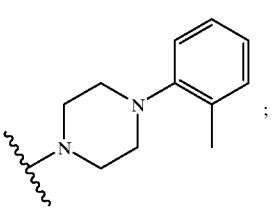
(36) 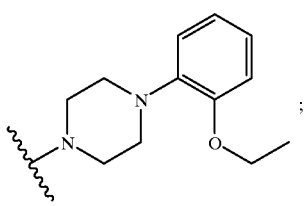
(37) 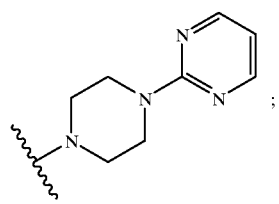
(38) 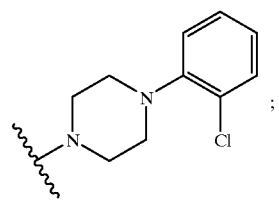
(39) 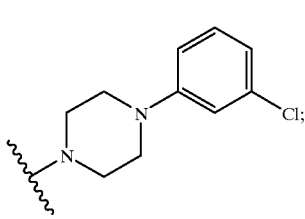
(40) 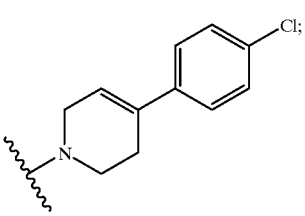
(41) 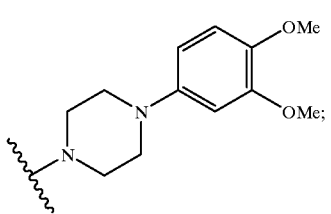
(42) 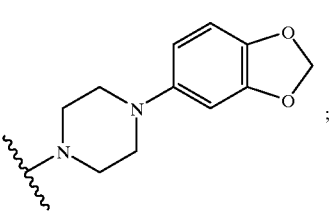

-continued
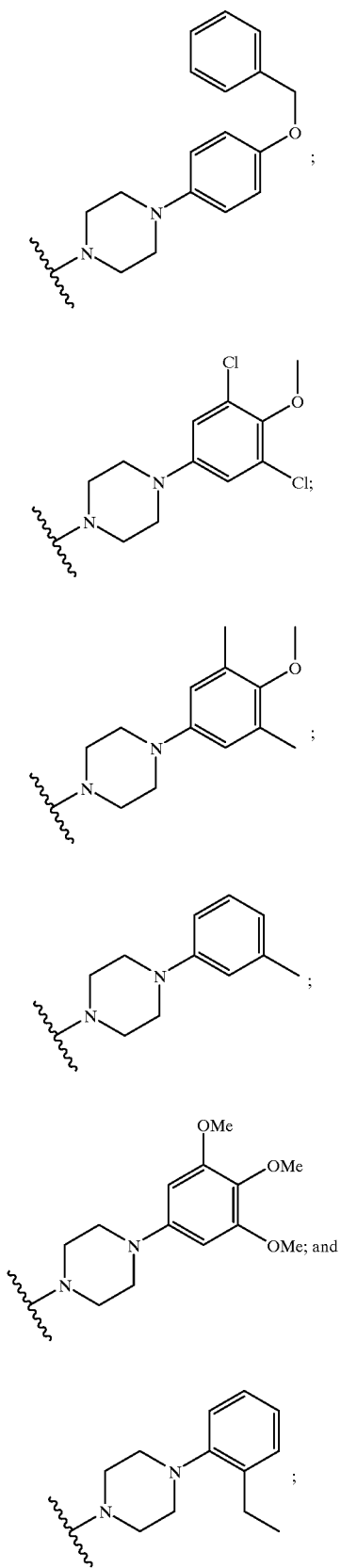
(J) a compound wherein X is O, R is $CH_2-CH=N-R^x$, and $R^x$ is selected from the group consisting of:
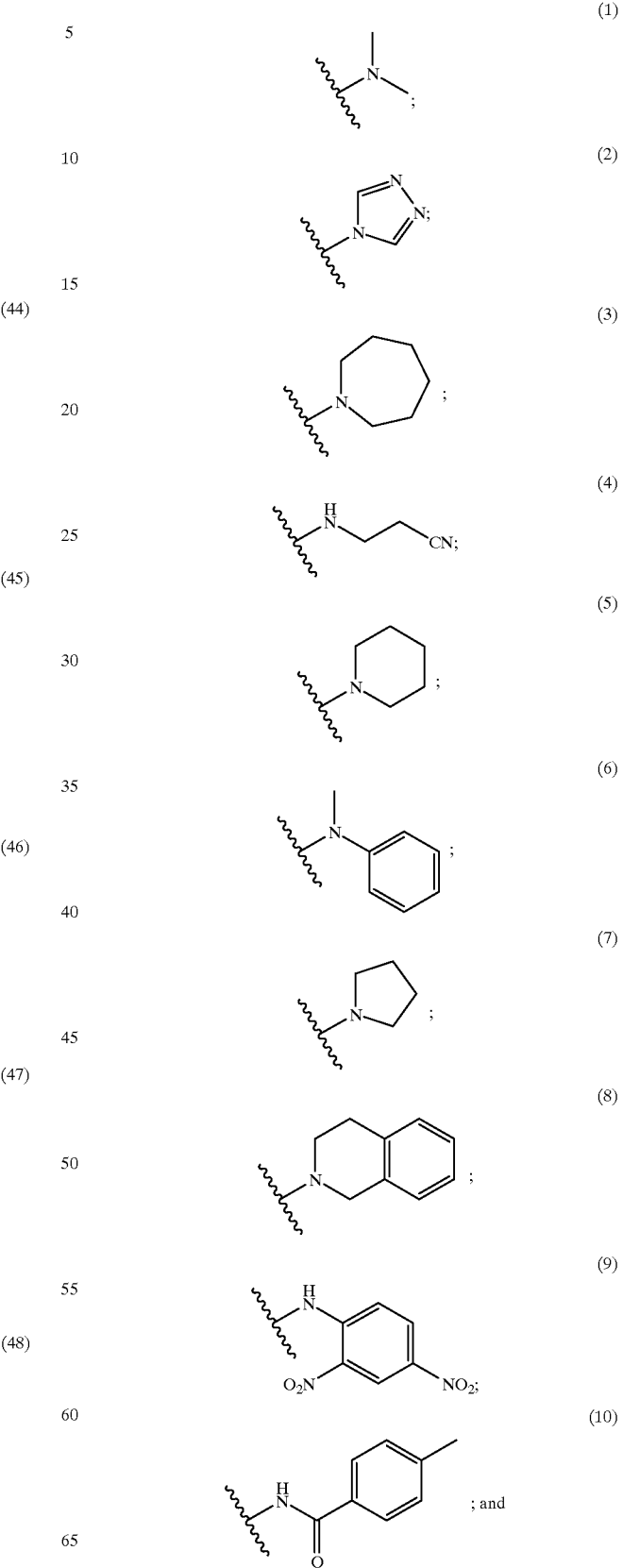

(11)

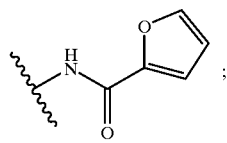

and (K) a compound wherein $R^a$ is OH; $R^b$ is H; $R^c$ is H; $R^d$ is RP; $R^e$ is methoxy; $R^f$ is RP; selected from the group consisting of compounds wherein:
(1) X is =N—O-(1-isopropoxycyclohexyl), R is allyl, RP is Trimethylsilyl
(2) X is =N—O-(1-isopropoxycyclohexyl), R is —CH$_2$-Phenyl, RP is Trimethylsilyl;
(3) X is =N—O-(1-isopropoxycyclohexyl), R is —CH$_2$-Phenyl, RP is H; and
(4) X is =N—OH, R is —CH$_2$-Phenyl, RP is H;
and pharmaceutically acceptable salts, esters and prodrugs thereof. Preferred compounds are those selected from the group consisting of
(A) a compound wherein $R^a$ is OH; $R^b$ is H; $R^c$ is H; $R^d$ is H; $R^e$ is methoxy; $R^f$ is H; selected from the group consisting of compounds wherein
(1) X is =O, R is —CH$_2$—CH=CH$_2$-(3-quinolinyl);
(2) X is =O, R is allyl;
(3) X is =N—OH, R is allyl;
(4) X is =O, R is propyl;
(5) X is =O, R is 2,3-dihydroxypropyl;
(6) X is =O, R is 2,3-epoxypropyl;
(7) X is =O, R is 2-hydroxy-3-(imidazol-1-yl)propyl;
(8) X is =O, R is 2-hydroxy-3-(morpholin-4-yl) propyl;
(9) X is =O, R is 2-hydroxy-3-(benzylamino)propyl;
(10) X is =O, R is 2-oxoethyl;
(11) X is =O, R is 2-oxopropyl;
(12) X is =N—O-(1-isopropoxycyclohexyl), R is —CH$_2$-C∫CH;
(13) R is —CH$_2$-C∫CH, X is =N—O—H;
(14) X is =O, R is —CH$_2$-C∫CH;
(15) X is =O, R is —CH$_2$—CHOH—CH$_2$—N$_3$;
(16) X is =O, R is —CH$_2$—CH=N—OH;
(17) X is =O, R is —CH$_2$—CH$_2$OH;
(18) X is =O, R is —CH$_2$—CH$_2$NH$_2$;
(19) X is =O, R is —CH$_2$—CN;
(20) X is =O, R is —CH$_2$-Phenyl;
(21) X is =O, R is —CH$_2$—CH=CH—Phenyl—;
(22) X is =O, R is —CH$_2$—CH=N—O—CH$_3$;
(23) X is =O, R is —CH$_2$—CH=N—O—CH$_2$-Phenyl;
(24) X is =O, R is —CH$_2$—CH=N—N(CH$_3$)$_2$;
(25) X is =O, R is —CH$_2$—CH=N—NH(CH$_3$);
(26) X is =O, R is —CH$_2$—CH=N-(4-Morpholinyl);
(27) X is =O, R is —CH$_2$—CH=N—NH(Phenyl); and
(28) X is =O, R is —CH$_2$—CH=N—N(Phenyl)$_2$;
(29) X=O, R=Phenylpropyl;
(30) X=O, R is —CH$_2$CH=CH-(4-methylphenyl);
(31) X=O, R is —CH$_2$—CH(OH)-Phenyl;
(32) X=O, R is —CH$_2$—CH(Br)-CH$_2$Br;
(33) X=O, R is —CH$_2$CH$_2$NHCH$_2$CH$_2$CH$_2$-Phenyl;
(34) X=O, R is —CH$_2$CH$_2$NHCH(CH$_2$Phenyl)CO$_2$Me;
(35) X=O, R is —CH$_2$CH$_2$NHCH$_2$CH$_2$CH$_3$;
(36) X=O, R is —CH$_2$CH$_2$NHCH$_2$CO$_2$CH$_2$CH$_2$;
(37) X=O, R is —CH$_2$CH$_2$NHCH$_2$CH$_2$-Phenyl;
(38) X=O, R is —CH$_2$CH$_2$NHCH$_2$CH$_2$-(4-hydroxyphenyl);
(39) X=O, R is —CH$_2$CH$_2$NHCH$_2$CH$_2$-(3-hydroxyphenyl);
(40) X=O, R is —CH$_2$CH$_2$NHCH$_2$CH$_2$-(3-methoxyphenyl);
(41) X=O, R is —CH$_2$CH$_2$NHCH$_2$CH$_2$-(2-methoxyphenyl);
(42) X=O, R is —CH$_2$CH$_2$NHCH$_2$CH$_2$-(4-methoxyphenyl);
(43) X=O, R is —CH$_2$CH$_2$NHCH$_2$-phenyl;
(44) X is =N—O-(1-isopropoxycyclohexyl), R is fluoromethyl;
(45) X=O, R is —CH$_2$CH$_2$NHCH$_2$CH$_2$-(3-chlorophenyl);
(46) X=O, R is —CH$_2$CH$_2$NHCH$_2$CH$_2$-(2-chlorophenyl);
(47) X=O, R is —CH$_2$CH$_2$NHCH$_2$CH$_2$-(4-chlorophenyl);
(48) X=O, R is —CH$_2$CH$_2$NHCH$_2$CH$_2$—O-phenyl);
(49) X=O, R is —CH$_2$CH$_2$NHCH$_2$CH$_2$CH$_2$-(4-quinolinyl);
(50) X=O, R is —CH$_2$CH$_2$NHCH$_2$CH$_2$CH$_2$-(3-quinolinyl);
(51) X=O, R is —CH$_2$CH$_2$NHCH$_2$CH$_2$CH$_2$CH$_2$-phenyl;
(52) X=O, R is —CH$_2$—CH=N—NH—C(O)—NH$_2$;
(53) X=O, R is —CH$_2$—CH=N—NH-(2-pyridinyl);
(54) X=O, R is —CH$_2$—CH=N-(4-methylpiperazinyl);
(55) X=O, R is —CH$_2$—CH=N—O-phenyl;
(56) X=O, R is —CH$_2$CH(OH)CH$_2$NHCH$_2$CH$_2$-phenyl;
(57) X=O, R is —CH$_2$CH(OH)CH$_2$NHCH$_2$-(4-pyridinyl);
(58) X is =O, R is (3-iodophenyl)methyl; and
(59) X is =O, R is (4-fluorophenyl)methyl;

(B) a compound wherein $R^a$ is OH; $R^b$ is H; $R^c$ is H; $R^d$ is H; $R^e$ is methoxy; $R^f$ is H; X is O; R is CH$_2$—CH(OH)—CH$_2$—$R^V$; and $R^V$ is selected from the group consisting of:

(1)

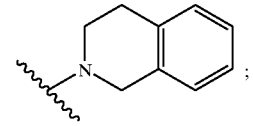

(2)

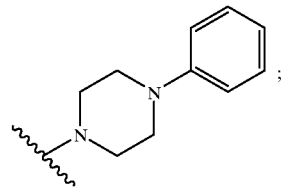

(3)

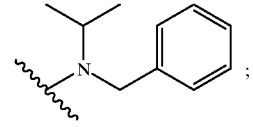

-continued (4) ;

(5) ;

(6) ;

(7) ;

(8) ;

(9) ;

(10) ;

(11) ;

(12) ;

(13) ;

(14) ;

(15) ;

(16) ;

(17) ;

(18) ;

(19) ;

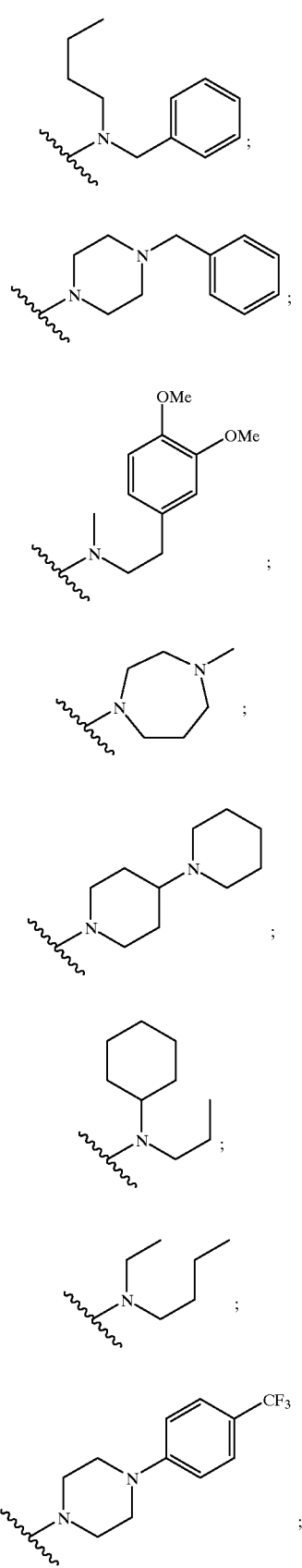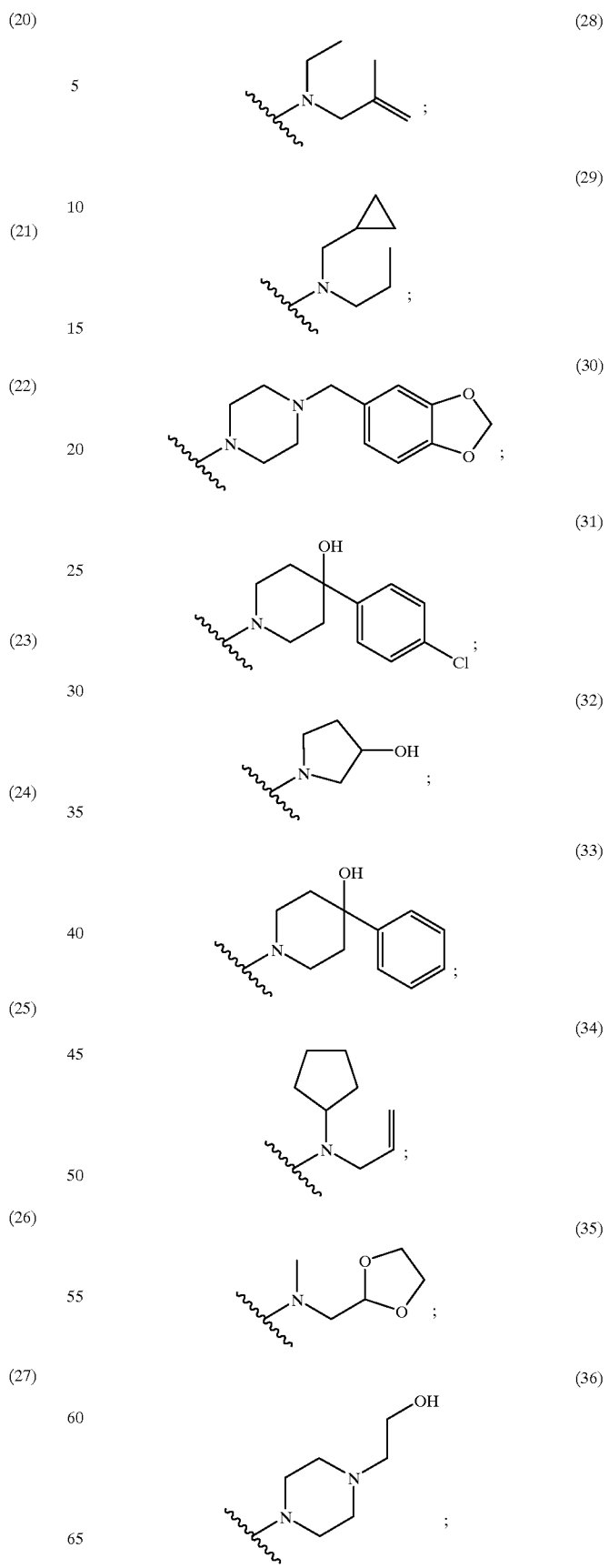

(37) 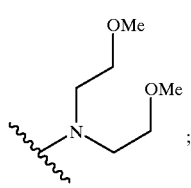
(38) 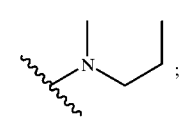
(39) 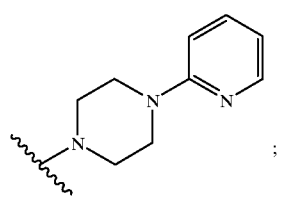
(40) 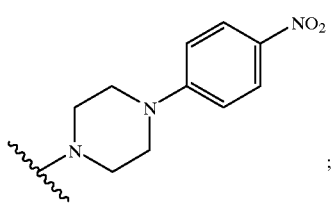
(41) 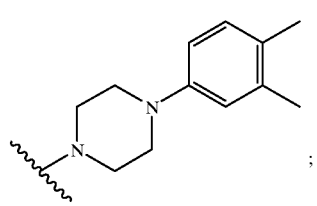
(42) 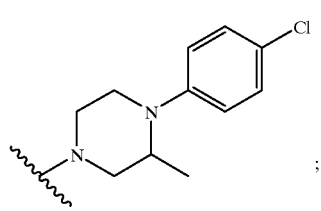
(43) 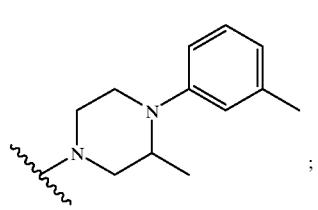
(44) 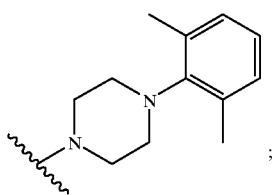
(45) 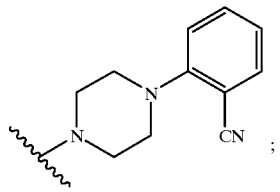
(46) 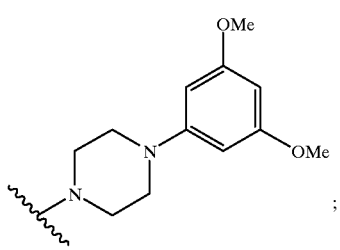
(47) 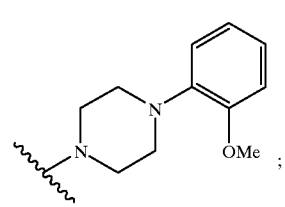
(48) 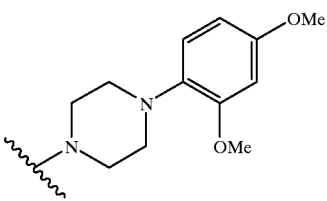
(49) 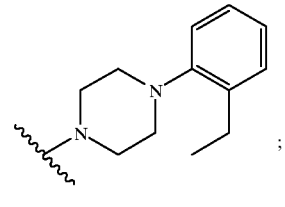
(50) 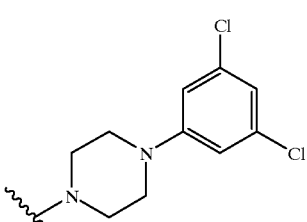

-continued
(51) 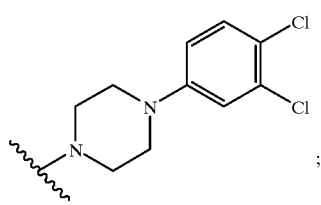
(52) 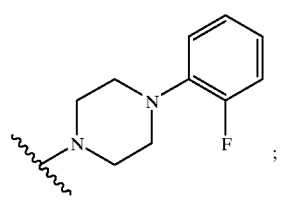
(53) 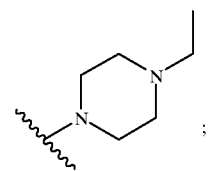
(54) 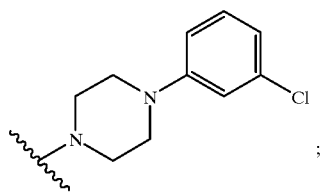
(55) 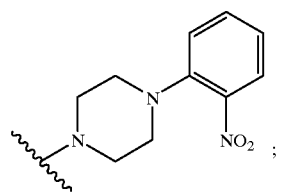
(56) 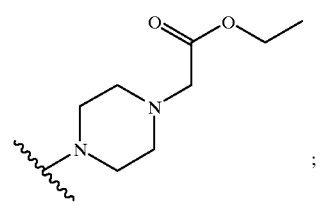
(57) 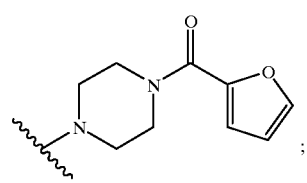
-continued
(58) 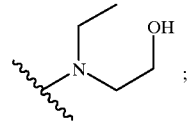
(59) 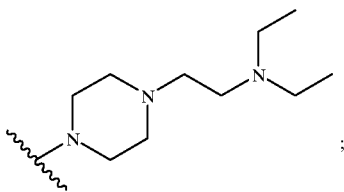
(60) 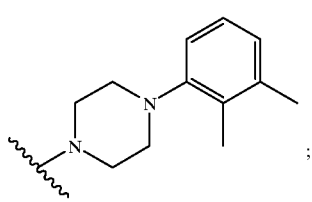
(61) 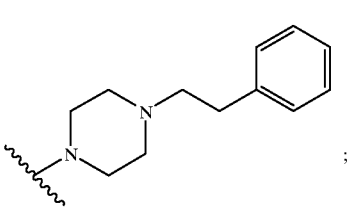
(62) 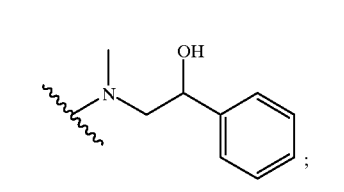
(63) 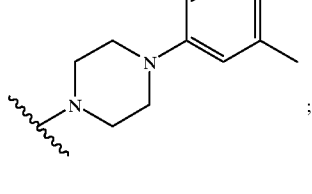
(64) 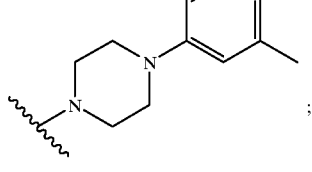

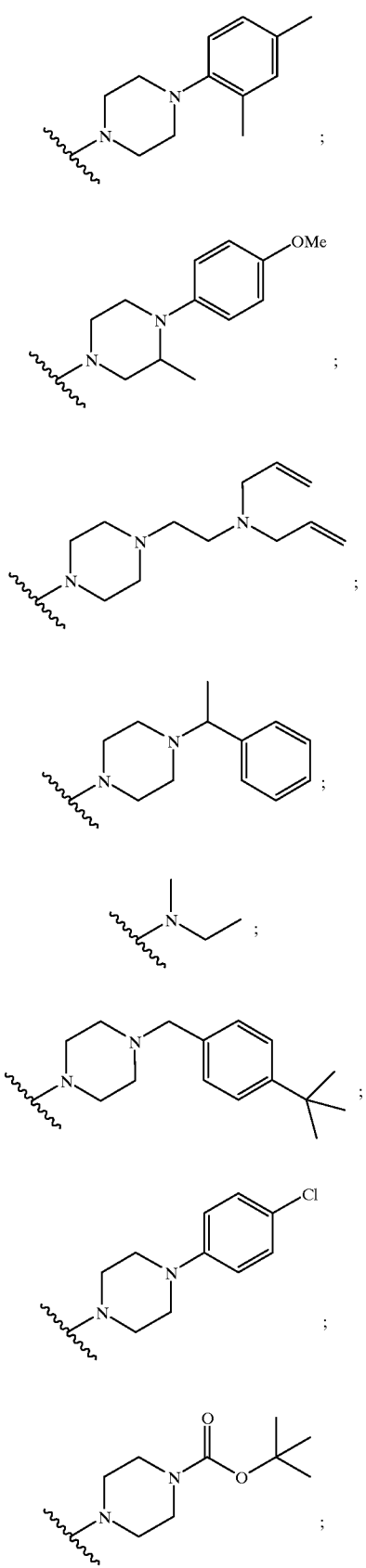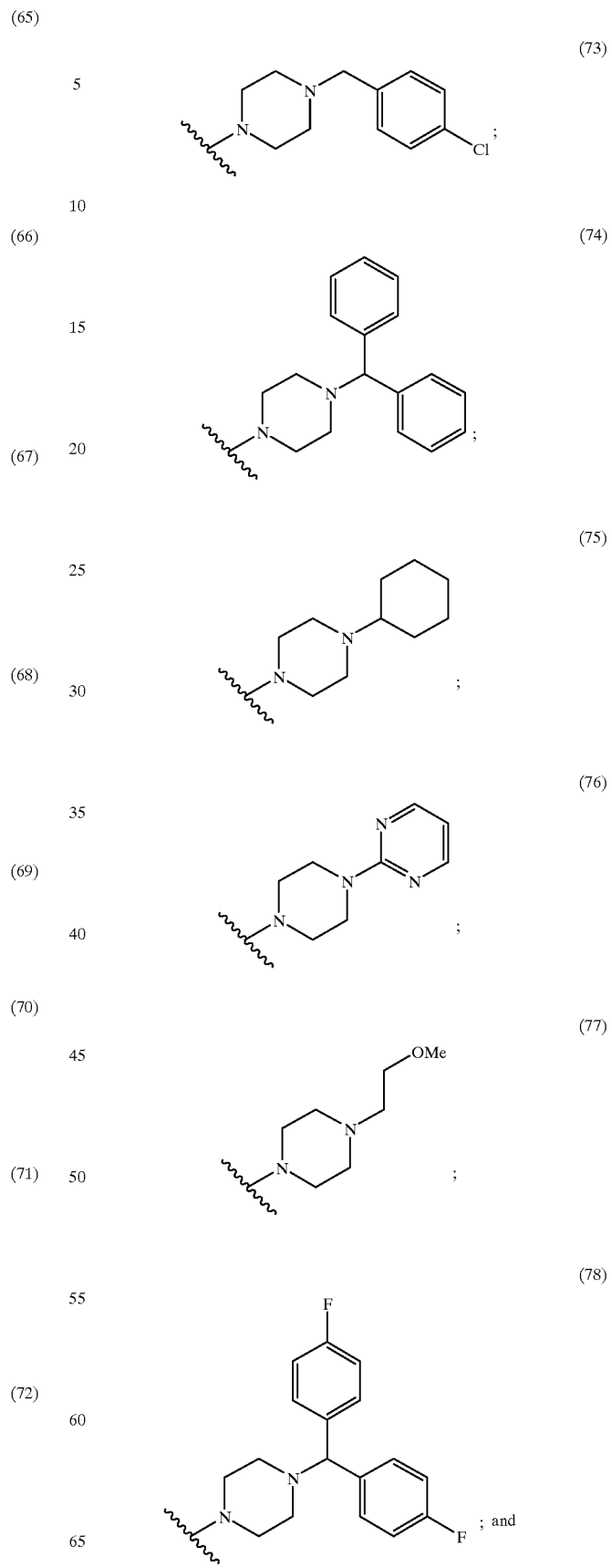

(79) 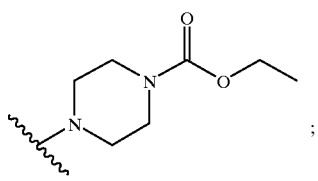
(C) a compound wherein X is O, R is CH$_2$—CH$_2$—R$^W$, and R$^W$ is selected from the group consisting of:
(1) 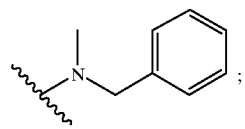
(2) 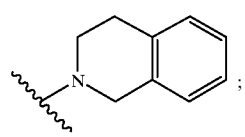
(3) 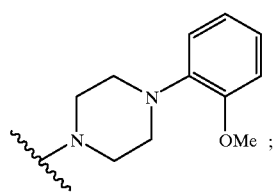
(4) 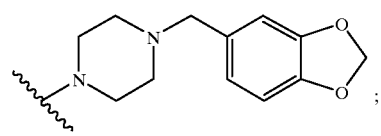
(5) 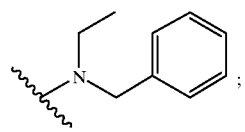
(6) 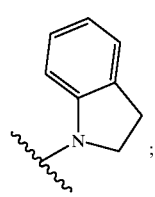
(7) 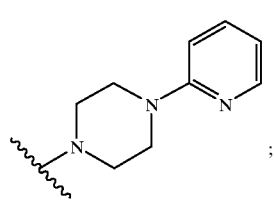
(8) 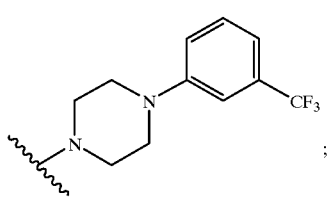
(9) 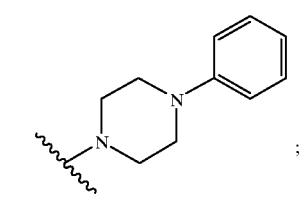
(10) 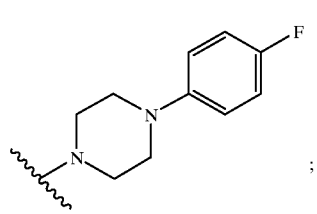
(11) 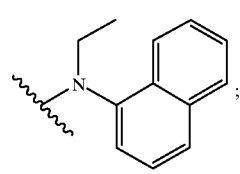
(12) 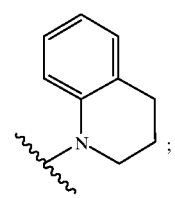
(13) 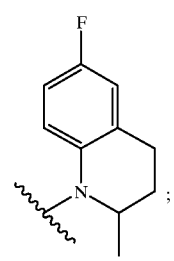
(14) 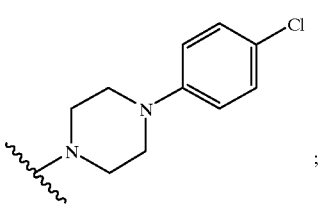

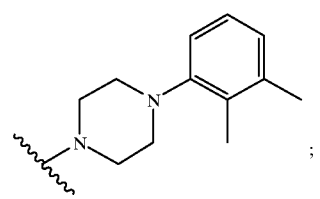 (15);
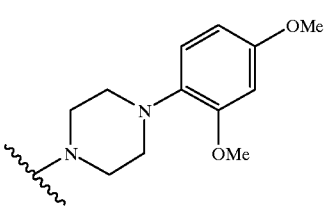 (16);
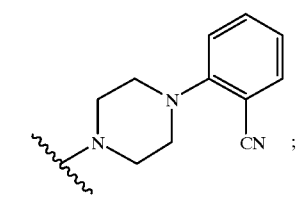 (17);
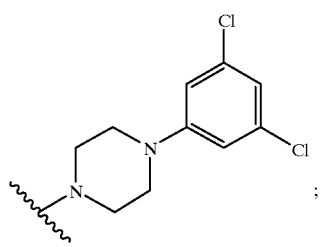 (18);
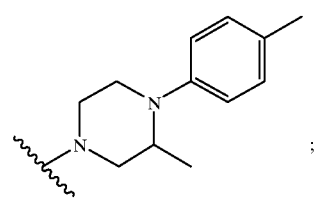 (19);
 (20);
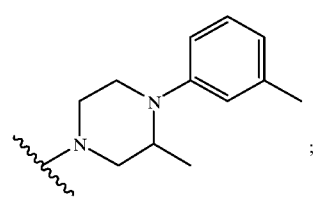 (21);
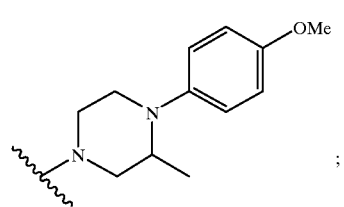 (22);
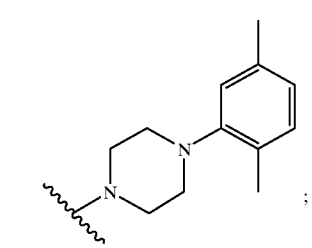 (23);
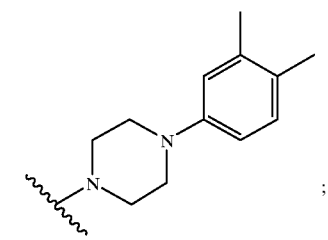 (24);
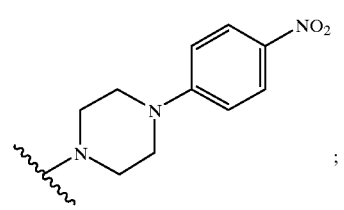 (25);
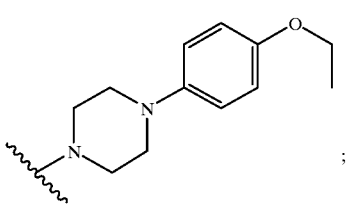 (26);
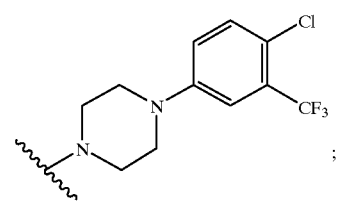 (27);

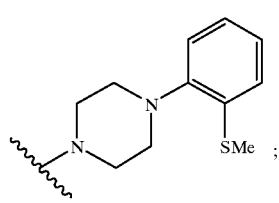 (28)
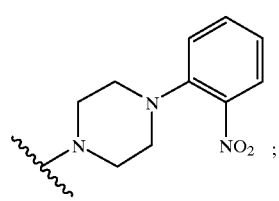 (29)
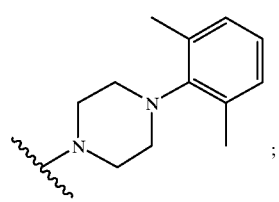 (30)
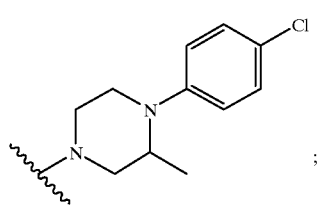 (31)
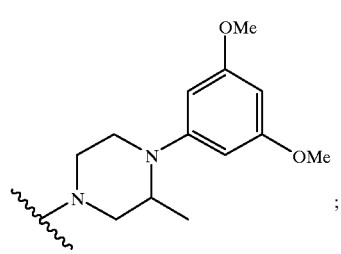 (32)
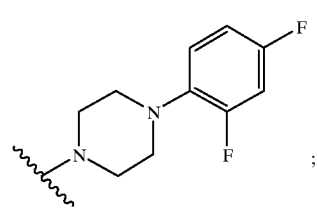 (33)
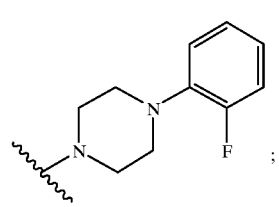 (34)
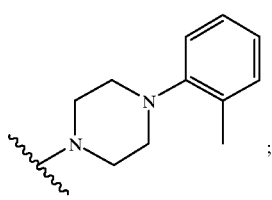 (35)
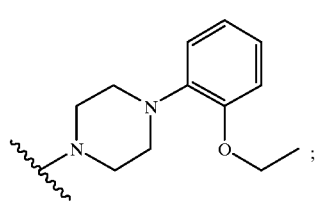 (36)
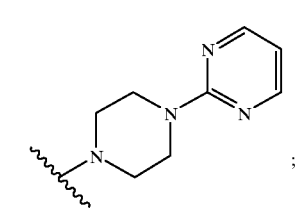 (37)
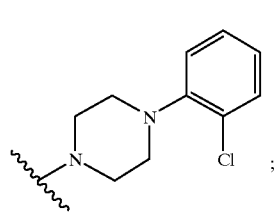 (38)
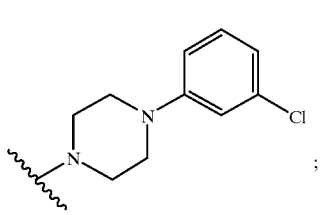 (39)
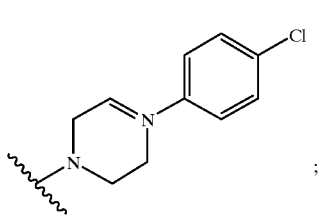 (40)
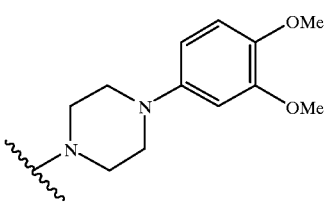 (41)

(42) 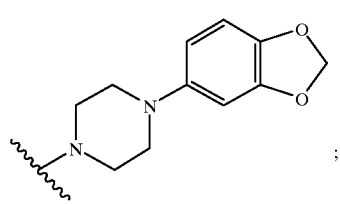;
(43) 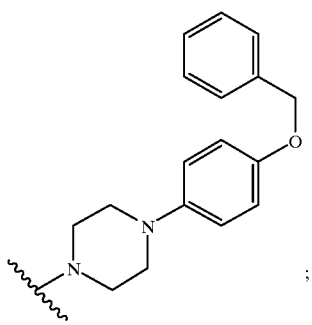;
(44) 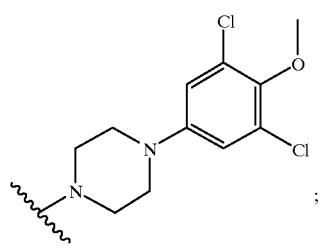;
(45) 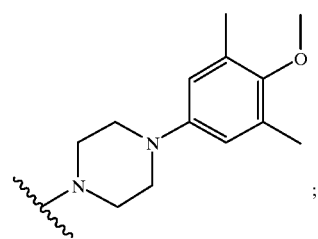;
(46) 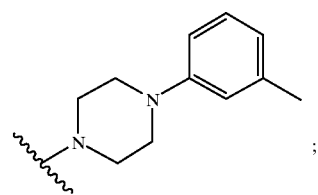;
(47) 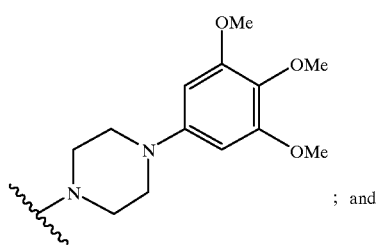; and
(48) 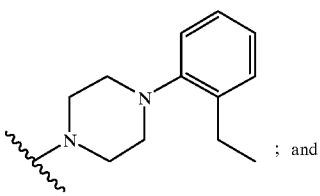; and
(D) a compound wherein X is O, R is CH$_2$—CH=N—R$^x$, and R$^x$ is selected from the group consisting of:
(1) 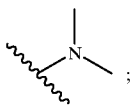;
(2) 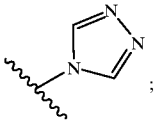;
(3) 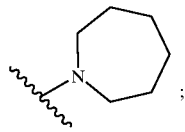;
(4) 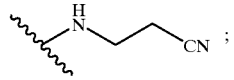;
(5) 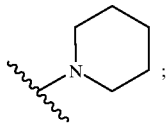;
(6) 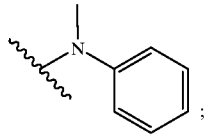;
(7) 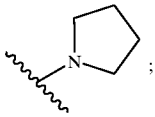;
(8) 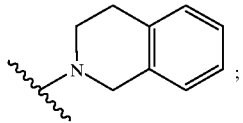;

(9)

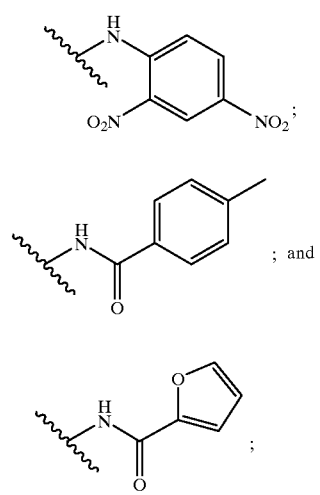

(10)

; and (11)

as well as the pharmaceutically acceptable salts, esters and prodrugs thereof.

More preferred compounds are selected from the group consisting of:

Compound of Formula (X): X is =O, R is —CH$_2$—CH=CH$_2$-(3-quinolinyl);
Compound of Formula (X): X is =O, R is allyl;
Compound of Formula (X): X is =O, R is 2-hydroxy-3-(benzylamino)propyl;
Compound of Formula (X): X is =O, R is 2-oxopropyl;
Compound of Formula (X): X is =O, R is —CH$_2$-C≡CH;
Compound of Formula (X): X is =O, R is —CH$_2$—CH=N—OH;
Compound of Formula (X): X is =O, R is —CH$_2$—CH$_2$OH;
Compound of Formula (X): X is =O, R is —CH$_2$—CH$_2$NH$_2$; and
Compound of Formula (X): X is =O, R is —CH$_2$—CN;

as well as the pharmaceutically acceptable salts, esters and prodrugs thereof.

A process for the preparation of 6-O-substituted macrolide derivatives having the Formulae:

(II)

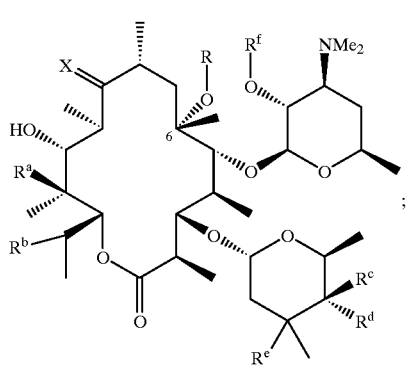

(III)

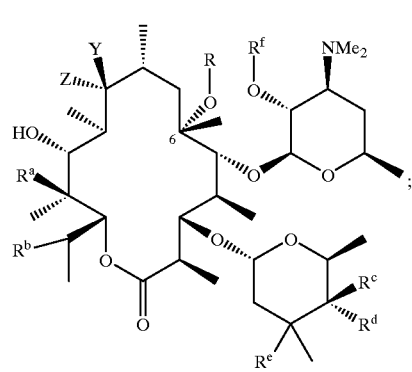

(IV)

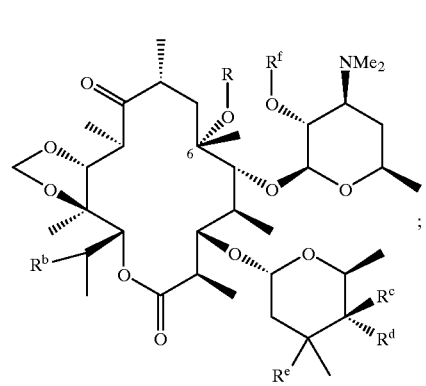

(V)

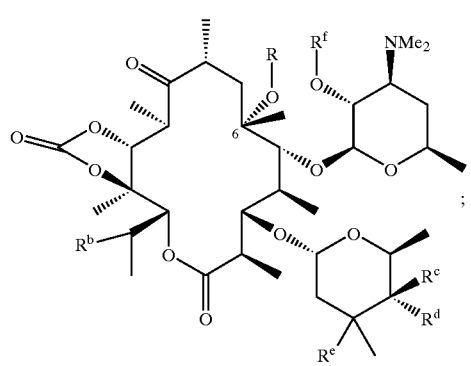

(VI)

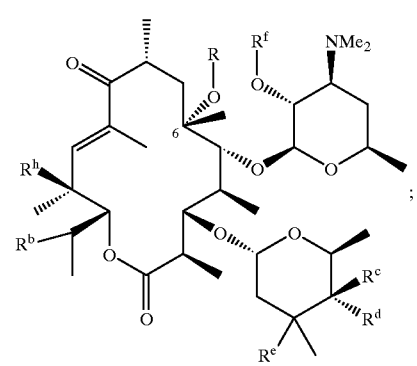

-continued

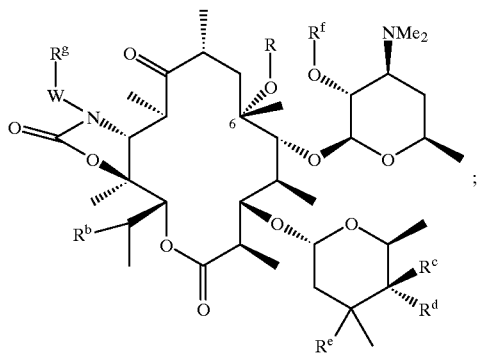
(VII)

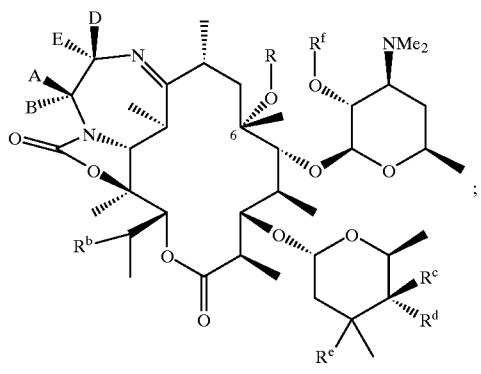
(VIII)

and

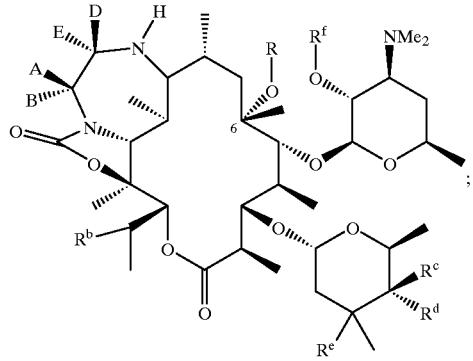
(IX)

wherein

X is selected from the group consisting of
(1) =O,
(2) =N—OH,
(3) =N—O—R$^1$ where R$^1$ is selected from the group consisting of
  (a) unsubstituted C$_1$–C$_{12}$-alkyl,
  (b) C$_1$–C$_{12}$-alkyl substituted with aryl,
  (c) C$_1$–C$_{12}$-alkyl substituted with substituted aryl,
  (d) C$_1$–C$_{12}$-alkyl substituted with heteroaryl,
  (e) C$_1$–C$_{12}$-alkyl substituted with substituted heteroaryl,
  (f) C$_3$–C$_{12}$-cycloalkyl,
  (g) —Si—(R$^2$)(R$^3$)(R$^4$) wherein R$^2$, R$^3$ and R$^4$ are each independently selected from C$_1$–C$_{12}$-alkyl, and
  (h) —Si—(Aryl)$_3$;
and (4) =N—O—C(R$^5$)(R$^6$)—O—R$^1$ where R$^1$ is as defined above and R$^5$ and R$^6$ are each independently selected from the group consisting of
  (a) hydrogen,
  (b) unsubstituted C$_1$–C$_{12}$-alkyl,
  (c) C$_1$–C$_{12}$-alkyl substituted with aryl,
  (d) C$_1$–C$_{12}$-alkyl substituted with substituted aryl,
  (e) C$_1$–C$_{12}$-alkyl substituted with heteroaryl, and
  (f) C$_1$–C$_{12}$-alkyl substituted with substituted heteroaryl,
or
  R$^5$ and R$^6$ taken together with the atom to which they are attached form a C$_3$–C$_{12}$-cycloalkyl ring;

R$^a$ is hydrogen or hydroxy;
R$^b$ is hydrogen or hydroxy;
one of R$^c$ and R$^d$ is hydrogen and the other of R$^c$ and R$^d$ is selected from the group consisting of
(1) hydroxy,
(2) protected hydroxy,
(3) halogen,
(4) NR$^7$R$^8$ where R$^7$ and R$^8$ are independently selected from the group consisting of
  (a) hydrogen,
  (b) C$_1$–C$_{12}$-alkyl,
  (c) substituted C$_1$–C$_{12}$-alkyl,
  (d) C$_1$–C$_8$-cycloalkyl,
  (e) substituted C$_1$–C$_8$-cycloalkyl,
  (f) C$_1$–C$_{12}$-alkyl substituted with aryl,
  (g) C$_1$–C$_{12}$-alkyl substituted with substituted aryl,
  (h) C$_1$–C$_{12}$-alkyl substituted with heterocycloalkyl,
  (i) C$_1$–C$_{12}$-alkyl substituted with substituted heterocycloalkyl,
  (j) C$_1$–C$_{12}$-alkyl substituted with C$_1$–C$_8$-cycloalkyl,
  (k) C$_1$–C$_{12}$-alkyl substituted with substituted C$_1$–C$_8$-cycloalkyl,
  (l) C$_1$–C$_{12}$-alkyl substituted with heteroaryl, and
  (m) C$_1$–C$_{12}$-alkyl substituted with substituted heteroaryl,
or
  R$^7$ and R$^8$ taken together with the atom to which they are attached form a 3–10 membered heterocycloalkyl ring,
(5) O—CO—NH-aryl,
(6) O—CO—NH-heteroaryl,
(7) O—CO—NR$^7$R$^8$, where R$^7$ and R$^8$ are as defined above,
(8) O—SO2—C$_1$–C$_6$-alkyl,
(9) O—SO$_2$-(substituted C$_1$–C$_6$-alkyl), and
(10) O—SO$_2$-CH$_2$—CH$_2$—NR$^7$R$^8$, where R$^7$ and R$^8$ are as defined above,
or
R$^c$ and R$^d$ taken together form the grouping selected from the group consisting of
(1) =O,
(2) =N—OH, and
(3) =N—OR$^1$ wherein R$^1$ is as defined above;

R$^e$ is methoxy, fluorine or hydroxy;
R$^f$ is hydrogen or a hydroxy protecting group;
W is absent or selected from the group consisting of
  —O—, —NH—CO—, —N=CH— and —NH—;
R$^g$ is selected from the group consisting of
(1) hydrogen, (2) $C_1$–$C_6$-alkyl optionally substituted with one or more substituents selected from the group consisting of
  (a) aryl,
  (b) substituted-aryl,
  (c) heteroaryl,
  (d) substituted-heteroaryl,
  (e) hydroxy,
  (f) $C_1$–$C_6$-alkoxy,
  (g) $NR^9R^{10}$, where $R^9$ and $R^{10}$ are independently selected from hydrogen and $C_1$–$C_6$-alkyl, or $R^9$ and $R^{10}$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$–$C_6$-alkyl—)—, —N(aryl)—, —N(aryl-$C_1$–$C_6$-alkyl—)—, —N(substituted-aryl-$C_1$–$C_6$-alkyl—)—, —N(heteroaryl)—, —N(heteroaryl-$C_1$–$C_6$-alkyl—)—, —N(substituted-heteroaryl-$C_1$–$C_6$-alkyl—)—, and —S— or —S(O)$_n$—, wherein n is 1 or 2, and
  (h) —$CH_2$—M—$R^{11}$
    wherein M is selected from the group consisting of:
    (i) —C(O)—NH—,
    (ii) —NH—C(O)—,
    (iii) —NH—,
    (iv) —N=,
    (v) —N($CH_3$)—,
    (vi) —NH—C(O)—O—
    (vii) —NH—C(O)—NH—
    (viii) —O—C(O)—NH—
    (ix) —O—C(O)—O—
    (x) —O—,
    (xi) —S(O)$_n$—, wherein n is 0, 1 or 2,
    (xii) —C(O)—O—,
    (xiii) —O—C(O)—,
    and
    (xiv) —C(O)—,
    and
    $R^{11}$ is selected from the group consisting of:
    (i) $C_1$–$C_6$-alkyl, optionally substituted with a substituent selected from the group consisting of
      (aa) aryl,
      (bb) substituted-aryl,
      (cc) heteroaryl, and
      (dd) substituted-heteroaryl,
    (ii) aryl,
    (iii) substituted-aryl,
    (iv) heteroaryl,
    (v) substituted-heteroaryl, and
    (vi) heterocycloalkyl,
(3) $C_3$–$C_7$-cycloalkyl,
(4) aryl,
(5) substituted-aryl,
(6) heteroaryl, and
(7) substituted-heteroaryl;
$R^h$ is selected from the group consisting of
(1) hydrogen,
(2) hydroxy,
(3) —O—C(O)-imidazolyl,
(4) —O—C(O)—O—$C_1$–$C_6$-alkyl,
(5) —O—C(O)—O-aryl,
(6) —O—C(O)—O-(substituted aryl),
(7) —O—C(O)-Cl, and
(8) —O—C(O)—$NH_2$;
R is selected from the group consisting of
  (1) methyl substituted with a moiety selected from the group consisting of
    (a) CN,
    (b) F,
    (c) —$CO_2R^{12}$ wherein $R^{12}$ is $C_1$–$C_3$-alkyl or aryl substituted $C_1$–$C_3$-alkyl, or heteroaryl substituted $C_1$–$C_3$-alkyl,
    (d) $S(O)_nR^{12}$ where n is 0, 1 or 2 and $R^{12}$ is as defined above,
    (e) $NHC(O)R^{12}$ where $R^{12}$ is as defined above,
    (f) $NHC(O)NR^{13}R^{14}$ wherein $R^{13}$ and $R^{14}$ are independently selected from hydrogen and $C_1$–$C_3$-alkyl,
    (g) aryl,
    (h) substituted aryl,
    (i) heteroaryl,
    and
    (j) substituted heteroaryl,
  (2) $C_2$–$C_{10}$-alkyl,
  (3) $C_2$–$C_{10}$-alkyl substituted with one or more substituents selected from the group consisting of
    (a) halogen,
    (b) hydroxy,
    (c) $C_1$–$C_3$-alkoxy,
    (d) $C_1$–$C_3$-alkoxy-$C_1$–$C_3$-alkoxy,
    (e) oxo,
    (f) —$N_3$,
    (g) —CHO,
    (h) O—$SO_2$-(substituted $C_1$–$C_6$-alkyl),
    (i) —$NR^{15}R^{16}$ wherein $R^{15}$ and $R^{16}$ are selected from the group consisting of
      (i) hydrogen,
      (ii) $C_1$–$C_{12}$-alkyl,
      (iii) substituted $C_1$–$C_{12}$-alkyl,
      (iv) $C_1$–$C_{12}$-alkenyl,
      (v) substituted $C_1$–$C_{12}$-alkenyl,
      (vi) $C_1$–$C_{12}$-alkynyl,
      (vii) substituted $C_1$–$C_{12}$-alkynyl,
      (viii) aryl,
      (ix) $C_3$–$C_8$-cycloalkyl,
      (x) substituted $C_3$–$C_8$-cycloalkyl,
      (xi) substituted aryl,
      (xii) heterocycloalkyl,
      (xiii) substituted heterocycloalkyl,
      (xiv) $C_1$–$C_{12}$-alkyl substituted with aryl,
      (xv) $C_1$–$C_{12}$-alkyl substituted with substituted aryl,
      (xvi) $C_1$–$C_{12}$-alkyl substituted with heterocycloalkyl,
      (xvii) $C_1$–$C_{12}$-alkyl substituted with substituted heterocycloalkyl,
      (xviii) $C_1$–$C_{12}$-alkyl substituted with $C_3$–$C_8$-cycloalkyl,
      (xix) $C_1$–$C_{12}$-alkyl substituted with substituted $C_3$–$C_8$-cycloalkyl,
      (xx) heteroaryl,
      (xxi) substituted heteroaryl,
      (xxii) $C_1$–$C_{12}$-alkyl substituted with heteroaryl, and
      (xxiii) $C_1$–$C_{12}$-alkyl substituted with substituted heteroaryl, or
      $R^{15}$ and $R^{16}$ are taken together with the atom to which they are attached form a 3–10 membered heterocycloalkyl ring which may be substituted with one or more substituents independently selected from the group consisting of
(i) halogen,
(ii) hydroxy,
(iii) $C_1$–$C_3$-alkoxy,
(iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl,
and
(vii) $C_1$–$C_3$-alkoxy-$C_1$–$C_3$-alkyl,
(j) —$CO_2R^{12}$ wherein $R^{12}$ is as defined above,
(k) —$C(O)NR^{13}R^{14}$ wherein $R^{13}$ and $R^{14}$ are as defined above,
(l) =N—O—$R^{12}$ wherein $R^{13}$ is as previously defined,
(m) —C≡N,
(n) O—$S(O)_nR^{12}$ wherein n is 0, 1 or 2 and $R^{12}$ is as defined above,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) heterocycloalkyl,
(w) substituted heterocycloalkyl,
(x) $NHC(O)R^{12}$ where $R^{12}$ is as previously defined,
(y) $NHC(O)NR^{13}R^{14}$ wherein $R^{13}$ and $R^{14}$ are as previously defined,
(z) =N—$NR^{15}R^{16}$ wherein $R^{15}$ and $R^{16}$ are as previously defined,
(aa) =N—$R^{11}$ wherein $R^{11}$ is as previously defined,
(bb) =N—$NHC(O)R^{12}$ wherein $R^{12}$ is as previously defined,
and
(cc) =N—$NHC(O)NR^{13}R^{14}$ wherein $R^{13}$ and $R^{14}$ are as previously defined;
(4) $C_3$-alkenyl substituted with a moiety selected from the group consisting of
(a) halogen,
(b) —CHO,
(c) —$CO_2R^{12}$ where $R^{12}$ is as defined above,
(d) —C(O)—$R^{11}$ where $R^{11}$ is as defined above,
(e) —$C(O)NR^{13}R^{14}$ wherein $R^{13}$ and $R^{14}$ are as previously defined,
(f) —C≡N,
(g) aryl,
(h) substituted aryl,
(i) heteroaryl,
(j) substituted heteroaryl,
(k) $C_3$–$C_7$-cycloalkyl,
and
(l) $C_1$–$C_{12}$-alkyl substituted with heteroaryl,
(5) $C_4$–$C_{10}$-alkenyl;
(6) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^{12}$ where $R^{12}$ is as defined above,
(f) —$C(O)NR^{13}R^{14}$ wherein $R^{13}$ and $R^{14}$ are as previously defined,
(g) —$NR^{15}R^{16}$ wherein $R^{15}$ and $R^{16}$ are as previously defined,
(h) =N—O—$R^{12}$ where $R^{12}$ is as previously defined,
(i) —C≡N,
(j) O—$S(O)_nR^{12}$ where n is 0, 1 or 2 and $R^{12}$ is as previously defined,
(k) aryl,
(l) substituted aryl,
(m) heteroaryl,
(n) substituted heteroaryl,
(o) $C_3$–$C_7$-cycloalkyl,
(p) $C_1$–$C_{12}$-alkyl substituted with heteroaryl,
(q) $NHC(O)R^{12}$ where $R^{12}$ is as previously defined,
(r) $NHC(O)NR^{13}R^{14}$ wherein $R^{13}$ and $R^{14}$ are as previously defined,
(s) =N—$NR^{15}R^{16}$ wherein $R^{15}$ and $R^{16}$ are as previously defined,
(t) =N—$R^{11}$ wherein $R^{11}$ is as previously defined,
(u) =N—$NHC(O)R^{12}$ where $R^{12}$ is as previously defined,
and
(v) =N—$NHC(O)NR^{13}R^{14}$ wherein $R^{13}$ and $R^{14}$ are as previously defined;
(7) $C_3$–$C_{10}$-alkynyl;
and
(8) $C_3$–$C_{10}$-alkynyl substituted with one or more substituents selected from the group consisting of
(a) trialkylsilyl,
(b) aryl,
(c) substituted aryl,
(d) heteroaryl,
and
(e) substituted heteroaryl;
one of Y and Z is hydrogen and the other is selected from a group consisting of
(1) hydrogen,
(2) hydroxy,
(3) protected hydroxy,
and
(4) $NR^7R^8$ wherein $R^7$ and $R^8$ are as defined above;
and
A, B, D and E, with the provision that at least two of A, B, D and E are hydrogen, are independently selected from the group consisting of:
(a) hydrogen;
(b) $C_1$–$C_6$-alkyl, optionally substituted with one or more substituents selected from the group consisting of:
(i) aryl;
(ii) substituted-aryl;
(iii) heteroaryl;
(iv) substituted-heteroaryl;
(v) heterocycloalkyl;
(vi) hydroxy;
(vii) $C_1$–$C_6$-alkoxy;
(viii) halogen consisting of Br, Cl, F or I; and
(ix) $NR^9R^{10}$, wherein $R^9$ and $R^{10}$ are as defined above;
(c) $C_3$–$C_7$-cycloalkyl;
(d) aryl;
(e) substituted-aryl;
(f) heteroaryl;
(g) substituted-heteroaryl;
(h) heterocycloalkyl; and
(i) a group selected from option (b) above further substituted with —M—$R^{11}$, wherein M and $R^{11}$ are as defined above;
or any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N(C$_1$-C$_6$-alkyl—)—, —N(aryl-C$_1$-C$_6$-alkyl—)—, —N(substituted-aryl-C$_1$-C$_6$-alkyl—)—, —N(heteroaryl-C$_1$-C$_6$-alkyl—)—, —N(substituted-heteroaryl-C$_1$-C$_6$-alkyl—)—, —S— or —S(O)$_n$—, wherein n is 1 or 2, —C(O)—NH—, —C(O)—NR$^{12}$—, wherein R$^{12}$ is as defined above, —NH—C(O)—, —NR$^{12}$—C(O)—, wherein R$^{12}$ is as defined above, and —C(=NH)—NH—;

is a method comprising:

(a) treating a compound having the formulae

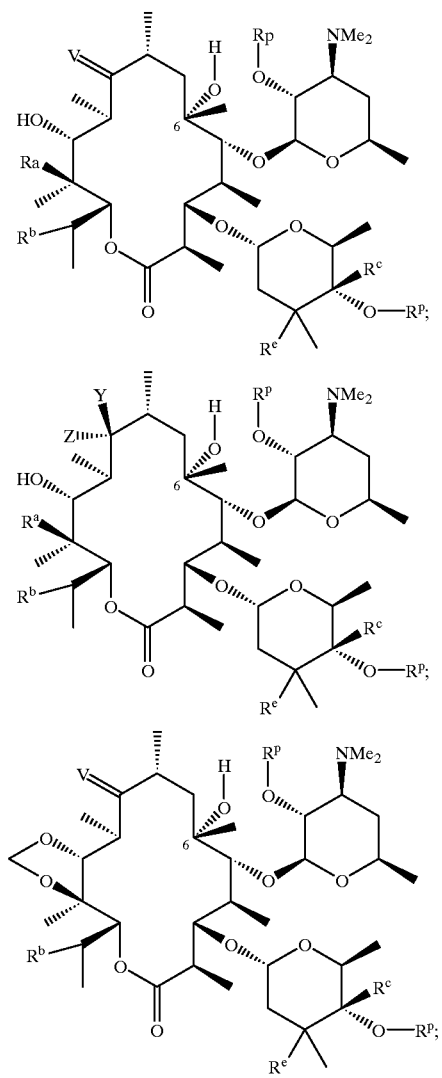

-continued

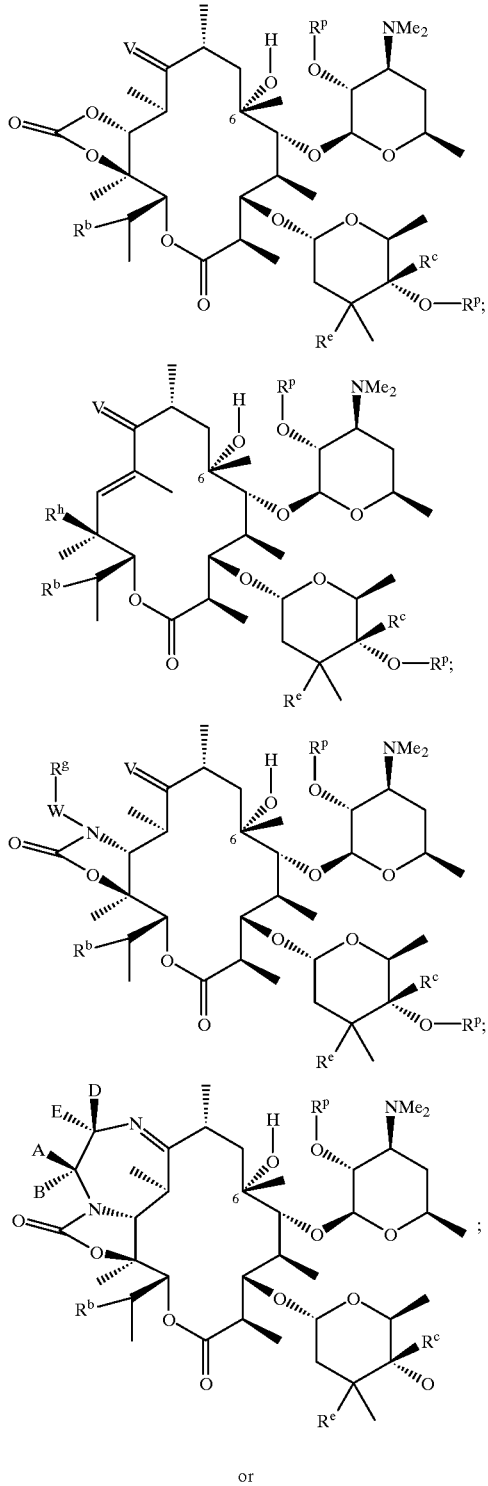

or

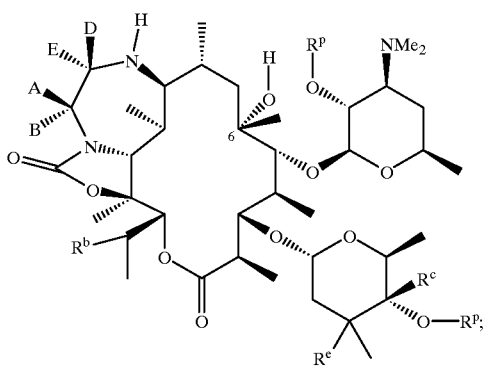
wherein RP is a hydroxy protecting group and V is =N—O—R$^1$ or =N—O—C(R$^9$)(R$^{10}$)—O—R$^1$ wherein R$^1$, R$^9$ and R$^{10}$ are as defined above, with a base in an aprotic solvent then with an alkylating agent to give a compound having the formula
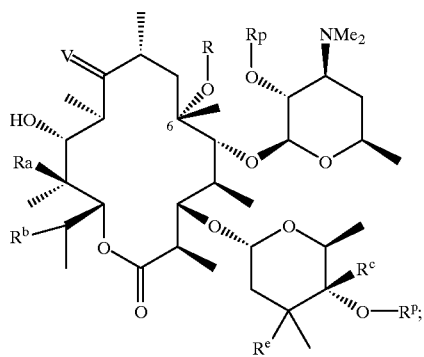
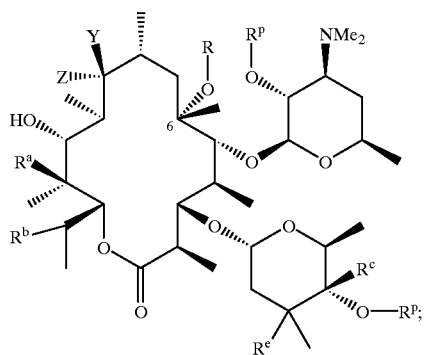
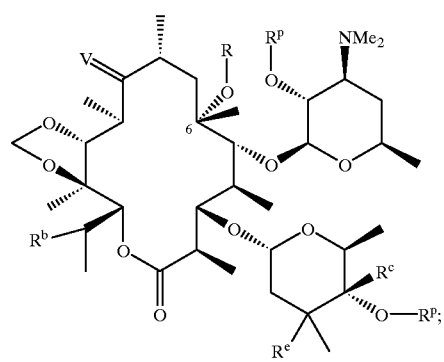
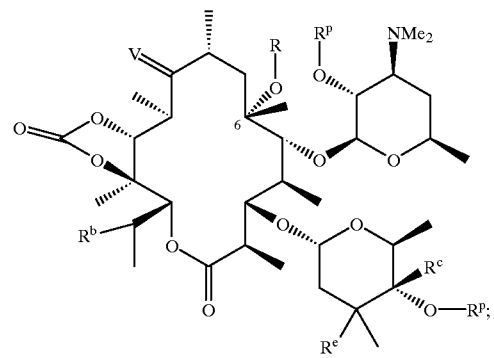
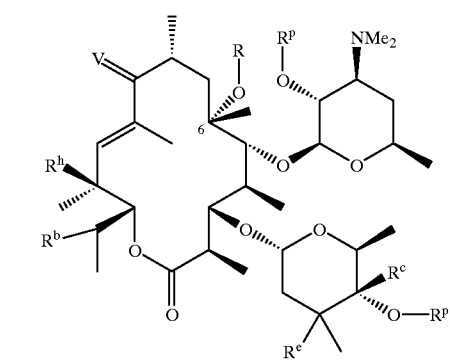
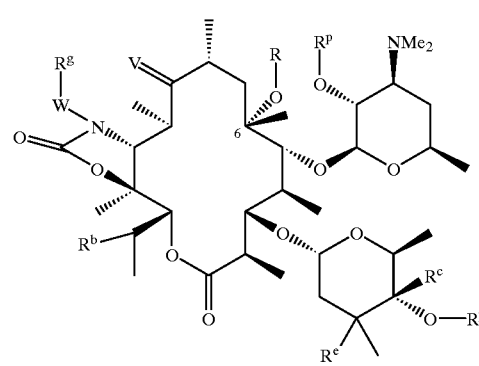
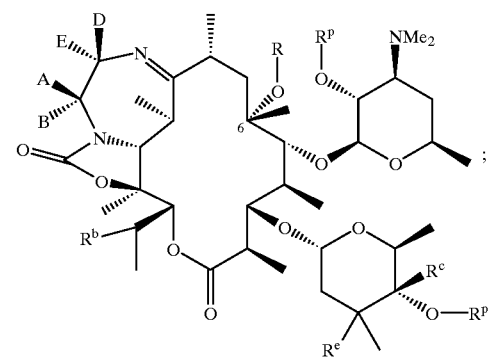
or

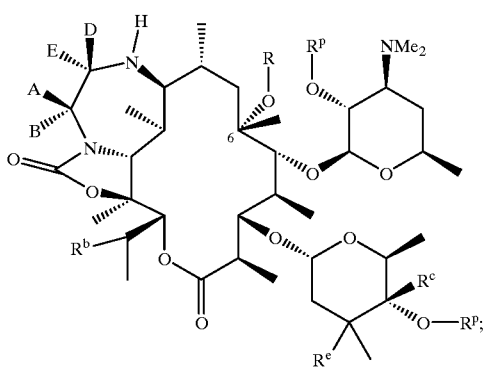
wherein A, B, D, E, W, X, Y, Z, $R^a$, $R^b$, $R^c$, $R^d$, $R^e$, $R^f$, $R^g$ and $R^h$ are as defined above, V is $=N-O-R^1$ or $=N-O-C(R^5)(R^6)-O-R^1$ wherein $R^1$, $R^5$ and $R^6$ are as defined above, and R is the "alkyl group" derived from the corresponding alkylating agent;
(b) deprotecting the 2'- and 4'-hydroxyl groups to give a compound of the formula
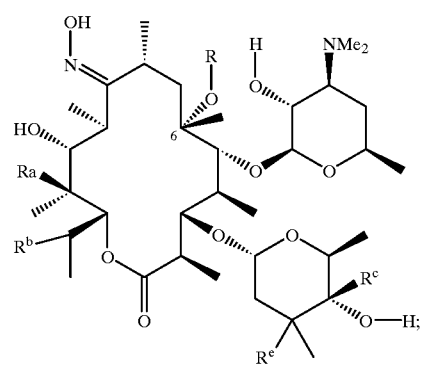
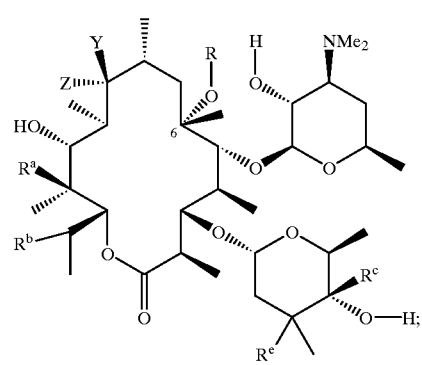
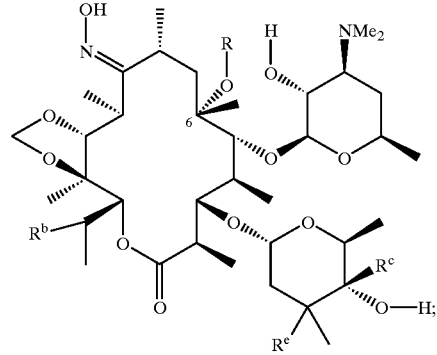
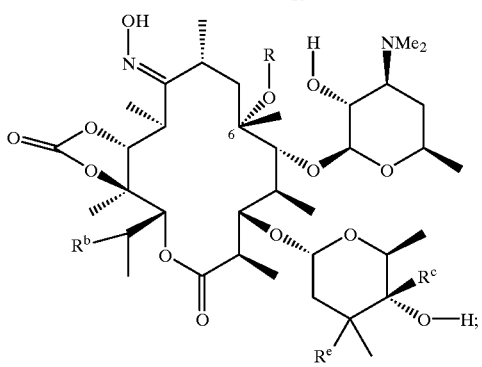
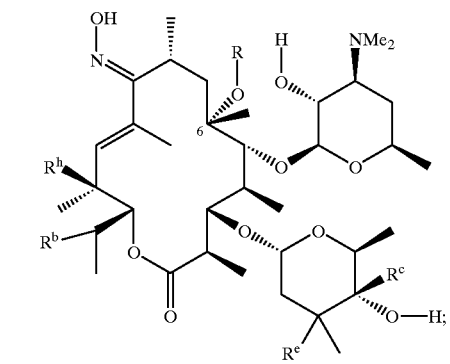
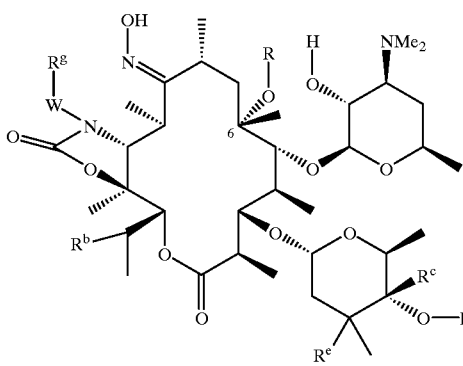

-continued

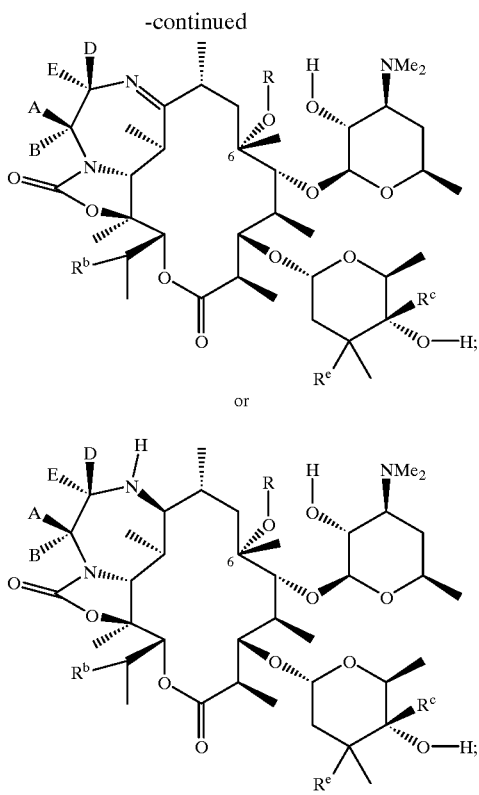

or wherein A, B, D, E, W, X, Y, Z, $R^a$, $R^b$, $R^c$, $R^d$, $R^e$, $R^f$, $R^g$ and $R^h$ are as defined above and R is the "alkyl group" derived from the corresponding alkylating agent; and (c) deoximation with an inorganic sulfur oxide salt or an inorganic nitrite salt in the presence of acid in a suitable solvent to give the desired products.

A preferred process for the preparation of 6-O-substituted macrolide compounds of the invention is the process immediately above wherein in step (a) the base is selected from the group consisting of potassium hydroxide, cesium hydroxide, tetraalkylammonium hydroxide, sodium hydride, potassium hydride, potassium isopropoxide, potassium tert-tbutoxide and potassium isobutoxide, the alkylating agent is selected from the group consisting of allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, allyl O-tosylate, 3-phenylpropyl-O-trifluoromethane sulfonate, and n-butyl-O-methanesulfonate, and the reaction is performed at a temperature from about −15° C. to about 50° C. for a period from 0.5 hours to 10 days;

In the preferred process in step (b) deprotection is accomplished by use of acetic acid in water and acetonitrile.

In the preferred process in step (c) the deoximating reagent is an inorganic sulfur oxide compound is selected from the group consisting of sodium hydrogen sulfite, sodium pyrosulfate, sodium thiosulfate, sodium sulfate, sodium sulfite, sodium hydrosulfite, sodium metabisulfite, sodium dithionate, potassium thiosulfate, and potassium metabisulfite, or an inorganic nitrite salt in the presence of acid selected from the group consisting of sodium nitrite and potassium nitrite, and the solvent is selected from the group consisting of water, methanol, ethanol, propanol, isopropanol, trimethylsilanol or a mixture of one or more thereof.

A preferred process of the invention is a process as described above for the preparation of 6-O-substituted macrolide compounds having formula (II) thereof wherein in step (a) the starting compound of has the formula

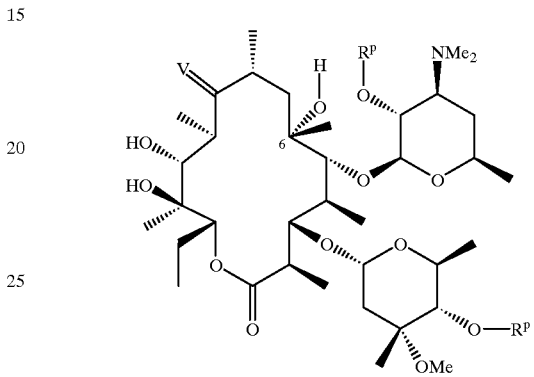

wherein $R^p$ is trimethylsilyl and V is a ketone protecting group and it is treated with potassium hydroxide in a mixture of THF and DMSO, in step (b) deprotection of the 2'- and 4'-hydroxyl groups is accomplished using acetic acid in water and acetonitrile to give a compound having the formula

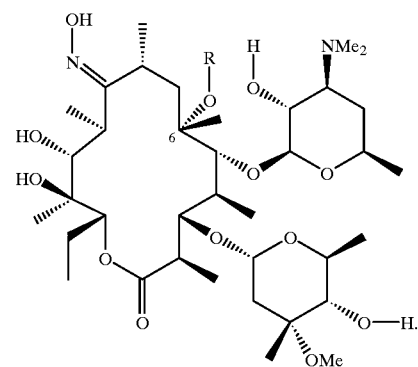

In this preferred process in step (c) the 9-oxime is deoximinated using $NaHSO_3$ and formic acid in ethanol-water.

In a more preferred process for the preparation of 6-O-substituted macrolide compounds having the formula having formula (II), in step (a) RP is trimethylsilyl and the ketone protecting group is O-(1-isopropoxycyclohexyl) oxime.

Definitions

The terms "$C_1$–$C_{12}$-alkyl" as used herein refer to saturated, straight- or branched-chain hydrocarbon radicals containing between one and twelve carbon atoms. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "$C_1$–$C_6$-alkoxy" as used herein refers to an $C_1$–$C_6$-alkyl group, as previously defined, attached to the parent molecular moiety through an oxygen atom. Examples of $C_1$–$C_6$-alkoxy, but are not limited to, methoxy, ethoxy, propoxy, isopropoxy, n-butoxy, tert-butoxy, neopentoxy and n-hexoxy.

The term "acylamino" as used herein refers to a $C_1$–$C_6$-alkyl, aryl, or substituted aryl group attached to the amino group via a carbonyl grouping. Examples of acylamino include, but are not limited to acetylamino, trifluoroacetylamino, propanoylamino, benzoylamino, 4-chlorbenzoylamino, and the like.

The term "alkenyl" as used herein refers to a branched or straight hydrocarbon chain comprising two to ten carbon atoms which also comprises one or more carbon-carbon double bonds. Representative alkenyl groups include 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "alkynyl" as used herein refers to a branched or straight hydrocarbon chain comprising two to ten carbon atoms which also comprises one or more carbon-carbon triple bonds. Representative alkynyl groups include ethynyl, 2-propynyl (propargyl), 1-propynyl and the like.

The term "$C_1$–$C_3$-alkyl-amino" as used herein refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chlorofom, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, N.Y., 1986.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "$C_3$–$C_{12}$-cycloalkyl" as used herein refers to carbocyclic groups of 3 to 12 carbons, respectively, for example, cyclopropyl, cyclobutyl, cyclopentyl, cyclohexyl, and cycloheptyl.

The term "$C_1$–$C_3$-alkyl-$C_3$–$C_5$-cycloalkyl", as used herein refers to a $C_3$–$C_5$-cycloalkyl radical, as defined above, attached to a $C_1$–$C_3$-alkyl radical by replacement of a hydrogen atom on the latter.

The terms "halo" and "halogen" as used herein refer to an atom selected from fluorine, chlorine, bromine and iodine.

The term "heteroaryl", as used herein, refers to a cyclic aromatic radical having from five to ten ring atoms of which one ring atom is selected from S, O and N; zero, one or two ring atoms are additional heteroatoms independently selected from S, and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycloalkyl rings include, but are not limited to, oxiranyl, aziranyl, oxetanyl, azetidinyl, pyrrolidinyl, piperidinyl, pyrazolinyl, pyrazolidinyl, piperazinyl, azacycloheptanyl, azacyclooctanyl, 1,4-diazacycloheptanyl, imidazolidinyl, oxazolidinyl, isoxazolidinyl, morpholinyl, thiazolidinyl, isothiazolidinyl, and tetrahydrofuryl.

Specific heterocycloalkyl rings contained in the examples below include: 3-methyl-4-(3-methylphenyl)piperazine, 3-methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-(3,4-direthoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichiorophenyl)piperazine, 4-(3,5-dimethoxyphenyl)piperazine, 4-(4-(phenylmethoxy)phenyl)piperazine, 4-(4-(1,1-dimethylethyl)phenylmethyl)piperazine, 4-(4-chloro-3-trifiuoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-((2-furanyl)carbonyl)piperazine, 4-((1,3-dioxolan-5-yl)methyl)piperazine, 6-fluoro-1,2,3,4-tetrahydro-2-methylquinoline, 1,4-diazacycloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*. 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

The term "ketone protecting group", as used herein, refers to an easily removable group which is known in the art to protect a ketone group against undesirable reactions during synthetic procedures and to be selectively removable. The use of ketone-protecting groups is well known in the art for protecting groups against undesirable reactions during a synthetic procedure and many such protecting groups are known, cf, for example, T. H. Greene and P. G. M. Wuts, *Protective Groups in Organic Synthesis*. 2nd edition, John Wiley & Sons, New York (1991). Examples of ketone-protecting groups include, but are not limited to, ketals, oximes, O-substituted oximes for example O-benzyl oxime, O-phenylthiomethyl oxime, 1-isopropoxycyclohexyl oxime, and the like.

A the term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, N.Y., 1986.

The term "substituted aryl" as used herein refers to an aryl group as defmed herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, substituted aryl, heteroaryl, or substituted heteroaryl, methoxymethoxy, amino, $C_1$–$C_3$-alkyl-amino, or ($C_1$–$C_3$-alkyl)$_2$-amino, acylamino; in addition, any one substituent may be an aryl, heteroary, or heterocycloalkyl group.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, substituted aryl, heteroaryl, or substituted heteroaryl, methoxymethoxy, amino, $C_1$–$C_3$-alkyl-amino, or ($C_1$–$C_3$-alkyl)$_2$-amino, acylamino; in addition, any one substituent may be an aryl, heteroary, or heterocycloalkyl group.

The term "substituted heterocycloalkyl" as used herein, refers to a heterocycloalkyl group, as defined above, substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, substituted aryl, heteroaryl, or substituted heteroaryl, methoxymethoxy, amino, $C_1$–$C_3$-alkyl-amino, or ($C_1$–$C_3$-alkyl)$_2$-amino, acylamino; in addition, any one substituent may be an aryl, heteroary, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*. 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptalble salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The term "pharmaceutically acceptable prodrugs" as used herein refers to those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in 'soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Opithalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: AIBN for azobisisobutyronitrile; Bu$_3$SnH for tributyltin hydride; CDI for carbonyldiimidazole; DBU for 1,8-diazabicyclo[5.4.0]undec-7-ene; DEAD for diethylazodicarboxylate; DMF for dimethylformamide; DMSO for dimethylsulfoxide; DPPA for diphenylphosphoryl azide; Et$_3$N for triethylamine; EtOAc for ethyl acetate; Et$_2$O for diethyl ether; EtOH for ethanol; HOAc for acetic acid; MeOH for methanol; NaN(TMS)$_2$ for sodium bis(trimethylsilyl)amide; NMMO for N-methylmorpholine N-oxide; TEA for triethylamine; THF for tetrahydrofuran; and TPP for triphenylphosphine.

Synthetic Methods

The compounds and processes of the present invention will be better understood in connection with the following synthetic schemes I–VI (to be found following the text describing the schemes) which illustrate the methods by which the compounds of the invention may be prepared. The groups A, B, D, E, W, X, Y, Z, R, $R^a$, $R^b$, $R^c$, $R^d$, $R^e$, $R^f$, $R^g$ and $R^h$ are as defined above unless otherwise noted below.

Scheme I illustrates the preparation of the starting material derived from erythromycin A, a compound of formula (XII). The preparation of protected erythromycin A is described in the following United States patents, U.S. Pat. No. 4,990,602; U.S. Pat. No. 4,331,803, U.S. Pat. No. 4,680,368, and U.S. Pat. No. 4,670,549 which are incorporated by reference. Also incorporated by reference is European Patent Application EP 260,938. In general, the 9-ketone of compound 1 is protected, for example as an oxime (V is =N—O—OR$^1$ or =N—O—C(R$^9$)(R$^{10}$)—O—R$^1$ where R$^1$, R$^9$ and R$^{10}$ are as defined above), and then either as a separate step or in the same pot, the 2'- and 4"-hydroxyls are protected.

The 9-ketone of compound (1) is protected to give compound (2) where V is =N—O— R$^1$ where R$^1$ is as defined above or =N—O—C(R$^9$)(R$^{10}$)—O—R$^1$ where R$^1$, R$^9$ and R$^{10}$ are as defined above. In a preferred embodiment of the process, V is O-(1-isopropoxycyclohexyl) oxime.

The 2'- and 4"-hydroxy groups of erythromycin A (2) are protected by reaction with a suitable hydroxy protecting reagent, such as those described by T. W. Greene and P. G. M. Wuts in *Protective Groups in Organic Synthesis*, 2nd ed., John Wiley & Son, Inc., 1991, which is incorporated by reference, for example, acetic anhydride, benzoic anhydride, benzyl chloroformate or a trialkylsilyl chloride in an aprotic solvent. Examples of aprotic solvents are dichloromethane, chloroform, DMF, tetrahydrofuran (THF), N-methyl pyirolidinone, dimethylsulfoxide, diethylsulfoxide, N,N-dimethylformamide, NN-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of erythromycin A thus affords compound (3) where RP is a hydroxy protecting group. In a preferred embodiment of the process, R$^p$ is trimethylsilyl.

Scheme II illustrates the general preparation of the compounds of the invention derived from erythromycin A. The alkylation of the 6-hydroxy group of compound (3) can be carried out with an alkylating agent in a solvent in the presence of a base at a temperature from about −15° C. to about 50° C. to give compound (4). Alkylating agents include alkyl chlorides, bromides, iodides or alkyl sulfonates. Specific examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromo chloromethane, bromomethyl phenyl sulfone, 1,3-dibromo-1-propene, and the like. Examples of alkyl sulfonates are: allyl O-tosylate, 3-phenylpropyl-O-trifluoromethane sulfonate, n-butyl -O-methanesulfonate and the like. It is sufficient to use 1 to 4 mole equivalents of alkylating agents relative to compound (3). Examples of the solvents used are aprotic solvents such as dimethylsulfoxide, diethylsulfoxide, N,N-dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like. The amount of base used is usually 1 to 4 equivalents relative to compound (3).

The deprotection of the 2'- and 4'-hydroxyl groups is carried out according to methods described in literature, for example, by T. W. Greene and P. G. M. Wuts in *Protective Groups in Organic Synthesis*, 2nd ed., John Wiley & Son, Inc., 1991, which is incorporated herein by reference. The conditions used for the deprotection of the 2'- and 4'-hydroxyl groups usually results in the conversion of X to =N—OH. (For example, using acetic acid in acetonitrile and water results in the deprotection of the 2'- and 4'-hydroxyl groups and the conversion of X from =N—O—OR$^1$ or =N—O—C(R$^9$)(R$^{10}$)—O—R$^1$ where R$^1$, R$^9$ and R$^{10}$ are as defined above to =N—OH.) If this is not the case, the conversion is carried out in a separate step.

The deoximation reaction can be carried out according to the methods described in the literature, for example by Greene and Wuts (op. cit.) and others. Examples of the deoximating agent are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite and the like. Deoximation may also be accomplished by treatment with an inorganic nitrite salt, for example sodium nitrite or potassium nitrite, in the presence of acid. Examples of the solvents used are protic solvents such as water, methanol, ethanol, propanol, isopropanol, trimethylsilanol or a mixture of one or more of the mentioned solvents and the like. The deoximation reaction is more conveniently carried out in the presence of an organic acid such as formic acid, acetic acid and trifluoroacetic acid, but may be accomplished with hydrochloric acid also. The amount of acid used is from about 1 to about 10 equivalents of the amount of compound 5 used. In a preferred embodiment, the deoximation is carried out using an organic acid such as formic acid in ethanol and water to give the desired product (6).

The desired 6-O-"alkylated" compound may be prepared directly as described above or obtained from chemical modification of an initially prepared 6-O-"alkylated" compound. Representative examples of further elaboration of the 6-position are shown in Scheme III and Scheme IV. For example, compound (6A), which is a compound of formula (6) wherein R is —CH$_2$CH=CH$_2$ (prepared with allyl bromide as the alkylating reagent) and wherein M represents the macrolide ring system, can be further derivatized. The double bond of the allyl compound can be (a) reduced to give the 6-O-propyl compound (7); (b) treated with osmium tetroxide to give the 2,3-dihydroxypropyl compound (8); (c) oxidized with 3-chloroperoxybenzoic acid to give the epoxy methyl compound (9), which can be opened with nucleophiles such as amines or N-containing heterocyclic compounds, for example, to give compounds with N-containing side chains (10); (d) oxidized under Wacker conditions (cf., Tsuji, in "Organic Synthesis with Palladium Compounds", N.Y., Springer-Verlan, 1980, pp. 6–12) to give the 6—O—CH$_2$–C(O)-CH$_3$ compound (11); (e) brominated with hydrogen bromide perbromide to give (12); (f) reacted with aryl halides under Heck conditions (R. F. Heck, Org. React., 1982, 27, 345–390.) to give (13); (g) oxidized with ozone to give the 6—O—CH$_2$—CHO compound (14) which can in turn be (i) converted to oxime (17) by reaction with H$_2$NOR', (ii) converted to hydrazone (15) by reaction with H₂NNR'R", and (iii) reductively aminated with primary amines, H₂NR', in the presence of NaCNBH₃ to give (16). Reaction of oxime (17), where R'=H, with diisopropylcarbodiimide in the presence of CuCl gives nitrile (18).

In Scheme IV, the propargylic compound (19), which is a compound of formula (6) of Scheme II wherein R is CH₂CCH (prepared with propargyl bromide as the alkylating reagent) can also be further derivatized. The triple bond can be coupled to aryl halides using Pd (II) or Pd(0) catalysts in amine solvents in the presence of co-catalytic CuI (Sonogashira et al., *Tetrahedron Lett.*, 1975, 50, 4467–4470.) to give the aryl substituted alkyne compound (20); brominated with N-bromosuccinimide in the presence of silver nitrate (Weichert, R., *Angew. Chem. Int. Ed. Engl.*, 1984, 23, 727–728) to provide the brominated alkyne (25); hydroborated with 9-BBN to give the boronated compound which is then treated with an aryl or alkenyl halide or sulfonate in the presence of Pd(0) catalysts according to the method of Suzuki (*Pure Appl. Chem.*, 1985, 57, 1749–1758) to give the aryl sustituted olefin or a conjugated diene compound (22); coupled to terminal alkynes in the presence of cupric salts under conditions of the Eglinton Reaction (Eglinton and McCrae, *Adv. Org. Chem.* 4, 225–328, 1963.) to generate diynes (24); or coupled with acyl halides utilizing cocatalytic Pd(II)/Cu(I) in amine solvents (Sonogashira, K.; Hagihara, N.; Tohda, Y. *Synthesis*, 1977, 777–778.) to give the alkynyl ketone (23). Compound (20) can be selectively reduced to the corresponding cis olefin (21) by catalytic hydrogenation in EtOH at atmospheric pressure in the presence of 5% Pd/BaSO₄ and quinoline.

Scheme V illustrates the preparation of compounds of formulae IV, V, VI, and VII of the invention. Compounds (6) (from Scheme II) are protected at the 2' and 4" hydroxy positions to give compounds (26). Compound 26 may be treated with formaldehyde in the presence of an acid, or with chloroiodomethane in the presence of base (according to the procedure of Hunt et al., *J. Antibiotics*, (1988), 41: 1644) to give the protected 11,12-methylenedioxy compound of formula (IV), which may optionally then be deprotected at the 2' and 4" positions by methods described above to give a 11,12-methylenedioxy compound of formula (IV).

To prepare compound (27) the compound (26) is reacted is reacted under anhydrous conditions with base such as sodium hydride, lithium hydride, potassium carbonate or dimethylaminopyridine and followed by phosgene, diphosgene, triphosgene or benzyl chloroformate in an aprotic solvent, as defined above. The reaction may require cooling or heating, depending upon the conditions used. The reaction temperature may be from −20° C. to 70° C., and preferably from 0° C. to room temperature. The reaction may require 0.5 hours to 10 days, and preferably 1–5 days, to complete. Compound (27) may optionally then be deprotected at the 2' and 4" positions by methods described above to give the 11,12-carbonate compound of formula (V).

Intermediate compound (28) may be prepared from compound (27) by treatment of the latter with under anhydrous conditions with NaH and CDI in an aprotic solvent, preferably THF, DMF or a mixture thereof. The reaction may require cooling or heating, depending upon the conditions used. The reaction temperature may be from −20° C. to 70° C., and preferably from 0° C. to room temperature. The reaction may require 0.5 hours to 10 days, and preferably 1–5 days, to complete.

Alternately, compound (28) may be prepared directly from compound (26) by reaction with sodium hydride or lithium hydride and CDI under anhydrous conditions in an aprotic solvent, as defined above, which does not adversely affect the reaction, preferably dichloromethane, chloroform, DMF, tetrahydrofuran (THF), N-methyl pyrrolidinone or a mixture thereof. The resulting alkoxide is then reacted with excess carbonyldiimidazole for 0.5 hours to 10 days in the same reaction mixture to produce (28). The preferred temperature is from −10° C. to ambient.

Hydrolysis of compound (28) gives the 10,11-anhydro compound of formula (VI).

To prepare compounds (29) which may converted to the unprotected compounds of Formula (VII), a compound (28) may be treated with several different reagents, each chosen to prepare a compound wherein the W group is unique. To prepare a compound (29) wherein W is absent, compound (28) is reacted with a primary amine RNH₂ in a suitable solvent at room temperature to reflux temperature for about 4 to about 48 hours. Suitable solvents include alcohols such as methanol, ethanol, propanol, isopropanol, butanol, t-butanol, and the like, aprotic solvents such as methylene chloride, tetrahydrofuran, N-methyl-pyrrolidinone, diethyl ether, bis-methoxymethyl ether, dimethyl formamide, and acetone, for example, as well as aqueous mixtures thereof. Preferred solvents are aqueous acetonitrile, aqueous DMF, and aqueous acetone.

In the primary amine $R^gNH_2$ and in the resulting compound of Formula (VII), $R^g$ may be hydrogen, $C_1$–$C_6$-alkyl, $C_3$–$C_7$-cycloalkyl, aryl, substituted-aryl, heteroaryl or substituted-heteroaryl. When $R^g$ is a $C_1$–$C_6$-alkyl substituent, the alkyl group may be optionally substituted with one or more substituents such as aryl, substituted-aryl, heteroaryl, substituted-heteroaryl, hydroxy, $C_1$–$C_6$-alkoxy, $NR^9R^{10}$, wherein $R^9$ and $R^{10}$ are independently selected from hydrogen and $C_1$–$C_6$-alkyl, or $NR^9R^{10}$, wherein $R^9$ and $R^{10}$ are taken with the nitrogen atom to which they are connected to form a 3- to 7-membered ring. In the instance wherein the $NR^9R^{10}$ substituent is a 5- to 7-membered ring, the ring may optionally contain a hetero function consisting of —O—, —NH—, —N($C_1$–$C_6$-alkyl—)—, —N(aryl)—, —N(aryl-$C_1$–$C_6$-alkyl—)—, —N(substituted-aryl-$C_1$–$C_6$-alkyl—)—, —N(heteroaryl)—, —N(heteroaryl-$C_1$–$C_6$-alkyl—)—, —N(substituted-heteroaryl-$C_1$–$C_6$-alkyl-)—, —S— or —S(O)$_n$—, wherein n is 1 or 2. Additionally, when $R^g$ is $C_1$–$C_6$-alkyl it may bear an optional substituent of the formula —CH₂—M—$R^{11}$, wherein M may be —NH—C(O)—O—, —NH— C(O)—NH—, —O—C(O)—NH—, —O—C(O)—O—, —O—, —S(O)$_n$—, wherein n is 0, 1 or 2, —C(O)—O—, —O— C(O)—, and —C(O)—, and $R^{11}$ may be aryl, substituted-aryl, heteroaryl, substituted-heteroaryl, heterocycloalkyl, or a $C_1$–$C_6$-alkyl optionally bearing one or more substituents such as aryl, substituted-aryl, heteroaryl, or substituted-heteroaryl. Chromatographic treatment of the crude reaction product affords both the natural and epi isomers at position C-10 of the molecule.

To prepare a compound wherein W is —NH—, compound (28) is reacted with a hydrazine reagent such as unsubstituted hydrazine or a substituted hydrazine in a solvent such as described immediately above to afford the desired compounds of (29) and the deprotected compounds of Formula (VII). The natural and C-10 epimers of these compounds may be isolated from the reaction mixture. Deprotection of the protected hydroxy groups may be accomplished by standard methods as described by Wuts and Greene (op. cit.).

Thus, treatment of compound (28) with unsubstituted hydrazine affords the compounds of (29) and Formula (VII) wherein W is —NH— and $R^g$ is H.

Also, treatment of (28) with a substituted hydrazine $R^gR^4NNH_2$, wherein $R^g$ is as defined above and $R^4$ is $C_1$–$C_6$-alkyl, gives the compounds of (29) and Formula (VII) wherein W is —N($C_1$–$C_6$-alkyl)—.

Optionally, the compound of Formula (VII) wherein W is —NH— and $R^g$ is H can be treated with an $R^g$-acyl acylating agent, wherein $R^g$ is as defined above, to afford a compound of Formula (VII) wherein W is —NH—CO—. The acylating agents can be, for example, an acid chloride, an acid fluoride, an acid anhydride, or a carboxylic acid in the presence of a carbodiimide coupling reagent such as carbonyldiimidazole or 1-(3-dimethylaminopropyl)-3-ethylcarbodiimide hydrochloride, for example, wherein $R^g$ is as defined above.

Optionally, the compound of Formula (VII) wherein W is —NH— and $R^g$ is H can be treated with an aldehyde $R^g$—CHO, wherein $R^g$ is as defined for Formula (I), to afford a compound of Formula (VII) wherein W is —N=CH—.

Optionally, the compounds of Formula (VII) wherein W is —N=CH— can be reduced to yield additional compounds of Formula (VII) above, wherein W is —NH— using reducing reagents such as sodium cyanoborohydride, sodium borohydride, sodium triacetoxyborohydride, borane-tetrahydrofuran complex, and borane-piperidine complex, for example.

Also shown in Scheme V is the procedure by which compounds of (29) and Formula (VII) wherein W is —O— and R is H or O—$C_1$–$C_6$-alkyl may be prepared. Under reaction conditions similar to those shown above for hydrazine reagents, treatment of compound (28) with unsubstituted hydroxylamine or an O—$C_1$–$C_6$-alkylated hydroxylamine affords the desired compound.

For example, treatment of compound (28) with an excess of hydroxylamine affords the compounds of (29) and Formula (VII) wherein W is —O— and R is H.

Treatment of compound (28) with an O—$C_1$–$C_6$-alkylated hydroxylamine affords the desired compounds of (29) and Formula (VII) wherein W is —O— and R is $C_1$–$C_6$-alkyl.

Optionally, it is possible to further treat the compound of Formula (VII) wherein W is —O— and $R^g$ is H with a suitable base and an appropriate electrophile to prepare a compound wherein W is —O— and $R^g$ is $C_1$–$C_6$-alkyl, $C_3$–$C_7$-cycloalkyl, aryl, substituted-aryl, heteroaryl or a substituted-heteroaryl group, wherein these terms are as defined for compounds of Formula (VII) above. The base may be an alkali metal hydride or an organo-alkali metal compound, including but not limited to sodium hydride, potassium hydride, lithium hydride, lithium diethylamide, and butyllithium. The electrophile is a compound having the formula $R^g$-L, wherein $R^g$ is as defined immediately above, and L is halide or another suitable leaving group, such as a methanesulfonyl or p-toluenesulfonyl moiety. Optional deprotection of any of the compounds wherein W is —O— may be accomplished by standard methods as described by Wuts and Greene (op. cit.).

As outlined in Scheme VI, compounds of Formulas (VIII) and (IX) may be synthesized. Thus, a starting material compound of formula (28), obtained according to Scheme V, is reacted with a 1,2-diamine compound having the formula:

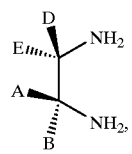

wherein A, B, D, and E are as defined above, in a suitable solvent at room temperature to reflux temperature for about 4 to about 48 hours to give the bicyclic compound of formula (29). The 1,2-diamine compound may have the substituents A, B, D and E, as defined above for the compounds of Formula (VIII), but with $C_2$ or $C_s$ symmetry or A=B=H. Suitable solvents include alcohols such as methanol, ethanol, propanol, isopropanol, butanol, t-butanol, and the like, aprotic solvents such as methylene chloride, tetrahydrofuran, N-methyl-pyrrolidinone, diethyl ether, bis-methoxymethyl ether, dimethyl formamide, and acetone, for example, as well as aqueous mixtures thereof. Preferred solvents are aqueous acetonitrile, aqueous DMF, and aqueous acetone.

Optionally, the 2'-and 4"-hydroxy protecting groups on compound (29) may removed by standard methods as described by Wuts and Greene (op. cit.). When $OR^f$ is an ester, for example, such as acetate or benzoate, the compound is preferably deprotected by treatment with methanol or ethanol. When $R^f$ is a trialkylsilyl group, the compound may be deprotected by treatment with fluoride in THF or acetonitrile. The reaction time required may be from about 1 to about 24 hours.

The deprotected compound (29) wherein $R^f$ is H is then cyclized to give compounds (30) by treatment with a dilute concentration of a strong acid at ambient temperature to reflux temperature for about 4 hours to about 10 days in a suitable organic solvent. Suitable acids include, but are not limited to, hydrochloric acid, sulfuric acid, dichloroacetic acid, trichloroacetic acid and the like. The reaction may be accomplished with a suspension of the reagents in aqueous alcohol, such as for example, methanol, ethanol, propanol, isopropanol, butanol, iso-butanol and t-butanol, for example.

Optionally, compound (29) may be deprotected by the standard methods as described by Wuts and Greene (op. cit.) to give compounds of Formula (VIII). In the event that the protecting groups were removed before the cyclization step, then compound (30) represents compounds of Formula (VIII).

The compounds having Formula (VIII) may be converted into compounds having Formula (IX)

Macrolides of the Formula (VIII) may be converted into compounds having Formula (IX) by treatment with reducing agents such as sodium cyanoborohydride at pH 4–5 or sodium borohydride in a suitable organic solvent.

Scheme VI also illustrates an alternate preparation for compounds of Formulas (VIII) and (IX). Starting material (28) is reacted with a compound having the formula:

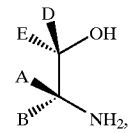

wherein A, B, D, and E are as defined above, in a suitable solvent at 0–70° C. for about 4 to about 48 hours to give compound (31). Suitable solvents are those such as methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF, and aqueous acetone, for example.

Compound (31) is then treated with triphenylphosphine and diphenylphosphoryl azide-DEAD in tetrahydrofuran under Mitsunobu reaction conditions to give the compound (32) wherein Y=$N_3$. Compound (32) wherein Y=$N_3$ is then deprotected by standard methods as described above.

Compound (32) wherein Y=N₃ is then reduced to the amino compound (32A) wherein Y=NH₂ (not shown). Preferable reducing reagents are triphenylphosphine-water, hydrogen with a catalyst, sodium borohydride, or dialkylaluminum hydride.

Compound (32A) wherein Y=NH₂ is then cyclized to prepare the compounds (30) and Formula (VIII) by treatment with a dilute concentration of a strong acid at ambient temperature to reflux temperature for about 4 hours to about 10 days in a suitable organic solvent. Suitable acids include, but are not limited to, hydrochloric acid, sulfuric acid, dichloroacetic acid, trichloroacetic acid and the like. The reaction may be accomplished with a suspension of the reagents in aqueous alcohol, such as for example, methanol, ethanol, propanol, iso-propanol, butanol, iso-butanol and t-butanol, for example. This treatment also removes protecting groups at positions $R^1$ and $R^2$, which eliminates the need to isolate and treat compound (30) separately.

In an another alternate series of reactions the hydroxy group (derived from the amino alcohol) in compound (31) may be activated by treatment with a sulfonating agent, such as sulfonyl chloride, alkyl or aryl sulfonic anhydride or trifluoromethanesufonic anhydride, in an aprotic solvent (e.g., diethyl ether, dichloromethane, tetrahydrofuran, chloroform, pyridine or a mixture thereof) to give the compound (32) wherein Y is a sulfonate ester. The reaction requires cooling or heating, depending on the conditions used. The reaction temperature is preferably −100° C. to 10° C. The reaction may require 20 minutes to 24 hours to complete. The sulfonate ester activated hydroxy group in (32) (for example, Y=—OSO₂CF₃) is then converted to an azide to give the second intermediate azide compound (32A, not shown) wherein Y=N₃ by reacting with an alkali metal azide, such as lithium azide or sodium azide, in the same solvent defined above. The reaction temperature is preferably about 0° C. to about 100° C. The azido compound is then converted to compounds (30) and Formulas (VIII) and (XI) according to the procedures described above.

It is understood that the foregoing chemistry is merely illustrative and is not to be taken as a limitation upon the scope of the invention. Various changes and modifications to the disclosed embodiments will be apparent to those skilled in the art, and may be made without departing from the spirit and scope thereof. Thus, while the foregoing chemistry is directed primarily to the preparation of compounds of formula II, the analogous compounds of formulae III, IV, V, VI, VII, VIII, and IX can be prepared in like manner.

Compounds of formula III wherein R is hydrogen, are described in United States patents U.S. Pat. No. 5,075,289 and U.S. Pat. No. 5,217,960 which are incorporated herein by reference. Chemistry relating to these macrolides is also described by Kirst et al. in *J. Med. Chem.*, 33: 3086 (1990) which is also incorporated herein by reference. Compounds of formula IV wherein R is hydrogen are described by Hunt et al. in *J. Antibiotics*, 41: 1644 (1989), which is incorporated herein by reference. Compounds of formula V, VI and VII wherein R is hydrogen are described by Baker et al. in *J. Org. Chem.*, 53: 2340 (1988), which is incorporated herein by reference. Compounds of formula VIII and IX wherein R is hydrogen are described in European Patent Application EP 559,896, which is incorporated herein by reference.

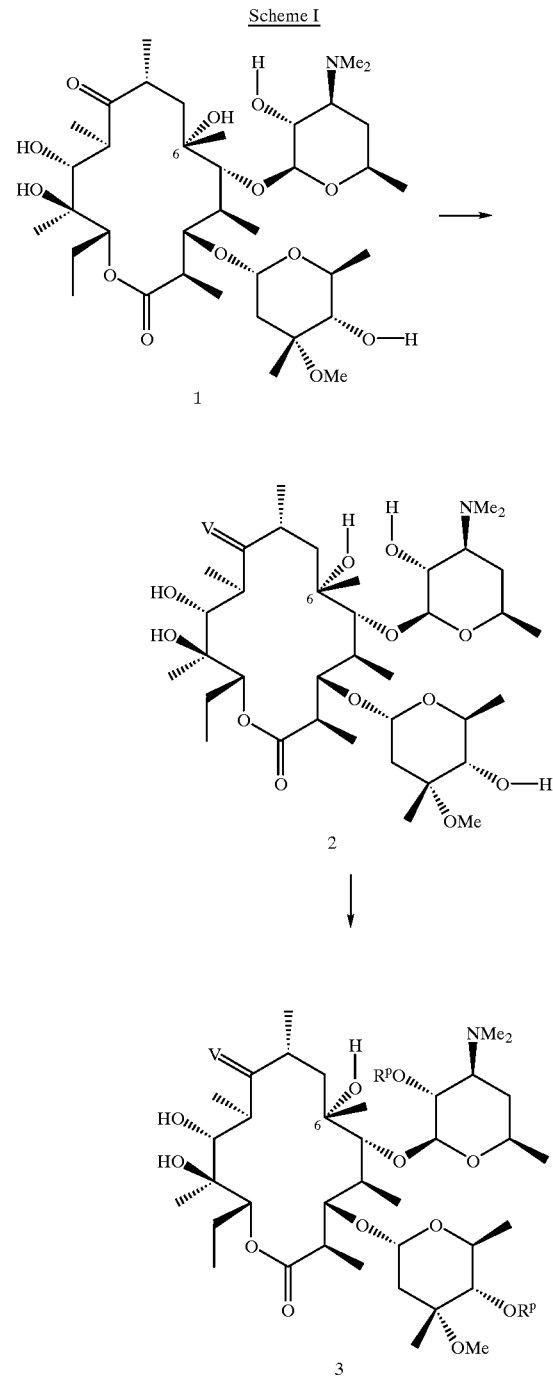

Scheme I

Scheme II
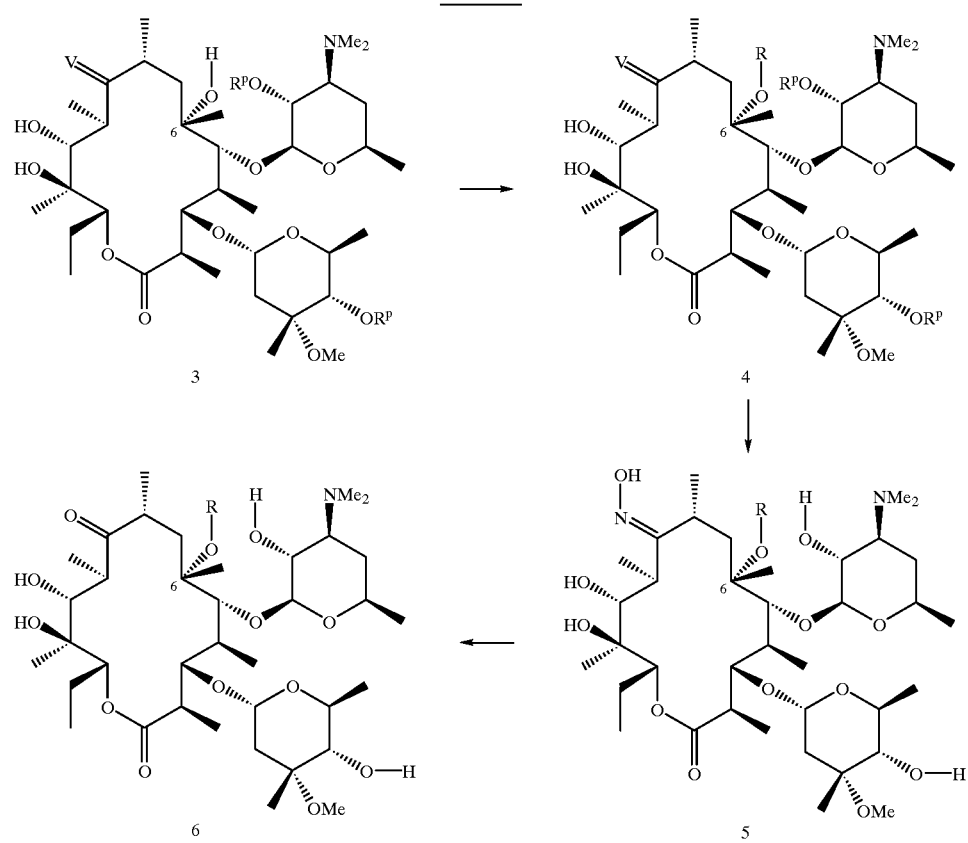
Scheme III
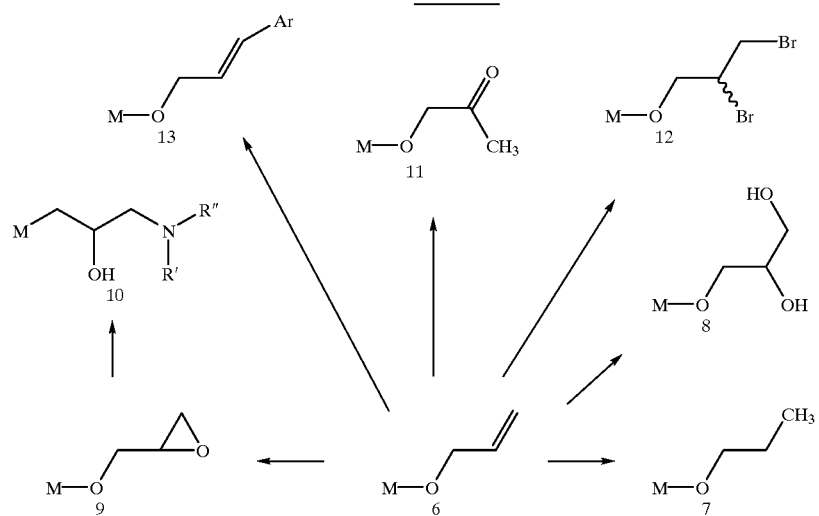

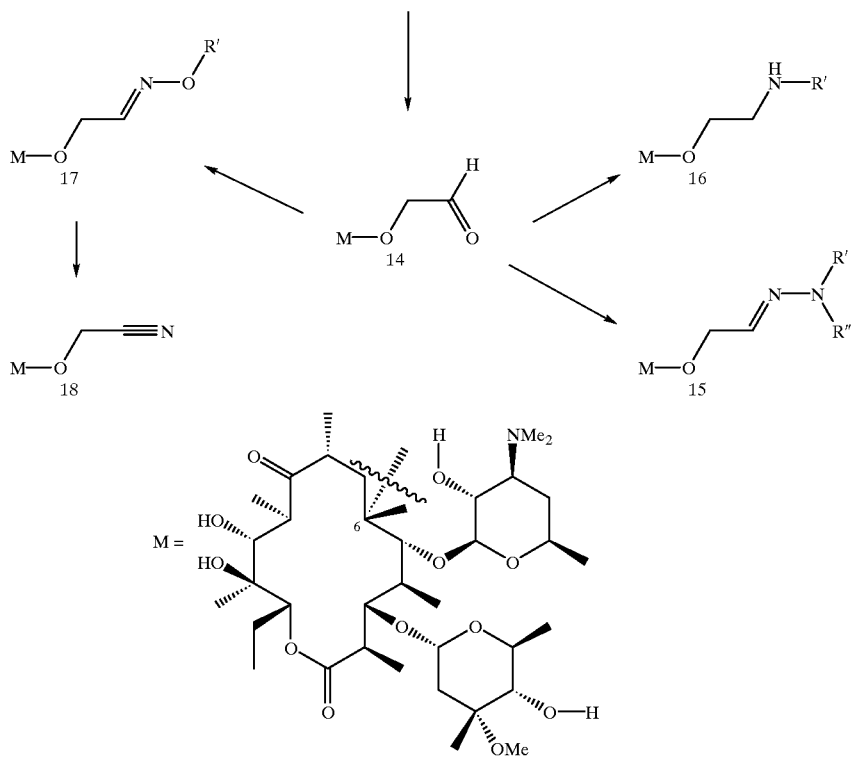
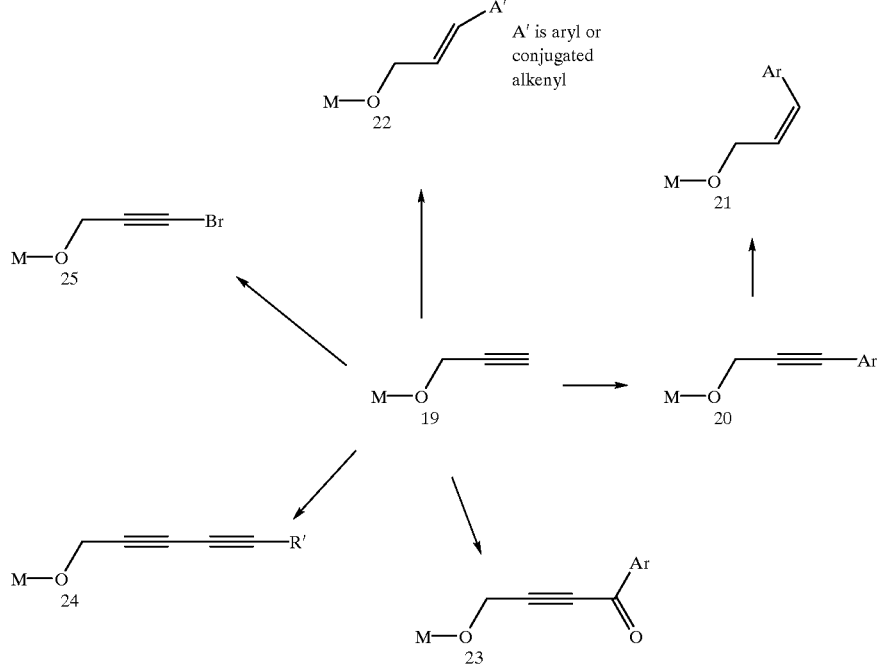
Scheme IV

M = 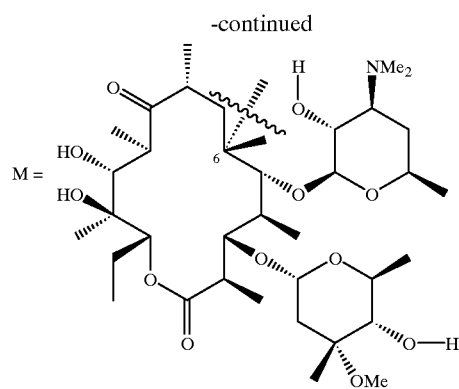
Scheme V
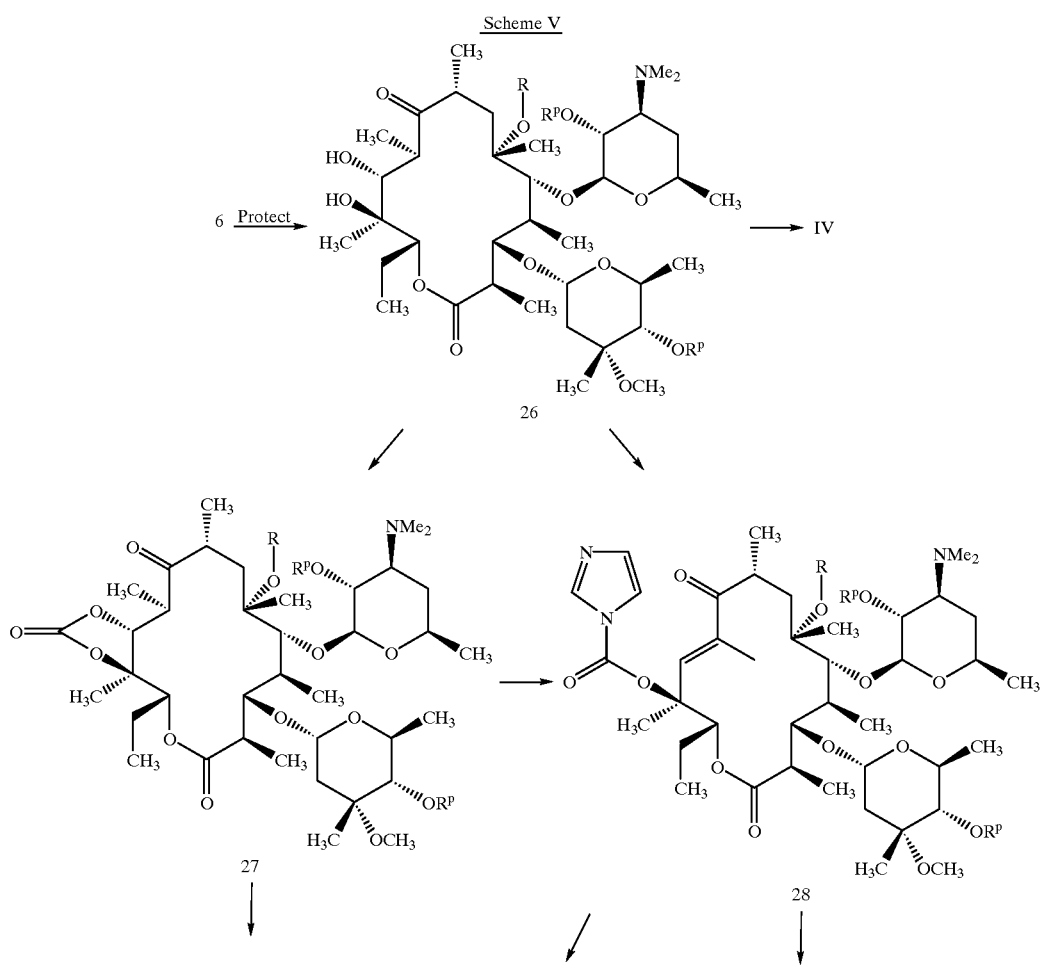

V
-continued
VI
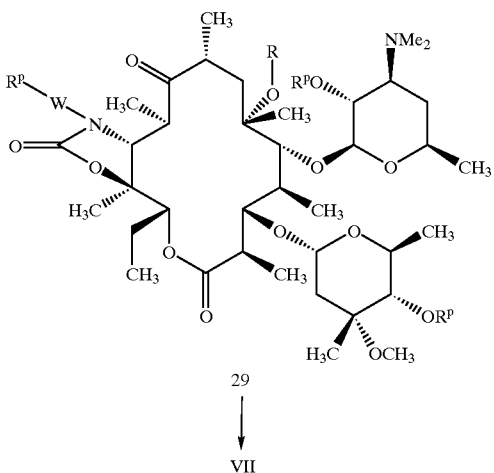
↓
VII
Scheme VI
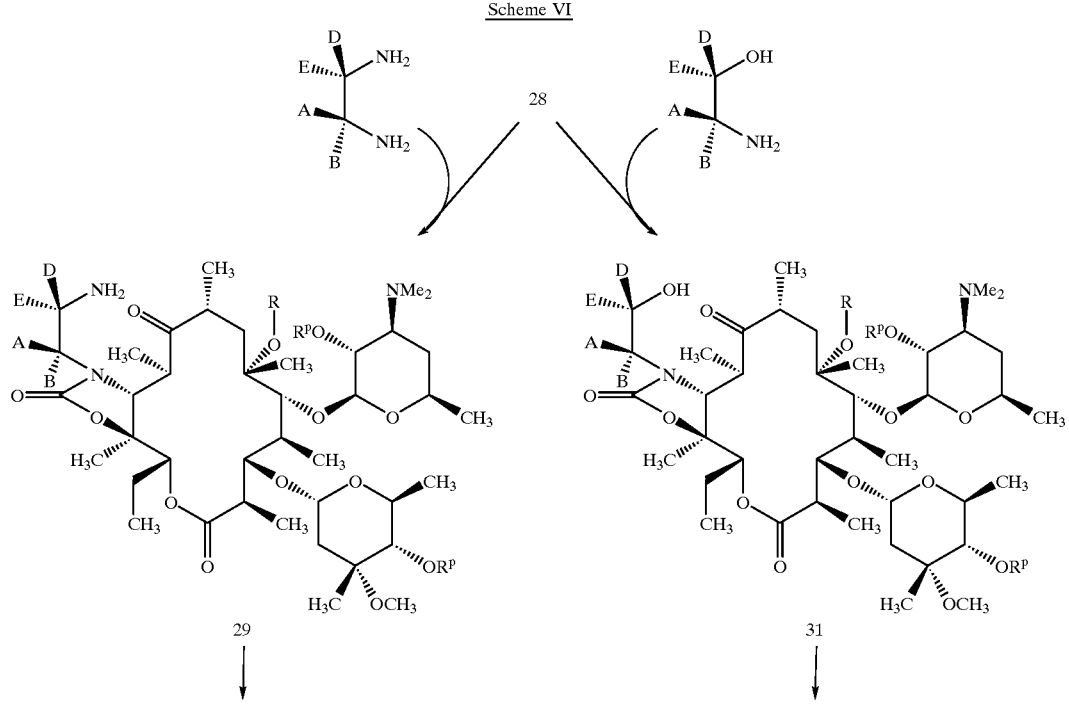

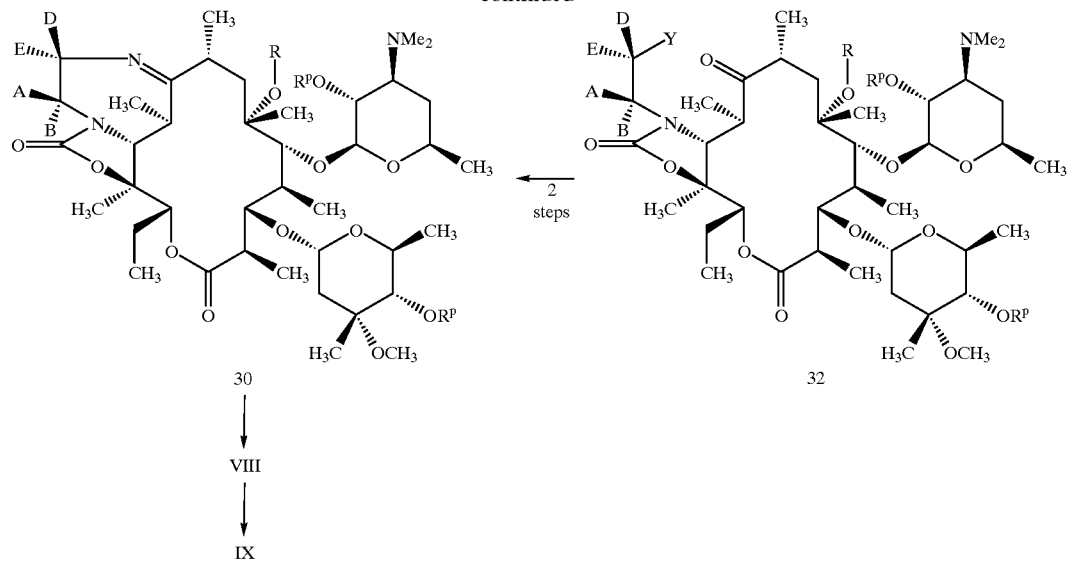

↓ 2 steps

30

↓

VIII

↓

IX

The compounds and processes of the present invention will be better understood in connection with the following examples, which are intended as an illustration of and not a limitation upon the scope of the invention.

EXAMPLE 1

Compound of Formula (X); X is =O, R is allyl

EXAMPLE 1A

Compound of Formula (XII); X is =N—O-(1-isopropoxycyclohexyl), R is allyl, $R^P$ is Trimethylsilyl To a 0° C. solution of 5 g of the compound of Formula XII where X is =N—O-(1-isopropoxycyclohexyl) and $R^P$ is trimethylsilyl in 15 mL of DMSO and 20 mL of THF was added 1.23 mL of freshly distilled allyl bromide. After approximately 10 minutes, a solution prepared by warming and stirring (556 mg, 2.05 equivalents) of powdered KOH in 25 mL of 1:1 THF-DMSO at 50° C. for 20–30 minutes was added dropwise over 5 minutes. After about 1 hour, the chilled reaction mixture was treated with 200 mL of EtOAc followed by 762 μL of allyl amine followed by 60 mL of water. The organic layer was washed with water followed by brine, dried over $MgSO_4$, filtered and concentrated in vacuo to afford 5.3 g of crude title compound. Purification by silica gel chromatography eluting with 5% acetone in hexanes containing 0.25% triethylamine afforded 2.35 g (45%) of the title compound.

EXAMPLE 1B

Alternate preparation of Compound of Formula (XII); X is =N—O-(1-isopropoxycyclohexyl), R is allyl, $R^P$ is Trimethylsilyl To a solution of 103.2 g (0.100 mmol) of the compound of Formula XII where X is =N—O-(1-isopropoxycyclohexyl) and $R^P$ is trimethylsilyl in 500 mL of DMSO and 500 mL of THF cooled to 0° C. and flushed with nitrogen was added freshly distilled allyl bromide (17.3 mL) over 10 minutes. A solution of potassium t-butoxide (120 mL 1M THF solution, 0.120 mmol) in THF (100 mL) and DMSO (230 mL) was added dropwise over 3.5 hours at 0° C., and the mixture was stirred at 0° C. under nitrogen for 2 hours. Additional potassium t-butoxide solution was added (50 mL 1M THF solution, 0.05 mmol, in 50 mL of DMSO) dropwise over 1 hour, and the mixture was stirred for 2 hours. The mixture was cooled and taken up in ethyl acetate (1.5 L). This solution was washed with water and brine, then dried over $Na_2SO_4$. Removal of the solvent under vacuum gave the title compound (125.1 g).

EXAMPLE 1C

Compound of Formula (X); X is =N—OH, R is allyl

To a solution of the compound resulting from Example 1A (1.7 g) in 17 mL of acetonitrile and 8.5 mL of water was added 9 mL of HOAc at ambient temperature. After several hours at ambient temperature, the reaction mixture was diluted with 200 mL of toluene and concentrated in vacuo. The residue obtained was found to contain unreacted starting material, so additional acetonitrile (15 mL), water (70 mL) and HOAc (2 mL) was added. After 2 hours, an additional 1 mL of HOAc was added. After approximately three more hours, the reaction mixture was placed in the freezer overnight. The reaction mixture was allowed to warm to ambient temperature, diluted with 200 mL of toluene and concentrated in vacuo. The residue was chased two times with toluene and dried to constant weight (1.524 g).

EXAMPLE 1D

Compound of Formula (X); X is =O, R is allyl

The compound resulting from Example 1C (1.225 g) in 16 mL of 1:1 EtOH-water was treated with $NaHSO_3$ (700 mg) and formic acid (141 μL) and warmed at 86° C. for 2.5 hours. After approximately three hours, the reaction mixture was allowed to cool to ambient temperature, diluted with 5–6 mL of water, basified with 1 N NaOH to pH 9–10 and extracted with EtOAc. The combined organic extracts were washed with brine (2x), dried over $MgSO_4$, filtered and concentrated in vacuo. The crude material was purified by column chromatography eluting with 1% MeOH in dichloromethane containing 1% ammonium hydroxide to give 686 mg (57%) of the title compound. $^{13}$C NMR (CDCl$_3$) δ 219.3 (C-9), 174.8 (C-1), 135.5, 116.3, 101.9 (C-1'), 95.9 (C-1"), 79.7 (C-5), 78.8 (C-6), 78.5 (C-3), 74.1 (C-12), 72.4 (C-3"), 70.6 (C-11), 68.1 (C-5'), 65.5 (allylic methylene), 65.1 (C2'), 49.0 (C-3" O-CH$_3$), 45.0 (C-2), 44.1 (C-8), 39.7 (NMe$_2$), 37.9 (C-4), 37.1 (C-10), 34.6 (C-2"), 28.4 (C-4'), 21.0, 20.6 (C-3" CH$_3$, C-6' CH$_3$), 20.8 (C-14), 18.3 (C-6"), 18.1 (C-8 CH$_3$), 15.7, 15.6 (C-2 CH$_3$, C-6 CH$_3$), 11.9 (C-10 CH$_3$), 10.1 (C-15), 8.9 (C-4 CH$_3$). MS (FAB)+m/e 774 (M+H)$^+$, 812 (M+K)+.

EXAMPLE 1E

Alternate preparation of Compound of Formula (X); X is =O, R is allyl

A sample of the compound prepared according to Example 1B (76.2 g) was dissolved in H$_2$O (120 mL) and EtOH (120 mL), then pellets of NaNO$_2$ (33.5 g, 0.485 mol, 5 equiv) were added to the solution and the reaction mixture was stirred until the NaNO$_2$ was dissolved. Hydrochloric acid (4N, 121 mL, 0.484 mol) was then added dropwise over a 10 minutes with rapid stirring. The reaction mixture was then heated to 70° C. and stirred for 2 hours. The reaction mixture was cooled, and solid NaHCO$_3$ was added slowly until the solution was saturated. The mixture was then concentrated to approximately half its volume under reduced pressure and extracted with ethyl acetate (3×). The organic extract was washed with brine and dried with Na$_2$SO$_4$. The solvent was removed under reduced pressure, and the residue was crystallized from acetonitrile to give 29.2 g of desired product. A second crop of crystals gave an additional 7.02 g of material. Analytical data was as in Example 1D above.

EXAMPLE 2

Compound of Formula (X); X is =O, R is propyl

The compound resulting from Example 1 (100 mg) was catalytically hydrogenated in MeOH (10 mL) using a palladium on carbon catalyst and hydrogen. The catalyst was removed by filtration, and the filtrate was concentrated in vacuo. The crude product (93 mg) was purified by column chromatography on silica gel eluting with 1% MeOH in dichloromethane containing 1% ammonium hydroxide to afford 38 mg (38%) of the title compound. $^{13}$C NMR (CDCl$_3$) δ 220.5 (C-9), 175.1 (C-1), 102.2 (C-1'), 96.4 (C-1"), 79.8 (C-5), 79.0 (C-3), 78.7 (C-6), 77.8 (C-4"), 76.4 (C-13), 74.4 (C-12), 72.8 (C-3") 71.1 (C-11), 68.8, 68.5, 66.0, 65.9, 65.6, 49.4 (C-3"-OMe), 45.3 (C-2), 44.5, 40.2 (—NMe$_2$), 38.4 (C-7), 38.2 (C-4), 37.4 (C-10), 35.1, 28.6, 21.8, 21.5 (C-14), 21.3, 21.0 (C-3" Me, 6 Me), (18.7, 18.6 (C-6" Me, 8 Me)), (16.2, 16.1 (C-2 Me, 6 Me)), 12.3 (C-10 Me), 10.5 (C-15), 10.1, 9.4 (C-4 Me). MS (DCI/NH$_3$) m/z 776 (M+H)$^+$.

EXAMPLE 3

Compound of Formula (X); X is =O, R is 2,3-dihydroxypropyl

To an ambient temperature solution of the compound resulting from Example 1 (100 mg) in 6 mL of THF was added N-methylmorpholine N-oxide (98 mg) followed by 32 μL of 4% by weight osmium tetroxide in water. The reaction mixture was stirred overnight and then quenched by the addition of 3 equivalents of NaHSO$_3$. After stirring at ambient temperature for 10 minutes, the reaction mixture was filtered through a silica gel plug eluting with 5% MeOH in dichloromethane containing 1% ammonium hydroxide to afford, after concentration at reduced pressure, the title compound (81 mg, 77%) as a mixture of epimers. $^{13}$C NMR (CDCl$_3$) δ 222.6, 221.6 (C-9), 176.9, 176.0 (C-1), 102.2 (C-1'), 102.1, 96.5 (C-1"), 96.4, 80.0, 79.9, 79.8, 78.8, 78.7, 77.6, 77.5, 77.2, 77.0, 76.7, 74.8, 74.7 (C-12), 72.8 (C-3"), 71.0, 71.0, 70.9 (C-11), 70.9, 68.9, 68.9, 68.5, 66.8, 66.5, 66.3, 66.2, 65.8, 65.6, 63.3, 63.0 (C-18), 55.3, 49.3 (—OCH$_3$), 45.6, 45.4 (C-2), 44.7 (C-8), 40.2 (—NMe$_2$), 38.4, 38.2, 38.2, 37.9, 37.6, 35.1 (C-2"), 35.0, 28.5, 28.5 (C-4'), 21.7, 21.5, 21.5, 21.4, 21.0, 20.9, 18.8, 18.6, 18.5, 16.2, 16.2, 16.0, 11.9 (C-10 CH$_3$), 10.4 (C-15), 10.4, 9.4 (C-4 CH$_3$), 9.3. MS m/z 808 (M+H)$^+$.

EXAMPLE 4

Compound of Formula (X); X is =O, R is 2,3-epoxypropyl

To an ambient temperature solution of the compound resulting from Example 1 (100 mg) in 1.5 mL of dichloromethane was added ~170 mg of m-chloroperoxybenzoic acid. The reaction mixture was stirred at ambient temperature overnight and concentrated in vacuo. The residue obtained was taken up in EtOAc and washed with saturated sodium bicarbonate solution (2×) followed by brine, dried over MgSO$_4$ and concentrated in vacua to afford 93 mg of crude product. The crude product was redissolved in EtOAc and washed with 1 M NaHSO$_3$ followed by NaHCO$_3$ solution and brine, dried over MgSO$_4$ and concentrated in vacuo. The residue obtained was chromatographed on silica gel eluting with 5% MeOH in dichloromethane containing 1% NH$_4$OH to afford the title compound as a mixture of epimers. $^{13}$C NMR (CDCl$_3$) δ 219.8, 219.0 (C-9), 175.5, 175.2 (C-1), 102.2, 102.2 (C-1'), 96.3, 96.2 (C-1"), 80.2, 79.9, 79.6, 79.0, 78.8, 77.8, 77.7, 76.6 (C-6,5,3,4",13)), 74.6 (C-12), 72.7 (C-3"), 71.0 (C-11), 68.8, 68.8, 68.5 (C-5'), (66.2, 66.0 (C-16)), (66.1, 65.6 (C-5",3')), 50.3, 49.8, 49.3 (3" OMe), 46.6, 45.5, (45.3, 45.2 (C-2)), 44.6, 44.6 (C-8), 40.2 (—NMe$_2$), 38.4 (C-7), 38.2, 38.2, (37.6, 37.5 (C-10)) 35.1 (C-2"), 35.0, 28.8 (C-4'), (21.4, 21.2, 21.1, 20.9 (C-3"Me, 6' Me, C-14), (18.7, 18.6, 18.5 (C-6" Me, 8 Me)), (16.1, 16.0, 15.9 (C-2 Me, 6 Me)), 12.2 (C-10 Me), 12.2, 10.5 (C-15), 9.3 (C-4 Me), 9.2. MS (FAB) m/e 790 (M+H)$^+$, 812 (M+Na)$^+$, 828 (M+K)$^+$. High Resolution Mass Spec m/z Calcd for C$_{40}$H$_{71}$NO$_{14}$K: 828.4512. Found: 828.4516.

EXAMPLE 5

Compound of Formula (X); X is =O, R is 2-hydroxy-3-(imidazol-1-yl)propyl

To an ambient temperature solution of the compound resulting from Example 4 (100 mg) in ~1 mL of chloroform was added 17 mg of imidazole. The reaction vessel was sealed and stirring was continued at ambient temperature for 1 hour. Two additional equivalents of imidazole were added, and stirring was continued for several days. The solvent was removed under reduced pressure, and the crude material obtained was purified by column chromatography eluting with 5% MeOH in dichloromethane containing 1% NH$_4$OH to afford 44 mg (41%) of the title compound. $^{13}$C NMR (CDCl$_3$) mixture of epimers δ 223.3, 221.2 (C-9), 176.4, 175.9 (C-1), 137.9, 128.7, 120.1, 119.9, 102.2, 102.1 (C-1'), 96.5 (C-1"), 80.3, 80.0, 79.7, 79.2, 78.9, 77.6, 77.6, 77.4, 77.2, 77.0, 77.0, 76.7, 74.7, 74.6, 72.7, 72.7, 71.0, 69.7, 69.4, 69.0, 69.0, 68.5, 68.5, 66.8 (C-16), 66.0, 65.5, 65.4, 50.2, 49.3 (C-18), 49.3 (C-3"-OMe), 45.5 (C-2), 45.2 (C-2), 44.7 (C-8), 40.1 (—NMe$_2$), 38.2 (C-7), 38.1 (C-7), 37.8, 37.5, 35.0, 34.9 (C-2"), 28.4 (C-4'), 21.4, 21.3, 21.3, 21.2, 20.9, 20.8, 18.9, 18.8, 18.7, 18.6, 16.2, 16.1 16.0 (C-2 Me, C-6 Me), 11.9 (C-10 Me), 10.4 (C-15), 9.3 (C-4 Me). MS m/z 858 (M+H)$^+$. High Resolution Mass Spec m/z Calcd for C$_{43}$H$_{76}$N$_3$O$_{14}$: 858.5327. Found: 858.5320.

EXAMPLE 6

Compound of Formula (X); X is =O, R is 2-hydroxy-3-(morpholin-4-yl)propyl

To an ambient temperature solution of the compound resulting from Example 4 (100 g) in 1 mL of chloroform was added 22 μL of morpholine. The reaction vessel was sealed and stirring was continued at ambient temperature for 1 hour. Two additional equivalents of morpholine was added and stirring was continued for several days. The solvent was removed under reduced pressure, and the crude material obtained was chromatographed on silica gel eluting with 3% MeOH in dichloromethane containing 1% NH$_4$OH to give 35 mg (33%) of the title compound. $^{13}$C NMR (CDCl$_3$) mixture of epimers δ 220.3, 219.1 (C-9), 176.1, 175.5 (C-1), 102.1, 102.1 (C-1'), 96.2, 96.1 (C-1"), 80.0, 79.8, 79.7, 79.1, 78.6, 78.5, 77.8, 77.7, 77.1, 76.6, 75.0, 75.0, 72.8, 71.0, 68.5, 68.2, 67.8, 67.0, 66.9, 66.4, 66.0, 65.9, 65.5, 65.5, 61.4, 60.8, 53.9, 53.8, 49.3, 49.3 (—OMe), 45.5, 45.4 (C-2), 44.8, 44.7 (C-8), 40.2 (—NMe$_2$), 38.3 (C-10,4), 38.2, 38.1, 37.9, 37.7 (C-7), 35.0, 28.5 (C-4'), 21.7, 21.5, 21.4, 21.4, 21.3, 21.3 (C-14, 3"-Me, 6'-Me), 21.1, 19.0, 18.7, 18.6, (C-8 Me, C-6" Me), 16.3, 16.2, 16.0 (C-2 Me, 6 Me), 12.1, 12.0 (C-10 Me), 10.6, 10.5 (C-15), 9.3 (C-4 Me). MS (FAB) m/e 877 (M+H)$^+$, 915 (M+K)$^+$.

EXAMPLE 7

Compound of Formula (X); X is =O, R is 2-hydroxy-3-(benzylamino)propyl

To an ambient temperature solution of the compound resulting from Example 4 (140 mg) in 1.5 mL of chloroform was added 3 equivalents (58 μL) of benzylamine. The reaction mixture was stirred overnight at ambient temperature and then warmed at 62° C. for approximately 3 hours and then stirred overnight at ambient temperature. The reaction mixture was then heated at 70° C. for 2 hours and then concentrated in vacuo. The residue was chased two times with toluene to afford 170 mg of crude title compound. Crude product was purified by silica gel chromatography eluting with 2% MeOH in dichloromethane containing 1% NH$_4$OH to give the title compound as a mixture of epimers. $^3$C NMR (CDCl$_3$) δ 221.7, 220.1 (C-9), 176.4 (C-1), 175.7, 140.7, 128.5, 128.2, 128.1, 128.1, 126.7, 126.6, 126.5, 102.2 (C-11), 96.2 (C-1"), 79.6, 79.3, 78.8, 78.7, 77.6, 77.6, 76.8, 76.7, 74.9, 72.7, 72.7, 71.0, 69.7, 69.1, 68.7, 68.5, 67.9, 67.8 (C-16), 66.0, 65.6, 53.8, 53.6, 51.6, 51.3, 49.3 (—OCH$_3$), 45.5 (C-2), 45.4, 44.7, 44.6 (C-8), 40.2 (—NMe$_2$), 38.2, 38.2 (C-7), 38.0, 37.9 (C-10, 4), 35.0, 34.8 (C-2"), 28.5 (C-4'), 21.7, 21.4, 21.4, 21.1, 21.1, 18.9, 18.6, 18.6, 16.2, 16.2, 16.0, 15.9, 12.1, 12.0 (C-10 CH$_3$), 10.5 (C-15), 9.3, 9.3 (C-4 CH$_3$). MS m/z 897 (M+H)$^+$.

EXAMPLE 8

Compound of Formula (X); X is =O, R is 2-oxoethyl

Method A.

To a solution of the compound from Example 3 (275 mg) in 6.5 mL of a 20% aqueous THF was added 87 mg of NaIO$_4$. The reaction was stirred at ambient temperature for 2 hours and then 0.5 equivalents of NaIO$_4$ was added. After 2 additional hours, another 0.5 equivalent of NaIO$_4$ was added. After two more hours, the reaction mixture was filtered through a silica gel plug eluting with 4% MeOH in dichloromethane containing 1% NH$_4$OH to afford 195 mg (65%) of the title compound. $^{13}$C NMR (CDCl$_3$) δ 221.0 (C-9), 203.2 (CHO), 175.5 (C-1), 102.4 (C-1"), 96.3 (C-1"), 80.5, 79.8, 78.8, 77.7, 76.7, 74.5 (C-12), 72.7 (C-3"), 71.0, 70.3, 68.9, 68.7, 66.1, 65.6, 49.4 (C-3" OMe), 45.3, 44.7, 40.2 (NMe$_2$), 38.4 (C-4), 38.2 (C-7), 37.4 (C-10), 34.9 (C-2"), 28.5 (C-4'), (21.5, 21.4, 21.1 (C-3" Me, 6 Me)), 21.0, (18.8, 18.5 (C-8 Me, 6" Me)), 16.0 (C-2 Me), 12.2 (C-10 Me), 10.4 (C-15), 9.2 (C-4 Me). Mass Spec m/z 776 (M+H)$^+$.

Method B.

A solution of the compound from Example 3 (8 g) in 350 dichloromethane (8 mL) was cooled to −78° C., ozone was bubbled into it until a blue color persisted, and nitrogen was then bubbled through it until the blue color disappeared. Methyl sulfide (6 mL) was added, the solution was warmed to 0° C. and stirred for 30 minutes. The solvent was removed under vacuum, the residue was redissolved in THF (90 mL), and triphenylphosphine (7.5 g) was added. The mixture was stirred at 55° C. for 4.5 hours, then concentrated in vacuo and dried under high vacuum to give the crude product (16.5 g). Flash chromatography on silica gel (10:1) eluting with acetonelhexanes/triethylamine (75:25:0.35) gave of the title compound (4.9 g, 61%). Mass Spec m/z 776 (M+H)$^+$.

EXAMPLE 9

Compound of Formula (X); X is =O, R is 2-oxopropyl

A mixture of 1.5 mL of 7:1 DMF-H$_2$O, 5 mg PdCl$_2$ and 21 mg of CuCl was stirred under an oxygen atmosphere for ~1.33 hours. To this mixture was added a solution of the compound resulting from Example 1 (150 mg) in 1.5 mL of 7:1 DMF-H$_2$O dropwise over 10 minutes. The reaction mixture was warmed to 50° C. and maintained at that temperature for approximately 1 hour and at ambient temperature overnight. Additional portions of PdCl$_2$ (5 mg) and CuCl (21 mg) were added. The reaction mixture was warmed to 54° C. and maintained at that temperature for about 3 hours. The reaction mixture was allowed to cool to ambient temperature and then O$_2$ was bubbled through the reaction mixture which was stirred overnight at ambient temperature. Additional PdCl$_2$ (10 mg) and CuCl (42 mg) were added, and the O$_2$ was continued. The reaction mixture was warmed to 40° C. for about 3 hours and then stirred over the weekend at ambient temperature. The reaction mixture was diluted with EtOAc and washed two times with 30% aqueous ammonium hydroxide solution and two times with brine, dried over MgSO$_4$ and concentrated in vacuo to afford 85 mg of crude title compound. Purification by eluting through a silica gel plug with 1% MeOH in dichloromethane containing 1% ammonium hydroxide afforded 47 mg of the title compound. $^3$C NMR (CDCl$_3$) δ 217.9, 205.3, 175.0, 102.4, 96.5, 80.6, 79.0, 78.9, 77.7, 76.7, 75.1, 72.7, 71.0, 69.6, 68.7, 68.3, 66.1, 65.6, 49.4, 44.8, 40.2, 38.4, 37.6, 35.0, 28.5, 26.5, 21.4, 21.3, 19.2, 18.7, 16.2, 15.9, 12.2, 10.6, 9.3. High Resolution Mass Spec (FAB) Calcd for m/z (M+H)$^+$ $C_{40}H_{72}NO_{12}$: 790.4953. Found: m/z 790.4932.

EXAMPLE 10

Compound of Formula (X); X is =O, R is
—CH—C≡CH

EXAMPLE 10A

Compound of Formula (X); X is =N—O-(1-isopropoxycyclohexyl), R is —CH$_2$—C≡CH

A solution of 1.14 g of powdered KOH in 30 mL of anhydrous DMSO and 30 mL of anhydrous freshly distilled THF was added via addition funnel to a 0° C. solution of the compound of Formula XII where X is =N—O-(1-isopropoxycyclohexyl) and R$^p$ is trimethylsilyl (10 g) in 60 mL of 1:1 DMSO-THF. This was followed by a solution containing 2.38 mL of propargyl bromide (80%) in toluene added over 10–15 minutes. The reaction mixture was stirred at 0° C. for about one hour and then 2 additional equivalents of propargyl bromide was added at 0° C. After 2 hours, 2 equivalents of powdered KOH (~1 g) was added at 0° C., and the reaction mixture was placed in the refrigerator overnight. The next day an additional 4 mL of propargyl bromide was added at 0° C. When tlc indicated that the reaction was complete, the reaction was quenched with 10 equivalents of allylamine at 0° C. and stirred for 5 minutes. The mixture was diluted with H$_2$O and EtOAc, and the organic layer was washed with water and brine, then dried over MgSO4 and concentrated under reduced pressure to afford 11.5 g of crude title compound. Filtration through a silica gel plug eluting with 10% acetone in hexane containing 0.25% Et$_3$N afforded 9.3 of purified title compound.

EXAMPLE 10B

Compound of Formula (X); R is —CH$_2$—C≡CH, X is =N—O—H

To the compound resulting from Example 10A (9.3 g) in 50 mL of acetonitrile and 35 mL of water was added 50 mL of HOAc. The reaction mixture was stirred at ambient temperature for 2 hours and placed in the refrigerator overnight. The reaction mixture was allowed to warm to ambient temperature, diluted with toluene and concentrated in vacuo.

The residue obtained was used without further purification.

EXAMPLE 10C

Compound of Formula (X); X is =O, R is
—CH$_2$—C≡CH

The compound resulting from Example 10B (8.16 g) in 1:1 EtOH-H$_2$O (140 ml) was treated with 4 equivalents of NaHSO$_3$ and formic acid (960 μL, 2.4 equivalents) and warmed to ~82° C. After approximately 2.5 hours, the reaction mixture was allowed to cool to ambient temperature, basified to pH 10 with 1 N NaOH solution and extracted with EtOAc. The combined organic extracts were washed, dried and concentrated in vacuo. The crude product obtained was chromatographed on silica gel eluting with 1% MeOH in dichloromethane containing 1% ammonium hydroxide to afford 2.9 g (40%) of the title compound which was recrystallized from acetonitrile. $^{13}$C NMR (CDCl$_3$) δ 219.7 (C-9), 175.2 (C-1), 102.6 (C-1'), 96.2 (C-1"), 80.7 (C-5), 80.3 (C-6), 78.8 (C-3), 77.9 (C-4") 76.6, 74.5, 73.9 (C-12), 72.7, 71.0 (C-2'), 68.7 (C-5'), 65.8, 65.6, 51.8 (C-16), 49.4 (C-3'OMe), 45.2 (C-2), 44.8 (C-8), 40.2 (NMe$_2$), 38.6 (C-7), 38.5 (C-4), 37.5 (C-10), 35.0 (C-2"), 28.6 (C-4"), 21.5 (C-3"Me, 6'Me), 21.2 (C-14), 21.0 (C-6 Me), (18.7, 18.4 (C-2 Me, 6 Me)), 16.1, 16.0, 12.3 (C-10 Me), 10.6 (C-15), 9.2 (C-4 Me). MS (FAB) m/e 772 (M+H)$^+$, 810 (M+K)$^+$.

EXAMPLE 11

Compound of Formula (X); X is =O, R is
—CH$_2$—CHOH—CH$_2$—N$_3$

To an ambient temperature solution of the compound resulting from Example 4 (100 mg) in 0.75 mL of DMF was added 12 mg of NaN$_3$. The reaction mixture was stirred at ambient temperature approximately 5.5 hours and then an additional 8 mg of NaN$_3$ was added. The reaction mixture was stirred at ambient temperature overnight, heated at 70° C.–90° C. for 3 hours and then treated with an additional 14 mg of NaN$_3$. The reaction mixture was heated at 60° C. overnight. Four drops of water were added, and the reaction mixture was heated at 80° C. for 4 hours. One equivalent of ammonium chloride was added and heating was continued at 80° C. for 2 hours. The reaction mixture was allowed to cool to ambient temperature, diluted with ethyl acetate and washed with 0.5 N NaOH solution and brine, dried and concentrated in vacuo. The residue obtained was filtered through a silica gel plug eluting with 4% MeOH in dichloromethane containing 1% ammonium hydroxide to give 47 mg (50%) of the title compound containing trace amounts of DMF. The DMF was removed by dissolving the compound in 1:1 EtOAc-Et$_2$O, washing with water followed by brine, drying over magnesium sulfate and concentrating in vacuo to give 45 mg of title compound which was further purified by filtering through silica gel eluting with 4% MeOH in dichloromethane containing 1% ammonium hydroxide to give the title compound. $^{13}$C NMR (CDCl$_3$) mixture of epimers δ 222.8, 221.2 (C-9), 176.6, 175.8 (C-1), (102.2, 102.1 (C-1')), (96.4, 96.3 (C-1")), 80.2, 80.1, 79.4, 78.9, 78.7, 77.6, 77.5, 77.4, 77.0, 76.6, 74.8, 74.7, 72.8, 71.0 (C-11), 70.0, 68.9, 68.6, 67.3, 66.8, 66.2, 65.6, 53.8, 53.2 (C-18), 49.3 (C-3"OMe), 45.6 (C-2), 45.4, 44.7 (C-8), 40.2 (—NMe$_2$), 38.4, 38.2 37.6, (35.1, 35.0 (C-2")), 28.5 (C-4'), 21.8, 21.5, 21.2, (21.1, 21.0 (C-14)), 20.9, 18.8, 18.2, 16.1, 12.0 (C-10 Me), 12.0, 10.4 (C-15), 9.3, 9.3 (C-4 Me). MS (FAB) m/e 833 (M+H)$^+$, 871 (M+K)$^+$. High Resolution Mass Spec m/z (M+H)+ Calcd for $C_{40}H_{73}N_4O_{14}$: 833.5123. Found: 833.5137.

EXAMPLE 12

Compound of Formula (X); X is =O, R is
—CH$_2$—CH=N—OH

To a solution of the compound resulting from Example 8 (600 mg) in 5 mL of MeOH was added a solution of 80 mg of hydroxylamine hydrochloride and 255 μL of N-methylmorpholine in 2 mL of MeOH. The reaction mixture was stirred at ambient temperature for 5 hours and then concentrated in vacuo. The residue obtained was purified by eluting from silica gel using 4% MeOH in dichloromethane containing 1% ammonium hydroxide to give the title compound as a 1: 1 mixture of oxime isomers. $^{13}$C NMR (CDCl$_3$) δ 220.8, 219.9 (C-9), 175.4, 175.3 (C-1), 151.7 (CH=N), 149.2 (CH=N), 102.4, 102.3 (C-1'), 96.3 (C-1"), 80.0, 80.0, 79.9, 79.8, 78.8, 78.8, 77.7, 77.3, 77.0, 76.7, 76.5, 76.4, 74.5, 74.4 (C-12), 72.7 (C-3"), 72.7, 71.1, 68.8, 68.7, 68.5, 68.5, 66.0, 65.9, 65.4, 61.4, 58.6, 49.4, 49.3 (3"—OCH$_3$), 45.2, 45.2, 44.6, 40.2 (—NMe$_2$), (38.4, 38.3 (C-4)), 38.2 (C-7), 37.4, 37.2 (C-10), 35.0 (C-2"), 28.6 (C-4"), 21.4, 21.4, 21.2, 21.1, 21.0, 20.9, 20.5, 18.7, 18.6, (18.4, 18.4 (C-8 Me, 6"Me)), 16.1, 16.0, 16.0 (C-2 Me), 15.9, 12.2 (C-10 Me), 10.4 (C-15), 9.2 (C-4 Me). MS m/z 791 (M+H)$^+$.

EXAMPLE 13

Compound of Formula (X); X is =O, R is —CH$_2$—CH$_2$OH

To a −78° C. solution of the compound resulting from Example 8 (75 mg) in 1 mL of anhydrous THF was added 1.1 equivalents of L-Selectride dropwise over 2 minutes. The reaction mixture was stirred at −78° C. for approximately one hour and then quenched at −78° C. with an aqueous solution of tris-hydroxymethylaminomethane followed by EtOAc. The organic phase was washed twice with brine, dried over magnesium sulfate and concentrated in vacuo. The crude material (76 mg) was chromatographed on silica gel eluting with 3% MeOH in dichloromethane containing 1% ammonium hydroxide to afford 20 mg of the desired title compound. $^{13}$C NMR (CDCl$_3$) δ 222.1 (C-9), 175.9 (C-1), 102.1, 96.3, 83.8, 80.2, 79.6, 78.8, 77.7, 77.0, 74.8, 72.8, 71.1, 68.8, 68.5, 66.1, 66.0, 65.6, 62.0, 49.4, 45.6, 44.7, 40.2 (NMe$_2$), 38.6, 38.1, 37.8, 35.1 (C-2"), 28.5 (C-4'), 21.6, 21.5, 21.4, 21.0, 18.7, 18.6, 16.2, 12.1, 10.5, 9.4. MS m/e 778 (M+H)$^+$.

EXAMPLE 14

Compound of Formula (X); X is =O, R is —CH$_2$—CH$_2$NH$_2$

The compound resulting from Example 12 (160 mg) was subjected to catalytic hydrogenation using a Raney nickel catalyst under 4 atmospheres of hydrogen over 20 hours. The catalyst was removed by filtration, and the filtrate was concentrated under reduced pressure to afford 159 mg of crude title compound. Purification by column chromatography on silica gel eluting with 7% MeOH in dichloromethane containing 1% ammonium hydroxide afforded 87 mg (55%) of the title compound. $^{13}$C NMR (CDCl$_3$) δ 219.9 (C-9), 175.5 (C-1), 101.6 (C-1'), 96.1 (C-1"), 79.3 (C-5), 78.9 (C-3), 78.4 (C-6), 77.3 (C-4"), 76.3 (C-13), 74.8 (C-12), 72.5 (C-3"), 71.1 (C-11), (68.0, 67.7, 65.6, 64.4, 64.2 (C-2',3',5",5',16)), 48.8 (C-3"OMe), 45.0 (C-2), 44.4, 40.6, 39.6 (NMe$_2$), (37.9, 37.8 (C-4, 10)), 37.5 (C-7), 34.8 (C-2"), 29.0 (C-4'), 21.0, 20.9, 20.8 (C-17), 20.7, (18.4, 18.1 (C-8 Me, 6"Me), (15.9, 15.4 (C-2 Me, 6 Me), 11.4 (C-10 Me), 10.0 (C-15), 9.0 (C-4 Me). MS m/z 777 (M+H)$^+$.

EXAMPLE 15

Compound of Formula (X); X is =O, R is —CH$_2$—CN

To a solution of the compound resulting from Example 12 (165 mg) in 5 mL of freshly distilled THF was added 2 equivalents of diisopropylcarbodiimide (65 µL) followed by a catalytic amount of CuCl. After stirring approximately 2 hours at ambient temperature, two additional aliquots of diisopropylcarbodiimide (65 µL) were added plus additional CuCl. After 3 more hours, the reaction was complete and the solvent was removed in vacuo to afford the title compound. Mass Spec m/z 773 (M+H)$^+$.

EXAMPLE 16

Compound of Formula (X); X is =O, R is —CH$_2$-Phenyl

EXAMPLE 16A

Compound of Formula (XII); X is =N—O-(1-isopropoxycyclohexyl), R is —CH$_2$-Phenyl, R$^p$ is Trimethylsilyl To a 0° C. solution of 30 mL of a 1:1 solution of THF and DMSO containing 5 g of the compound of Formula (X) wherein X is =N—O-(1-isopropoxycyclohexyl) and R is hydrogen was added 1.2 mL of benzyl bromide. A second solution of 30 mL of 1:1 DMSO and THF containing 560 mg of powdered KOH was added in portions over 45 minutes at 0° C. with good stirring. Upon completion of the addition, stir at 0° C. under nitrogen for 1 hour and then allylamine (700 µL) and ethyl acetate were added. The solution was washed wtih water and brine (2×), dried over magnesium sulfate, filtered and concentrated in vacuo to afford 6 g of the title compound.

EXAMPLE 16B

Compound of Formula (XII); X is =N—O-(1-isopropoxycyclohexyl), R is —CH$_2$-Phenyl, R$^p$ is H To a room temperature solution of 6 g of the compound resulting from Example 16A in 65 mL of anhydrous THF was added 14.5 mL of 1 M tetrabutylammonium fluoride. After several hours, the solvent was removed under reduced pressure and the residue was dried to constant weight. Purification by column chromatography eluting with 4% methanol in dichloromethane containing 1% ammonium hydroxide afforded 2.8 g of the title compound.

EXAMPLE 16C

Compound of Formula (XII); X is =N—OH, R is —CH$_2$-Phenyl, R$^p$ is H

To the compound resulting from Example 16B (2.8 g) in 26 mL of acetonitrile was added 14 mL of water followed by 14 mL of acetic acid. The reaction mixture was stirred for ~4 hours at ambient temperature and then placed in the freezer overnight. The volatiles were removed in vacuo, and the residue was chased twice with toluene and dried to constant weight to afford 2.73 g of the title compound.

EXAMPLE 16D

Compound of Formula (X); X is =O, R is —CH$_2$-Phenyl

To the compound resulting from Example 16C (2.7 g) in 23 mL of EtOH and water (23 mL) was added 1.4 g of NaHSO$_3$. This was followed by 292 µL of formic acid, and the reaction mixture was warmed to 80° C. After approximately 90 minutes, the reaction mixture was allowed to cool to ambient temperature, basified to pH ~10–11 with 2 N NaOH solution and extracted with ethyl acetate. The combined organic extracts were washed with water followed by brine, dried over magnesium sulfate, filtered and concentrated in vacuo. The crude material (1.95 g) was chromatographed on silica gel eluting with 1% methanol in dichloromethane containing 1% ammonium hydroxide followed by 2% methanol in dichloromethane containing 1% ammonium hydroxide to afford 715 mg of the title compound. Further purification was effected by chromatography on silica gel eluting with 2% ammonium hydroxide in dichloromethane followed by 2% methanol in dichloromethane containing 1% ammonium hydroxide to afford 435 mg of the title compound. $^{13}$C NMR (CDCl$_3$) δ 219.28, 174.69, 139.20, 128.51, 127.95, 127.12, 102.20, 96.42, 80.14, 79.80, 78.96, 77.79, 77.42, 77.00, 76.56, 74.77, 72.84, 71.11, 68.75, 68.56, 66.39, 66.21, 65.61, 49.41, 45.15, 44.62, 40.27, 38.02, 37.91, 35.19, 28.54, 21.95, 21.56, 21.53, 21.28, 19.2, 18.82, 16.25, 16.09, 12.24, 10.61, 9.56. MS (FAB) m/e 824 (M+H)$^+$.

EXAMPLE 17

Compound of Formula (X); X is =O, R is
—CH$_2$—CH=CH—Phenyl

The title compound was prepared by the procedures described in Example 16 substituting 3-phenyl allyl bromide for benzyl bromide. For conversion of the oxime to the ketone, the reaction mixture was heated about 3 hours and then placed in the freezer overnight. Chromatography on silica gel eluting with 1% methanol in dichloromethane containing 1% ammonium hydroxide afforded ~700 mg (17% yield for three steps) of the title compound. H. Res. MS: 850.5338.

EXAMPLE 18

Compound of Formula (X); X is =O, R is
—CH$_2$—CH=N—O—CH$_3$

To a room temperature solution of 150 mg of the compound resulting from Example 8 in 1 mL of methanol was added a solution of 14 mg of methoxylamine hydrochloride in 0.5 mL methanol containing 64 μL of N-methyl morpholine in one portion. The reaction mixture was stirred at ambient temperature under a nitrogen atmosphere for about 6 hours and then treated with 0.75 equivalents (12 mg) of methoxylamine hydrochloride. The reaction mixture was stirred at ambient temperature for 1 hour and then placed in the refrigerator overnight. The volatiles were removed under reduced pressure to afford 215 mg of crude title compound. Purification by column chromatography on silica gel eluting with 1% methanol in dichloromethane containing 1% ammonium hydroxide afforded 120 mg (78%) of the title compound as a 1:1 syn:anti mixture. $^{13}$C NMR (CDCl$_3$) δ 219.3, 218.4, 173.8, 173.7, 157.9, 149.5, 146.8, 100.8, 100.7, 94.7, 94.5, 93.0, 78.4, 78.2, 77.3, 77.1, 76.2, 75.9, 75.4, 75.0, 74.9, 74.8, 72.9, 72.7, 71.2, 71.1, 69.4, 67.2, 67.1, 67.0, 65.3, 64.5, 64.4, 64.0, 59.9, 57.3, 47.8, 47.8, 44.8, 43.7, 43.6, 43.0, 38.6, 36.8, 36.7, 36.7, 35.7, 33.4, 26.9, 19.9, 19.8, 19.4, 18.9, 17.1, 16.9, 16.8, 14.4, 14.4, 10.6, 8.9, 8.8, 7.6, 7.5. MS (FAB) m/e 805 (M+H)$^+$.

EXAMPLE 19

Compound of Formula (X); X is =O, R is
—CH$_2$—CH=N—O—CH$_2$-Phenyl

The title compound was prepared as a 1:1 syn:anti mixture by the procedures described in Example 18 substituting O-benzyl hydroxylamine hydrochloride for methoxylamine hydrochloride to afford 118 mg (70%). $^{13}$C NMR (CDCl$_3$) δ 219.3, 218.5, 173.8, 173.7, 149.8, 147.6, 136.6, 126.5, 126.5, 126.2, 125.8, 125.8, 100.8, 100.8, 94.7, 94.5, 93.0, 78.5, 78.4, 78.2, 77.2, 76.2, 76.2, 75.8, 75.4, 75.0, 74.9, 74.2, 74.0, 72.8, 72.7, 71.2, 71.1, 69.4, 67.2, 67.1, 67.0, 65.3, 64.4, 64.4, 60.1, 57.5, 53.8, 47.8, 47.8, 44.8, 43.6, 43.0, 38.6, 36.8, 36.8, 36.7, 36.7, 35.6, 33.4, 33.4, 26.9, 19.9, 19.8, 19.8, 19.5, 19.4, 19.0, 17.1, 17.0, 16.8, 16.8, 14.4, 14.4, 10.6, 10.6, 8.9, 7.6. MS (FAB) m/e 881 (M+H)$^+$.

EXAMPLE 20

Compound of Formula (X); X is =O, R is
—CH$_2$—CH=N—N(CH$_3$)$_2$

The title compound was prepared by the procedures described in Example 18 substituting N,N-dimethyl hydrazine for methoxylamine hydrochloride. Purification by column chromatography eluting with 2% methanol in dichloromethane containing 1% ammonium hydroxide afforded 115 mg (73%) of the title compound as a single (syn or anti) isomer. $^3$C NMR (CDCl$_3$) δ 217.8, 173.5, 132.4, 100.5, 94.5, 92.7, 78.1, 77.4, 76.0, 75.6, 75.2, 74.7, 74.6, 72.6, 70.9, 69.2, 66.7, 64.1, 63.7, 63.0, 47.5, 43.4, 42.7, 41.0, 38.4, 36.6, 36.5, 35.4, 33.1, 26.7, 19.6, 19.6, 19.4, 19.2, 16.8, 16.6, 14.3, 14.0, 10.4, 8.8, 7.4. MS (FAB) m/e 818 (M+H)$^+$.

EXAMPLE 21

Compound of Formula (X); X is =O, R is
—CH$_2$—CH=N—NH(CH$_3$)

The title compound was prepared by the procedures described in Example 18 substituting N-methyl hydrazine for methoxylamine hydrochloride. Purification by column chromatography eluting with 2% methanol in dichloromethane containing 1% ammonium hydroxide afforded 89 mg (58%) of the title compound as a single pure isomer of unknown stereochemistry. $^{13}$C NMR (CDCl$_3$) δ 219.7, 175.5, 136.2, 102.5, 96.5, 80.1, 79.4, 79.1, 77.9, 77.2, 77.0, 76.7, 76.5, 74.5, 72.8, 71.1, 68.7, 66.1, 65.7, 64.4, 49.4, 45.3, 44.6, 40.3, 38.6, 38.5, 37.4, 35.1, 34.8, 28.6, 21.5, 21.5, 21.3, 21.0, 18.8, 18.5, 16.2, 15.9, 12.3, 10.7, 9.2. MS (FAB) m/e 804 (M+H)$^+$.

EXAMPLE 22

Compound of Formula (X); X is =O, R is
—CH$_2$—CH=N-(4-Morpholinyl)

The title compound was prepared by the procedures described in Example 18 substituting N-amino morpholine for methoxylamine hydrochloride. Purification by column chromatography eluting with 5% methanol in dichloromethane containing 1% ammonium hydroxide followed by re-chromatography eluting with 2% methanol in dichloromethane containing 1% ammonium hydroxide afforded 125 mg (75%) of the title compound as a single pure isomer of unknown stereochemistry. Diagnostic peaks $^1$H NMR (CDCl$_3$, 500 MHz) δ 0.84 (t, 3H), 2.29 (s, 6H), 3.12 (m, 4H), 3.34 (s, 3H), 3.85 (t, 4H), 4.50 (d, 1H), 4.92 (d, 1H), 5.06 (d of d, 1H). MS (FAB) m/e 860 (M+H)$^+$.

EXAMPLE 23

Compound of Formula (X); X is =O, R is
—CH$_2$—CH=N—NH(Phenyl)

The title compound was prepared by the procedures described in Example 18 substituting N-phenyl hydrazine for methoxylamine hydrochloride. Purification by column chromatography eluting with 1% methanol in dichloromethane containing 1% ammonium hydroxide afforded 50 mg of the title compound as a single pure isomer of unknown stereochemistry. $^1$MS (FAB) m/e 866 (M+H)$^+$.

EXAMPLE 24

Compound of Formula (X); X is =O, R is
—CH$_2$—CH=N—N(Phenyl)$_2$

The title compound was prepared by the procedures described in Example 18 substituting N,N-diphenyl hydrazine for methoxylamine hydrochloride. Purification by column chromatography eluting with 2% methanol in dichloromethane containing 1% ammonium hydroxide afforded 156 mg of the title compound as a single pure isomer of unknown stereochemistry. Diagnostic peaks $^1$H NMR (CDCl$_3$, 300 MHz) δ 7.07–7.39 (m, 10H), (m, 6.46 (t, 1H). MS (FAB) m/e 942 (M+H)$^+$.

EXAMPLES 26–105

Compounds having Formula (X) wherein X is O, R is CH$_2$—CH(OH)—CH$_2$—R$^V$, and R$^V$ is as shown In accordance with the procedures of Examples 5, 6,7 or 210, except replacing the reagent amines from those examples with the appropriate amine, the compounds of Examples 26–105, which are compounds having Formula (X) wherein

111

X is O, R is CH$_2$—CH(OH)—CH$_2$—R$^V$, and R$^V$ is as shown in Table 1 below, were prepared.

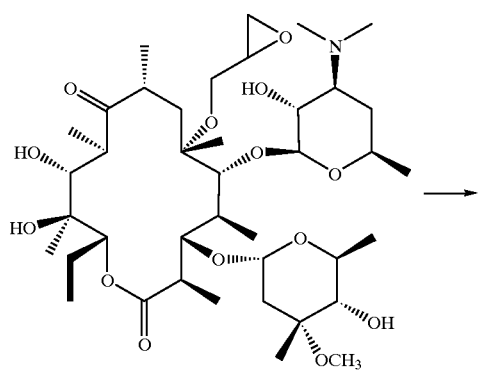 → 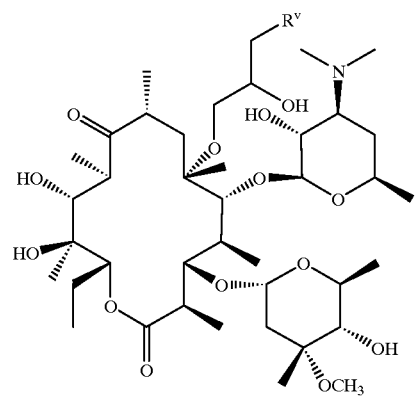

TABLE 1

Examples 26–105

Compounds having Formula (X) wherein X is O, R is CH$_2$—CH(OH)—CH$_2$—R$^V$, and R$^V$ is as shown

| Exam No. | R$^V$ | molecular formula | Calcd. exact mass | MS analysis |
|---|---|---|---|---|
| 26 | (1,2,3,4-tetrahydroisoquinolin-2-yl) | C$_{49}$H$_{82}$N$_2$O$_{14}$ | 922.6 | 922.1, 461.4 |
| 27 | (4-phenylpiperazin-1-yl) | C$_{50}$H$_{85}$N$_3$O$_{14}$ | 951.6 | 952.0, 476.2 |
| 28 | N(iPr)(CH$_2$Ph) | C$_{50}$H$_{86}$N$_2$O$_{14}$ | 938.6 | 937.8, 470.2 |
| 29 | N(CH$_2$Ph)$_2$ | C$_{54}$H$_{86}$N$_2$O$_{14}$ | 986.6 | 985.8, 493.8 |

TABLE 1-continued
Examples 26–105
Compounds having Formula (X) wherein X is O,
R is CH$_2$—CH(OH)—CH$_2$—R$^V$, and R$^V$ is as shown
| Exam No. | R$^V$ | molecular formula | Calcd. exact mass | MS analysis |
|---|---|---|---|---|
| 30 | 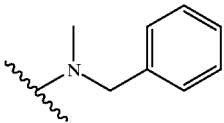 | C$_{48}$H$_{82}$N$_2$O$_{14}$ | 910.6 | 911.1, 456.3 |
| 31 | 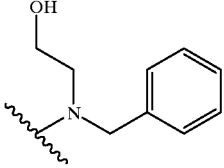 | C$_{49}$H$_{84}$N$_2$O$_{15}$ | 940.6 | 939.8, 470.9 |
| 32 | 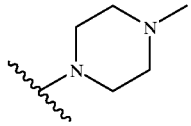 | C$_{45}$H$_{83}$N$_3$O$_{14}$ | 889.6 | 889.0, 445.3 |
| 33 | 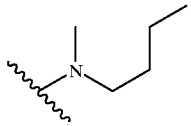 | C$_{45}$H$_{84}$N$_2$O$_{14}$ | 876.6 | 877.0, 439.4 |
| 34 | 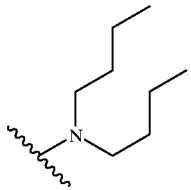 | C$_{48}$H$_{90}$N$_2$O$_{14}$ | 918.6 | 918.5, 459.9 |
| 35 | 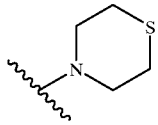 | C$_{44}$H$_{80}$N$_2$O$_{14}$S | 892.5 | 891.8, 447.0 |
| 36 | 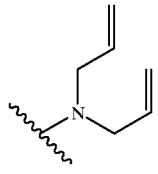 | C$_{46}$H$_{82}$N$_2$O$_{14}$ | 886.6 | 886.1, 444.2 |
| 37 | 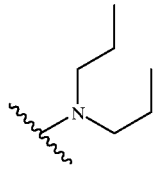 | C$_{46}$H$_{86}$N$_2$O$_{14}$ | 890.6 | 889.9, 446.2 |

TABLE 1-continued

Examples 26–105
Compounds having Formula (X) wherein X is O,
R is CH$_2$—CH(OH)—CH$_2$—R$^V$, and R$^V$ is as shown

| Exam No. | R$^V$ | molecular formula | Calcd. exact mass | MS analysis |
|---|---|---|---|---|
| 38 | | C$_{47}$H$_{84}$N$_2$O$_{16}$ | 932.6 | 931.8, 467.3 |
| 39 | | C$_{46}$H$_{84}$N$_2$O$_{14}$ | 888.6 | 887.6, 445.0 |
| 40 | | C$_{44}$H$_{79}$N$_3$O$_{14}$ | 873.6 | 872.8, 437.3 |
| 41 | | C$_{47}$H$_{86}$N$_2$O$_{14}$ | 902.6 | 901.9, 451.7 |
| 42 | | C$_{47}$H$_{86}$N$_2$O$_{14}$ | 902.6 | 901.9, 451.7 |
| 43 | | C$_{49}$H$_{88}$N$_2$O$_{14}$ | 928.6 | 928.0, 465.0 |
| 44 | | C$_{50}$H$_{84}$FN$_3$O$_{14}$ | 969.6 | 970.2, 485.2 |
| 45 | | C$_{51}$H$_{88}$N$_2$O$_{14}$ | 952.6 | 952.4, 476.8 |

TABLE 1-continued
Examples 26–105
Compounds having Formula (X) wherein X is O,
R is CH₂—CH(OH)—CH₂—R$^V$, and R$^V$ is as shown
| Exam No. | R$^V$ | molecular formula | Calcd. exact mass | MS analysis |
|---|---|---|---|---|
| 46 | 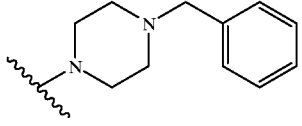 | $C_{51}H_{87}N_3O_{14}$ | 965.6 | 964.8, 483.4 |
| 47 | 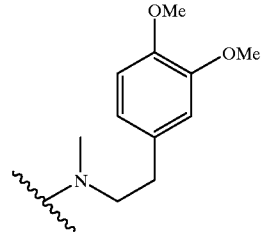 | $C_{51}H_{88}N_2O_{16}$ | 984.6 | 985.1, 492.8 |
| 48 | 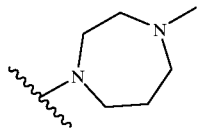 | $C_{46}H_{85}N_3O_{14}$ | 903.6 | 904.2, 452.0 |
| 49 | 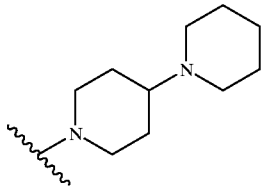 | $C_{50}H_{91}N_3O_{14}$ | 957.7 | 957.4, 479.1 |
| 50 | 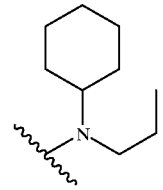 | $C_{44}H_{88}N_2O_{14}$ | 916.6 | 915.9, 458.6 |
| 51 | 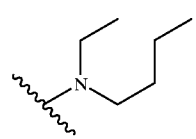 | $C_{46}H_{86}N_2O_{14}$ | 890.6 | 889.9, 446.0 |
| 52 | 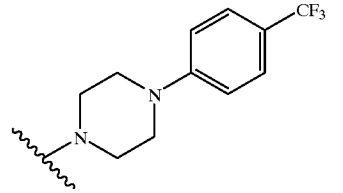 | $C_{51}H_{84}F_3N_3O_{14}$ | 1019.6 | 1020.1, 510.0 |

TABLE 1-continued
Examples 26–105
Compounds having Formula (X) wherein X is O,
R is CH$_2$—CH(OH)—CH$_2$—R$^V$, and R$^V$ is as shown
| Exam No. | R$^V$ | molecular formula | Calcd. exact mass | MS analysis |
|---|---|---|---|---|
| 53 | 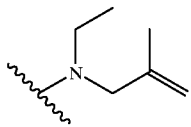 | C$_{46}$H$_{84}$N$_2$O$_{14}$ | 888.6 | 889.4, 444.8 |
| 54 | 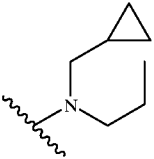 | C$_{47}$H$_{86}$N$_2$O$_{14}$ | 902.6 | 902.1, 452.0 |
| 55 | 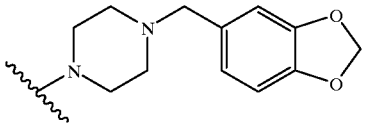 | C$_{52}$H$_{87}$N$_3$O$_{16}$ | 1009.6 | 1010.0, 505.7 |
| 56 | 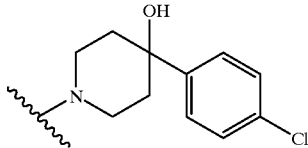 | C$_{51}$H$_{85}$ClN$_2$O$_{15}$ | 1000.6 | 1000.9, 501.4 |
| 57 | 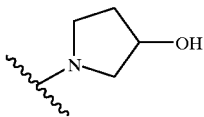 | C$_{44}$H$_{80}$N$_2$O$_{15}$ | 876.6 | 877.1, 439.1 |
| 58 | 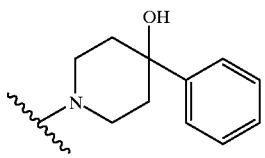 | C$_{51}$H$_{86}$N$_2$O$_{15}$ | 966.6 | 965.6, 483.8 |
| 59 | 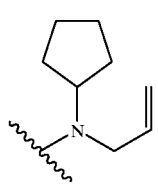 | C$_{48}$H$_{86}$N$_2$O$_{14}$ | 914.6 | 915.0, 457.8 |
| 60 | 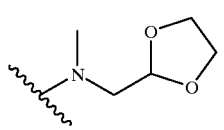 | C$_{45}$H$_{82}$N$_2$O$_{16}$ | 906.6 | 907.3, 453.9 |

TABLE 1-continued

Examples 26–105
Compounds having Formula (X) wherein X is O,
R is CH$_2$—CH(OH)—CH$_2$—R$^V$, and R$^V$ is as shown

| Exam No. | R$^V$ | molecular formula | Calcd. exact mass | MS analysis |
|---|---|---|---|---|
| 61 | piperazine-N-CH$_2$CH$_2$OH | C$_{46}$H$_{85}$N$_3$O$_{15}$ | 919.6 | 920.2, 460.6 |
| 62 | N(CH$_2$CH$_2$OMe)$_2$ | C$_{46}$H$_{86}$N$_2$O$_{16}$ | 922.6 | 923.3, 461.8 |
| 63 | N(Me)(propyl) | C$_{44}$H$_{82}$N$_2$O$_{14}$ | 862.6 | 863.2, 431.9 |
| 64 | 4-(2-pyridyl)piperazinyl | C$_{49}$H$_{84}$N$_4$O$_{14}$ | 952.6 | 952.0, 476.9 |
| 65 | 4-(4-nitrophenyl)piperazinyl | C$_{50}$H$_{84}$N$_4$O$_{16}$ | 996.6 | 996.9, 499.2 |
| 66 | 4-(3,4-dimethylphenyl)piperazinyl | C$_{52}$H$_{89}$N$_3$O$_{14}$ | 979.6 | 980.2, 490.4 |
| 67 | 4-(4-chlorophenyl)-2-methylpiperazinyl | C$_{51}$H$_{86}$ClN$_3$O$_{14}$ | 999.6 | 999.1, 500.9 |

TABLE 1-continued

Examples 26–105
Compounds having Formula (X) wherein X is O,
R is CH$_2$—CH(OH)—CH$_2$—R$^V$, and R$^V$ is as shown

| Exam No. | R$^V$ | molecular formula | Calcd. exact mass | MS analysis |
|---|---|---|---|---|
| 68 | 3-methylphenyl-2-methylpiperazinyl | C$_{52}$H$_{89}$N$_3$O$_{14}$ | 979.6 | 980.0, 490.2 |
| 69 | 2,6-dimethylphenylpiperazinyl | C$_{52}$H$_{89}$N$_3$O$_{14}$ | 979.6 | 978.8, 490.3 |
| 70 | 2-cyanophenylpiperazinyl | C$_{51}$H$_{84}$N$_4$O$_{14}$ | 976.6 | 977.2, 488.8 |
| 71 | 3,5-dimethoxyphenylpiperazinyl | C$_{52}$H$_{89}$N$_3$O$_{16}$ | 1011.6 | 1010.7, 506.2 |
| 72 | 2-methoxyphenylpiperazinyl | C$_{51}$H$_{87}$N$_3$O$_{15}$ | 981.6 | 982.1, 491.1 |
| 73 | 2,4-dimethoxyphenylpiperazinyl | C$_{52}$H$_{89}$N$_3$O$_{16}$ | 1011.6 | 1012.2, 506.3 |

TABLE 1-continued

Examples 26–105
Compounds having Formula (X) wherein X is O,
R is CH$_2$—CH(OH)—CH$_2$—R$^V$, and R$^V$ is as shown

| Exam No. | R$^V$ | molecular formula | Calcd. exact mass | MS analysis |
|---|---|---|---|---|
| 74 | piperazine-N-(2-ethylphenyl) | C$_{52}$H$_{89}$N$_3$O$_{14}$ | 979.6 | 978.8, 490.4 |
| 75 | piperazine-N-(3,5-dichlorophenyl) | C$_{50}$H$_{83}$Cl$_2$N$_3$O$_{14}$ | 1019.5 | 1019.8, 510.8 |
| 76 | piperazine-N-(3,4-dichlorophenyl) | C$_{50}$H$_{83}$Cl$_2$N$_3$O$_{14}$ | 1019.5 | 1019.9, 510.6 |
| 77 | piperazine-N-(2-fluorophenyl) | C$_{50}$H$_{84}$FN$_3$O$_{14}$ | 969.6 | 970.2, 485.2 |
| 78 | N-ethylpiperazine | C$_{46}$H$_{85}$N$_3$O$_{14}$ | 903.6 | 902.9, 452.3 |
| 79 | piperazine-N-(3-chlorophenyl) | C$_{50}$H$_{84}$ClN$_3$O$_{14}$ | 985.6 | 984.8, 493.7 |

TABLE 1-continued

Examples 26–105
Compounds having Formula (X) wherein X is O,
R is CH$_2$—CH(OH)—CH$_2$—R$^V$, and R$^V$ is as shown

| Exam No. | R$^V$ | molecular formula | Calcd. exact mass | MS analysis |
|---|---|---|---|---|
| 80 | | C$_{50}$H$_{84}$N$_4$O$_{16}$ | 996.6 | 997.0, 498.9 |
| 81 | | C$_{48}$H$_{87}$N$_3$O$_{16}$ | 961.6 | 960.6, 481.2 |
| 82 | | C$_{49}$H$_{83}$N$_3$O$_{16}$ | 969.6 | 968.7, 485.7 |
| 83 | | C$_{44}$H$_{82}$N$_2$O$_{15}$ | 878.6 | 878.5, 440.0 |
| 84 | | C$_{50}$H$_{94}$N$_3$O$_{14}$ | 974.7 | 973.8, 487.6 |
| 85 | | C$_{52}$H$_{89}$N$_3$O$_{14}$ | 979.6 | 979.4, 490.3 |
| 86 | | C$_{52}$H$_{89}$N$_3$O$_{14}$ | 979.6 | 978.8, 490.4 |

TABLE 1-continued
Examples 26–105
Compounds having Formula (X) wherein X is O,
R is CH$_2$—CH(OH)—CH$_2$—R$^V$, and R$^V$ is as shown
| Exam No. | R$^V$ | molecular formula | Calcd. exact mass | MS analysis |
|---|---|---|---|---|
| 87 | 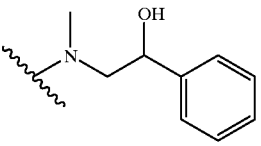 | C$_{49}$H$_{84}$N$_2$O$_{15}$ | 940.6 | 941.2, 470.6 |
| 88 | 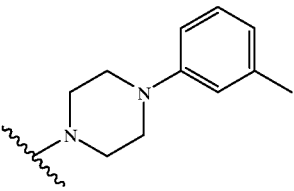 | C$_{51}$H$_{87}$N$_3$O$_{14}$ | 965.6 | 965.9, 483.8 |
| 89 | 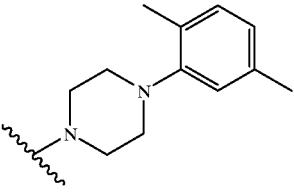 | C$_{52}$H$_{89}$N$_3$O$_{14}$ | 979.6 | 978.8, 490.6 |
| 90 | 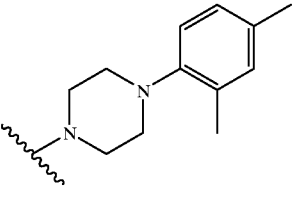 | C$_{52}$H$_{89}$N$_3$O$_{14}$ | 979.6 | 980.1, 490.3 |
| 91 | 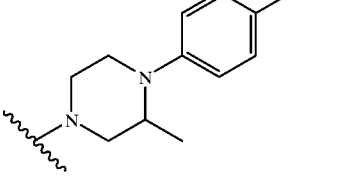 | C$_{52}$H$_{89}$N$_3$O$_{15}$ | 995.6 | 994.9, 498.5 |
| 92 | 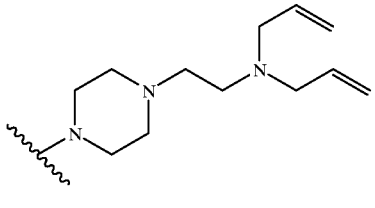 | C$_{52}$H$_{94}$N$_4$O$_{14}$ | 998.7 | 999.2, 499.7 |
| 93 | 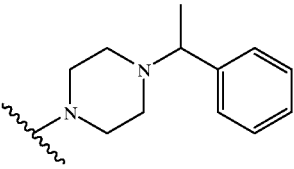 | C$_{52}$H$_{89}$N$_3$O$_{14}$ | 979.6 | 978.8, 490.6 |

TABLE 1-continued

Examples 26–105
Compounds having Formula (X) wherein X is O,
R is CH$_2$—CH(OH)—CH$_2$—R$^V$, and R$^V$ is as shown

| Exam No. | R$^V$ | molecular formula | Calcd. exact mass | MS analysis |
|---|---|---|---|---|
| 94 |  | C$_{43}$H$_{80}$N$_2$O$_{14}$ | 848.6 | 848.0, 425.1 |
| 95 |  | C$_{55}$H$_{95}$N$_3$O$_{14}$ | 1021.7 | 1020.8, 511.2 |
| 96 |  | C$_{50}$H$_{84}$ClN$_3$O$_{14}$ | 985.6 | 986.1, 493.9 |
| 97 |  | C$_{49}$H$_{89}$N$_3$O$_{16}$ | 975.6 | 974.8, 488.5 |
| 98 |  | C$_{51}$H$_{86}$ClN$_3$O$_{14}$ | 999.6 | 999.89, 500.8 |
| 99 |  | C$_{57}$H$_{91}$N$_3$O$_{14}$ | 1041.7 | 1041.2, 521.8 |
| 100 |  | C$_{50}$H$_{91}$N$_3$O$_{14}$ | 957.6 | 957.0, 479.7 |

TABLE 1-continued

Examples 26–105
Compounds having Formula (X) wherein X is O,
R is CH₂—CH(OH)—CH₂—R$^V$, and R$^V$ is as shown

| Exam No. | R$^V$ | molecular formula | Calcd. exact mass | MS analysis |
|---|---|---|---|---|
| 102 | 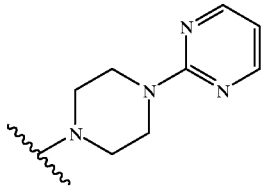 | C$_{48}$H$_{83}$N$_5$O$_{14}$ | 953.6 | 952.7, 477.2 |
| 103 | 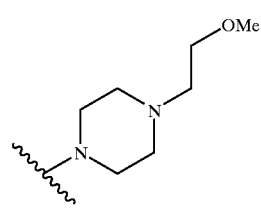 | C$_{47}$H$_{87}$N$_3$O$_{15}$ | 933.6 | 934.2, 467.1 |
| 104 | 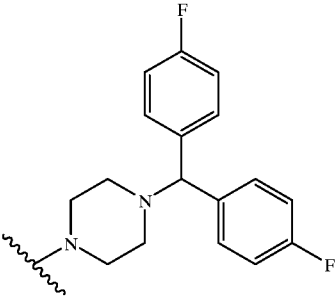 | C$_{57}$H$_{89}$F$_2$N$_3$O$_{14}$ | 1077.6 | 1076.5, 539.4 |
| 105 | 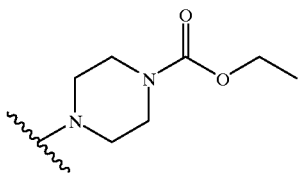 | C$_{47}$H$_{85}$N$_3$O$_{16}$ | 947.6 | 946.8, 474.5 |

EXAMPLES 106–153

Compounds having Formula (X) wherein X is O; R is CH₂—CH₂—R$^W$; and R$^W$ is as shown Treating the compound of Example 8 with an appropriate reagent amine in the presence of sodium cyanoborohydride in methanol and acetic acid, the compounds of Examples 106–153, which are compounds having Formula (X) wherein X is O, R is CH₂—CH₂—R$^W$; and R$^W$ is as shown in Table 2 below, were prepared.

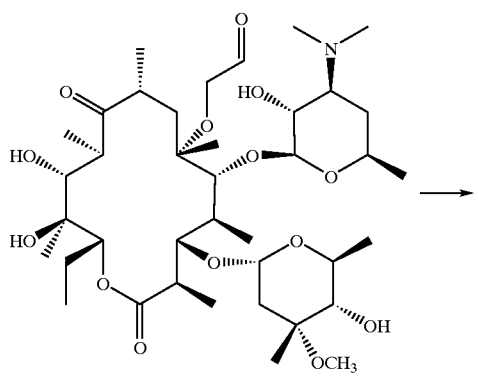 → 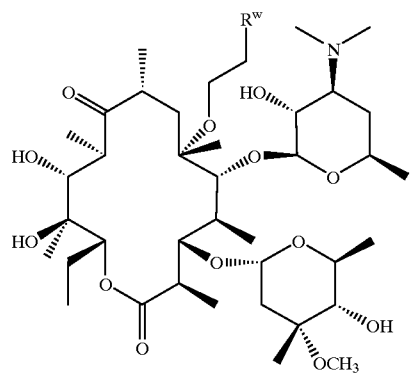
TABLE 2
Examples 106–153
Compounds having Formula (X) wherein X is O; R CH2—CH2—R$^w$; and R$^w$ is as shown
| Exam No. | R$^w$ | molecular formula | Calcd. exact mass | MS analysis |
|---|---|---|---|---|
| 106 | ~N(Me)–CH2–Ph | $C_{47}H_{80}N_2O_{13}$ | 880.6 | 881.4, 880.2, 440.9 |
| 107 | ~N-tetrahydroisoquinoline | $C_{48}H_{80}N_2O_{13}$ | 892.6 | 893.5, 892.1, 447.2 |
| 108 | ~N-piperazine-(2-OMe-phenyl) | $C_{50}H_{85}N_3O_{14}$ | 951.6 | 953.2, 951.1, 477.1, 476.3 |
| 109 | ~N-piperazine-CH2-(3,4-methylenedioxyphenyl) | $C_{51}H_{85}N_3O_{15}$ | 979.6 | 980.1, 979.1, 490.6 |
| 110 | ~N(Et)–CH2–Ph | $C_{48}H_{82}N_2O_{13}$ | 894.6 | 895.4, 894.1, 448.1 |
| 111 | ~N-indoline | $C_{47}H_{78}N_2O_{13}$ | 878.6 | 879.2, 878.1, 439.9 |

TABLE 2-continued
Examples 106–153
Compounds having Formula (X) wherein X is O; R CH2—CH2—R$^W$; and R$^W$ is as shown
| Exam No. | R$^W$ | molecular formula | Calcd. exact mass | MS analysis |
|---|---|---|---|---|
| 112 | 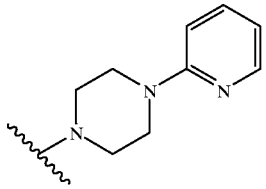 | $C_{48}H_{82}N_4O_{13}$ | 922.6 | 923.5, 922.1, 462.0 |
| 113 | 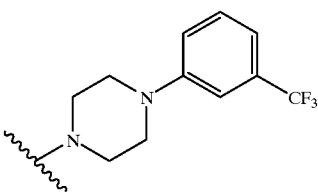 | $C_{50}H_{82}F_3N_3O_{13}$ | 989.6 | 990.3, 989.0, 495.8 |
| 114 | 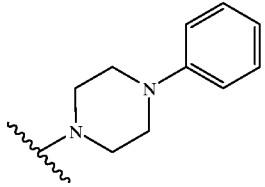 | $C_{49}H_{83}N_3O_{13}$ | 921.6 | 922.4, 921.3, 461.6 |
| 115 | 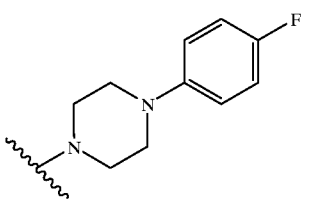 | $C_{49}H_{82}FN_3O_{13}$ | 939.6 | 940.7, 939.1, 470.5 |
| 116 | 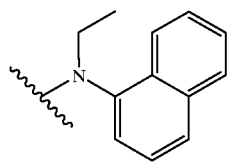 | $C_{51}H_{82}N_2O_{13}$ | 930.6 | 931.3, 930.1, 777.1, 778.4, 466.6, 465.6 |
| 117 | 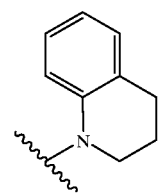 | $C_{48}H_{80}N_2O_{13}$ | 892.6 | 892.1, 446.8 |

TABLE 2-continued
Examples 106–153
Compounds having Formula (X) wherein X is O; R CH2—CH2—R$^W$; and R$^W$ is as shown
| Exam No. | R$^W$ | molecular formula | Calcd. exact mass | MS analysis |
|---|---|---|---|---|
| 118 | 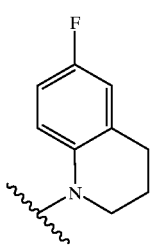 | C$_{49}$H$_{81}$FN$_2$O$_{13}$ | 924.6 | 925.4, 924.3, 923.4, 462.8 |
| 119 | 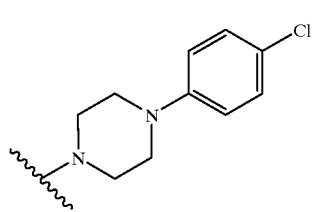 | C$_{49}$H$_{82}$ClN$_3$O$_{13}$ | 955.6 | 958.4, 957.3, 956.2, 955.0, 479.1 |
| 120 | 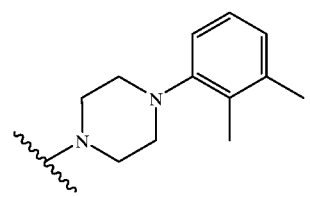 | C$_{51}$H$_{87}$N$_3$O$_{13}$ | 949.6 | 950.6, 949.3, 475.4 |
| 121 | 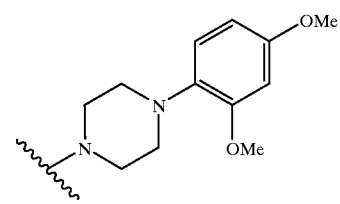 | C$_{51}$H$_{87}$N$_3$O$_{15}$ | 981.6 | 982.5, 981.1, 491.7 |
| 122 | 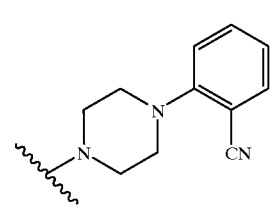 | C$_{50}$H$_{82}$N$_4$O$_{13}$ | 946.6 | 947.4, 946.1, 474.3 |
| 123 | 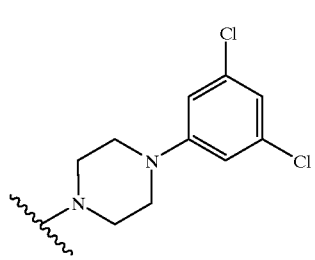 | C$_{49}$H$_{81}$Cl$_2$N$_3$O$_{13}$ | 989.5 | 992.3, 991.2, 990.1, 496.8, 495.4 |

TABLE 2-continued
Examples 106–153
Compounds having Formula (X) wherein X is O; R CH2—CH2—R^W; and R^W is as shown
| Exam No. | R^W | molecular formula | Calcd. exact mass | MS analysis |
|---|---|---|---|---|
| 124 | 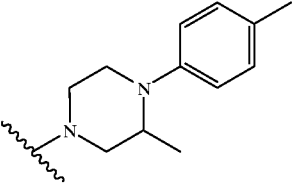 | $C_{51}H_{87}N_3O_{13}$ | 949.6 | 950.4, 949.1, 475.5 |
| 125 | 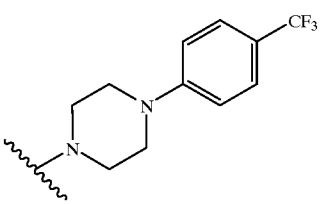 | $C_{50}H_{82}F_3N_3O_{13}$ | 989.6 | 990.0, 989.0, 495.7 |
| 126 | 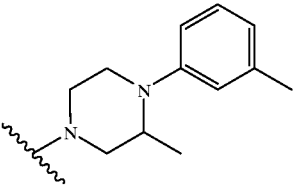 | $C_{51}H_{87}N_3O_{13}$ | 949.6 | 949.9, 949.0, 475.4 |
| 127 | 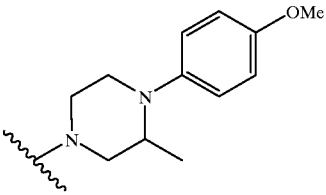 | $C_{51}H_{87}N_3O_{14}$ | 965.6 | 966.5, 965.1, 483.5 |
| 128 | 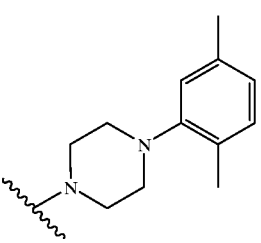 | $C_{51}H_{87}N_3O_{13}$ | 949.6 | 950.2, 949.4, 475.7 |
| 129 | 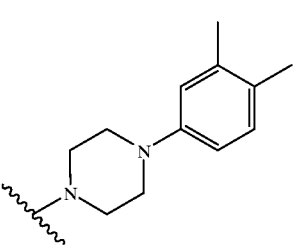 | $C_{51}H_{87}N_3O_{13}$ | 949.6 | 950.5, 949.1, 476.2, 475.3 |

TABLE 2-continued

Examples 106–153

Compounds having Formula (X) wherein X is O; R CH2—CH2—R^W; and R^W is as shown

| Exam No. | R^W | molecular formula | Calcd. exact mass | MS analysis |
|---|---|---|---|---|
| 130 | 4-nitrophenyl piperazine | $C_{49}H_{82}N_4O_{15}$ | 966.6 | 967.4, 966.1, 484.2 |
| 131 | 4-ethoxyphenyl piperazine | $C_{51}H_{87}N_3O_{14}$ | 965.6 | 966.3, 964.9, 483.6 |
| 132 | 4-chloro-3-trifluoromethylphenyl piperazine | $C_{50}H_{81}ClF_3N_3O_{13}$ | 1023.5 | 1026.3, 1025.3, 1024.0, 1022.9, 512.9 |
| 133 | 2-methylthiophenyl piperazine | $C_{50}H_{85}N_3O_{13}S$ | 967.6 | 968.4, 967.2, 484.4 |
| 134 | 2-nitrophenyl piperazine | $C_{49}H_{82}N_4O_{15}$ | 966.6 | 967.3, 966.2, 484.0 |
| 135 | 2,6-dimethylphenyl piperazine | $C_{51}H_{87}N_3O_{13}$ | 949.6 | 950.5, 949.3, 475.3 |

TABLE 2-continued
Examples 106–153
Compounds having Formula (X) wherein X is O; R CH2—CH2—R$^W$; and R$^W$ is as shown
| Exam No. | R$^W$ | molecular formula | Calcd. exact mass | MS analysis |
|---|---|---|---|---|
| 136 | 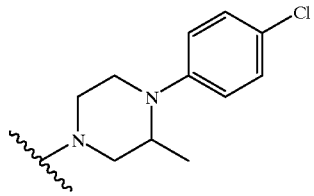 | $C_{50}H_{84}ClN_3O_{13}$ | 969.6 | 972.4, 971.5, 970.2, 969.1, 486.1 |
| 137 | 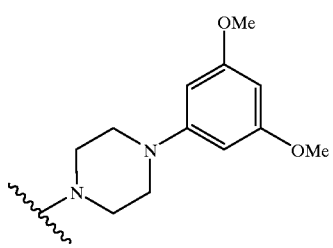 | $C_{51}H_{87}N_3O_{15}$ | 981.6 | 982.4, 981.1 492.1, 491.3 |
| 138 | 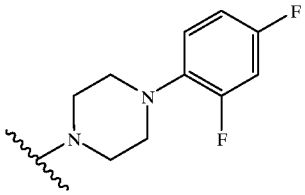 | $C_{49}H_{81}F_2N_3O_{13}$ | 957.6 | 958.3, 957.0, 479.7 |
| 139 | 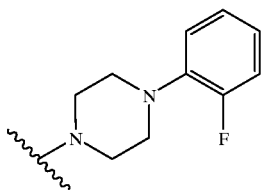 | $C_{49}H_{82}FN_3O_{13}$ | 939.6 | 940.4, 939.1, 470.4 |
| 140 | 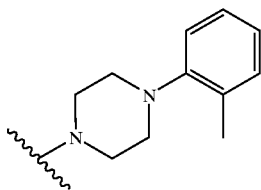 | $C_{50}H_{85}N_3O_{13}$ | 935.6 | 936.4, 935.1, 468.6 |
| 141 | 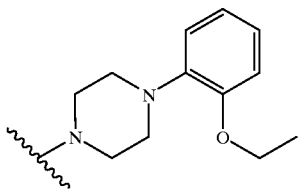 | $C_{51}H_{87}N_3O_{14}$ | 965.6 | 966.1, 965.1, 483.4 |

TABLE 2-continued
Examples 106–153
Compounds having Formula (X) wherein X is O; R CH2—CH2—R^W; and R^W is as shown
| Exam No. | R^W | molecular formula | Calcd. exact mass | MS analysis |
|---|---|---|---|---|
| 142 | 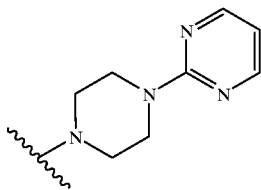 | $C_{47}H_{81}N_5O_{13}$ | 923.6 | 924.4, 923.1, 463.1, 462.2 |
| 143 | 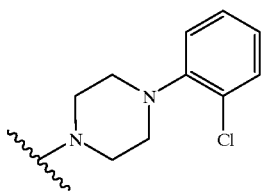 | $C_{49}H_{82}ClN_3O_{13}$ | 955.6 | 958.4, 957.3, 956.2, 955.0, 478.6 |
| 144 | 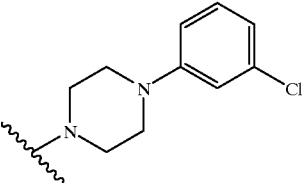 | $C_{49}H_{82}ClN_3O_{13}$ | 955.6 | 958.4, 957.3, 956.4, 955.3, 479.1 |
| 145 | 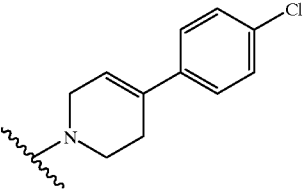 | $C_{50}H_{81}ClN_2O_{13}$ | 952.5 | 955.3, 954.3, 953.2, 952.0, 477.1 |
| 146 | 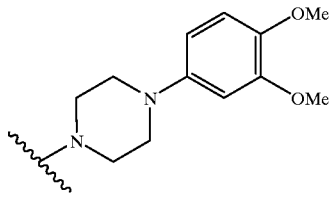 | $C_{51}H_{87}N_3O_{15}$ | 981.6 | 982.4, 981.0, 491.4 |
| 147 | 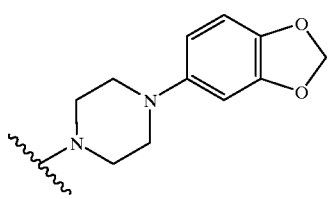 | $C_{50}H_{83}N_3O_{15}$ | 965.6 | 966.3, 964.9, 483.8 |

TABLE 2-continued
Examples 106–153
Compounds having Formula (X) wherein X is O; R CH2—CH2—R$^W$; and R$^W$ is as shown
| Exam No. | R$^W$ | molecular formula | Calcd. exact mass | MS analysis |
|---|---|---|---|---|
| 148 | 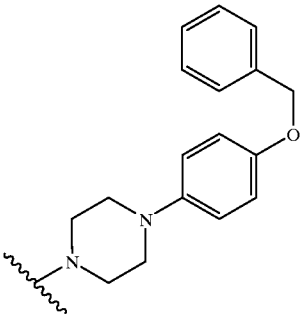 | $C_{56}H_{89}N_3O_{14}$ | 1027.6 | 1028.3, 1027.0, 514.3 |
| 149 | 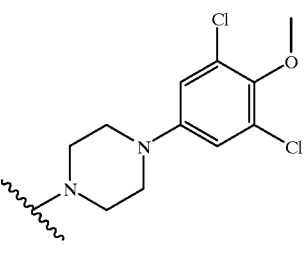 | $C_{50}H_{83}Cl_2N_3O_{14}$ | 1019.5 | 1022.3, 1021.2, 1019.9, 1018.7, 510.8 |
| 150 | 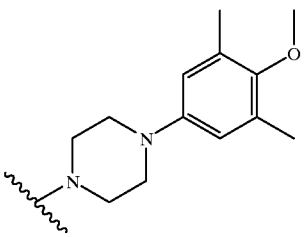 | $C_{52}H_{89}N_3O_{14}$ | 979.6 | 979.0, 490.4 |
| 151 | 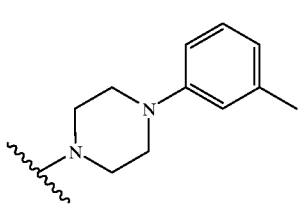 | $C_{50}H_{85}N_3O_{13}$ | 935.6 | 936.4, 468.7 |
| 152 | 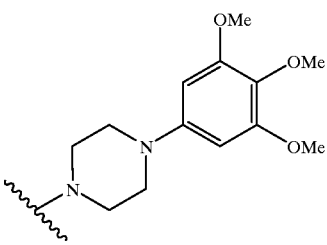 | $C_{52}H_{89}N_3O_{16}$ | 1011.6 | 1012.1, 1011.1, 507.0, 506.1 |

TABLE 2-continued

Examples 106–153
Compounds having Formula (X) wherein X is O; R CH2—CH2—R^W; and R^W is as shown

| Exam No. | R^W | molecular formula | Calcd. exact mass | MS analysis |
|---|---|---|---|---|
| 153 | 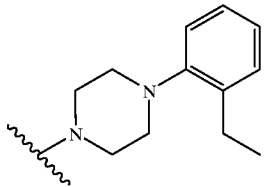 | $C_{51}H_{87}N_3O_{13}$ | 949.6 | 950.4, 949.2, 475.8 |

EXAMPLES 154–164

Compounds having Formula (X) wherein X is O, R is $CH_2$—CH=N—$R^x$, and $R^x$ is as shown Treating the compound of Example 8 according to the procedures of Example 12, except subtituting the appropriate substituted hydroxyl amine reagent for the unsubstituted hydroxylamine reagent of Example 12, the compounds of Examples 154–164, which are compounds having Formula (X) wherein X is O, R is $CH_2$—CH=N—$R^x$ and $R^x$ is as shown in Table 3 below were prepared.

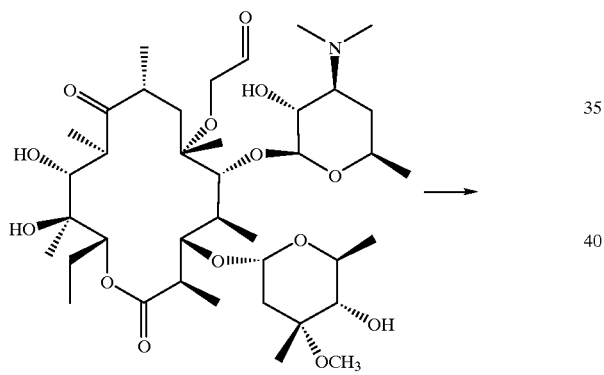

→

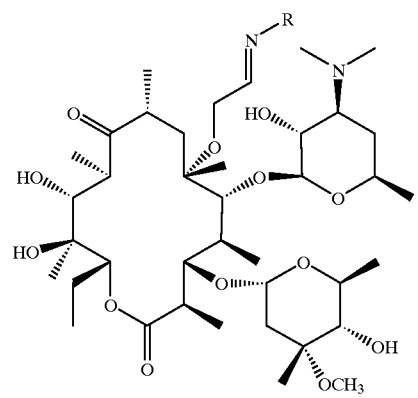

TABLE 3

Examples 154–164
Compounds having Formula (X) wherein X is O, R is CH2—CH=N—R^X, and R^X is as shown

| Exam. No. | R^X | molecular formula | Calcd. exact mass | MS analysis |
|---|---|---|---|---|
| 154 | 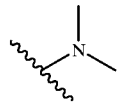 | $C_{41}H_{75}N_3O_{13}$ | 817.5 | 818.4, 817.3, 409.6 |
| 155 | 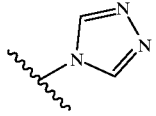 | $C_{41}H_{71}N_5O_{13}$ | 841.5 | 841.6, 421.6 |

TABLE 3-continued

Examples 154–164
Compounds having Formula (X) wherein X is O, R is CH2—CH=N—R$^x$, and R$^x$ is as shown

| Exam. No. | R$^x$ | molecular formula | Calcd. exact mass | MS analysis |
|---|---|---|---|---|
| 156 | 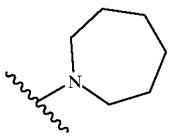 | C$_{45}$H$_{81}$N$_3$O$_{13}$ | 871.6 | 871.9, 436.5 |
| 157 | 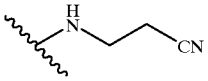 | C$_{42}$H$_{74}$N$_4$O$_{13}$ | 842.5 | 842.7 |
| 158 | 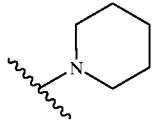 | C$_{44}$H$_{79}$N$_3$O$_{13}$ | 857.6 | 857.5, 429.4 |
| 159 | 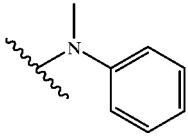 | C$_{46}$H$_{77}$N$_3$O$_{13}$ | 879.5 | 880.3, 879.1 |
| 160 | 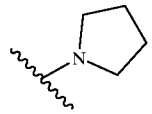 | C$_{43}$H$_{77}$N$_3$O$_{13}$ | 843.5 | 844.3, 843.4 |
| 161 | 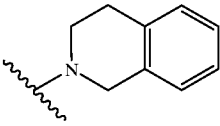 | C$_{48}$H$_{79}$N$_3$O$_{13}$ | 905.6 | 906.3, 904.9, 454.1, 453.2 |
| 162 | 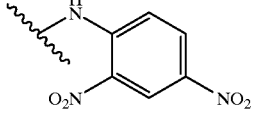 | C$_{45}$H$_{73}$N$_5$O$_{17}$ | 955.5 | 956.4, 955.1 |
| 163 | 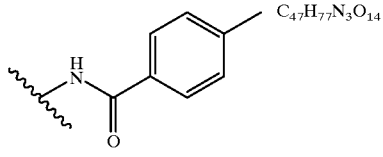 | C$_{47}$H$_{77}$N$_3$O$_{14}$ | 907.5 | 908.3, 907.2 |
| 164 | 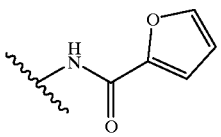 | C$_{44}$H$_{73}$N$_3$O$_{15}$ | 883.5 | 884.3, 883.2 |

EXAMPLE 165

Compound of Formula (V): R$^b$ is H; R$^c$ is H: R$^d$ is phenylmethyloxycarbonyl; R$^e$ is methoxy; R$^f$ is H; R is —CH$_2$—CH=CH$_2$ Step 165a. 2'-acetyl-6-O-allyl erythromycin A A solution of 6-O-allyl erythromycin A (10 g, the compound of Formula (X) wherein X is =O and R is —CH$_2$—C=CH$_2$, from Example 10 step c above) and triethylamine (2.25 mL) in dichloromethane (50 mL) was cooled to 0° C. and flushed with nitrogen. Acetic anhydride (2.4 mL) was added, the solution was stirred at 0° C. for 5 minutes, then the ice bath was removed and the mixture was stirred for 5 hours at ambient temperature. The mixture was quenched by addition of 1.5 M aqueous $KH_2PO_4$ (50 mL), then extracted with ethyl acetate. The organic phase was washed with water and brine, then dried over $MgSO_4$. The solvent was removed under vacuum, and the residue was dried. The residue was crystallized from acetonitrile to give the title compound (5.66 g).

165b. 2'-acetyl-4'-(phenylmethyloxycarbonyl)-6-O-allyl erythromycin A

To a solution of 2'-acetyl-6-O-allyl erythromycin A (5 g, from step 165a) in dry dichloromethane (50 mL) was added DMAP (3 g), and the solution was cooled to −40° C. The solution was flushed with nitrogen, and benzyl chloroformate (3 mL) waa added over 45 minutes. Then additional DMAP (585 mg) and benzyl chloroformate (0.585 mL over 45 minutes) was added. The mixture was stirred under nitrogen for 0.5 hours at −40° C. and at −20° C. for 40 hours, then diluted with ethyl acetate and quenched with saturated aqueous sodium bicarbonate. The organic phase was separated, washed with water and brine, then dried over $MgSO_4$. The solvent was removed, the residue (6.5 g) was triturated with ethyl acetate, and the solvent was washed, dried and removed under vacuum. The residue was crystallized from acetonitrile, then purified by chromatography on mixed alumina and silica gel to give the title compound (4.6 g).

Step 165c. Compound of Formula (V); $R^b$ is H; s H; $R^d$ is phenylmethyloxycarbonyl; $R^e$ is methoxy; $R^f$ is acetyl; R is $—CH_2—CH=CH_2$ To a solution of 2'-acetyl-4'-(phenylmethyloxycarbonyl)-6-O-allyl erythromycin A (4.5 g, from step 165b) in THF (90 mL) at −40° C. was added 1 M sodium bis(trimethylsilyl)amine (5.25 mL), and the mixture was stirred for 10 minutes. To this was added carbonyldiimidazole (2.7 g) in THF over 45 minutes, then the ice bath was removed and the mixture was stirred at ambient temperature for 40 minutes. The mixture was cooled to 0° C., quenched with 1 M aqueous $KH_2PO_4$, then extracted with ethyl acetate. The organic phase was washed with water and brine, then dried over $MgSO_4$. The solvent was removed under vacuum, and the residue was dried. The residue was crystallized from acetonitrile, then purified by chromatography on silica gel, eluting with 25–50% acetone/hexane to give the title compound (2.65 g).

Step 165d. Compound of Formula (V); $R^b$ is H; $R^c$ is H; $R^d$ is phenylmethyloxycarbonyl; $R^e$ is methoxy; $R^f$ is H; R is $—CH_2—CH=CH_2$ A solution of the compound from step 165c (400 mg) in methanol (30 mL) was stirred at room temperature for 20 hours and at 50° C. for 6 hours. The solvent was removed to give the title compound. H. Res. MS 934.5176 $(M+H)^+$.

EXAMPLE 166

Compound of Formula (V); $R^b$ is H; $R^c$ is H; $R^d$ is hydroxy; $R^e$ is methoxy; $R^f$ is H; R is $—CH_2—CH=CH_2$ To a sample of the compound from Example 165 in methanol was added 10% Pd/C (450 mg), and the mixture was shaken under 1 atm of hydrogen for 2.5 hours. The mixture was filtered, and the solvent was removed. The residue was purified by chromatography on silica gel, eluting with 25–50% acetone/hexane to give the title compound. H. Res. MS 802.4941 $(M+H)^+$.

EXAMPLE 167

Compound of Formula (VI); $R^b$ is H; $R^c$ is H; $R^d$ is phenylmethyloxycarbonyl; $R^e$ is methoxy; $R^f$ is acetyl; R is $—CH_2—CH=CH_2$ A solution of the compound of Example 165 step c (3.6 g) and DBU (4.4 mL) in benzene (136 mL) was heated at reflux for 8 hours. The solvent was removed under vacuum, and the residue was dissolved in ethyl acetate. This solution was extracted with 1M $NaH2PO_4$ and washed with brine, then dried over $MgSO_4$. The solvent was removed, and the residue was purified by chromatography on silica gel, eluting with 25% acetone/hexane to give the title compound (3.3 g).

EXAMPLE 168

Compound of Formula (VII); W is $—NH—$:$R^b$ is H; $R^c$ is H; $R^d$ is phenylmethloxycarbonyl; $R^e$ is methoxy; $R^f$ is H; $R^g$ is H; R is propyl Step 168a. Compound (28) of Scheme V: 2'-$R^p$ is acetyl; 4"-$R^p$ is phenylmethyloxycarbonyl; R is $—CH_2—CH=CH_2$ To a −10° C. solution of the compound of Example 167 (3.3 g) in THF (60 mL) flushed with nitrogen was added 60% NaH (284 mg), and the mixture was stirred at −10° C. for 15 minutes. The mixture was warmed to 0° C., and a solution of CDI (1.7 g) in THF (30 mL) was added over 15 minutes. The mixture was then stirred at room temperature under nitrogen for 2.5 hours. The mixture was cooled to 0° C., quenched with ethyl acetate, and saturated aqueous sodium bicarbonate solution was added. The organic phase was separated, washed with brine and dried over $MgSO_4$. The solvent was removed, and the residue was purified by chromatography on silica gel, eluting with 35% acetone/hexane to give the title compound (3.2 g).

Step 168b. Compound of Formula (VII); W is $—NH—$;$R^b$ is H; $R^c$ is H; $R^d$ is phenylmethyloxycarbonyl; $R^e$ is methoxy; $R^f$ is H; $R^g$ is H; R is propyl To a sample of the compound from step 168a (100 mg) in DMF (1 mL) was added hydrazine (0.048 mL), and the mixture was stirred at 60° C. under nitrogen for 43 hours. The mixture was diluted with ethyl acetate, then washed with aqueous sodium bicarbonate and dried over $MgSO_4$. The solvent was removed, and the treatment with hydrazine was repeated, heating for 24 hours at 60° C. The mixture was diluted with ethyl acetate, then washed with aqueous sodium bicarbonate and dried over $MgSO_4$. The solvent was removed, and the residue was purified by chromatography on silica gel, eluting with 1% methanol/dichloromethane containing 0.5% $NH_4OH$ to give the title compound (136 mg). H. Res. MS 950.5594 $(M+H)^+$.

EXAMPLE 169

Compound of Formula (VII); W is $—NH—$; $R^b$ is H; $R^c$ is H; $R^d$ is H; $R^e$ is methoxy; $R^f$ is H; $R^g$ is H; R is propyl To a sample of the compound from Example 168 (73 mg) in methanol (2 mL) was added 10% Pd/C (60 mg), and the mixture was shaken under 1 atm of hydrogen for 2 hours. The mixture was filtered, and the solvent was removed to give the title compound (56 mg). H. Res. MS 816.5198 $(M+H)^+$.

EXAMPLE 170

Compound of Formula (VII); W is $—NH—$; $R^b$ is H; $R^c$ is H; $R^d$ is phenylmethyloxycarbonyl; $R^e$ is methoxy; $R^f$ is H; $R^g$ is H; R is $—CH_2—CH=CH_2$ To a solution of the compound of Example 168 step a (3.3 g) in acetonitrile (26 mL) was added hydrazine (0.206 mL), and the mixture was stirred at room temperature for 22 hours. The mixture was diluted with ethyl acetate, and this solution was washed with water and brine and dried over MgSO$_4$. The solvent was removed, and the residue was dissolved in methanol and stirred under nitrogen at room temperature for 66 hours. The solvent was removed to give the title compound containing a mixture (2.20 g) of the C10 epimers. This material was dissolved in methanol (15 mL) and stirred at ambient temperature in a sealed tube with 2 M NH$_3$ in methanol (15 mL) for 5 days. The solvent was removed, and the residue (2.18 g) was purified by chromatography on silica gel, eluting with 7% methanol/ dichloromethane containing 3% NH$_4$OH to give the title compound (1.86 g). H. Res. MS 948.5440 (M+H)$^+$.

EXAMPLE 171

Compound of Formula (VII); W is absent; $R^b$ is H; $R^c$ is H; $R^d$ is phenylmethyloxycarbonyl; $R^e$ is methoxy; $R^f$ is acetyl; $R^g$ is 4-phenylbutyl: R is —CH$_2$—CH=CH$_2$ To a solution of the compound of Example 168 step a (2.0 g) in acetonitrile (22 mL) was added 4-phenylbutylamine (2.5 mL), and the mixture was stirred at room temperature for 66 hours. The solvent was removed, and the residue was purified by chromatography on silica gel, eluting with 1% ethyl acetae/hexane containing 1% NH$_4$OH to give the title compound (2.14 g).

EXAMPLE 172

Compound of Formula (VII); W is absent; $R^b$ is H; $R^c$ is H; $R^d$ is phenylmethyloxycarbonyl; $R^e$ is methoxy; $R^f$ is H; $R^g$ is 4-phenylbutyl; R is —CH$_2$—CH=CH$_2$ A solution of the compound of Example 171 (400 mg) in methanol (15 mL) was stirred under nitrogen at room temperature for 4 days. The solvent was removed, and the residue (2.18 g) was purified by chromatography on silica gel, eluting with 40% acetone/hexane to give the title compound (355 mg). MS 1065 (M+H)$^+$.

EXAMPLE 173

Compound of Formula (VII); W is absent; $R^b$ is H; $R^c$ is H; $R^d$ H; $R^e$ is methoxy: $R^f$ is H; $R^g$ is 4-phenylbutyl; R is propyl To a sample of the compound from Example 172 (220 mg) in methanol (4 mL) was added 10% Pd/C (200 mg), and the mixture was shaken under 1 atm of hydrogen for 3 hours. The mixture was filtered, and the solvent was removed to give a compound which was purified by chromatography on silica gel, eluting with 1% methanol/dichloromethane containing 10% NH$_4$OH to give the title compound (148 mg). Anal. Calcd. for C$_{51}$H$_{84}$N$_2$O$_{13}$: C, 65.63; H, 9.07; N, 3.00; Found: C, 65.25; H, 9.00; N, 2.87. H. Res. MS 933.6059 (M+H)$^+$.

EXAMPLE 174

Compound of Formula (VII); W is absent; $R^b$ is H; $R^c$ is H; $R^d$ is phenylmethyloxycarbonyl; $R^e$ is methoxy; $R^f$ is acetyl; $R^g$ is 4-phenylbutyl; R is —CH$_2$—CH=CH$_2$-(3-quinolinyl)

To a sample of the compound from Example 171 (500 mg, 0.452 mmol) in acetonitrile (5 mL) were added 3-bromoquinoline (188 mg, 0.904 mmol), palladium acetate (21 mg, 0.094 mmol), tri-(o-tolyl)phosphine (55 mg, 0.181 mmol) and triethylamine (0.126 mL, 0.904 mmol). The mixture was cooled to −78° C., degassed, sealed in a tube under nitrogen, and heated at 50° C. for 2 hours, and at 80° C. for 14 hours. Additional palladium acetate (20 mg, 0.094 mmol) and tri-(o-tolyl)phosphine (20 mg) were added, and the mixture was heated at 100° C. for 12 hours. Additional 3-bromoquinoline (0.046 mL) and triethylamine (0.065) were added, and the mixture was heated at 100° C. for 24 hours. The mixture was cooled and diluted with ethyl acetate, then washed with saturated brine, 1M tris (hydroxymethyl)aminomethane, brine and dried over MgSO$_4$. The solvent was removed to give a compound which was purified by chromatography on silica gel, eluting with 25–40% acetone/hexane to give the title compound (444 mg).

EXAMPLE 175

Compound of Formula (VII); W is absent: $R^b$ is H; $R^c$ is H; $R^d$ is phenylmethyloxycarbonyl; $R^e$ is methoxy; $R^f$ is H; $R^g$ is 4-phenylbutyl; R is —CH$_2$—CH=CH$_2$-(3-quinolinyl)

A solution of the compound of Example 174 (444 mg) in methanol (20 mL) was stirred under nitrogen at 50° C. for 7 hours and at room temperature for 16 hours. The solvent was removed, and the residue (420 mg) was purified by chromatography on silica gel, eluting with 1% methanol/ dichloromethane to give the title compound (170 mg). H. Res. MS 1192.6678 (M+H)$^+$.

EXAMPLE 176

Compound of Formula (VII); W is absent; $R^b$ is H; $R^c$ is H; $R^d$ is H; $R^e$ is methoxy; $R^f$ is H; $R^g$ is 4-phenylbutyl; R is —CH$_2$—CH$_2$—CH$_2$-(3-quinolinyl)

To a sample of the compound from Example 175 (130 mg) in methanol (6 mL) was added 10% Pd/C (100 mg), and the mixture was shaken under 1 atm of hydrogen for 17 hours. The mixture was filtered, and the solvent was removed to give a compound which was purified by chromatography on silica gel, eluting with 2% methanol/ dichloromethane containing 1% NH$_4$OH to give the title compound (41 mg). H. Res. MS 1060.6453 (M+H)$^+$.

EXAMPLE 177

Compound of Formula (VI); $R^a$ is hydroxy; $R^b$ is H; $R^c$ is H; $R^d$ is H; $R^e$ is methoxy; $R^f$ is H; R is —CH$_2$—CH=CH$_2$ A mixture of 6-O-allyl erythromycin A (30 g, prepared according to Example 10 step c above), trethylamine (70 mL) and ethylene carbonate (24 g) was heated at 95° C. under nitrogen with stirring for 66 hours. The mixture was cooled and diluted with ethyl acetate and extracted with water. The organic phase was washed with water and brine and dried over MgSO$_4$. The solvent was removed under vacuum, and the residue was purified by chromatography on silica gel, eluting with 2% methanol/dichloromethane containing 1% NH$_4$OH to give the title compound (20.9 g). The compound was crystallized from acetonitrile with a yield of 14.6 g in the first crop. MS 756 (M+H)$^+$.

EXAMPLE 178

Compound of Formula (VII); W is absent; $R^b$ is H; $R^c$ is H; $R^d$ is H; $R^e$ is methoxy; $R^f$ is H; $R^g$ is H; R is —CH$_2$—CH=CH$_2$ Step 178a. Compound of Formula (VI); $R^a$ is hydroxy; $R^b$ is H; $R^c$ is H; $R^d$ is trimethylsilyl; $R^e$ is methoxy; $R^f$ is trimethylsilyl; R is —CH$_2$—CH=CH$_2$ To a solution of the compound from Example 177 (12.2 g) in acetonitrile (90 mL), THF (20 mL) and dichloromethane (6 mL) was added hexamethyldisilazane (10.1 mL), and the reaction was stirred at room temperature for 44 hours. The solvents were then removed under vacuum to give the title compound (15.1 g).

Step 178b. Compound (28) of Scheme V; 2'-$R^p$ is trimethylsilyl; 4"-$R^p$ is trimethylsilyl; R is —$CH_2$—CH=$CH_2$ To a −10° C. solution of the compound of step 178a (15.1 g) in freshly distilled THF (200 mL) was added 60% NaH (1.3 g), and the mixture was stirred for 10 minutes then warmed to 0° C. To this solution was added carbodiimidazole (6.5 g) in THF (100 mL) over 15 minutes, then the mixture was stirred at room temperature for 2 hours. The mixture was cooled to 0° C., diluted with ethyl acetate and quenched with 5% aqueous sodium bicarbonate solution. This mixture was extracted with ethyl acetate, and the organic phase was washed with water and brine, then dried over $MgSO_4$. The solvent was removed to give the title compound.

Step 178c. Compound of Formula (VII); W is absent; $R^b$ is H; $R^c$ is H; $R^d$ is trimethylsilyl; $R^e$ is methoxy; $R^f$ is trimethylsilyl; $R^g$ is H; R is —$CH_2$—CH=$CH_2$ A solution of the compound from step 178b (17.5 g) in acetonitrile (250 mL) and liquid ammonia (250 mL) at −78° C. was sealed in a tube and stirred at room temperature for 24 hours. After cooling to −78° C. the seal was broken, and the solution was stirred at room temperature to release the excess ammonia. The solvent was then removed under vacuum to give the title compound.

Step 178d. Compound of Formula (VII); W is absent; $R^b$ is H; $R^c$ is H; $R^d$ is H; $R^e$ is methoxy; $R^f$ is H; $R^g$ is H; R is —$CH_2$—CH=$CH_2$ To a solution of the compound of step 178c (17 g) in acetonitrile (200 mL) at 0° C. was added a solution of HF (48%, 2.3 mL) in acetonitrile (10 mL) over one minute. The mixture was stirred at room temperature for 1 hour, then cooled to 0° C. Solid sodium bicarbonate (9 g) was added, and the mixture was stirred for 30 minutes. The solution was diluted with ether (350 mL) and water (200 mL), and the phases were separated. The organic phase was washed with water and brine, then dried over $MgSO_4$. The solvent was removed, and the residue was purified by chromatography on silica gel, eluting with 1% methanol/dichloromethane containing 1% $NH_4OH$ to give the title compound (12.3 g). H. Res. MS 799.4962 $(M+H)^+$.

EXAMPLE 179

Compound of Formula (VII); W is absent; $R^b$ is H; $R^c$ is H; $R^d$ is H; $R^e$ is methoxy; $R^f$ is H; $R^g$ is H; R is propyl To a sample of the title compound of Example 178 (150 mg) in methanol (3 mL) was added 10% Pd/C (120 mg), and the mixture was treated with 1 atm of hydrogen at room temperature for 5.5 hours. The catalyst and the solvent were removed, and the residue was purified by chromatography on silica gel, eluting with 1% methanol/dichloromethane containing 1% $NH_4OH$ to give the title compound (84 mg). H. Res. MS 801.5110 $(M+H)^+$.

EXAMPLE 180

Compound of Formnula (VII); W is absent; $R^b$ is H; $R^c$ is H; $R^d$ is H; $R^e$ is methoxy; $R^f$ is H; $R^g$ is H; R is —$CH_2$—C(O)—H A sample of the title compound (6 g) from Example 178 was treated with ozone according to the procedure of Example 8b to give the title compound (4.5 g).

EXAMPLE 181

Compound of Formula (VII); W is absent: $R^b$ is H; $R^c$ is H; $R^d$ is H; $R^e$ is methoxy; $R^f$ is H; $R^g$ is H; R is —$CH_2$—C=N—O—$CH_2$-phenyl To a sample of the title compound (200 mg) from Example 180 in methanol (1 mL) was added a solution of O-benzylhydroxylamine hydrochloride (76 mg) in methanol (1 mL) and 0.082 mL of N-methylmorpholine. The mixture was stirred at room temperature for 16 hours, then diluted with ethyl acetate, washed with water and brine, and dried over $MgSO_4$. The solvent was removed, and the residue was purified by chromatography on silica gel, eluting with 1% methanol/dichloromethane containing 1% $NH_4OH$ to give the title compound (125 mg, 56%) as a mixture of syn/anti isomers. H. Res. MS 906.5314 $(M+H)^+$.

EXAMPLE 182

Compound of Formula (VII); W is absent; $R^b$ is H; $R^c$ is H; $R^d$ is H; $R^e$ is methoxy; $R^f$ is H; $R^g$ is H; R is —$CH_2$—$CH_2$—NH—$CH_2$-phenyl To a sample of the title compound (150 mg) from Example 180 in methanol (2 mL) at 0° C. was added benzylamine (0.024 mL), acetic acid (0.034 mL) and sodium cyanoborohydride (82 mg, in three portions). The mixture was stirred at room temperature for 2 hours, then quenched by addition of 5% aqueous sodium bicarbonate and extracted into ethyl acetate. The organic phase was washed with water and brine, and dried over $MgSO_4$. The solvent was removed, and the residue was purified by chromatography on silica gel, eluting with 2% methanol/dichloromethane containing 1% $NH_4OH$ to give the title compound (35 mg). H. Res. MS 892.5526 $(M+H)^+$.

EXAMPLE 183

Compound of formula (X); X=O, R=Phenylpropyl

A sample of the compound prepared according to Example 17 (70 mg) was catalytically hydrogenated by procedures described in Example 2. The crude product (64 mg) was purified by column chromatography on silica gel eluting with 98:1:1 dichloromethane/methanol/ammonium hydroxide to afford the title compound (44 mg, 44%). MS m/z 852 $(M+H)^+$.

EXAMPLE 184

Compound of formula (X); X=O, R is —$CH_2$CH=CH-(4-methylphenyl)

To a mixture of NaH (60%, 19 mg) in THF (2 mL) at 0° C. was added tris(4-methylphenyl)phosphonium chloride (172 mg) over 3 minutes. The mixture was stirred at ambient temperature for 40 minutes, then re-ecooled to 0° C. To this mixture was added a THF solution (2 mL) containing a sample of the compound of Example 8 (300 mg). The reaction was sealed under nitrogen and stirred at ambient temperature for 30 hours. The reaction mixture was taken up in EtOAc and washed successively with water, aqueous 5% sodium bicarbonate and brine. The organic layers were dried over $MgSO_4$ and concentrated in vacuo. The crude product (428 mg) was purified by column chromatography on silica gel eluting with 8% methanol in dichloromethane to afford the title compound (120 mg, 42%). High Res. MS: Calculated m/z for $(M+H)^+$: $C_{47}H_{78}NO_{13}$: 864.5473; Found: 864.5444.

EXAMPLE 185

Compound of formula (X); X=O, R is —CH$_2$—CH(OH)-Phenyl

To a solution of the compound of Example 8 (500 mg) in THF (15 mL) at −10° C. was added phenylmagnesium bromide (6.6 mL, 1 molar solution in THF) over 20 minutes under a nitrogen atmosphere. The reaction was stirred at ambient temperature for 2 hours, then cooled to 0° C. Water (1 mL) was added, the mixture was stirred for 3 minutes, then extracted with EtOAc. The organic layers were washed with brine, dried over MgSO$_4$ and concentrated in vacuo. Chromatography on silica gel eluting with dichloromethane/MeOH/ammonium hydroxide (98:1:1) gave the title compound (300 mg). High Res. MS: calculated m/z for (M+H)$^+$: C$_{45}$H$_{76}$NO$_{14}$: 854.5266; Found: 854.5264.

EXAMPLE 186

Compound of formula (X); X=O, R is —CH$_2$—CH(Br)—CH$_2$Br

To a solution of the compound of Example 1D (200 mg) in dichloromethane (5 mL) 0° C. was added acetic acid (0.073 mL) and pyridinium bromide perbromide (134 mg). After 1 hour at 0° the reaction was warmed to ambient temperature and stirred for 16 hours. The reaction mixture was concentrated in vacuo, the residue was dissolved in EtOAc which was washed with water (2x) and brine, then dried over MgSO$_4$ and concentrated in vacuo. Chromatography on silica gel eluting with 8% MeOH in dichloromethane gave 155 mg (65%) of the title compound. High resolution Mass Spec: calculated m/z for (M+H)$^+$: C$_{40}$H$_{72}$NO$_{13}$$^{79}$Br$_2$:932.3370; Found: 932.3376.

EXAMPLE 187

Compound of formula (X); X=O, R is —CH$_2$CH$_2$NHCH)CH$_2$CH$_2$-Phenyl

To a solution of the compound of Example 8 (150 mg) and 3-phenylpropylamine (0.033 mL) in ethanol (2 mL) was added acetic acid (0.044 mL). After stirring at ambient temperature for 30 minutes, Pd/C (10%, 125 mg) was added under a nitrogen atmosphere. The reaction was stirred for 16 hours under 1 atm hydrogen, then the mixture was filtered and concentrated. The residue was dissolved in EtOAc and washed with 5% sodium bicarbonate and brine. After drying over MgSO$_4$ and concentrating in vacuo, the crude residue was purified with column chromatography on silica gel eluting with dichloromethane/MeOH/ammonium hydroxide (97:2:1) to afford of the title compound (90 mg, 55%). High resolution Mass Spec: calculated m/z for (M+H)$^+$: C$_{48}$H$_{83}$N$_2$O$_{13}$:895.5895; Found: 895.5905.

EXAMPLE 188

Compound of formula (X); X=O, R is —CH$_2$CH$_2$NHCH(CH$_2$Phenyl)CO$_2$Me

To a solution of the compound of Example 8 (150 mg), L-phenylalanine methyl ester hydrochloride (250 mg), acetic acid (0.066 mL) in methanol (2 mL) was added sodium cyanoborohydride (120 mg in 3 portions) over 5 minutes under nitrogen. The reaction was stirred at ambient temperature for 4.5 hours, then was quenched with aqueous 5% sodium bicarbonate. Following an EtOAc extraction and brine wash, the organic layer was dried over MgSO$_4$. The EtOAc extracts were filtered and concentrated in vacuo. Purification was performed with column chromatography on silica gel eluting with dichloromethane/methanol/ammonium hydroxide (98:1:1) to give the title compound (127 mg, 70%). High resolution Mass Spec: calculated m/z for (M+H)$^+$: C$_{49}$H$_{83}$N$_2$O$_{15}$: 939.5793; Found: 939.5798.

EXAMPLE 189

Compound of formula (X); X=O, R is —CH$_2$CH$_2$NHCH$_2$CH$_2$CH$_3$

The title compound was prepared by procedures described in Example 187 except substituting propylamine for phenylpropylamine to give the title compound (90 mg, 57%). H. Res. MS 819.5583 (M+H)$^+$.

EXAMPLE 190

Compound of formula (X); X=O, R is —CH$_2$CH$_2$NHCH$_2$CO$_2$CH$_2$CH$_2$

The title compound was prepared by procedures described in Example 187 except substituting glycine ethyl ester for phenylpropylamine to give the title compound (72 mg, 46%). H. Res. MS 863.5472 (M+H)$^+$.

EXAMPLE 191

Compound of formula (X); X=O, R is —CH$_2$CH$_2$NHCH$_2$CH$_2$-Phenyl

The title compound was prepared by procedures described in Example 187 except substituting phenethylamine for phenylpropylamine to give of the title compound (55 mg, 34%). H. Res. MS 881.5762 (M+H)$^+$.

EXAMPLE 192

Compound of formula (X); X=O, R is —CH$_2$CH$_2$NHCH$_2$CH$_2$-(4-hydroxyphenyl)

The title compound was prepared by procedures described in Example 187 except substituting 4-hydroxyphenethylamine for phenylpropylamine to give of the title compound (80 mg, 48%). H. Res. MS 897.5674 (M+H)$^+$.

EXAMPLE 193

Compound of formula (X); X=O, R is —CH$_2$CH$_2$NHCH$_2$CH$_2$-(3-hydroxyphenyl)

The title compound was prepared by procedures described in Example 187 except substituting 3-hydroxyphenethylamine for phenylpropylamine to give the title compound (69 mg, 40%). MS 897 (M+H)$^+$.

EXAMPLE 194

Compound of formula (X); X=O, R is —CH$_2$CH$_2$NHCH$_2$CH$_2$-(3-methoxyphenyl)

The title compound was prepared by procedures described in Example 187 except substituting 3-methoxyphenethylamine for phenylpropylamine to give the title compound (76 mg, 43%). H. Res. MS 911.5829 (M+H)$^+$.

EXAMPLE 195

Compound of formula (X); X=O, R is —CH$_2$CH$_2$NHCH$_2$CH$_2$-(2-methoxyphenyl)

The title compound was prepared by procedures described in Example 187 except substituting 2-methoxyphenethylamine for phenylpropylamine to give the title compound (36 mg, 20%). H. Res. MS 911.5833 (M+H)+.

EXAMPLE 196

Compound of formula (X); X=O, R is —CH$_2$CH$_2$NHCH$_2$C$_{22}$-(4-methoxyphenyl)

The title compound was prepared by procedures described in Example 187 except substituting 4-methoxyphenethylamine for phenylpropylamine to give the tide compound (78 mg, 44%). H. Res. MS (M+H)+.

EXAMPLE 197

Compound of formula (X); X=O, R is —CH$_2$CH$_2$NHCH$_2$-phenyl

The title compound was prepared by procedures described in Example 188 except substituting benzyl amine for L-phenylalanine methyl ester hydrochloride to give the title compound (64 mg, 38%). H. Res. MS 911.5833 (M+H)+.

EXAMPLE 198

Compound of Formula (X); X is =N—O-(1-isopropoxycyclohexvl), R is fluoromethyl

Step 198a. Compound of Formula (XII); X is =N—O-(1-isopropoxycyclohexyl), R is fluoromethyl, R$^p$ is Trimethylsilyl To a 0° C. solution of 15 g of the compound of Formula XII where X is =N—O-(1-isopropoxycyclohexyl) and R$^p$ is trimethylsilyl in 150 mL of DMSO and 150 mL of THF was added 113.1 g of bromofluoromethane. A solution of potassium t-butoxide (1 M in THF, 25.4 mL) was added dropwise over 6 hours. The reaction was quenched by addition of allyl amine with stirring for 10 minutes, followed by dilution with water. Ethyl acetate was added, and the organic layer was separated and washed with water and brine, then dried over MgSO$_4$, filtered and concentrated in vacuo to afford 16.5 g of title compound.

Step 198b. Compound of Formula (XII); X is =N—O-(1-isopropoxycyclohexyl), R is fluoromethyl, R$^p$ is H To a room temperature solution of 14.5 g of the compound resulting from step xxxx in 150 mL of anhydrous THF was added 41 mL of 1 M tetrabutylammonium fluoride. After two hours, the solvent was removed under reduced pressure and the residue was dried to constant weight. Purification by column chromatography eluting with 2% methanol in dichloromethane containing 1% ammonium hydroxide afforded 10.24 g of the title compound.

EXAMPLE 199

Compound of formula (X); X=O, R is —CH$_2$CH$_2$NHCH$_2$CH$_2$-(3-chlorophenyl)

The title compound was prepared by procedures described in Example 188 except substituting 3-chlorophenethylamine for L-phenylalanine methyl ester hydrochloride to give the title compound (94 mg, 53%). H. Res. MS 915.5320 (M+H)+.

EXAMPLE 200

Compound of formula (X); X=O, R is —CH$_2$CH$_2$NHCH$_2$CH$_2$-(2-chlorophenyl)

The title compound was prepared by procedures described in Example 188 except substituting 2-chlorophenethylamine for L-phenylalanine methyl ester hydrochloride to give the title compound (88 mg, 50%). H. Res. MS 915.5340 (M+H)+.

EXAMPLE 201

Compound of formula (X); X=O, R is —CH$_2$CH$_2$NHCH$_2$CH$_2$-(4-chlorophenyl)

The title compound was prepared by procedures described in Example 188 except substituting 4-chlorophenethylamine for L-phenylalanine methyl ester hydrochloride to give the title compound (84 mg, 47%). H. Res. MS 915.5338 (M+H)+.

EXAMPLE 202

Compound of formula (X); X=O, R is —CH$_2$CH$_2$NHCH$_2$CH$_2$—O-phenyl)

The title compound was prepared by procedures described in Example 188 except substituting 2-phenoxyethylamine for L-phenylalanine methyl ester hydrochloride to give the title compound (71 mg, 41%). H. Res. MS 897.5654 (M+H)+.

EXAMPLE 203

Compound of formula (X); X=O, R is —CH$_2$CH$_2$NHCH$_2$CH$_2$-(4-quinolinyl)

The title compound was prepared by procedures described in Example 188 except substituting 4-(propylamino)quinoline for L-phenylalanine methyl ester hydrochloride to give the title compound (60 mg, 33%). H. Res. MS 946.5967 (M+H)+.

EXAMPLE 204

Compound of formula (X); X=O, R is —CH$_2$CH$_2$NHCH$_2$CH$_2$CH$_2$-(3-quinolinyl)

The title compound was prepared by procedures described in Example 188 except substituting 3-(propylamino)quinoline for L-phenylalanine methyl ester hydrochloride to give the title compound. H. Res. MS 946.6022 (M+H)+.

EXAMPLE 205

Compound of formula (X); X=O, R is —CH$_2$CH$_2$NHCH$_2$CH$_2$CH$_2$CH$_2$-phenyl The title compound was prepared by procedures described in Example 188 except substituting 4-phenylbutylamine for L-phenylalanine methyl ester hydrochloride to give the title compound. H. Res. MS 909.6046 (M+H)+.

EXAMPLE 206

Compound of formula (X); X=O, R is —CH$_2$—CH=N—NH—C(O)—NH$_2$

The tide compound was prepared by procedures described in Example 18 except substituting semicarbazide hydrochloride for methoxylamine hydrochloride to give the title compound as a 10:1 anti/syn mixture of isomers. H. Res. MS 833.5153 (M+H)+.

EXAMPLE 207

Compound of formula (X); X=O, R is —CH$_2$—CH=N—NH-(2-pyridinyl)

The title compound was prepared by procedures described in Example 18 except substituting 2-hydrazinopyridine for methoxylamine hydrochloride to give the title compound as a 1:1 anti/syn mixture of isomers. H. Res. MS 867.5351 $(M+H)^+$.

EXAMPLE 208

Compound of formula (X); X=O, R is —CH$_2$—CH=N-(4-methylpiperazinyl)

The title compound was prepared by procedures described in Example 18 except substituting 1-amino-4-methylpiperazine for methoxylamine hydrochloride to give the title compound as a trans isomer. H. Res. MS 873.5765 $(M+H)^+$.

EXAMPLE 209

Compound of formula (X); X=O, R is —CH$_2$—CH=N—O-phenyl

The title compound was prepared by procedures described in Example 18 except substituting O-phenylhydroxylamine hydrochloride for methoxylamine hydrochloride to give the title compound as a 1:1 anti/syn mixture of isomers. H. Res. MS 867.5198 $(M+H)^+$.

EXAMPLE 210

Compound of formula (X); X=O, R is —CH$_2$CH(OH)CH$_2$NHCH$_2$CH$_2$-phenyl

To a solution of the compound from Example 4 (200 mg) in DMF (1 mL) was added benzylamine (0.160 mL), and the reaction was heated at 65° C. for 20 hours. The mixture was diluted with EtOAC (30 mL) and washed successively with water, 5% sodium bicarbonate and brine. The EtOAc layers were then dried over MgSO$_4$ and concentrated in vacuo. The residue was chromatographed on silica gel eluting with dichloromethane/methanol/ammonium hydroxide (96:3:1) to afford of the title compound (109 mg) as a mixture of diastereomers. H. Res. MS 911.5853 $(M+H)^+$.

EXAMPLE 211

Compound of formula (X); X=O, R is —CH$_2$CH(OH)CH$_2$NHCH$_2$-(4-pyridinyl

The title compound was prepared by procedures described in Example 210 except substituting 4-(aminoethyl)pyridine for benzylamine to give the title compound (50 mg, 34%). H. Res. MS 898.5635 $(M+H)^+$.

EXAMPLE 212

Compound of Formula (VII); W is absent; $R^b$ is H; $R^c$ is H; $R^d$ is H; $R^e$ is methoxy, $R^f$ is H; $R^g$ is H; R is —CH$_2$—C=N—O—H (anti-isomer)

The title compound was prepared by procedures described in Example 181 substituting hydroxylamine hydrochloride for O-benzylhydroxylamine hydrochloride. The crude product was obtained as a mixture of syn/anti isomers. After chromatography on silica gel eluting with dichloromethane/methanol/ammonium hydroxide (96:3:1) the title compound was obtained as a single anti isomer. H. Res. MS 816.4835 $(M+H)^+$.

EXAMPLE 213

Compound of Formula (VII); W is absent; $R^b$ is H; $R^c$ is H; $R^d$ is H; $R^e$ is methoxy: $R^f$ is H; $R^g$ is H; R is —CH$_2$—C=N—O—H (syn-isomer)

After chromatography of the mixture of syn and anti isomers from Example 212 on silica gel eluting with dichloromethane/methanol/ammonium hydroxide (96:3:1) the title compound was obtained as a single syn isomer. H. Res. MS 816.4835 $(M+H)^+$.

EXAMPLE 214

Compound of Formula (VII); W is absent; $R^b$ is H; $R^c$ is H; $R^d$ is H; $R^e$ is methoxy: $R^e$ is H; $R^g$ is H; R is —CH$_2$—C=N—O-phenyl The title compound was prepared by procedures described in Example 181 substituting O-phenylhydroxylamine hydrochloride for O-benzylhydroxylamine hydrochloride. The title compound was obtained as a mixture of syn/anti isomers. H. Res. MS 892.5151 $(M+H)^+$.

EXAMPLE 215

Compound of Formula (VII); W is absent; $R^b$ is H; $R^c$ is H; $R^d$ is H; $R^e$ is methoxy: $R^f$ is H; $R^g$ is H; R is —CH$_2$—C=N—O—CH$_2$-(4-nitrophenyl)

The title compound was prepared by procedures described in Example 181 substituting O-(4nitrobenzyl)hydroxylamine hydrochloride for O-benzylhydroxylamine hydrochloride. The title compound was obtained as a mixture of syn/anti isomers. H. Res. MS 951.5197 $(M+H)^+$.

EXAMPLE 216

Compound of Formula (VII); W is absent; $R^b$ is H; $R^c$ is H; $R^d$ is H; $R^e$ is methoxy; $R^f$ is H; $R^g$ is H; R is —CH$_2$—C=N—O—CH$_2$-(4-quinolinyl)

To a solution of 130 mgs of the title compound of Example 180 in 2 mL MeOH was added 100 mg O-(4-quinolyl)hydroxylamine and catalytic p-toluenesulfonic acid. The reaction was heated at 60° C. for 16 hours. The reaction was concentrated in vacuo. The residue obtained was chromatographed on silica gel eluting with dichloromethane/methanol/ammonium hydroxide (98:1:1) to afford 85 mg (62%) of the title compound as a mixture of syn/anti isomers. H. Res. MS 957.5443 $(M+H)^+$.

EXAMPLE 217

Compound of Formula (VII); W is absent; $R^b$ is H; $R^c$ is H; $R^d$ is H; $R^e$ is methoxy; $R^f$ is H; $R^g$ is H; R is —CH$_2$—C=N—O-(phenyl)$_3$ The title compound was prepared by procedures described in Example 216 except substituting O-tritylhydroxylamine for O-(4-quinolyl)hydroxylamine. The title compound was obtained as a mixture of syn/anti isomers. MS 1058 $(M+H)^+$.

EXAMPLE 218

Compound of Formula (VII); W is absent; $R^b$ is H; $R^c$ is H; $R^d$ is H; $R^e$ is methoxy; $R^f$ is H; $R^g$ is H; R is —CH$_2$—CH$_2$—NH$_2$ A 150 mg sample of the title compound from Example 180 was dissolved in 2 mL of dichloromethane and 24 microliters of benzylamine and 50 mg MgSO$_4$ were added. The reaction was stirred at ambient temperature for 16 hours, filtered and concentrated in vacuo. The residue obtained was dissolved in EtOH and 120 mg 10% Pd/C was added under a nitrogen atmosphere. The reaction was then placed under 1 atm hydrogen and stirred for 16 hours. The reaction was filtered and concentrated in vacuo. The residue obtained was purified with column chromatography on silica gel eluting with dichloromethane/MeOH/ammonium hydroxide (97:2:1) to afford 40 mg of the title compound. MS 802 (M+H)$^+$.

EXAMPLE 219

Compound of Formula (VII); W is absent; $R^b$ is H; $R^c$ is H; $R^d$ is H; $R^e$ is methoxy; $R^f$ is H; $R^g$ is H; R is —CH$_2$—CH$_2$—NH—CH$_2$-phenyl To a solution of 150 mg of the title compound from Example 180, 24 microliters of benzylamine and 34 microliters of acetic acid in 2 mL of MeOH was added 82 mg sodium cyanoborohydride in 3 portions over 5 minutes under a nitrogen atmosphere. The reaction was stirred at ambient temperature for 4.5 hours and was quenched with aqueous 5% sodium bicarbonate. Following an EtOAc extraction and brine wash the organic layer was dried over MgSO$_4$. The EtOAc extracts were filtered and concentrated in vacuo. Purification was performed with column chromatography on silica gel eluting with dichloromethane/methanol/ammonium hydroxide (97:2:1) to give 35 mg (21%) of the title compound. H. Res. MS 892.5526 (M+H)$^+$.

EXAMPLE 220

Compound of Formula (VII): W is absent; $R^b$ is H; $R^c$ is H; $R^d$ is H; $R^e$ is methoxy: $R^f$ is H; $R^g$ is H; R is —CH$_2$—CH$_2$—NH—CH$_2$CH$_2$-phenyl A 200 mg sample of the title compound from Example 180 was dissolved in 2 mL of dichloromethane, and 36 microliters of phenethylamine and 50 mgs of MgSO$_4$ were added. The reaction was stirred at ambient tremperature for 16 hours, then filtered and concentrated in vacuo. The residue obtained was dissolved in EtOH, and 150 mg 10% Pd/C was added under a nitrogen atmosphere. The reaction was then placed under 1 atm hydrogen and stirred for 20 hours. The reaction mixture was filtered and concentrated in vacuo, and the residue obtained was purified with column chromatography on silica gel eluting with dichloromethane/MeOH/ammonium hydroxide (97:2: 1) to afford 104 mg (46%) of the title compound. H. Res. MS 906.5713 (M+H)$^+$.

EXAMPLE 221

Compound of Formula (VII); W is absent; $R^b$ is H; $R^c$ is H; $R^d$ is H; $R^e$ is methoxy; $R^f$ is H; $R^g$ is H; R is —CH$_2$—CH$_2$NH—CH$_2$—CH$_2$—CH$_2$-phenyl The title compound was prepared by the procedures described in Example 220 except substituting phenylpropylamine for phenethylamine. H. Res. MS 920.5863 (M+H)$^+$.

EXAMPLE 222

Compound of Formula (X); X is =O, R is (3-iodophenyl)methyl

Step 222a. Compound of Formula (XII); X is =N—O-(1-isopropoxycyclohexyl), R is (3-iodophenyl)methyl, $R^p$ is Trimethylsilyl To a 0° C. solution flushed with nitrogen of 33.5 g (0.032 mmol) of the compound of Formula XII where X is =N—O-(1-isopropoxycyclohexyl) and $R^p$ is trimethylsilyl in 120 mL of DMSO and 120 mL of THF was added 24 g (0.081 mmol) of 3-iodobenzyl bromide over 10 minutes. A solution of potassium t-butoxide (1 M in THF, 65 mL, 0.065 mmol) was added at 0° C. over 6 hours. The reaction was stirred for an additional hour, then taken up inn ethyl acetate. The organic layer was separated, washed with water and brine, then dried over MgSO$_4$, filtered and concentrated in vacuo to afford 40 g of title compound. MS 1249 (M+H)$^+$.

Step 222b. Compound of Formula (XII); X is =N—O-(1-isopropoxycyclohexyl), R is (3-iodophenyl)methyl, $R^p$ is H The compound from step 222a was suspended in acetonitrile (130 mL), and water (65 mL) and acetic acid (65 mL) were added to provide a clear solution. The reaction mixture was stirred at room temperature for 20 hours, and the solvent was removed under reduced pressureto give the title compound (32 g). MS 965 (M+H)$^+$.

Step 222c. Compound of Formula (X); X is =O, R is (3-iodophenyl)methyl

The compound from step 222b (32 g, 0.032 mol) in 500 mL of 1:1 EtOH-water was treated with NaHSO$_3$ (67.39 g, 0.65 mol) and formic acid (6.11 mL) and warmed at 80° C. under nitrogen for 1 hour. The ethanol was removed under vacuum, and the resulting solution was adjusted to pH 10 with sodium carbonate (27.5 g, 0.259 mol) and extracted with EtOAc. The organic phase was washed with water and brine (2x), dried over MgSO4, filtered and concentrated in vacuo. The crude material (9.1 g) was purified by column chromatography eluting with 1% MeOH in dichloromethane containing 1% ammonium hydroxide to give the pure title compound. MS 950 (M+H)$^+$.

EXAMPLE 223

Compound of Formula (X); X is =O, R is (4-fluorophenyl)methyl

Following the procedures of Example 222, except substituting 4-fluorobenzyl bromide for the 3-iodobenzyl bromide thereof, the title compound was prepared. MS 842 (M+H)$^+$.

EXAMPLE 224

Compound of Formula (X); X is =O, R is —CH$_2$—CH=CH$_2$-(3-quinolinyl)

To a sample of the compound from Example 1 (3.09 g, 4 mmol) in acetonitrile (70 mL) were added 3-bromoquinoline (1.08 mL, 8.0 mmol), palladium acetate (180 mg, 0.8 mmol), tri-(o-tolyl)phosphine (365 mg, 1.2 mmol) and triethylamine (1.40 mL, 10 mmol). The mixture was degassed by bubbling N$_2$ through it for 30 minutes, sealed in a tube under nitrogen, and heated at 60° C. for 1 hour and at 100° C. for 14 hours. The mixture was cooled to room temperature and diluted with ethyl acetate. The organic phase was separated, washed with saturated NaHCO$_3$ and brine, and dried over MgSO$_4$. The solvent was removed to give crude product which was purified by chromatography on silica gel, eluting with 40–60% acetonelhexane to give the title compound (2.73g). MS 901 (M+H)$^+$.

EXAMPLE 225

Compound of Formula (II); X is =O, $R^b$ is H; $R^c$ is H; $R^d$ is acetyl; $R^e$ is methoxy; $R^f$ is acetyl; R is —CH$_2$—CH=CH$_2$ To a solution of the compound of Example 1 (80 g, 103 mmol and DMAP (4.0 g, 32.7 mmol) in dichloromethane (200 mL) was added acetic anhydride (40 mL, 400 mmol). The solution was stirred for 5 hours at ambient temperature. The mixture was diluted with dichloromethane (800 mL). The organic phase was washed with 5% Na$_2$CO$_3$, saturated NaHCO$_3$ and brine and dried over MgSO$_4$. The solvent was removed under vacuum, and the residue was dried. The residue was crystallized from acetonitrile to give the title compound (60.0 g).

EXAMPLE 226

Compound of Formula (VII): W is absent; $R^b$ is H; $R^c$ is H; $R^d$ is acetyl; $R^e$ is methoxy; $R^f$ is acetyl; $R^g$ is H; R is —CH$_2$—CH=CH$_2$ Step 226a. (Compound (28) of Scheme V; 2'-$R^p$ is acetyl; 4"-$R^p$ is acetyl; R is allyl To a solution of the compound of Example 225 (19.5 g, 22.75 mmol) in THF (125 mL) cooled to −48° C. in a dry ice-acetonitrile bath was added sodium bis(trimethylsilyl) amide (30.0 mL, 1 M in THF, 30.0 mmol) over 30 min. After 45 min, a solution of 15.0 g (91.0 mmol) of carbonyldiimidazole in 75 mL of THF and 50 mL of DMF was added. The mixture was stirred for 2.5 hrs at −48° C. and 18 hrs at room temperature. The reaction was quenched by adding a solution of 0.5 M NaH$_2$PO$_4$ (200 mL). The product was isolated by extraction of the reaction mixture with ethyl acetate. The extract was dried with MgSO$_4$ and concentrated to give the crude product, which was purified by flash chromatography using 40–60% acetone/hexanes, yielding 19.66 g (92%) of the title compound.

Step 226b. Compound (29) of Scheme V—which is also a Compound of Formula (VII); W is absent; $R^b$ is H; $R^c$ is H; $R^d$ is acetyl; $R^e$ is methoxy; $R^f$ is acetyl; $R^g$ is H; R is —CH$_2$—CH=CH$_2$ To a solution of compound from step 226a (40.0 g, 42.9 mmol) in acetonitrile (1000 mL) and THF (100 mL) was added concentrated ammonium hydroxide (28–30%, 120 mL). The mixture was stirred at room temperature for 7 days. Solvents were removed in vacuo, and the residue was taked up in ethyl acetate. The organic layers were washed with brine, dried over MgSO$_4$ and concentrated in vacuo. The residue was chromatographed on silica gel eluting with dichloromethane/MeOH/ammonium hydroxide (10:1:0.05) to give the title compound (23.07 g). HRMS: calculated m/z for (M+H)+: C45H74N2O15: 883.5164; Found: 883.5162.

EXAMPLE 227

Compound of Formula (VII); W is absent; $R^b$ is H; $R^c$ is H; $R^d$ is acetyl; $R^e$ is methoxy; $R^f$ is acetyl; $R^g$ is H; R is —CH$_2$—CH=CH$_2$-(3-quinolinyl)

To a sample of the title compound from Example 226 (20.5 g, 23.2 mmol) in acetonitrile (200 mL) were added 3-bromoquinoline (6.47 mL, 31.1 mmol), palladium acetate (1.07 g, 4.76 mmol), tri-(o-tolyl)phosphine (2.43 g, 7.97 mmol) and triethylamine (9.13 mL, 65.5 mmol). The mixture was degassed by bubbling N$_2$ through for 30 minutes, sealed in a tube under nitrogen, and heated at 60° C. for 1 hour and 14 hours at 100° C. The mixture was cooled and diluted with ethyl acetate, which was separated and washed with saturated NaHCO$_3$ and brine, then dried over MgSO$_4$. The solvents were removed and the crude product was purified by chromatography on silica gel eluting with 40–60% acetone/hexane to give the title compound (21.0 g). MS: [M+H]+ at m/z 883.

EXAMPLE 228

Compound of Formula (VII); W is absent; $R^b$ is H; $R^c$ is H; $R^d$ is acetyl; $R^e$ is methoxy; $R^f$ is H; $R^g$ is H; R is —CH$_2$CH=CH$_2$-(3-quinolinyl)

A sample of compound from Example 227 (109 mg, 0.108 mmol) in MeOH (3 mL) was heated at reflux for 4 hours. The solvent was removed by evaporation, and the crude product was purified by chromatography on silica gel with dichloromethane/MeOH/ammonium hydroxide (10:1:0.05) to give the title compound (70 mg). HRMS: calculated m/z for (M+H)+: C$_{52}$H$_{78}$N$_3$O$_{14}$: 968.5484; Found: 968.5485.

EXAMPLE 229

Compound of Formula (VII); W is absent; $R^b$ is H; $R^c$ is H; $R^d$ is acetyl; $R^e$ is methoxy; $R^f$ is H; $R^g$ is H; R is —CH$_2$CH=CH$_2$-(3-quinolinyl)

A sample of compound from Example 228 (2.53 g, 2.51 mmol) from above in MeOH (50 mL) was added 7.5 mL 2 N NaOH. The mixture was stirred at room temperature for 24 hours before it was diluted with ethyl acetate. The organic layers were washed with brine, dried over MgSO$_4$ and concentrated in vacuo. Chromatography on silica gel eluting with dichloromethane/MeOH/ammonium hydroxide (10:1:0.05) gave the title compound (1.42 g, 61%). H. Res. MS 926.5396.

EXAMPLE 230

Compound of Formula (VII); W is absent; $R^b$ is H; $R^c$ is H; $R^d$ is H; $R^e$ is methoxy; $R^f$ is acetyl; $R^g$ is H; R is —CH$_2$CH=CH$_2$-(3-quinolinyl)

A sample of compound from Example 227 (1.42 g, 1.53 mmol) in dichloromethane (30 mL) was treated with triethylamine (0.25 mL, 1.79 mmol) and acetic anhydride (0.29 mL, 2.12 mmol) at room temperature for 12 hours. The mixture was washed with a saturated solution of NaHCO3, dried over MgSO4, and concentrated in vacuo. Crude product was further purifed by recrystalization from hot acetonitrile to give 1.40 g of the title compound.

EXAMPLE 231

Compound of Formula (VII); W is absent; $R^b$ is H; $R^c$ is H; $R^d$ is methoxy; $R^e$ is methoxy; $R^f$ is H; $R^g$ is H; R is —CH$_2$CH=CH$_2$-(3-quinolinyl)

A sample of compound from Example 230 (0.1 g, 0.103 mmol) in THF (2 mL) at 8° C. was added NaN(TMS)2 (1 M in THF, 0.19 mL). After 30 min, iodomethane (0.027 g, 0.189 mmol) was added. After stirred at room temperature for 12 hours,the mixture was diluted with AcOEt. Organic layers were washed with water, brine, and dried over Na2SO4, concentrated in vacuo to give crude product. This material was then dissolved in methanol (3 mL) and heated at reflux for 4 hours. Solvent was removed by evaporation in vacuo, residue was purified by chromatography on silica gel eluted with 95:5:1 dichloromethane:MeOH:NH4OH to give title compound.

EXAMPLE 232

Compound of Formula (VII); W is absent; $R^b$ is H; $R^c$ is H; $R^e$ is methoxy; $R^d$ is ethenesulfonyloxy: $R^f$ is acetyl; $R^g$ is H; R is —CH$_2$—CH=CH$_2$-(3-quinolinyl)

A sample of compound from Example 231 (0.49 g, 0.51 mmol) was dissolved in pyridine (15 mL) and cooled to 0° C. 2-Chloroethanesulfonyl chloride (0.262 g, 1.61 mmol) was added dropwise, the mixture was stirred at 8° C. for 15 minutes and at room temperature for 48 hours. The mixture was diluted with AcOEt, and washed with 5% NaHCO$_3$. The aqueous phase was extracted with AcOEt, and the combined organic layers were washed with brine, dried over MgSO$_4$, filtered and concentraded in vacuo. The crude product was purified by flash chromatography with 95:5:1 dichloromethane:MeOH:NH4OH to give 0.28 g title compound as a yellow foam.

EXAMPLE 233

Compound of Formula (VII); W is absent; R$^b$ is H; R$^c$ is H; R$^e$ is methoxy; R$^d$ is 2-(dimethylamino) ethylsulfonyloxy; R$^f$ is acetyl; R$^g$ is H; R is —CH$_2$CH=CH$_2$-(3-guinolinyl)

To a sample of compound from Example 232 (70 mg, 0.066 mmol) in CH$_3$CN (3 mL) was added dimethylamine (2 M in THF, 0.4 mL, 0.079 mmol), and the mixture was stirred for 12 hours at room temperature. The mixture was evaporated to dryness, and the residue was dissolved in 5 mL MeOH and heated at reflux for 4 hours. The solvent was removed by evaporation, and the crude product was purified by chromatography on silica gel with dichloromethane/MeOH/ammonium hydroxide (20:1:0.05) to give the title compound (32 mg). MS m/z 1061 [M+H]$^+$.

EXAMPLE 234

Compound of Formula (VII); W is absent, R$^b$ is H; R$^c$ is H; R$^d$ is methoxy; R$^e$ is 2-(phenylthio)ethoxy: R$^f$ is acetyl; R$^g$ is H; R is —CH$_2$CH=CH$_2$-(3-quinolinyl)

Following the procedure of Example 233, except substituting thiophenol for the dimethylamine thereof, the title compound was prepared (25 mg).

EXAMPLE 235

Compound of Formula (VII); W is absent; R$^b$ is H; R$^c$ and R$^e$ taken together is =O; R$^e$ is methoxy; R$^f$ is H; R$^g$ is H; R is —CH$_2$CH=CH$_2$-(3-quinolinyl)

To a solution of N-chlorosuccinimide (110.5 mg, 0.827 mmol) in dichlomethane (3 mL) was added dimethylsulfide (64.3 mg, 1.03 mmol) at −18° C. After 10 min, a solution of compound from Example 231 (400 mg, 0.414 mmol) in dichlomethane (3 mL) was added. The mixture was stirred at −10° C. to 0° C. for 45 minutes and triethylamine (144 mL, 1.03 mmol) was added. The mixture was diluted with dichloromethane (10 mL), washed with NaHCO$_3$ and brine, dried over MgSO$_4$, and concentrated in vacuo to give 400 mg of the 2'acetyl compound. A 40 mg sample of this material was heated in refluxing MeOH (3 mL) for 3 hours. Methanol was evaporated, and the residue was purified by chromatography on silica gel eluting with dichloromethane/MeOH/ammonium hydroxide (20:1:0.05) to give the title compound (32 mg). MS: [M+H]+at m/z 924.

EXAMPLE 236

Compound of Formula (VII); W is absent; R$^b$ is H; R$^c$ is H; R$^d$ is methoxy; R$^e$ is (2-nitrophenyl) aminocarbonyloxy; R$^f$ is H; R$^g$ is H; R is —CH$_2$CH=CH$_2$-(3-quinolinyl)

A sample of the compound from Example 231 (50 mg, 0.054 mmol), 2-nitrophenylisocyanate (13 mg, 0.081 mmol) and DAMP (7.0 mg, 0.057 mmol) in toluene (2 mL) was heated at 108° C. for 3 hrs. After 5 mL MeOH was added, the mixture was heated at reflux for 4 hours. Solvents were removed in vacua, and the residue was purified by flash chromatography on silica gel eluted with-dichloromethane/MeOH/ammonium hydroxide (20:1:0.05) to give the title compound, 38 mg. MS: [M+H]+at m/z 1090.

EXAMPLES 237–283

Using the procedures described in the preceeding examples and schemes and methods known in the synthetic organic chemistry art, the following compounds having the formula (X) wherein R is as described below can be prepared.

| Ex. No. | Structure of R |
|---|---|
| 237 | —CH$_2$CH$_2$CH$_2$OH |
| 238 | —CH$_2$C(=O)OH |
| 239 | —CH$_2$CH$_2$NHCH$_3$ |
| 240 | —CH$_2$CH$_2$CH$_2$NHCH$_3$ |
| 241 | —CH$_2$CH$_2$N(CH$_3$)$_2$ |
| 242 | —CH$_2$CH$_2$-morpholinyl |
| 243 | —CH$_2$C(=O)NH$_2$ |
| 244 | —CH$_2$CH$_2$NHC(=O)NH$_2$ |
| 245 | —CH$_2$CH$_2$NHC(=O)CH$_3$ |

-continued (X) [macrolide structure with R group at position 6]

| Ex. No. | Structure of R |
|---|---|
| 246 | ~~~O~CH₃ (propyl methyl ether) |
| 247 | ~~~CH₃ (propyl) |
| 248 | CH₃-C(CH₃)=CH-CH₂- (3-methyl-2-butenyl) |
| 249 | (CH₃)₂CH-CH₂-CH₂- (isopentyl) |
| 250 | ~~O~~O~CH₃ |
| 251 | ~S~CH₃ |
| 252 | cyclopropylmethyl |
| 253 | ~O~CH₃ |
| 254 | ~~F |
| 255 | ~cyclopropyl |
| 256 | ~~CH₃ |
| 257 | ~~CHO |
| 258 | CH₃-CH₂-C(O)-CH₂-CH₂- |
| 259 | 4-nitrophenethyl |

-continued (X) [macrolide structure with R group at position 6]

| Ex. No. | Structure of R |
|---|---|
| 260 | 4-chlorophenethyl |
| 261 | 4-methoxyphenethyl |
| 262 | 4-cyanophenethyl |
| 263 | ~~/=\~CO₂CH₃ |
| 264 | ~~/=\~CH₃ |
| 265 | ~~~/=\~CH₃ |
| 266 | ~~~/=\~~CH₃ |
| 267 | CH₃CH₂-CH=CH-S(O)₂-C₆H₅ |
| 268 | CH₃CH₂-C≡C-Si(CH₃)₃ |
| 269 | CH₃CH₂-C≡C-(CH₂)₄-CH₃ |
| 270 | CH₃CH₂-C≡C-CH₃ |

-continued (X)

| Ex. No. | Structure of R |
|---|---|
| 271 | ethyl-2-pyridine |
| 272 | ethyl-3-pyridine |
| 273 | ethyl-4-pyridine |
| 274 | ethyl-4-quinoline |
| 275 | CH₃CH₂NO₂ (ethyl nitro) |
| 276 | propanoate methyl ester |
| 277 | ethyl methyl ether |
| 278 | propanamide |
| 279 | 1-phenylpropan-1-one |

-continued (X)

| Ex. No. | Structure of R |
|---|---|
| 280 | pentan-3-one |
| 281 | ethyl chloride |
| 282 | ethyl phenyl sulfone |
| 283 | 1-bromo-1-butene |

EXAMPLES 284–315

Using the procedures described in the preceeding examples and schemes and methods known in the synthetic organic chemistry art, the following compounds can be prepared. The macrolide ring systems are selected from the group consisting of:

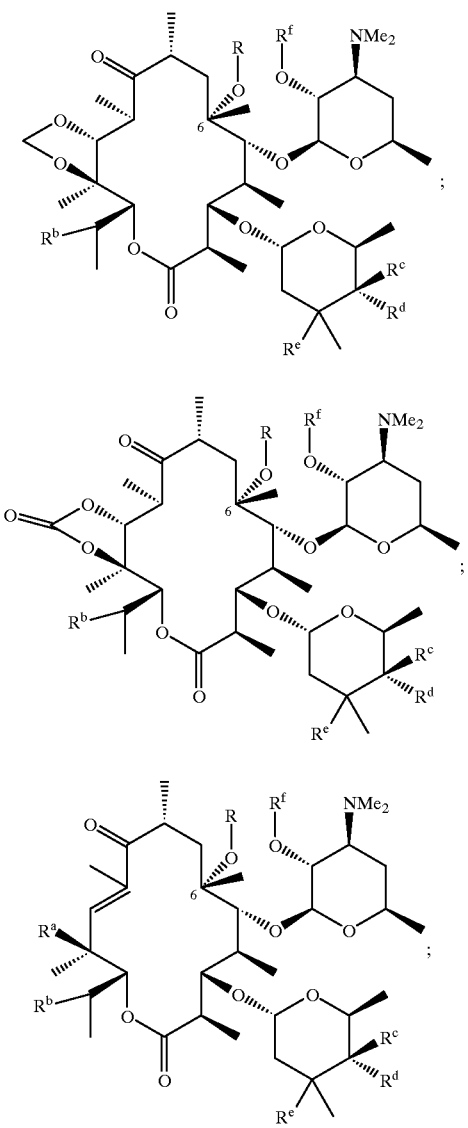
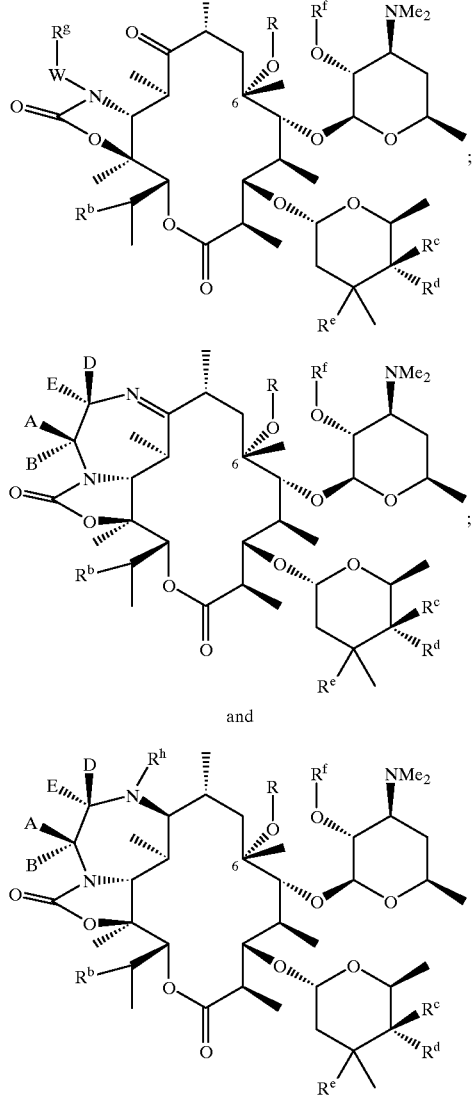
wherein A, B, D, E, W, X, Y, Z, R, $R^a$, $R^b$, $R^c$, $R^d$, $R^e$, $R^f$, $R^g$ and $R^h$ are as previously defined.
| Ex. No. | Precursor of R | Structure of R |
|---|---|---|
| 284 | Allyl bromide | |
| 285 | Propargyl bromide | |

-continued
| Ex. No. | Precursor of R | Structure of R |
|---|---|---|
| 286 | Benzyl bromide | 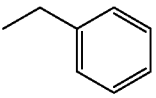 |
| 287 | 2-Fluoroethyl bromide | 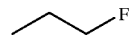 |
| 288 | 4-Nitrobenzyl bromide | 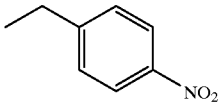 |
| 289 | 4-Chlorobenzyl bromide | 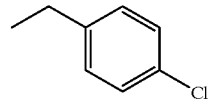 |
| 290 | 4-Methoxybenzyl bromide | 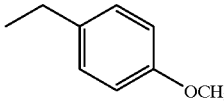 |
| 291 | α-Bromo-p-tolunitrile | 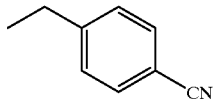 |
| 292 | Cinnamyl bromide | 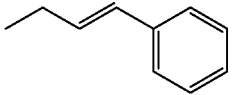 |
| 293 | Methyl 4-bromocrotonate | 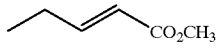 |
| 294 | Crotyl bromide | 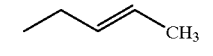 |
| 295 | 1-Bromo-2-pentene |  |
| 296 | 3-Bromo-1-propenyl phenyl sulfone | 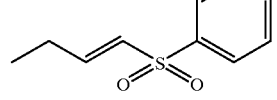 |
| 297 | 3-Bromo-1-trimethylsilyl-1-propyne | 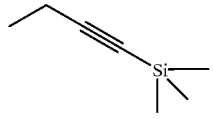 |
| 298 | 3-Bromo-2-octyne | 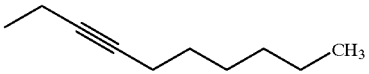 |
| 299 | 1-Bromo-2-butyne |  |

-continued
| Ex. No. | Precursor of R | Structure of R |
| --- | --- | --- |
| 300 | 2-Picolyl chloride | 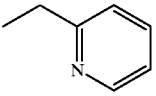 |
| 301 | 3-Picolyl chloride | 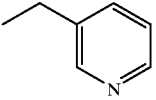 |
| 302 | 4-Picolyl chloride | 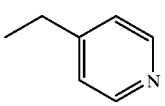 |
| 303 | 4-Bromomethyl quinoline | 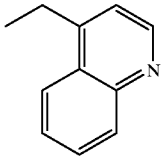 |
| 304 | Bromoacetonitrile | 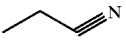 |
| 305 | Epichlorohydrin | 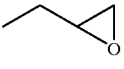 |
| 306 | Bromofluoromethane |  |
| 307 | Bromonitromethane |  |
| 308 | Methyl bromoacetate | 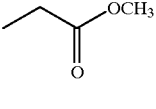 |
| 309 | Methoxymethyl chloride |  |
| 310 | Bromoacetamide | 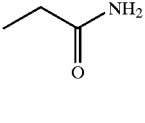 |
| 311 | 2-Bromoacetophenone | 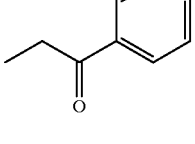 |
| 312 | 1-Bromo-2-butanone | 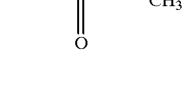 |
| 313 | Bromo chloromethane |  |

-continued

| Ex. No. | Precursor of R | Structure of R |
|---|---|---|
| 314 | Bromomethyl phenyl sulfone | |
| 315 | 1,3-Dibromo-1-propene | |

EXAMPLE 316

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 4 demonstrate the antibacterial activity of the compounds of the invention.

TABLE 4

Antibacterial Activity (MIC's) of Selected Compounds

| Microorganism | Ery. A | Example 1B | Example 1C |
|---|---|---|---|
| Staphylococcus aureus ATCC 6538P | 0.2 | 0.78 | 0.78 |
| Staphytococcus aureus A5177 | 3.1 | 12.5 | 12.5 |
| Staphylococcus aureus A-5278 | >100 | >100 | >100 |
| Staphylococcus aureus CMX 642A | 0.39 | 1.56 | 1.56 |
| Staphylococcus aureus NCTC10649M | 0.39 | 3.1 | 0.78 |
| Staphylococcus aureus CMX 553 | 0.39 | 1.56 | 0.78 |
| Staphytococcus aureus 1775 | >100 | >100 | >100 |
| Staphylococcus epidermidis 3519 | 0.39 | 0.39 | 0.39 |
| Enterococcus faecium ATCC 8043 | 0.05 | 0.2 | 0.2 |
| Streptococcus bovis A-5169 | 0.02 | 0.02 | 0.01 |
| Streptococcus agalactiae CMX 508 | 0.05 | 0.1 | 0.01 |
| Streptococcus pyogenes EES61 | | | |
| Streptococcus pyogenes 930 | >100 | >100 | >100 |
| Streptococcus pyogenes PIU 2548 | 3.1 | 6.2 | 3.1 |
| Micrococcus luteus ATCC 9341 | 0.05 | 0.2 | 0.1 |
| Micrococcus luteus ATCC 4698 | 0.2 | 3.1 | 1.56 |

TABLE 4-continued

Antibacterial Activity (MIC's) of Selected Compounds

| Microorganism | Ery. A | Example 1B | Example 1C |
|---|---|---|---|
| Escherichia coli JUHL | >100 | >100 | 100 |
| Escherichia coli SS | 0.78 | 3.1 | 0.78 |
| Escherichia coli DC-2 | >100 | >100 | >100 |
| Escherichia coli H560 | 50 | 100 | 100 |
| Escherichia coli KNK437 | 100 | >100 | >100 |
| Enterobacter aerogenes ATCC 13048 | >100 | >100 | >100 |
| Klebsiella pneumoniae ATCC 8045 | >100 | >100 | >100 |
| Providencia struartii CMX 640 | >100 | >100 | >100 |
| Pseudomonas aeruginosa BMH10 | >100 | >100 | >100 |
| Pseudomonas aeruginosa 5007 | >100 | >100 | >100 |
| Pseudomonas aeruginosa K799/WT | 100 | >100 | >100 |
| Pseudomonas aeruginosa K799/61 | 1.56 | 6.2 | 6.2 |
| Pseudomonas capacia 2961 | >100 | >100 | >100 |
| Actinetobacter calcoaceticus CMX 669 | 12.5 | 50 | 50 |
| Pseudonwnas aeruginosa DPHD-5263 | >100 | >100 | >100 |
| Pseudomonas aeruginosa DPHD-2862 | >100 | >100 | >100 |
| Candida albicans CCH 442 | >100 | >100 | >100 |

TABLE 2

Antibacterial Activity (MIC's) of Selected Compounds Continued

| Microorganism | Ery. A | Example 2 | Example 3 |
|---|---|---|---|
| Staphylococcus aureus ATCC 6538P | 0.2 | 3.1 | 1.56 |
| Staphylococcus aureus A5177 | 3.1 | 25 | 50 |
| Staphylococcus aureus A-5278 | >100 | >100 | >100 |
| Staphylococcus aureus CMX 642A | 0.39 | 12.5 | 1.56 |
| Staphylococcus aureus NCTC10649M | 0.39 | 6.2 | 1.56 |
| Staphylococcus aureus CMX 553 | 0.39 | 3.1 | 3.1 |
| Staphylococcus aureus 1775 | >100 | >100 | >100 |
| Staphylococcus epidermidis 3519 | 0.39 | 1.56 | 0.78 |
| Enterococcus faecium ATCC 8043 | 0.05 | 3.1 | 0.39 |
| Streptococcus bovis A-5169 | 0.02 | 0.05 | 0.2 |
| Streptococcus agalactiae CMX 508 | 0.05 | 0.2 | 0.39 |
| Streptococcus pyogenes EES61 | 0.05 | 0.2 | |
| Streptococcus pyogenes 930 | >100 | >100 | >100 |
| Streptococcus pyogenes PIU 2548 | 3.1 | 6.2 | 12.5 |
| Micrococcus luteus ATCC 9341 | 0.05 | 0.2 | 0.1 |
| Micrococcus luteus ATCC 4698 | 0.2 | 3.1 | 1.56 |
| Escherichia coli JUHL | >100 | >100 | 50 |
| Escherichia coli SS | 0.78 | 1.56 | 1.56 |
| Escherichia coli DC-2 | >100 | >100 | 50 |
| Escherichiacoli H560 | 50 | >100 | 25 |
| Escherichia coli KNK437 | 100 | >100 | 160 |
| Enterobacter aerogenes ATCC 13048 | >100 | >100 | >100 |
| Klebsiella pneumoniae ATCC 8045 | >100 | >100 | >100 |
| Providencia struartii CMX 640 | >100 | >100 | >100 |
| Pseudomonas aeruginosa BMH10 | >100 | >100 | >100 |

TABLE 2-continued

Antibacterial Activity (MIC's) of Selected Compounds Continued

| Microorganism | Ery. A | Example 5 | Example 6 |
|---|---|---|---|
| Pseudomonas aeruginosa 5007 | >100 | >100 | >100 |
| Pseudomonas aeruginosa K799/WT | 100 | 6.2 | >100 |
| Pseudomonas aeruginosa K799/61 | 1.56 | >100 | 1.56 |
| Pseudomonas capacia 2961 | >100 | 50 | >100 |
| Actinetobacter calcoaceticus CMX 669 | 12.5 | >100 | 12.5 |
| Pseudomonas aeruginosa DPHD-5263 | >100 | >100 | >100 |
| Pseudomonas aeruginosa DPHD-2862 | >100 | >100 | >100 |
| Candida albicans CCH 442 | >100 | 0.1 | >100 |
| Mycobacterium smegmatis ATCC 114 | 3.1 | — | 0.78 |

| Microorganism | Ery. A | Example 5 | Example 6 |
|---|---|---|---|
| Staphylococcus aureus ATCC 6538P | 0.2 | 0.78 | 0.78 |
| Staphylococcus aureus A5177 | 3.1 | 12.5 | 25 |
| Staphylococcus aureus A-5278 | >100 | >100 | >100 |
| Staphylococcus aureus CMX 642A | 0.39 | 0.78 | 1.56 |
| Staphylococcus aureus NCTC10649M | 0.39 | 0.78 | 0.78 |
| Staphylococcus aureus CMX 553 | 0.39 | 0.78 | 0.78 |
| Staphylococcus aureus 1775 | >100 | >100 | >100 |
| Staphylococcus epidermidis 3519 | 0.39 | 1.56 | 0.78 |
| Enterococcus faecium ATCC 8043 | 0.05 | 0.39 | 0.39 |
| Streptococcus bovis A-5169 | 0.02 | 0.05 | — |
| Streptococcus agalactiae CMX 508 | 0.05 | 0.1 | 0.1 |
| Streptococcus pyogenes EES61 | — | 0.05 | 0.05 |
| Streptococcus pyogenes 930 | >100 | >100 | >100 |
| Streptococcus pyogenes PIU 2548 | 3.1 | — | 6.2 |
| Micrococcus luteus ATCC 9341 | 0.05 | 0.1 | 0.1 |
| Micrococcus luteus ATCC 4698 | 0.2 | 3.1 | 1.56 |
| Escherichia coli JUHL | >100 | 25 | >100 |
| Escherichia coli SS | 0.78 | 0.78 | 0.78 |
| Escherichia coli DC-2 | >100 | 50 | >100 |
| Escherichia coli H560 | 50 | 50 | 100 |
| Escherichia coli KNK437 | 100 | 50 | >100 |
| Enterobacter aerogenes ATCC 13048 | >100 | 100 | >100 |
| Klebsiella pneumoniae ATCC 8045 | >100 | 100 | >100 |
| Providencia struartii CMX 640 | >100 | >100 | >100 |
| Pseudomonas aeruginosa BMH10 | >100 | 100 | >100 |
| Pseuaomonas aeruginosa 5007 | >100 | >100 | >100 |
| Pseudomonas aeruginosa K799/WT | 100 | >100 | >100 |
| Pseudomonas aeruginosa K799/61 | 1.56 | 1.56 | 12.5 |
| Pseudomonas capacia 2961 | >100 | >100 | >100 |
| Actinetobacter calcoaceticus CMX 669 | 12.5 | 12.5 | 25 |
| Pseudomonas aeruginosa DPHD-5263 | >100 | >100 | >100 |
| Pseudomonas aeruginosa DPHD-2862 | >100 | >100 | >100 |
| Candida albicans CCH442 | >100 | >100 | >100 |
| Mycobacterium smegmatis ATCC 114 | 3.1 | 1.56 | 0.2 |

| Microorganism | Ery. A | Example 7 | Example 8 |
|---|---|---|---|
| Staphylococcus aureus ATCC 6538P | 0.2 | 0.39 | 0.78 |
| Staphylococcus aureus A5177 | 3.1 | 3.1 | 12.5 |
| Staphylococcus aureus A-5278 | >100 | >100 | >100 |
| Staphylococcus aureus CMX 642A | 0.39 | 0.39 | 0.78 |
| Staphylococcus aureus NCTC10649M | 0.39 | 0.39 | 0.78 |
| Staphylococcus aureus CMX 553 | 0.39 | 0.39 | 0.78 |
| Staphylococcus aureus 1775 | >100 | >100 | >100 |
| Staphylococcus epidermidis 3519 | 0.39 | 0.39 | 0.78 |
| Enterococcus faecium ATCC 8043 | 0.05 | 0.39 | 0.39 |
| Streptococcus bovis A-5169 | 0.02 | 0.01 | 0.2 |
| Streptococcus agalactiae CMX 508 | 0.05 | 0.01 | 0.39 |
| Streptococcus pyogenes EES61 | — | 0.01 | 0.1 |
| Streptococcus pyogenes 930 | >100 | >100 | >100 |
| Streptococcus pyogenes PIU 2548 | 3.1 | — | 25 |
| Micrococcus luteus ATCC 9341 | 0.05 | 0.02 | 0.1 |
| Micrococcus luteus ATCC 4698 | 0.2 | 0.78 | 1.56 |
| Escherichia coli JUHL | >100 | 12.5 | 100 |
| Escherichia coli SS | 0.78 | 0.2 | 1.56 |
| Escherichia coli DC-2 | >100 | 6.2 | >100 |
| Escherichia coli H560 | 50 | 1.56 | 50 |
| Escherichia coli KNK437 | 100 | 12.5 | >100 |
| Enterobacter aerogenes ATCC 13048 | >100 | 50 | >100 |
| Klebsiella pneumoniae ATCC 8045 | >100 | 25 | >100 |
| Providencia struartii CMX 640 | >100 | >100 | >100 |
| Pseudomonas aeruginosa BMH10 | >100 | 25 | >100 |
| Pseudomonas aeruginosa 5007 | >100 | >100 | >100 |
| Pseudomonas aeruginosa K799/WT | 100 | 100 | >100 |
| Pseudomonas aeruginosa K799/61 | 1.56 | 0.39 | 3.1 |
| Pseudomonas capacia 2961 | >100 | >100 | >100 |
| Actinetobacter calcoaceticus CMX 669 | 12.5 | 12.5 | 50 |
| Pseudomonas aeruginosa DPHD-5263 | >100 | >100 | >100 |
| Pseudomonas aeruginosa DPHD-2862 | >100 | >100 | >100 |
| Candida albicans CCH 442 | >100 | >100 | >100 |
| Mycobacterium smegmatis ATCC 114 | 3.1 | 0.2 | 6.2 |
| | | | 0.39 |

| Microorganism | Ery. A | Example 9 | Example 10 |
|---|---|---|---|
| Staphylococcus aureus ATCC 6538P | 0 2 | 3.1 | 0 2 |
| Staphylococcus aureus A5177 | 3.1 | — | 6.2 |
| Staphylococcus aureus A-5278 | >100 | >100 | >100 |
| Staphylococcus aureus CMX 642A | 0.39 | 3.1 | 0.39 |
| Staphylococcus aureus NCTC10649M | 0.39 | 3.1 | 0.39 |
| Staphylococcus aureus CMX 553 | 0.39 | — | 0.39 |
| Staphylococcus aureus 1775 | >100 | >100 | >100 |
| Staphylococcus epidermidis 3519 | 0.39 | 3.1 | 0.2 |
| Enterococcus faecium ATCC 8043 | 0.05 | 3.1 | 0.1 |
| Streptococcus bovis A-5169 | 0.02 | 3.1 | 0.01 |
| Streptococcus agalactiae CMX 508 | 0.05 | 3.1 | 0.05 |
| Streptococcus pyogenes EES61 | — | — | 0.01 |
| Streptococcus pyogenes 930 | >100 | >100 | >100 |
| Streptococcus pyogenes PIU 2548 | 3.1 | 12.5 | — |
| Micrococcus luteus ATCC 9341 | 0.05 | 3.1 | 0.05 |
| Micrococcus luteus ATCC 4698 | 0.2 | — | 0.78 |
| Escherichia coli JUHL | >100 | >100 | 50 |
| Escherichia coli SS | 0.78 | — | 0.78 |
| Escherichia coli DC-2 | >100 | — | 100 |
| Escherichia coli H560 | 50 | >100 | 25 |
| Escherichia coli KNK437 | 100 | >100 | >100 |
| Enterobacter aerogenes ATCC 13048 | >100 | >100 | >100 |
| Klebsiella pneumoniae ATCC 8045 | >100 | >100 | >100 |
| Providencia struartii CMX 640 | >100 | >100 | >100 |
| Pseudomonas aeruginosa BMH10 | >100 | >100 | 100 |
| Pseudomonas aeruginosa 5007 | >100 | >100 | >100 |
| Pseudomonas aeruginosa K799/WT | 100 | >100 | >100 |
| Pseudomonas aeruginosa K799/61 | 1.56 | 12.5 | 3.1 |
| Pseudomonas capacia 296I | >100 | >100 | >100 |
| Actinetobacter calcoaceticus CMX 669 | 12.5 | 50 | 12.5 |
| Pseudomonas aeruginosa DPHD-5263 | >100 | >100 | >100 |
| Pseudomonas aeruginosa DPHD-2862 | >100 | >100 | >100 |
| Candida albicans CCH 442 | >100 | >100 | >100 |
| Mycobacterium smeginatis ATCC 114 | 3.1 | 3.1 | 0.39 |
| Nocarrdia asteroides ATCC 9970 | | | |

| Microorganism | Ery. A | Example 11 | Example 12 |
|---|---|---|---|
| Staphylococcus aureus ATCC 6538P | 0.2 | 0.78 | 0.39 |
| Staphylococcus aureus A5177 | 3.1 | 6.2 | — |
| Staphylococcus aureus A-5278 | >100 | >100 | >100 |
| Staphylococcus aureus CMX 642A | 0.39 | 1.56 | 0.39 |
| Staphylococcus aureus NCTC10649M | 0.39 | 0.78 | 0.39 |
| Staphylococcus aureus CMX 553 | 0.39 | 0.78 | 0.39 |
| Staphylococcus aureus 1775 | >100 | >100 | >100 |
| Staphylococcus epidermidis 3519 | 0.39 | 0.78 | 0.39 |
| Enterococcus faecium ATCC 8043 | 0.05 | 0.39 | 0.1 |
| Streptococcus bovis A-5169 | 0.02 | 0.2 | 0.05 |
| Streptococcus agalactiae CMX 508 | 0.05 | 0.05 | 0.05 |
| Streptococcus pyogenes EES61 | — | 0.05 | 0.05 |
| Streptococcus pyogenes 930 | >100 | >100 | >100 |
| Streptococcus pyogenes PIU 2548 | 3.1 | 25 | 12.5 |
| Micrococcus luteus ATCC 9341 | 0.05 | 0.05 | 0.05 |
| Micrococcus luteus ATCC 4698 | 0.2 | — | 0.78 |
| Escherichia coli JUHL | >100 | 100 | 50 |
| Escherichia coli SS | 0.78 | 1.56 | 0.78 |
| Escherichia coli DC-2 | >100 | >100 | >100 |
| Escherichia coli H560 | 50 | 50 | 25 |
| Escherichia coli KNK437 | 100 | >100 | 100 |
| Enterobacter aerogenes ATCC 13048 | >100 | >100 | >100 |
| Klebsiella pneumoniae ATCC 8045 | >100 | >100 | >100 |
| Providencia struartii CMX 640 | >100 | >100 | >100 |
| Pseudomonas aeruginosa BMH10 | >100 | >100 | >100 |

TABLE 2-continued

Antibacterial Activity (MIC's) of Selected Compounds Continued

| Microorganism | | | |
|---|---|---|---|
| Pseudomonas aeruginosa 5007 | >100 | >100 | >100 |
| Pseudomonas aeruginosa K799/WT | 100 | >100 | >100 |
| Pseudomonas aeruginosa K799/61 | 1.56 | — | 1.56 |
| Pseudomonas capacia 2961 | >100 | >100 | >100 |
| Actinetobacter calcoaceticus CMX 669 | 12.5 | 25 | 12.5 |
| Pseudomonas aeruginosa DPHD-5263 | >100 | >100 | >100 |
| Pseudomonas aeruginosa DPHD-2862 | >100 | >100 | >100 |
| Candida albicans CCH 442 | >100 | >100 | >100 |
| Mycobacterium smegmatis ATCC 114 | 3.1 | 0.39 | 0.78 |
| Nocarrdia asteroides ATCC 9970 | | 0.1 | |

TABLE 2

Antibacterial Activity (MIC's) of Selected Compounds Continued

| Microorganism | Ery, A | Example 11 | Example 12 |
|---|---|---|---|
| Staphylococcus aureus ATCC 6538P | 0.2 | 0.78 | 0.39 |
| Staphylococcus aureus A5177 | 3.1 | 6.2 | — |
| Staphylococcus aureus A-5278 | >100 | >100 | >100 |
| Stapylococcus aureus CMX 642A | 0.39 | 1.56 | 0.39 |
| Staphylococcus aureus NCTC10649M | 0.39 | 0.78 | 0.39 |
| Staphylococcus aureus CMX 553 | 0.39 | 0.78 | 0.39 |
| Staphylococcus aureus 1775 | >100 | >100 | >100 |
| Staphylococcus epidermidis 3519 | 0.39 | 0.78 | 0.39 |
| Enterococcus faecium ATCC 8043 | 0.05 | 0.39 | 0.1 |
| Streptococcus bovis A-5169 | 0.02 | 0.2 | 0.05 |
| Streptococcus agalactiae CMX 508 | 0.05 | 0.05 | 0.05 |
| Streptococcus pyogenes EES61 | — | 0.05 | 0.05 |
| Streptococcus pyogenes 930 | >100 | >100 | >100 |
| Streptococcus pyogenes PIU 2548 | 3.1 | 25 | 12.5 |
| Micrococcus luteus ATCC 9341 | 0.05 | 0.05 | 0.05 |
| Micrococcus luteus ATCC 4698 | 0.2 | — | 0.78 |
| Escherichia coli JUHL | >100 | 100 | 50 |
| Escherichia coli SS | 0.78 | 1.56 | 0.78 |
| Escherichia coli DC-2 | >100 | >100 | >100 |
| Escherichia coli H560 | 50 | 50 | 25 |
| Escherichia coli KNK 437 | 100 | >100 | 100 |
| Enterobacter aerogenes ATCC 13048 | >100 | >100 | >100 |
| Klebsiella pneumoniae ATCC 8045 | >100 | >100 | — |
| Providencia struartii CMX 640 | >100 | >100 | >100 |
| Pseudomonas aeruginosa BMH10 | >100 | >100 | >100 |
| Pseudomonas aeruginosa 5007 | >100 | >100 | >100 |
| Pseudomonas aeruginosa K799/WT | 100 | >100 | >100 |
| Pseudomonas aeruginosa K799/61 | 1.56 | — | 1.56 |
| Pseudomonas capacia | >100 | >100 | >100 |

TABLE 2-continued

Antibacterial Activity (MIC's) of Selected Compounds Continued

| Microorganism | Ery, A | Example 11 | Example 12 |
|---|---|---|---|
| 2961 | | | |
| Actinetobacter calcoaceticus CMX 669 | 12.5 | 25 | 12.5 |
| Pseudomonas aeruginosa DPHD-5263 | >100 | >100 | >100 |
| Pseudomonas aeruginosa DPHD-2862 | >100 | >100 | >100 |
| Candida albicans CCH 442 | >100 | >100 | >100 |
| Mycobacterium smegmatis ATCC 114 | 3.1 | 0.39 | 0.78 |
| Nocarrdia asteroides ATCC 9970 | | 0.1 | |

It is understood that the foregoing detailed description and accompanying examples are merely illustrative and are not to be taken as limitations upon the scope of the invention which is defined solely by the appended claims and their equivalents. Various changes and modifications to the disclosed embodiments will be apparent to those skilled in the art, and may be made without departing from the spirit and scope thereof.

What is claimed is:

1. A compound having the formula

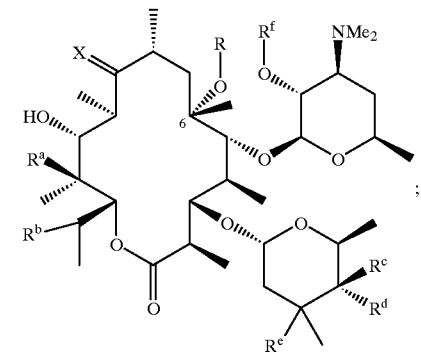

(II)

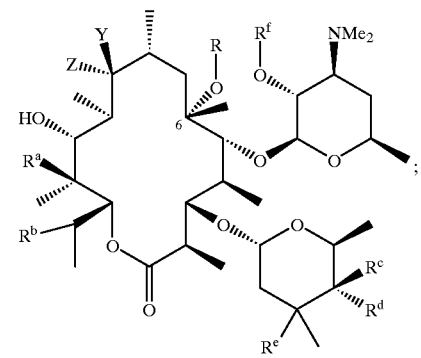

(III)

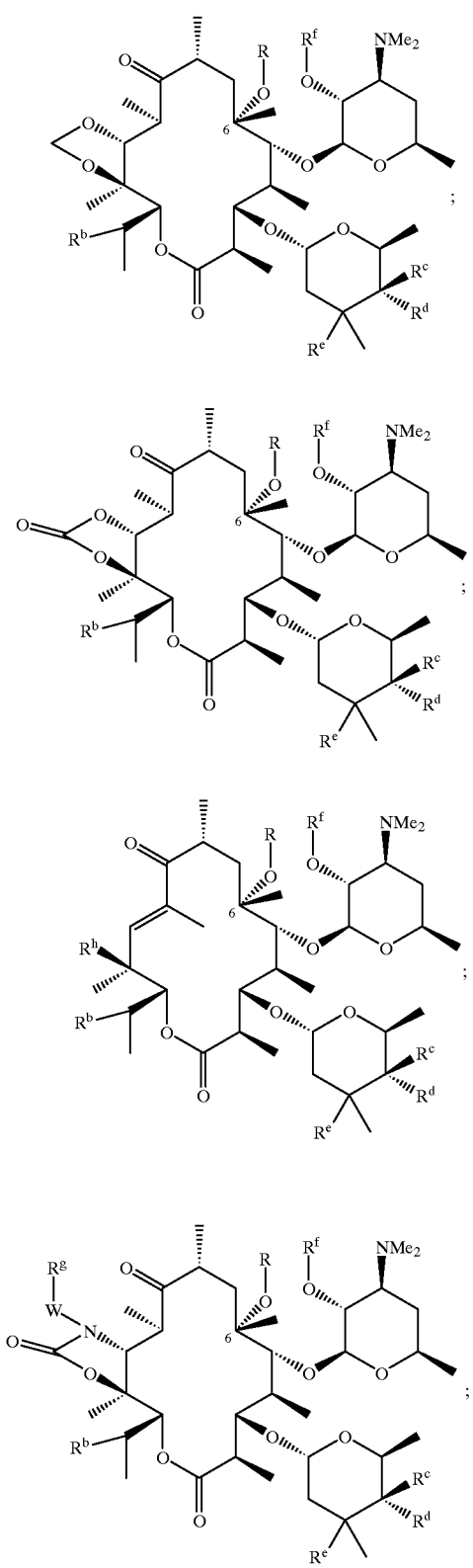

or a pharmaceutically acceptable salt, esters or prodrug thereof; wherein

X is selected from the group consisting of
(1) =O,
(2) =N—OH,
(3) =N—O—R$^1$ where R$^1$ is selected from the group consisting of
  (a) unsubstituted C$_1$–C$_{12}$-alkyl,
  (b) C$_1$–C$_{12}$-alkyl substituted with aryl,
  (c) C$_1$–C$_{12}$-alkyl substituted with substituted aryl,
  (d) C$_1$–C$_{12}$-alkyl substituted with heteroaryl,
  (e) C$_1$–C$_{12}$-alkyl substituted with substituted heteroaryl,
  (f) C$_3$–C$_{12}$-cycloalkyl,
  (g) —Si—(R$^2$)(R$^3$)(R$^4$) wherein R$^2$, R$^3$ and R$^4$ are each independently selected from C$_1$–C$_{12}$-alkyl, and
  (h) —Si—(Aryl)$_3$;
and
(4) =N—O—C(R$^5$)(R$^6$)—O—R$^1$ where R$^1$ is as defined above and R$^5$ and R$^6$ are each independently selected from the group consisting of
  (a) hydrogen,
  (b) unsubstituted C$_1$–C$_{12}$-alkyl,
  (c) C$_1$–C$_{12}$-alkyl substituted with aryl,
  (d) C$_1$–C$_{12}$-alkyl substituted with substituted aryl,
  (e) C$_1$–C$_{12}$-alkyl substituted with heteroaryl,
  and (f) $C_1$–$C_{12}$-alkyl substituted with substituted heteroaryl, or $R^5$ and $R^6$ taken together with the atom to which they are attached form a $C_3$–$C_{12}$-cycloalkyl ring;

$R^a$ is hydrogen or hydroxy;

$R^b$ is hydrogen or hydroxy;

one of $R^c$ and $R^d$ is hydrogen and the other of $R^c$ and $R^d$ is selected from the group consisting of
(1) hydroxy,
(2) protected hydroxy,
(3) halogen,
(4) $NR^7R^8$ where $R^7$ and $R^8$ are independently selected from the group consisting of
  (a) hydrogen,
  (b) $C_1$–$C_{12}$-alkyl,
  (c) substituted $C_1$–$C_{12}$-alkyl,
  (d) $C_1$–$C_8$-cycloalkyl,
  (e) substituted $C_1$–$C_8$-cycloalkyl,
  (f) $C_1$–$C_{12}$-alkyl substituted with aryl,
  (g) $C_1$–$C_{12}$-alkyl substituted with substituted aryl,
  (h) $C_1$–$C_{12}$-alkyl substituted with heterocycloalkyl,
  (i) $C_1$–$C_{12}$-alkyl substituted with substituted heterocycloalkyl,
  (j) $C_1$–$C_{12}$-alkyl substituted with $C_1$–$C_8$-cycloalkyl,
  (k) $C_1$–$C_{12}$-alkyl substituted with substituted $C_1$–$C_8$-cycloalkyl,
  (l) $C_1$–$C_{12}$-alkyl substituted with heteroaryl, and
  (m) $C_1$–$C_{12}$-alkyl substituted with substituted heteroaryl, or $R^7$ and $R^8$ taken together with the atom to which they are attached form a 3–10 membered heterocycloalkyl ring,
(5) O—CO—NH-aryl,
(6) O—CO—NH-heteroaryl,
(7) O—CO—$NR^7R^8$, where $R^7$ and $R^8$ are as defined above,
(8) O—$SO_2$—$C_1$–$C_6$-alkyl,
(9) O—$SO_2$-(substituted $C_1$–$C_6$-alkyl), and
(10) O—$SO_2$—$CH_2$—$CH_2$—$NR^7R^8$, where $R^7$ and $R^8$ are as defined above, or $R^c$ and $R^d$ taken together form the grouping selected from the group consisting of
(1) =O,
(2) =N—OH, and
(3) =N—$OR^1$ wherein $R^1$ is as defined above;

$R^e$ is methoxy, fluorine or hydroxy;

$R^f$ is hydrogen or a hydroxy protecting group;

W is absent or selected from the group consisting of —O—, —NH—CO—, —N=CH— and —NH—;

$R^g$ is selected from the group consisting of
(1) hydrogen,
(2) $C_1$–$C_6$-alkyl optionally substituted with one or more substituents selected from the group consisting of
  (a) aryl,
  (b) substituted-aryl,
  (c) heteroaryl,
  (d) substituted-heteroaryl,
  (e) hydroxy,
  (f) $C_1$–$C_6$-alkoxy,
  (g) $NR^9R^{10}$, where $R^9$ and $R^{10}$ are independently selected from hydrogen and $C_1$–$C_6$-alkyl, or $R^9$ and $R^{10}$ are taken with the nitrogen atom to which they are connected to form a 3- to 7-membered ring which, when the ring is a 5- to 7-membered ring, may optionally contain a hetero function selected from the group consisting of —O—, —NH—, —N($C_1$–$C_6$-alkyl—)—, —N(aryl)—, —N(aryl-$C_1$–$C_6$-alkyl—)—, —N(substituted-aryl-$C_1$–$C_6$-alkyl—)—, —N(heteroaryl)—, —N(heteroaryl-$C_1$–$C_6$-alkyl—)—, —N(substituted-heteroaryl-$C_1$–$C_6$-alkyl—)—, and —S— or —S(O)$_n$—, wherein n is 1 or 2, and
(h) —$CH_2$—M—$R^{11}$
  wherein M is selected from the group consisting of:
  (i) —C(O)—NH—,
  (ii) —NH—C(O)—,
  (iii) —NH—,
  (iv) —N=,
  (v) —N($CH_3$)—,
  (vi) —NH—C(O)—O—
  (vii) —NH—C(O)—NH—
  (viii) —O—C(O)—NH—
  (ix) —O—C(O)—O—
  (x) —O—,
  (xi) —S(O)$_n$—, wherein n is 0, 1 or 2,
  (xii) —C(O)—O—,
  (xiii) —O—C(O)—, and
  (xiv) —C(O)—, and $R^{11}$ is selected from the group consisting of:
  (i) $C_1$–$C_6$-alkyl, optionally substituted with a substituent selected from the group consisting of
    (aa) aryl,
    (bb) substituted-aryl,
    (cc) heteroaryl, and
    (dd) substituted-heteroaryl,
  (ii) aryl,
  (iii) substituted-aryl,
  (iv) heteroaryl,
  (v) substituted-heteroaryl, and
  (vi) heterocycloalkyl,
(3) $C_3$–$C_7$-cycloalkyl,
(4) aryl,
(5) substituted-aryl,
(6) heteroaryl, and
(7) substituted-heteroaryl;

$R^h$ is selected from the group consisting of
(1) hydrogen,
(2) hydroxy,
(3) —O—C(O)-imidazolyl,
(4) —O—C(O)—O—$C_1$–$C_6$-alkyl,
(5) —O—C(O)—O-aryl,
(6) —O—C(O)—O-(substituted aryl),
(7) —O—C(O)—Cl, and
(8) —O—C(O)—$NH_2$;

R is selected from the group consisting of
(1) methyl substituted with a moiety selected from the group consisting of
  (a) CN,
  (b) F, (c) —$CO_2R^{12}$ wherein $R^{12}$ is $C_1$–$C_3$-alkyl or aryl substituted $C_1$–$C_3$-alkyl, or heteroaryl substituted $C_1$–$C_3$-alkyl,
(d) $S(O)_nR^{12}$ where n is 0, 1 or 2 and $R^{12}$ is as defined above,
(e) $NHC(O)R^{12}$ where $R^{12}$ is as defined above,
(f) $NHC(O)NR^{13}R^{14}$ wherein $R^{13}$ and $R^{14}$ are independently selected from hydrogen and $C_1$–$C_3$-alkyl,
(g) aryl,
(h) substituted aryl,
(i) heteroaryl, and
(j) substituted heteroaryl,
(2) $C_2$–$C_{10}$-alkyl,
(3) $C_2$–$C_{10}$-alkyl substituted with one or more substituents selected from the group consisting of
(a) halogen,
(b) hydroxy,
(c) $C_1$–$C_3$-alkoxy,
(d) $C_1$–$C_3$-alkoxy-$C_1$–$C_3$-alkoxy,
(e) oxo,
(f) —$N_3$,
(g) —CHO,
(h) O—$SO_2$-(substituted $C_1$–$C_6$-alkyl),
(i) —$NR^{15}R^{16}$ wherein $R^{15}$ and $R^{16}$ are selected from the group consisting of
(i) hydrogen,
(ii) $C_1$–$C_{12}$-alkyl,
(iii) substituted $C_1$–$C_{12}$-alkyl,
(iv) $C_1$–$C_{12}$-alkenyl,
(v) substituted $C_1$–$C_{12}$-alkenyl,
(vi) $C_1$–$C_{12}$-alkynyl,
(vii) substituted $C_1$–$C_{12}$-alkynyl,
(viii) aryl,
(ix) $C_3$–$C_8$-cycloalkyl,
(x) substituted $C_3$–$C_8$-cycloalkyl,
(xi) substituted aryl,
(xii) heterocycloalkyl,
(xiii) substituted heterocycloalkyl,
(xiv) $C_1$–$C_{12}$-alkyl substituted with aryl,
(xv) $C_1$–$C_{12}$-alkyl substituted with substituted aryl,
(xvi) $C_1$–$C_{12}$-alkyl substituted with heterocycloalkyl,
(xvii) $C_1$–$C_{12}$-alkyl substituted with substituted heterocycloalkyl,
(xviii) $C_1$–$C_{12}$-alkyl substituted with $C_3$–$C_8$-cycloalkyl,
(xix) $C_1$–$C_{12}$-alkyl substituted with substituted $C_3$–$C_8$-cycloalkyl,
(xx) heteroaryl,
(xxi) substituted heteroaryl,
(xxii) $C_1$–$C_{12}$-alkyl substituted with heteroaryl, and
(xxiii) $C_1$–$C_{12}$-alkyl substituted with substituted heteroaryl,
or
$R^{15}$ and $R^{16}$ are taken together with the atom to which they are attached form a 3–10 membered heterocycloalkyl ring which may be substituted with one or more substituents independently selected from the group consisting of
(i) halogen,
(ii) hydroxy,
(iii) $C_1$–$C_3$-alkoxy,
(iv) $C_1$–$C_3$-alkoxy-$C_1$–$C_3$-alkoxy,
(v) oxo,
(vi) $C_1$–$C_3$-alkyl,
(vii) halo-$C_1$–$C_3$-alkyl, and
(vii) $C_1$–$C_3$-alkoxy-$C_1$–$C_3$-alkyl,
(j) —$CO_2R^{12}$ wherein $R^{12}$ is as defined above,
(k) —$C(O)NR^{13}R^{14}$ wherein $R^{13}$ and $R^{14}$ are as defined above,
(l) =N—O—$R^{12}$ wherein $R^{13}$ is as previously defined,
(m) —C≡N,
(n) O—$S(O)_nR^{12}$ wherein n is 0, 1 or 2 and $R^{12}$ is as defined above,
(o) aryl,
(p) substituted aryl,
(q) heteroaryl,
(r) substituted heteroaryl,
(s) $C_3$–$C_8$-cycloalkyl,
(t) substituted $C_3$–$C_8$-cycloalkyl,
(u) $C_1$–$C_{12}$-alkyl substituted with heteroaryl,
(v) heterocycloalkyl,
(w) substituted heterocycloalkyl,
(x) $NHC(O)R^{12}$ where $R^{12}$ is as previously defined,
(y) $NHC(O)NR^{13}R^{14}$ wherein $R^{13}$ and $R^{14}$ are as previously defined,
(z) =N—$NR^{15}R^{16}$ wherein $R^{15}$ and $R^{16}$ are as previously defined,
(aa) =N—$R^{11}$ wherein $R^{11}$ is as previously defined,
(bb) =N—$NHC(O)R^{12}$ wherein $R^{12}$ is as previously defined, and
(cc) =N—$NHC(O)NR^{13}R^{14}$ wherein $R^{13}$ and $R^{14}$ are as previously defined;
(4) $C_3$-alkenyl substituted with a moiety selected from the group consisting of
(a) halogen,
(b) —CHO,
(c) —$CO_2R^{12}$ where $R^{12}$ is as defined above,
(d) —C(O)—$R^{11}$ where $R^{11}$ is as defined above,
(e) —$C(O)NR^{13}R^{14}$ wherein $R^{13}$ and $R^{14}$ are as previously defined,
(f) —C≡N,
(g) aryl,
(h) substituted aryl,
(i) heteroaryl,
(j) substituted heteroaryl,
(k) $C_3$–$C_7$-cycloalkyl, and
(l) $C_1$–$C_{12}$-alkyl substituted with heteroaryl,
(5) $C_4$–$C_{10}$-alkenyl;
(6) $C_4$–$C_{10}$-alkenyl substituted with one or more substituents selected from the group consisting of
(a) halogen,
(b) $C_1$–$C_3$-alkoxy,
(c) oxo,
(d) —CHO,
(e) —$CO_2R^{12}$ where $R^{12}$ is as defined above,
(f) —$C(O)NR^{13}R^{14}$ wherein $R^{13}$ and $R^{14}$ are as previously defined,
(g) —$NR^{15}R^{16}$ wherein $R^{15}$ and $R^{16}$ are previously defined,
(h) =N—O—$R^{12}$ where $R^{12}$ is as previously defined,
(i) —C≡N,
(j) O—$S(O)_nR^{12}$ where n is 0, 1 or 2 and $R^{12}$ is as previously defined,
(k) aryl, (l) substituted aryl,
(m) heteroaryl,
(n) substituted heteroaryl,
(o) $C_3$–$C_7$-cycloalkyl,
(p) $C_1$–$C_{12}$-alkyl substituted with heteroaryl,
(q) $NHC(O)R^{12}$ where $R^{12}$ is as previously defined,
(r) $NHC(O)NR^{13}R^{14}$ wherein $R^{13}$ and $R^{14}$ are as previously defined,
(s) $=N-NR^{15}R^{16}$ wherein $R^{15}$ and $R^{16}$ are as previously defined,
(t) $=N-R^{11}$ wherein $R^{11}$ is as previously defined,
(u) $=N-NHC(O)R^{12}$ where $R^{12}$ is as previously defined,
and
(v) $=N-NHC(O)NR^{13}R^{14}$ wherein $R^{13}$ and $R^{14}$ are as previously defined;
(7) $C_3$–$C_{10}$-alkynyl;
and
(8) $C_3$–$C_{10}$-alkynyl substituted with one or more substituents selected from the group consisting of
(a) trialkylsilyl,
(b) aryl,
(c) substituted aryl,
(d) heteroaryl,
and
(e) substituted heteroaryl;
one of Y and Z is hydrogen and the other is selected from a group consisting of
(1) hydrogen,
(2) hydroxy,
(3) protected hydroxy,
and
(4) $NR^7R^8$ wherein $R^7$ and $R^8$ are as defined above;
and
A, B, D and E, with the provision that at least two of A, B, D and E are hydrogen, are independently selected from the group consisting of:
(a) hydrogen;
(b) $C_1$–$C_6$-alkyl, optionally substituted with one or more substituents selected from the group consisting of:
(i) aryl;
(ii) substituted-aryl;
(iii) heteroaryl;
(iv) substituted-heteroaryl;
(v) heterocycloalkyl;
(vi) hydroxy;
(vii) $C_1$–$C_6$-alkoxy;
(viii) halogen consisting of Br, Cl, F or I; and
(ix) $NR^9R^{10}$, wherein $R^9$ and $R^{10}$ are as defined above;
(c) $C_3$–$C_7$-cycloalkyl;
(d) aryl;
(e) substituted-aryl;
(f) heteroaryl;
(g) substituted-heteroaryl;
(h) heterocycloalkyl; and
(i) a group selected from option (b) above further substituted with $-M-R^{11}$, wherein M and $R^{11}$ are as defined above;

or
any one pair of substituents, consisting of AB, AD, AE, BD, BE or DE, is taken together with the atom or atoms to which they are attached to form a 3- to 7-membered ring optionally containing a hetero function selected from the group consisting of —O—, —NH—, —N($C_1$–$C_6$-alkyl—)—, —N(aryl-$C_1$–$C_6$-alkyl—)—, —N(substituted-aryl-$C_1$–$C_6$-alkyl—)—, —N(heteroaryl-$C_1$–$C_6$-alkyl—)—, —N(substituted-heteroaryl-$C_1$–$C_6$-alkyl—)—, —S— or —S(O)$_n$—, wherein n is 1 or 2, —C(O)—NH—, —C(O)—$NR^{12}$—, wherein $R^{12}$ is as defined above, —NH—C(O)—, —$NR^{12}$—C(O)—, wherein $R^{12}$ is as defined above, and —C(=NH)—NH—.

2. A compound according to claim 1 having the formula

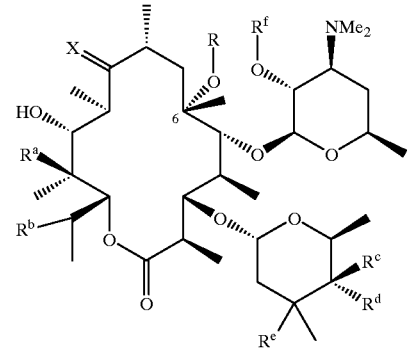

wherein X, R, $R^a$, $R^b$, $R^c$, $R^d$, $R^e$ and $R^f$ are as defined in claim 1.

3. A compound according to claim 2 wherein $R^a$ is hydroxy, $R^b$ is hydrogen, $R^c$ is hydrogen, $R^d$ is hydroxy, $R^e$ is methoxy, and $R^f$ is hydrogen.

4. A compound according to claim 1 having the formula

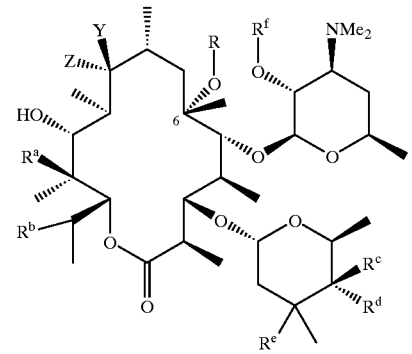

wherein Y, Z, R, $R^a$, $R^b$, $R^c$, $R^d$, $R^e$ and $R^f$ are as defined in claim 1.

5. A compound according to claim 3 wherein $R^a$ is hydroxy, $R^b$ is hydrogen, $R^c$ is hydrogen, $R^d$ is hydroxy, $R^e$ is methoxy, and $R^f$ is hydrogen.

6. A compound according to claim 1 having the formula

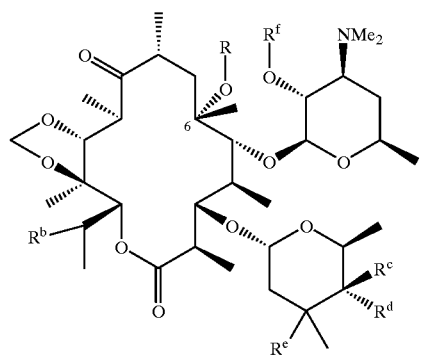

wherein R, $R^b$, $R^c$, $R^d$, $R^e$ and $R^f$ are as defined in claim 1.

7. A compound according to claim 1 having the formula

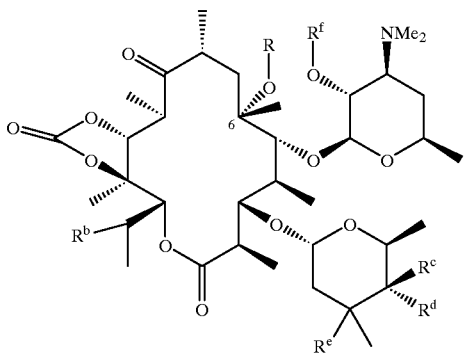

wherein R, $R^b$, $R^c$, $R^d$, $R^e$ and $R^f$ are as defined in claim 1.

8. A compound according to claim 1 having the formula

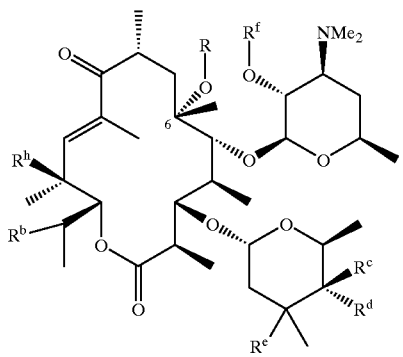

wherein R, $R^b$, $R^c$, $R^d$, $R^e$, $R^f$ and $R^h$, are as defined in claim 1.

9. A compound according to claim 1 having the formula

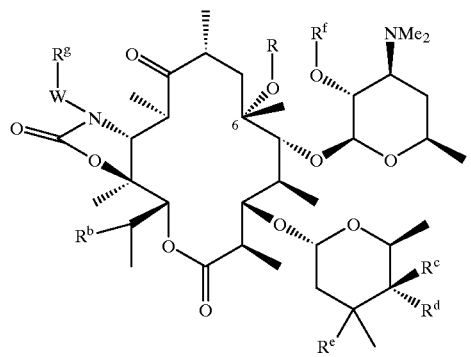

wherein W, R, $R^b$, $R^c$, $R^d$, $R^e$, $R^f$ and $R^g$ are as defined in claim 1.

10. A compound according to claim 1 having the formula

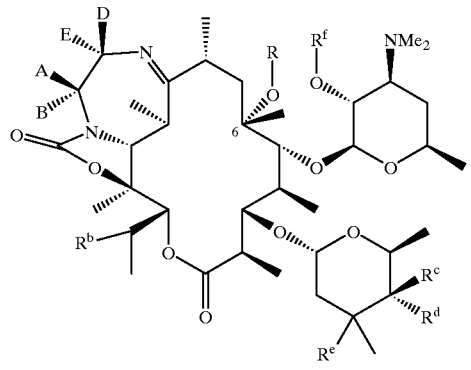

wherein A, B, D, E, R, $R^b$, $R^c$, $R^d$, $R^e$ and $R^f$ are as defined in claim 1.

11. A compound according to claim 1 having formula

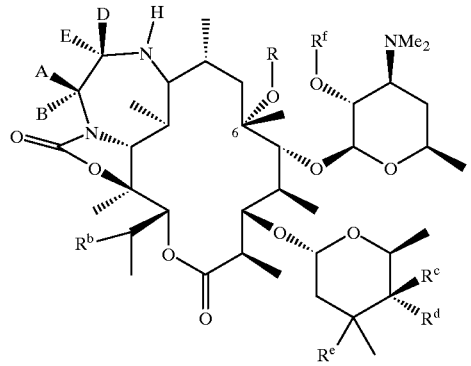

wherein A, B, D, E, R, $R^b$, $R^c$, $R^d$, $R^e$ and $R^f$ are as defined in claim 1.

12. A compound according to claim 1 which is selected from the group consisting of:

(A) compound wherein A, B, D, E, W, X, Y, Z, R, $R^a$, $R^b$, $R^c$, $R^d$, $R^e$, $R^f$, $R^g$, and $R^h$ are as defined in claim 1, and R is selected from the group consisting of:

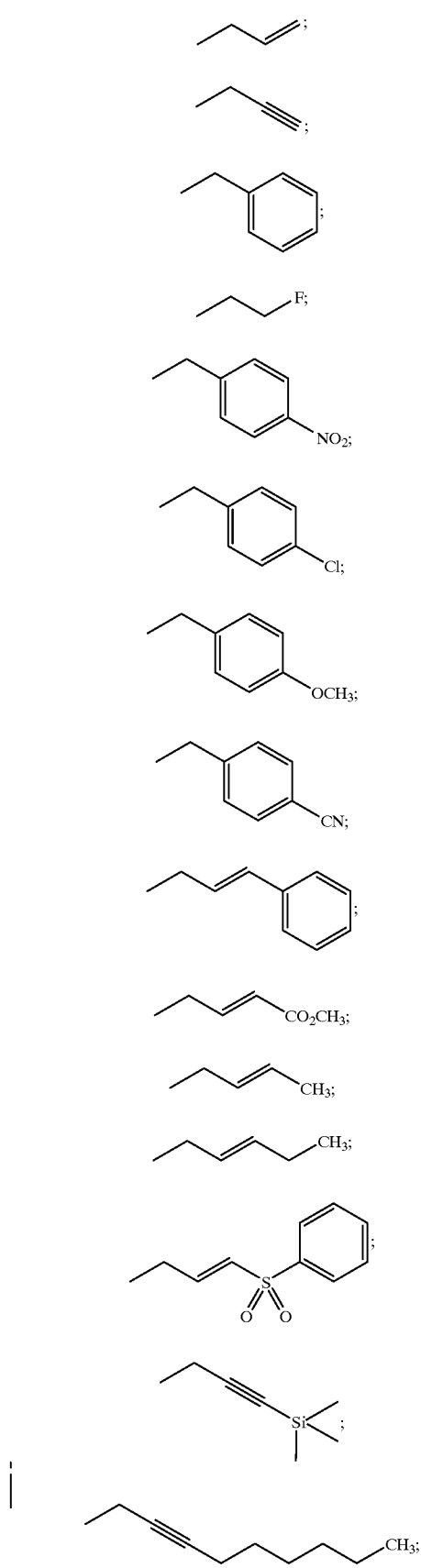
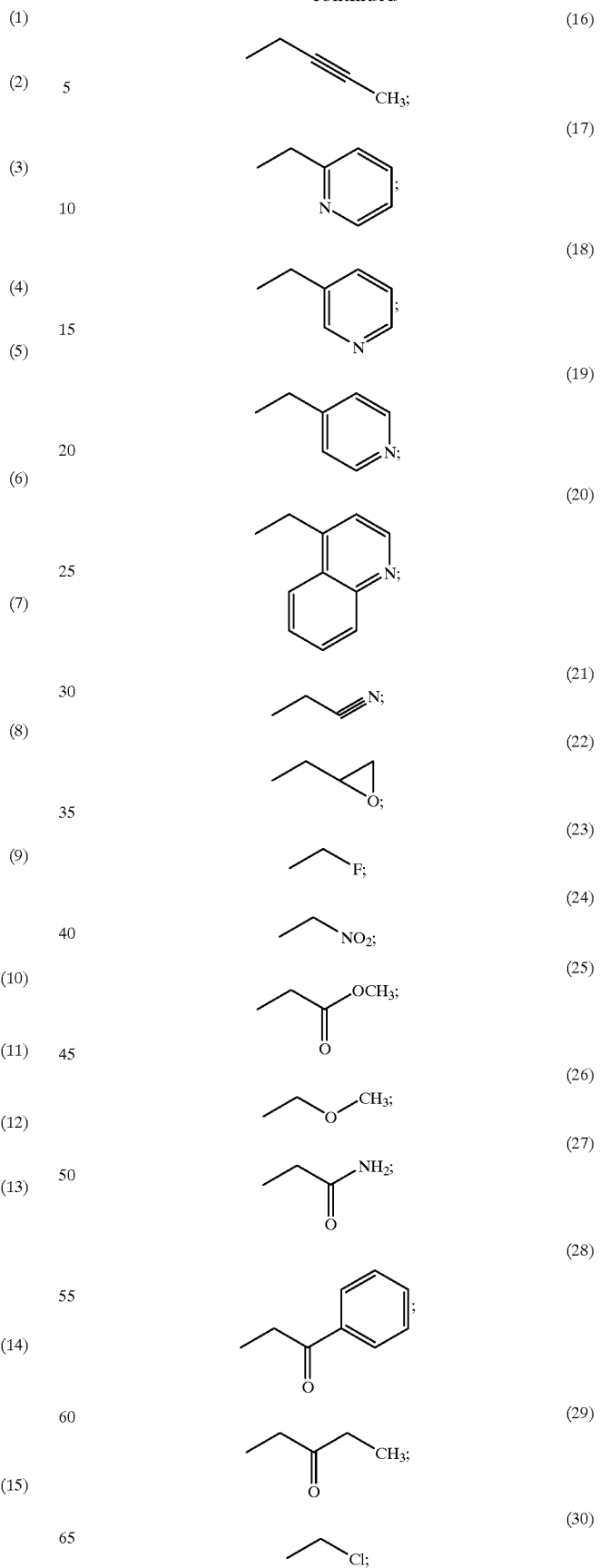

(31) 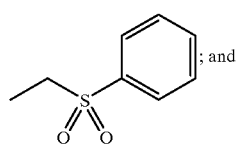 ; and

(32) 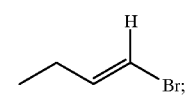

(B) compounds of formula X wherein $R^a$ is OH; $R^b$ is OH; $R^c$ is H; $R^d$ is H; $R^e$ is methoxy; $R^f$ is H; wherein R is selected from the group consisting of:

(1) 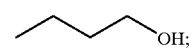

(2) 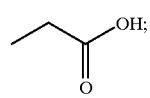

(3) 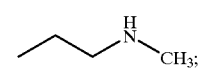

(4) 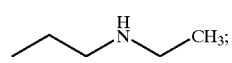

(5) 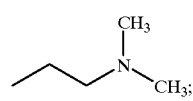

(6) 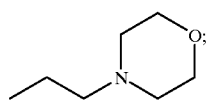

(7) 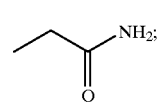

(8) 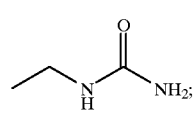

(9) 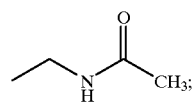

(10) 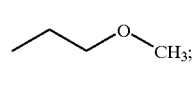

(11) 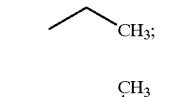

(12) 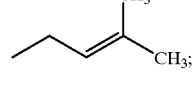

(13) 
![structure](CH3 branched pentyl);

(14) 
;

(15) 
;

(16) 
![cyclopropyl methyl];

(17) 
;

(18) 
;

(19) 
;

(20) 
;

(21) 
;

(22) 
![structure](methyl ketone with propyl-CH3);

(23) 
![structure](4-nitro ethylbenzene);

(24) 
![structure](4-chloro ethylbenzene);

(25) 
![structure](4-methoxy ethylbenzene);

(26) 
![structure](4-cyano ethylbenzene);

(27) 
;

(28) 
;

(29) 
![structure](CH=CH-CH3 longer chain);

(30) 
![structure](CH=CH-CH3 hexenyl);

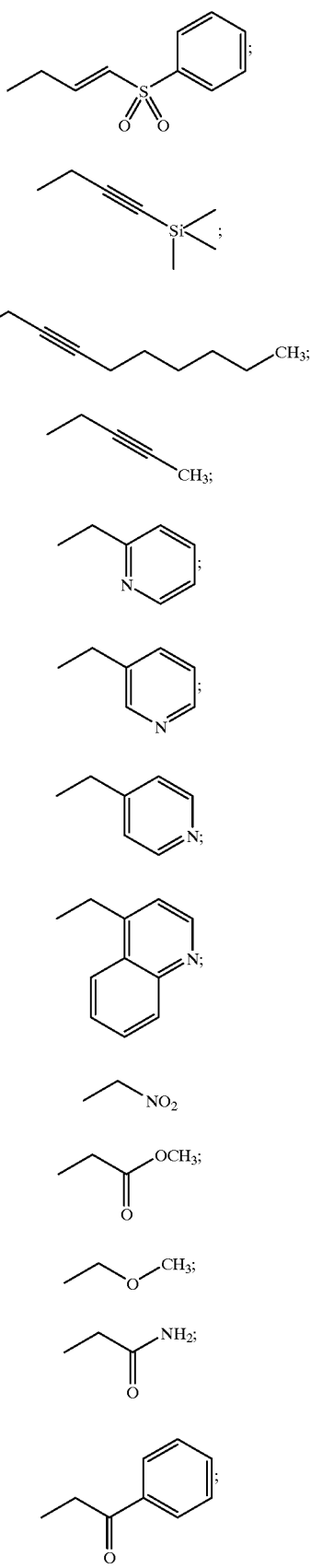

(C) a compound of Formula (II) therein wherein X is =O, $R^b$ is H; $R^c$ is H; $R^d$ is acetyl; $R^e$ is methoxy; $R^f$ is acetyl; R is —$CH_2$—CH=$CH_2$;

(D) a compound of Formula (V) therein which is selected from the group wherein
  (1) $R^b$ is H; $R^c$ is H; $R^d$ is phenylmethyloxycarbonyl; $R^e$ is methoxy; $R^f$ is H; R is —$CH_2$—CH=$CH_2$; and
  (2) $R^b$ is H; $R^c$ is H; $R^d$ is hydroxy; $R^e$ is methoxy; $R^f$ is H; R is —$CH_2$—CH=$CH_2$;

(E) a compound of Formula (VI) therein which is selected from the group wherein
  (1) $R^b$ is H; $R^c$ is H; $R^d$ is phenylmethyloxycarbonyl; $R^e$ is methoxy; $R^f$ is acetyl; R is —$CH_2$—CH=$CH_2$; and
  (2) $R^a$ is hydroxy; $R^b$ is H; $R^c$ is H; $R^d$ is H; $R^e$ is methoxy; $R^f$ is H; R is —$CH_2$—CH=$CH_2$;

(F) a compound of Formula (VII) therein which is selected from the group wherein
  (1) W is —NH—; $R^b$ is H; $R^c$ is H; $R^d$ is phenylmethyloxycarbonyl; $R^e$ is methoxy; $R^f$ is H; $R^g$ is H; R is propyl;
  (2) W is —NH—; $R^b$ is H; $R^c$ is H; $R^d$ is H; $R^e$ is methoxy; $R^f$ is H; $R^g$ is H; R is propyl;
  (3) W is —NH—; $R^b$ is H; $R^c$ is H; $R^d$ is phenylmethyloxycarbonyl; $R^e$ is methoxy; $R^f$ is H; $R^g$ is H; R is —$CH_2$—CH=$CH_2$;
  (4) W is absent; $R^b$ is H; $R^c$ is H; $R^d$ is phenylmethyloxycarbonyl; $R^e$ is methoxy; $R^f$ is acetyl; $R^g$ is 4-phenylbutyl; R is —$CH_2$—CH=$CH_2$;
  (5) W is absent; $R^b$ is H; $R^c$ is H; $R^d$ is phenylmethyloxycarbonyl; $R^e$ is methoxy; $R^f$ is H; $R^g$ is 4-phenylbutyl; R is —$CH_2$—CH=$CH_2$;
  (6) W is absent; $R^b$ is H; $R^c$ is H; $R^d$ is H; $R^e$ is methoxy; $R^f$ is H; $R^g$ is 4-phenylbutyl; R is propyl;
  (7) W is absent; $R^b$ is H; $R^c$ is H; $R^d$ is phenylmethyloxycarbonyl; $R^e$ is methoxy; $R^f$ is acetyl; $R^g$ is 4-phenylbutyl; R is —$CH_2$—CH=$CH_2$-(3-quinolinyl);
  (8) W is absent; $R^b$ is H; $R^c$ is H; $R^d$ is phenylmethyloxycarbonyl; $R^e$ is methoxy; $R^f$ is H; $R^g$ is 4-phenylbutyl; R is —$CH_2$—CH=$CH_2$-(3-quinolinyl);
  (25) W is absent; $R^b$ is H; $R^c$ is H; $R^d$ is acetyl; $R^e$ is methoxy; $R^f$ is acetyl; $R^g$ is H; R is —$CH_2$—CH=$CH_2$;
  (26) W is absent; $R^b$ is H; $R^c$ is H; $R^d$ is acetyl; $R^e$ is methoxy; $R^f$ is acetyl; $R^g$ is H; R is —$CH_2$—CH=$CH_2$-(3-quinolinyl);

(27) W is absent; $R^b$ is H; $R^c$ is H; $R^d$ is acetyl; $R^e$ is methoxy; $R^f$ is H; $R^g$ is H; R is —CH$_2$CH=CH$_2$-(3-quinolinyl);
(30) W is absent; $R^b$ is H; $R^c$ is H; $R^d$ is methoxy; $R^e$ is methoxy; $R^f$ is H; $R^g$ is H; R is —CH$_2$CH=CH$_2$-(3-quinolinyl);
(31) W is absent; $R^b$ is H; $R^c$ is H; $R^e$ is methoxy; $R^d$ is ethenesulfonyloxy; $R^f$ is acetyl; $R^g$ is H; R is —CH$_2$CH=CH$_2$-(3-quinolinyl);
(32) W is absent; $R^b$ is H; $R^c$ is H; $R^e$ is methoxy; $R^d$ is 2-(dimethylamino)ethylsulfonyloxy; $R^f$ is acetyl; $R^g$ is H; R is —CH$_2$CH=CH$_2$-(3-quinolinyl);
(33) W is absent; $R^b$ is H; $R^c$ is H; $R^d$ is methoxy; $R^e$ is 2-(phenylthio)ethoxy; $R^f$ is acetyl; $R^g$ is H; R is —CH$_2$CH=CH$_2$-(3-quinolinyl);
(34) W is absent; $R^b$ is H; $R^c$ is H; $R^d$ is methoxy; $R^e$ is (2-nitrophenyl)aminocarbonyloxy; $R^f$ is H; $R^g$ is H; R is —CH$_2$CH=CH$_2$-(3-quinolinyl); and
(35) W is absent; $R^b$ is H; $R^c$ is H; $R^d$ is methoxy; $R^e$ is (2-nitrophenyl)aminocarbonyloxy; $R^f$ is H; $R^g$ is H; R is —CH$_2$CH=CH$_2$-(3-quinolinyl);

(G) a compound of formula X wherein $R^a$ is OH; $R^b$ is OH; $R^c$ is H; $R^d$ is H; $R^e$ is methoxy; $R^f$ is H; selected from the group consisting of compounds wherein
(1) X is =O, R is —CH$_2$—CH=CH$_2$-(3-quinolinyl);
(2) X is =O, R is allyl;
(3) X is =N—OH, R is allyl;
(4) X is =O, R is propyl;
(5) X is =O, R is 2,3-dihydroxypropyl;
(6) X is =O, R is 2,3-epoxypropyl;
(7) X is =O, R is 2-hydroxy-3-(imidazol-1-yl)propyl;
(8) X is =O, R is 2-hydroxy-3-(morpholin-4-yl)propyl;
(9) X is =O, R is 2-hydroxy-3-(benzylamino)propyl;
(10) X is =O, R is 2-oxoethyl;
(11) X is =O, R is 2-oxopropyl;
(12) X is =N—O—(1-isopropoxycyclohexyl), R is —CH$_2$-C∫CH;
(13) R is —CH$_2$—C∫CH, X is =N—O—H;
(14) X is =O, R is —CH$_2$—C∫CH;
(15) X is =O, R is —CH$_2$—CHOH—CH$_2$—N$_3$;
(16) X is =O, R is —CH$_2$—CH=N—OH;
(17) X is =O, R is —CH$_2$—CH$_2$OH;
(18) X is =O, R is —CH$_2$—CH$_2$NH$_2$;
(19) X is =O, R is —CH$_2$—CN;
(20) X is =O, R is —CH$_2$-Phenyl;
(21) X is =O, R is —CH$_2$—CH=CH—Phenyl—;
(22) X is =O, R is —CH$_2$—CH=N—O—CH$_3$;
(23) X is =O, R is —CH$_2$—CH=N—O—CH$_2$-Phenyl;
(24) X is =O, R is —CH$_2$—CH=N—N(CH$_3$)$_2$;
(25) X is =O, R is —CH$_2$—CH=N—NH(CH$_3$);
(26) X is =O, R is —CH$_2$—CH=N-(4-Morpholinyl);
(27) X is =O, R is —CH$_2$—CH=N—NH(Phenyl); and
(28) X is =O, R is —CH$_2$—CH=N—N(Phenyl)$_2$;
(29) X=O, R=Phenylpropyl;
(30) X=O, R is —CH$_2$CH=CH-(4-methylphenyl);
(31) X=O, R is —CH$_2$—CH(OH)-Phenyl;
(32) X=O, R is —CH$_2$—CH(Br)—CH$_2$Br;
(33) X=O, R is —CH$_2$CH$_2$NHCH$_2$CH$_2$CH$_2$-Phenyl;
(34) X=O, R is —CH$_2$CH$_2$NHCH(CH$_2$Phenyl)CO$_2$Me;
(35) X=O, R is —CH$_2$CH$_2$NHCH$_2$CH$_2$CH$_3$;
(36) X=O, R is —CH$_2$CH$_2$NHCH$_2$CO$_2$CH$_2$CH$_2$;
(37) X=O, R is —CH$_2$CH$_2$NHCH$_2$CH$_2$-Phenyl;
(38) X=O, R is —CH$_2$CH$_2$NHCH$_2$CH$_2$-(4-hydroxyphenyl);
(39) X=O, R is —CH$_2$CH$_2$NHCH$_2$CH$_2$-(3-hydroxyphenyl);
(40) X=O, R is —CH$_2$CH$_2$NHCH$_2$CH$_2$-(3-methoxyphenyl);
(41) X=O, R is —CH$_2$CH$_2$NHCH$_2$CH$_2$-(2-methoxyphenyl);
(42) X=O, R is —CH$_2$CH$_2$NHCH$_2$CH$_2$-(4-methoxyphenyl);
(43) X=O, R is —CH$_2$CH$_2$NHCH$_2$-phenyl;
(44) X is =N—O—(1-isopropoxycyclohexyl), R is fluoromethyl;
(45) X=O, R is —CH$_2$CH$_2$NHCH$_2$CH$_2$-(3-chlorophenyl);
(46) X=O, R is —CH$_2$CH$_2$NHCH$_2$CH$_2$-(2-chlorophenyl);
(47) X=O, R is —CH$_2$CH$_2$NHCH$_2$CH$_2$-(4-chlorophenyl);
(48) X=O, R is —CH$_2$CH$_2$NHCH$_2$CH$_2$—O-phenyl;
(49) X=O, R is —CH$_2$CH$_2$NHCH$_2$CH$_2$CH$_2$-(4-quinolinyl);
(50) X=O, R is —CH$_2$CH$_2$NHCH$_2$CH$_2$CH$_2$-(3-quinolinyl);
(51) X=O, R is —CH$_2$CH$_2$NHCH$_2$CH$_2$CH$_2$CH$_2$-phenyl;
(52) X=O, R is —CH$_2$—CH=N—NH—C(O)—NH$_2$;
(53) X=O, R is —CH$_2$—CH=N—NH-(2-pyridinyl);
(54) X=O, R is —CH$_2$—CH=N-(4-methylpiperazinyl);
(55) X=O, R is —CH$_2$—CH=N—O-phenyl;
(56) X=O, R is —CH$_2$CH(OH)CH$_2$NHCH$_2$CH$_2$-phenyl;
(57) X=O, R is —CH$_2$CH(OH)CH$_2$NHCH$_2$-(4-pyridinyl);
(58) X is =O, R is (3-iodophenyl)methyl; and
(59) X is =O, R is (4-fluorophenyl)methyl;

(H) a compound of formula X wherein $R^a$ is OH; $R^b$ is OH; $R^c$ is H; $R^d$ is H; $R^e$ is methoxy; $R^f$ is H; X is O; R is CH$_2$—CH(OH)—CH$_2$—$R^V$; and $R^V$ is selected from the group consisting of:

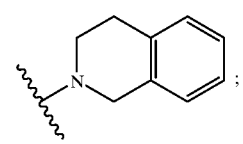

(1)

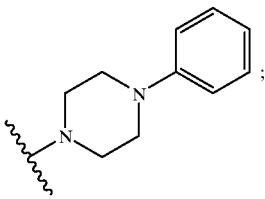

(2)

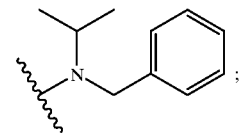

(3)

6,075,011
207
-continued
(4)
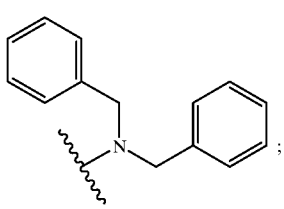
(5)
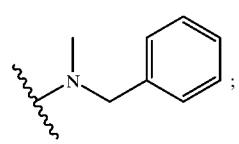
(6)
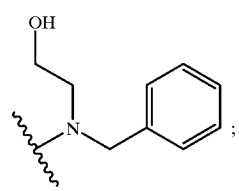
(7)
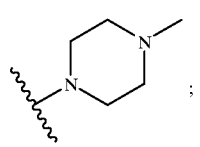
(8)
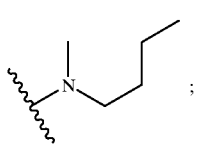
(9)
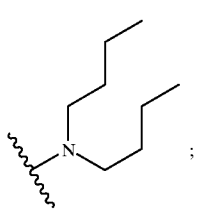
(10)
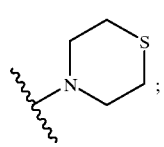
(11)
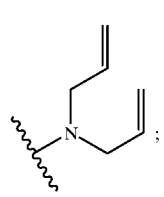
208
-continued
(12)
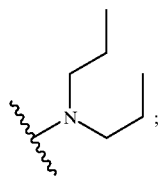
(13)
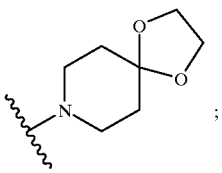
(14)
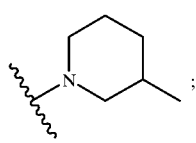
(15)
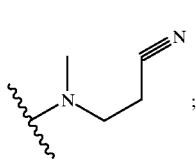
(16)
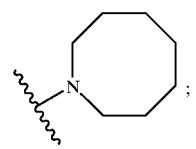
(17)
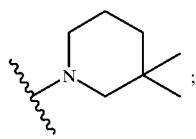
(18)
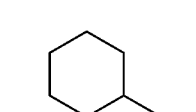
(19)
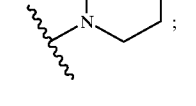

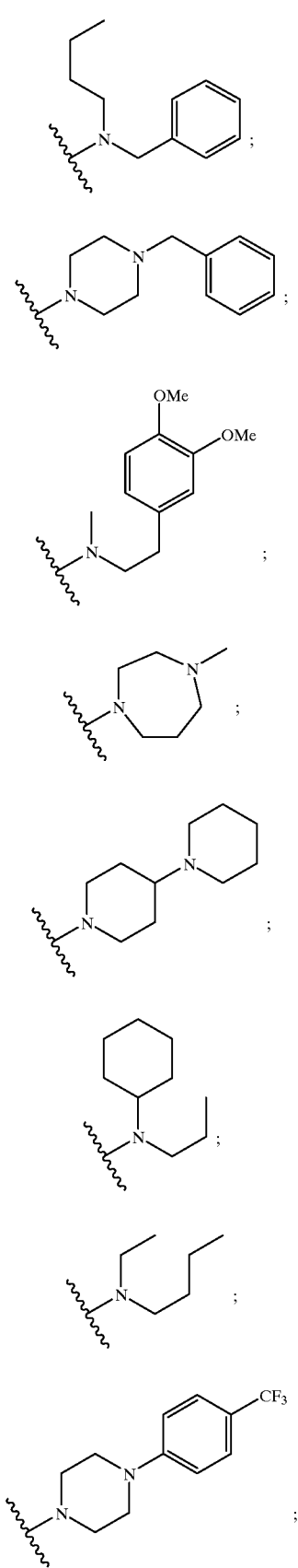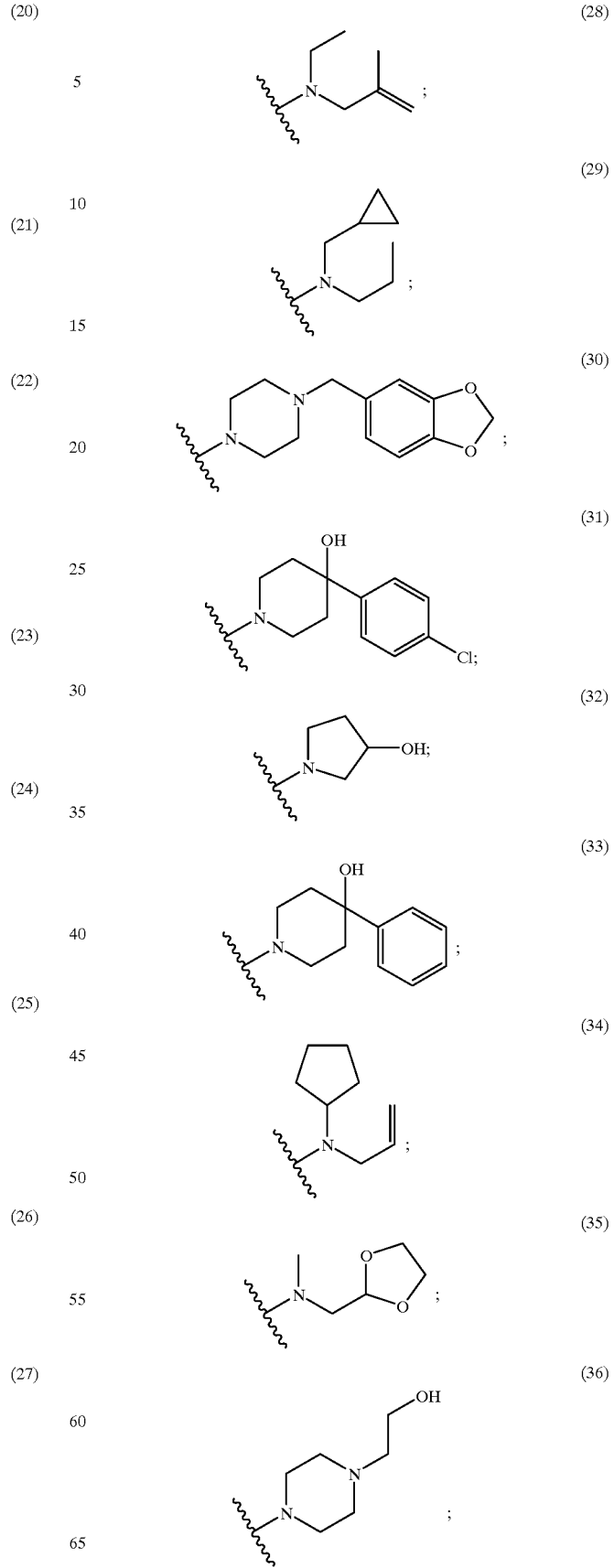

(37) 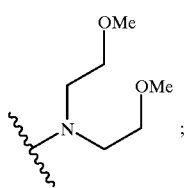
(38) 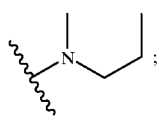
(39) 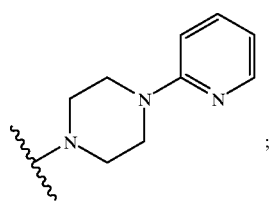
(40) 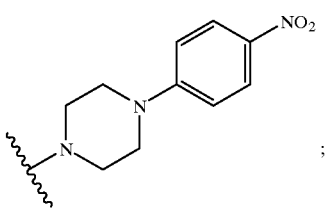
(41) 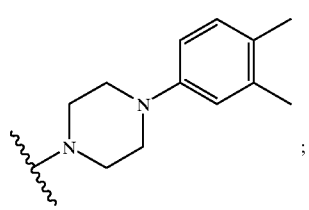
(42) 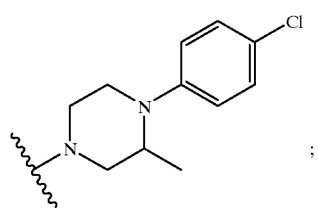
(43) 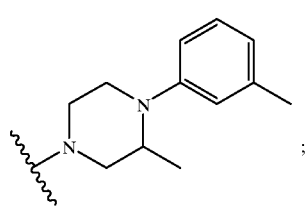
(44) 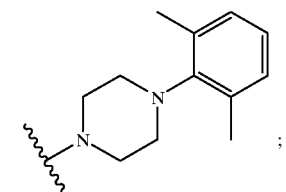
(45) 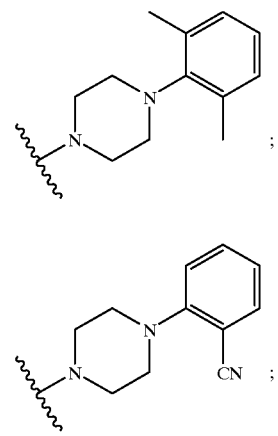
(46) 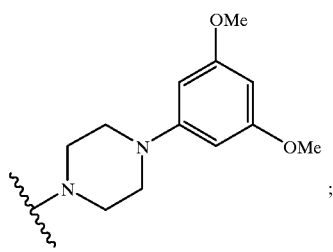
(47) 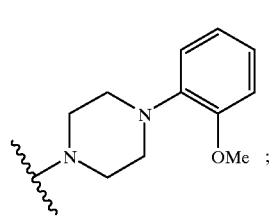
(48) 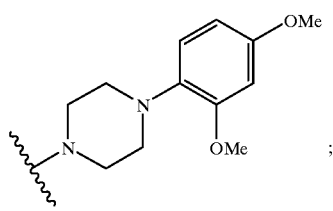
(49) 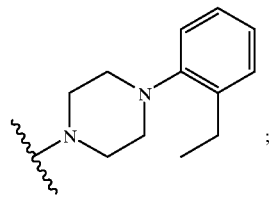
(50) 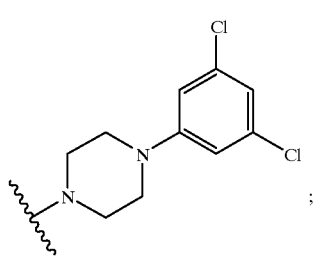

-continued
(51) 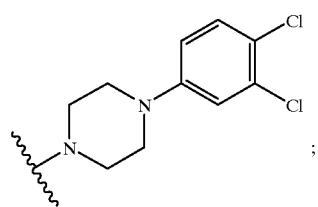
(52) 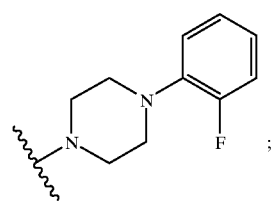
(53) 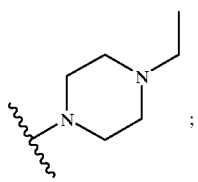
(54) 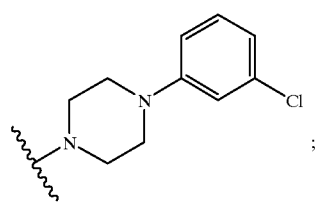
(55) 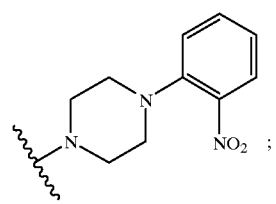
(56) 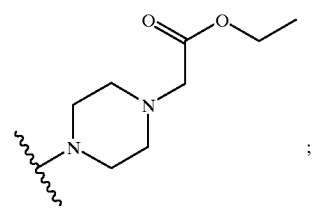
(57) 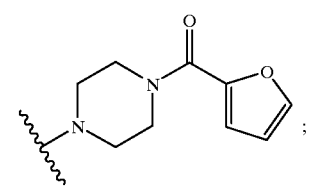
-continued
(58) 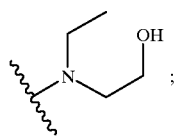
(59) 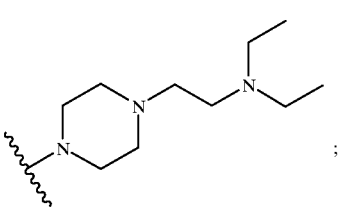
(60) 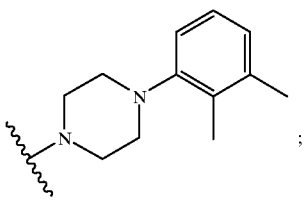
(61) 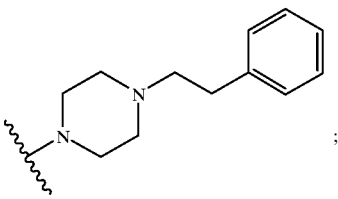
(62) 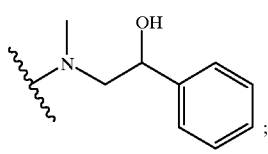
(63) 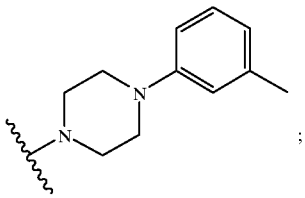
(64) 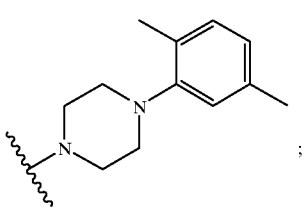

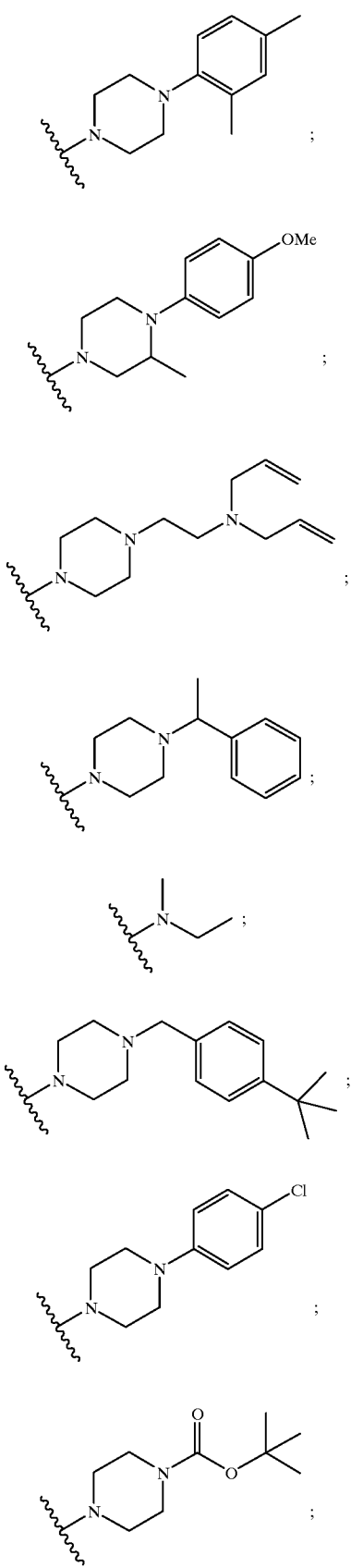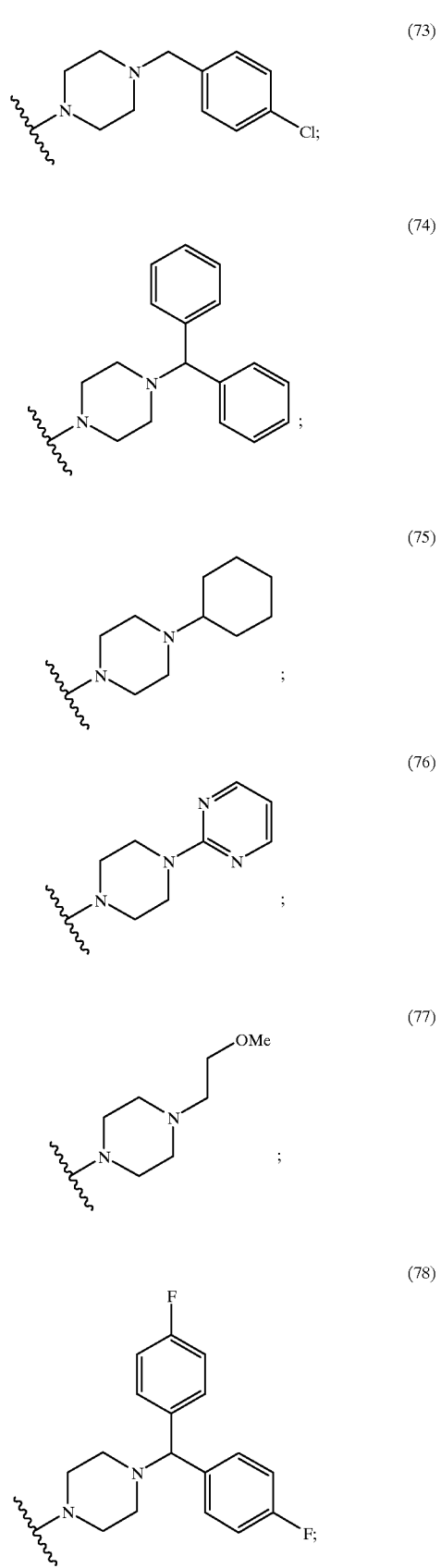

-continued
(79) 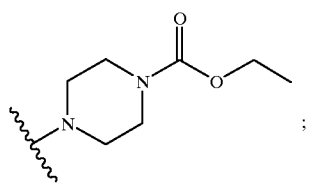
(I) a compound wherein X is O, R is CH$_2$—CH$_2$—R$^W$, and R$^W$ is selected from the group consisting of:
(1) 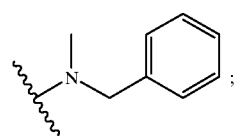
(2) 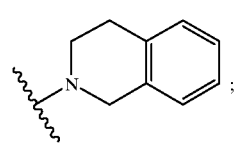
(3) 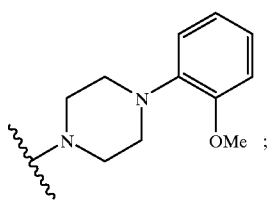
(4) 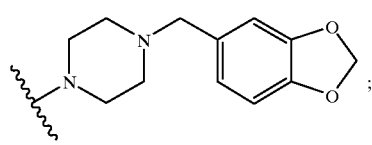
(5) 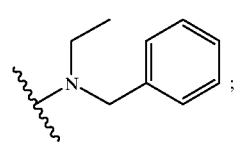
(6) 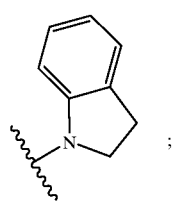
(7) 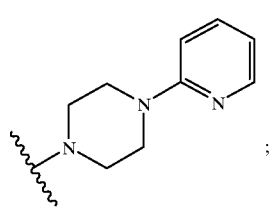
-continued
(8) 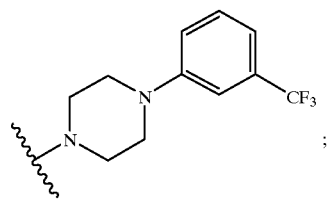
(9) 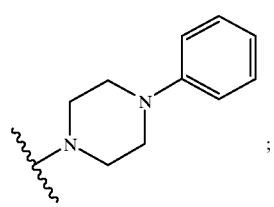
(10) 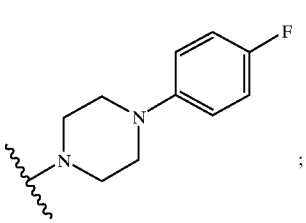
(11) 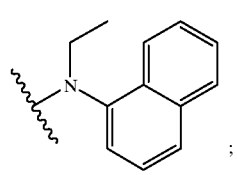
(12) 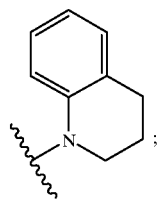
(13) 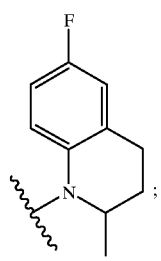
(14) 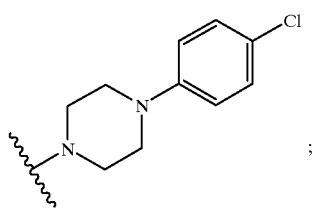

-continued
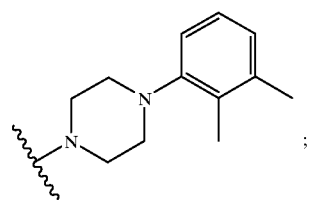 (15)
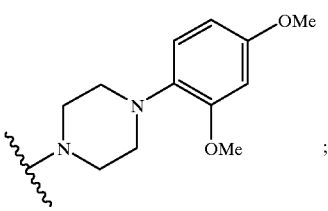 (16)
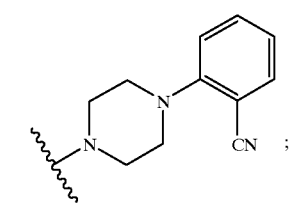 (17)
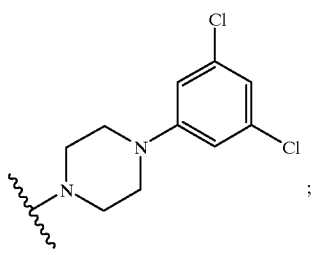 (18)
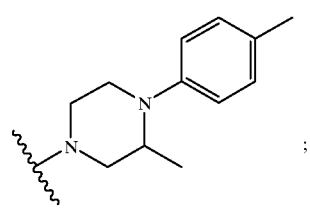 (19)
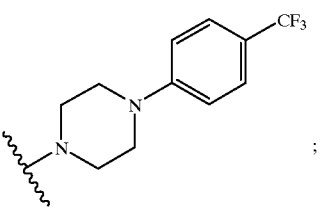 (20)
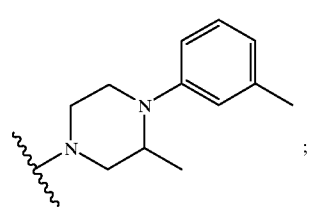 (21)
-continued
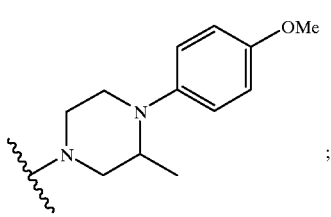 (22)
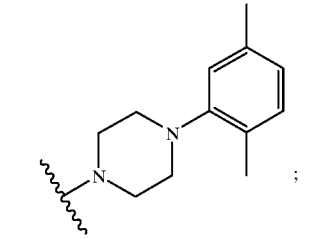 (23)
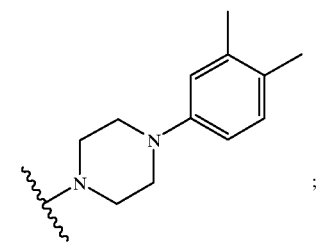 (24)
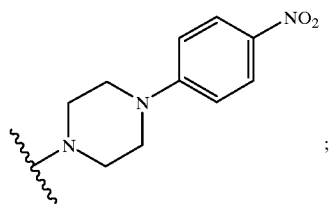 (25)
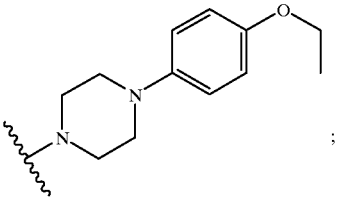 (26)
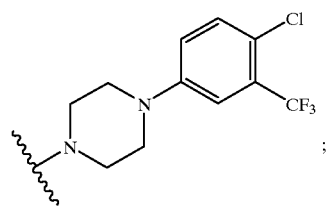 (27)

-continued
(28) 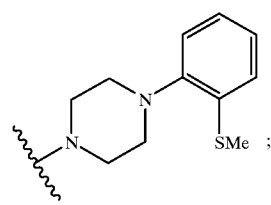
(29) 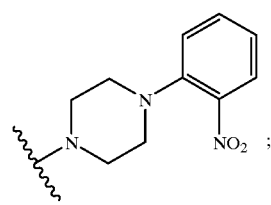
(30) 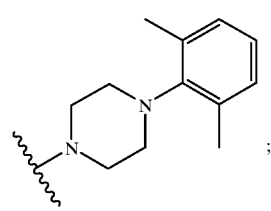
(31) 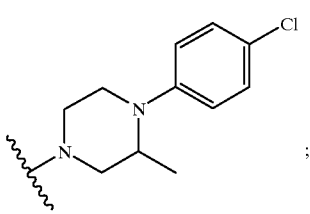
(32) 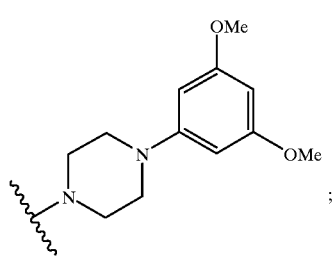
(33) 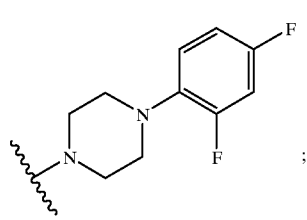
(34) 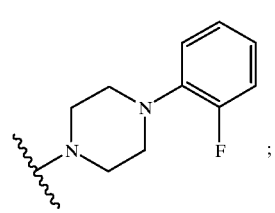
-continued
(35) 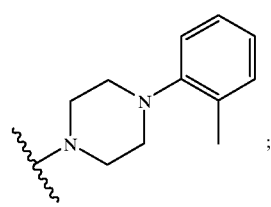
(36) 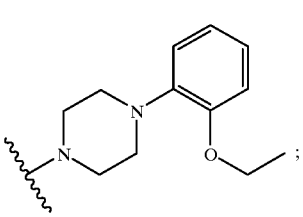
(37) 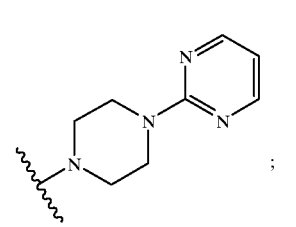
(38) 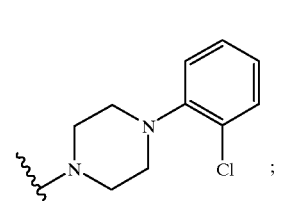
(39) 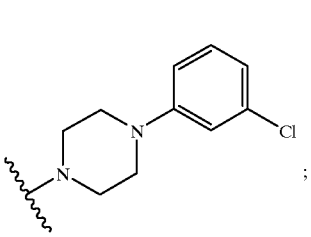
(40) 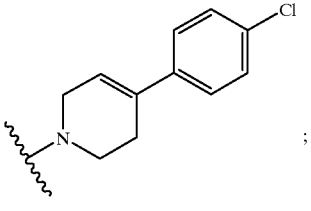
(41) 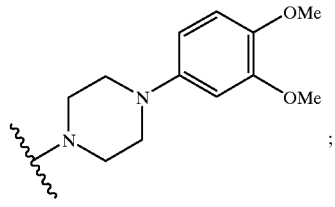

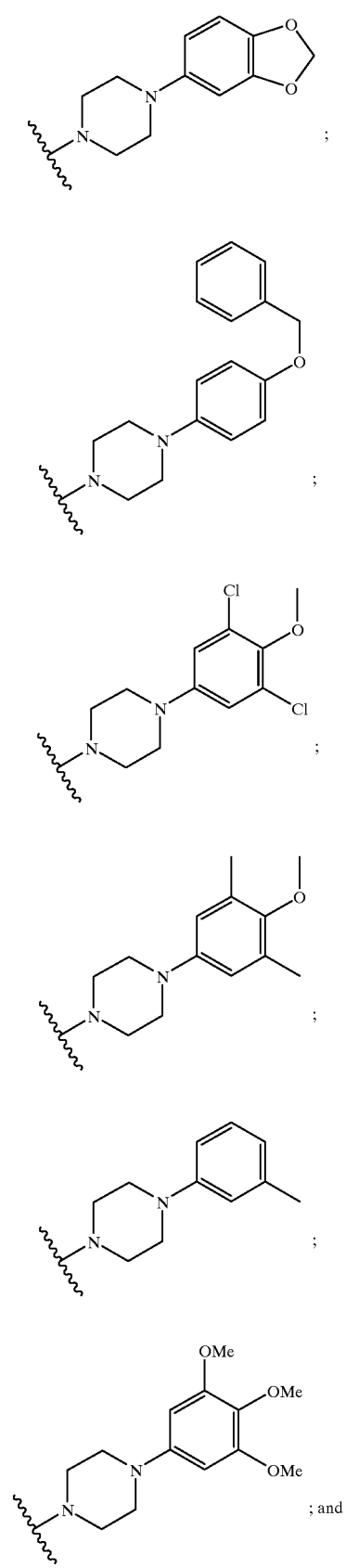
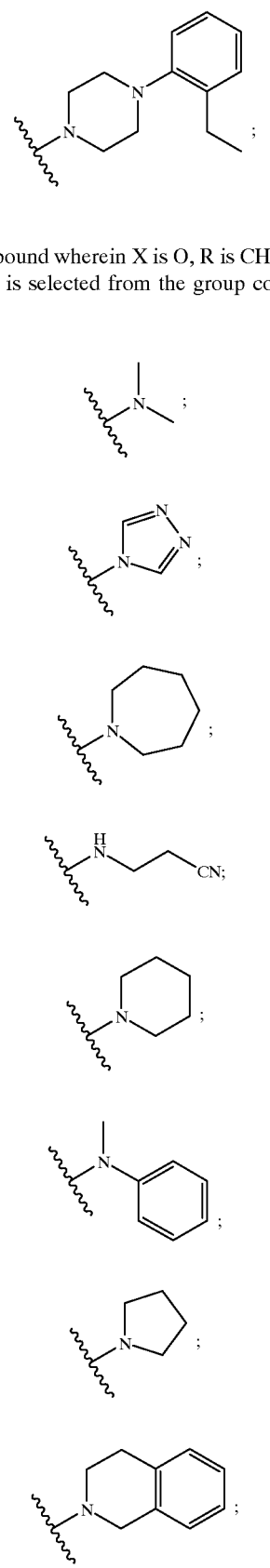
(J) a compound wherein X is O, R is $CH_2$—$CH$=$N$—$R^x$, and $R^x$ is selected from the group consisting of:

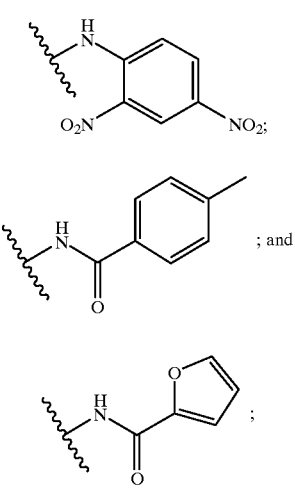

(9)

(10) ; and

(11) ;

and (K) a compound wherein $R^a$ is OH; $R^b$ is H; $R^c$ is H; $R^d$ is Rp; $R^e$ is methoxy; $R^f$ is Rp; selected from the group consisting of compounds wherein:
(1) X is =N—O-(1-isopropoxycyclohexyl), R is allyl, Rp is Trimethylsilyl
(2) X is =N—O-(1-isopropoxycyclohexyl), R is —CH$_2$-Phenyl, Rp is Trimethylsilyl;
(3) X is =N—O-(1-isopropoxycyclohexyl), R is —CH$_2$-Phenyl, Rp is H; and
(4) X is =N—OH, R is —CH$_2$-Phenyl, Rp is H; and pharmaceutically acceptable salts, esters and pro-drugs thereof.

13. A compound according to claim 3 which is selected from the group consisting of
(A) a compound wherein $R^a$ is OH; $R^b$ is OH; $R^c$ is H; $R^d$ is H; $R^e$ is methoxy; $R^f$ is H; selected from the group consisting of compounds wherein
(1) X is =O, R is —CH$_2$—CH=CH$_2$-(3-quinolinyl);
(2) X is =O, R is allyl;
(3) X is =N—OH, R is allyl;
(4) X is =O, R is propyl;
(5) X is =O, R is 2,3-dihydroxypropyl;
(6) X is =O, R is 2,3-epoxypropyl;
(7) X is =O, R is 2-hydroxy-3-(imidazol-1-yl)propyl;
(8) X is =O, R is 2-hydroxy-3-(morpholin-4-yl)propyl;
(9) X is =O, R is 2-hydroxy-3-(benzylamino)propyl;
(10) X is =O, R is 2-oxoethyl;
(11) X is =O, R is 2-oxopropyl;
(12) X is =N—O—(1-isopropoxycyclohexyl), R is —CH$_2$—C∫CH;
(13) R is —CH$_2$—C∫CH, X is =N—O—H;
(14) X is =O, R is —CH$_2$—C∫CH;
(15) X is =O, R is —CH$_2$—CHOH—CH$_2$—N$_3$;
(16) X is =O, R is —CH$_2$—CH=N—OH;
(17) X is =O, R is —CH$_2$—CH$_2$OH;
(18) X is =O, R is —CH$_2$—CH$_2$NH$_2$;
(19) X is =O, R is —CH$_2$—CN;
(20) X is =O, R is —CH$_2$-Phenyl;
(21) X is =O, R is —CH$_2$—CH=CH—Phenyl—;
(22) X is =O, R is —CH$_2$—CH=N—O—CH$_3$;
(23) X is =O, R is —CH$_2$—CH=N—O—CH$_2$-Phenyl;
(24) X is =O, R is —CH$_2$—CH=N—N(CH$_3$)$_2$;
(25) X is =O, R is —CH$_2$—CH=N—NH(CH$_3$);
(26) X is =O, R is —CH$_2$—CH=N-(4-Morpholinyl);
(27) X is =O, R is —CH$_2$—CH=N—NH(Phenyl); and
(28) X is =O, R is —CH$_2$—CH=N—N(Phenyl)$_2$;
(29) X=O, R=Phenylpropyl;
(30) X=O, R is —CH$_2$CH=CH—(4-methylphenyl);
(31) X=O, R is —CH$_2$—CH(OH)-Phenyl;
(32) X=O, R is —CH$_2$—CH(Br)—CH$_2$Br;
(33) X=O, R is —CH$_2$CH$_2$NHCH$_2$CH$_2$CH$_2$-Phenyl;
(34) X=O, R is —CH$_2$CH$_2$NHCH(CH$_2$Phenyl)CO$_2$Me;
(35) X=O, R is —CH$_2$CH$_2$NHCH$_2$CH$_2$CH$_3$;
(36) X=O, R is —CH$_2$CH$_2$NHCH$_2$CO$_2$CH$_2$CH$_2$;
(37) X=O, R is —CH$_2$CH$_2$NHCH$_2$CH$_2$-Phenyl;
(38) X=O, R is —CH$_2$CH$_2$NHCH$_2$CH$_2$-(4-hydroxyphenyl);
(39) X=O, R is —CH$_2$CH$_2$NHCH$_2$CH$_2$-(3-hydroxyphenyl);
(40) X=O, R is —CH$_2$CH$_2$NHCH$_2$CH$_2$-(3-methoxyphenyl);
(41) X=O, R is —CH$_2$CH$_2$NHCH$_2$CH$_2$-(2-methoxyphenyl);
(42) X=O, R is —CH$_2$CH$_2$NHCH$_2$CH$_2$-(4-methoxyphenyl);
(43) X=O, R is —CH$_2$CH$_2$NHCH$_2$-phenyl;
(44) X is =N—O—(1-isopropoxycyclohexyl), R is fluoromethyl;
(45) X=O, R is —CH$_2$CH$_2$NHCH$_2$CH$_2$-(3-chlorophenyl);
(46) X=O, R is —CH$_2$CH$_2$NHCH$_2$CH$_2$-(2-chlorophenyl);
(47) X=O, R is —CH$_2$CH$_2$NHCH$_2$CH$_2$-(4-chlorophenyl);
(48) X=O, R is —CH$_2$CH$_2$NHCH$_2$CH$_2$—O-phenyl);
(49) X=O, R is —CH$_2$CH$_2$NHCH$_2$CH$_2$-(4-quinolinyl);
(50) X=O, R is —CH$_2$CH$_2$NHCH$_2$CH$_2$-(3-quinolinyl);
(51) X=O, R is —CH$_2$CH$_2$NHCH$_2$CH$_2$CH$_2$-phenyl;
(52) X=O, R is —CH$_2$—CH=N—NH—C(O)—NH$_2$;
(53) X=O, R is —CH$_2$—CH=N—NH—(2-pyridinyl);
(54) X=O, R is —CH$_2$—CH=N—(4-methylpiperazinyl);
(55) X=O, R is —CH$_2$—CH=N—O-phenyl;
(56) X=O, R is —CH$_2$CH(OH)CH$_2$NHCH$_2$CH$_2$-phenyl;
(57) X=O, R is —CH$_2$CH(OH)CH$_2$NHCH$_2$-(4-pyridinyl;
(58) X is =O, R is (3-iodophenyl)methyl; and
(59) X is =O, R is (4-fluorophenyl)methyl;
(B) a compound wherein $R^a$ is OH; $R^b$ is OH; $R^c$ is H; $R^d$ is H; $R^e$ is methoxy; $R^f$ is H; X is O; R is CH$_2$—CH(OH)—CH$_2$—$R^V$; and $R^V$ is selected from the group consisting of:

(1)

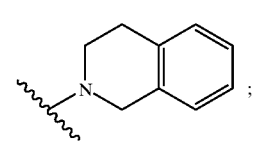

227
-continued
(2) 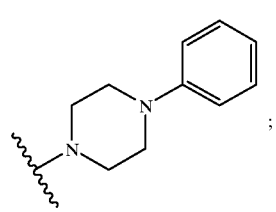
(3) 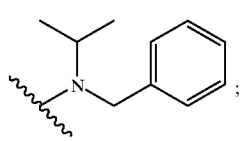
(4) 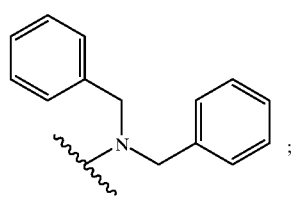
(5) 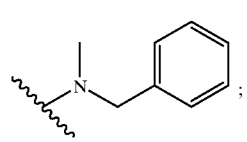
(6) 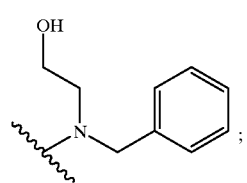
(7) 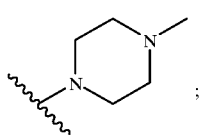
(8) 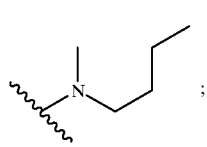
(9) 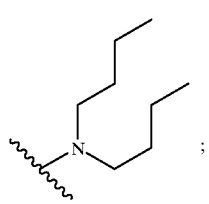
228
-continued
(10) 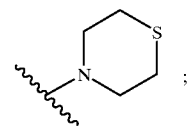
(11) 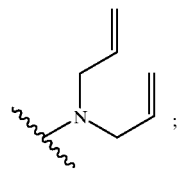
(12) 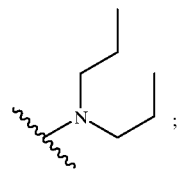
(13) 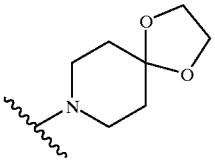
(14) 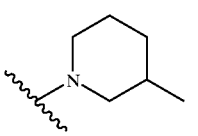
(15) 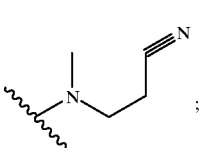
(16) 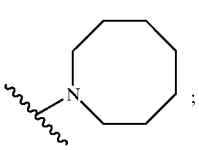
(17) 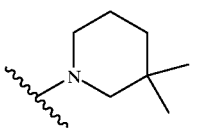
(18) 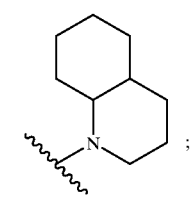

-continued
(19) 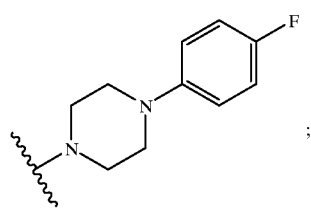
(20) 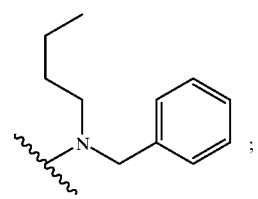
(21) 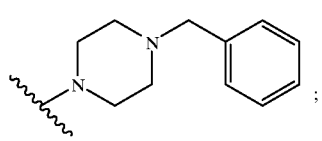
(22) 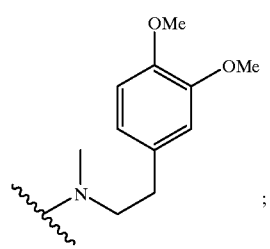
(23) 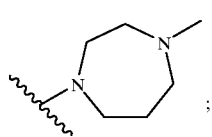
(24) 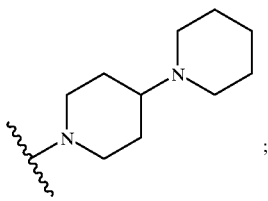
(25) 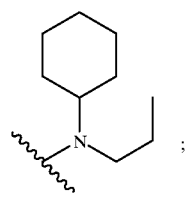
(26) 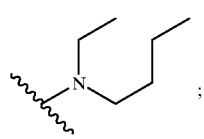
-continued
(27) 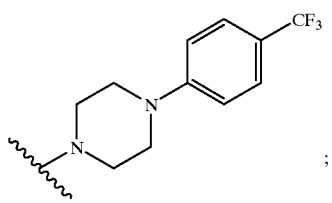
(28) 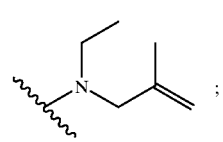
(29) 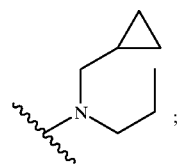
(30) 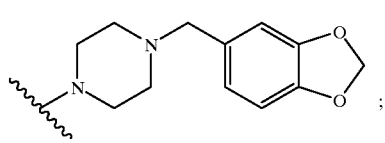
(31) 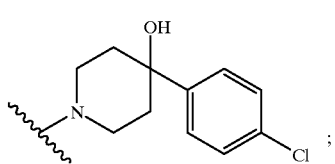
(32) 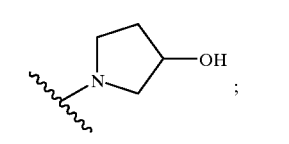
(33) 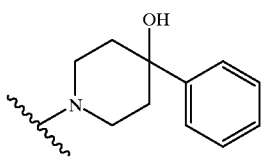
(34) 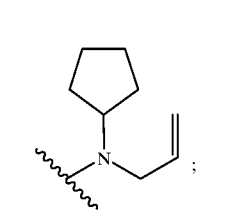
(35) 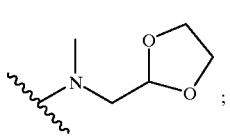

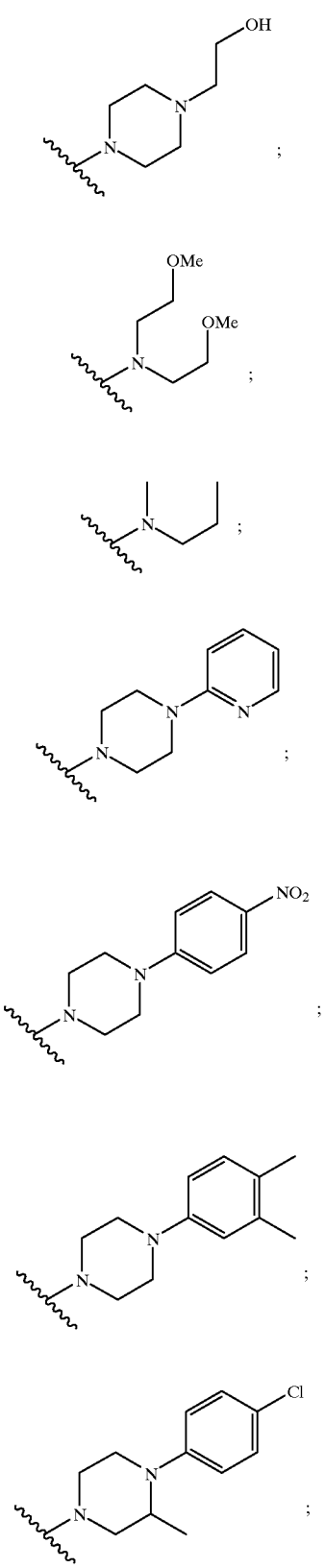
(36)
(37)
(38)
(39)
(40)
(41)
(42)
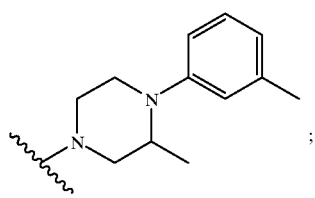
(43)
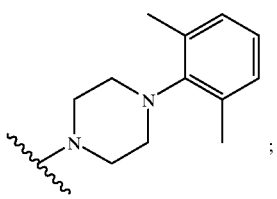
(44)
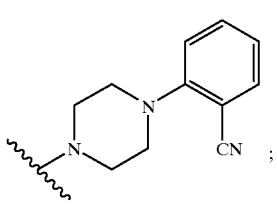
(45)
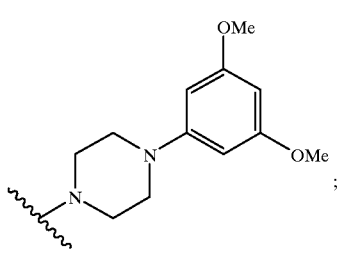
(46)
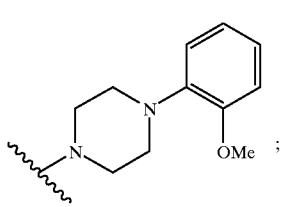
(47)
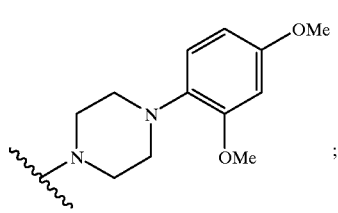
(48)
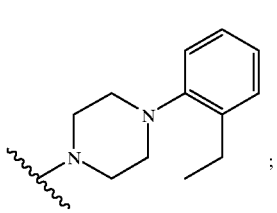
(49)

-continued
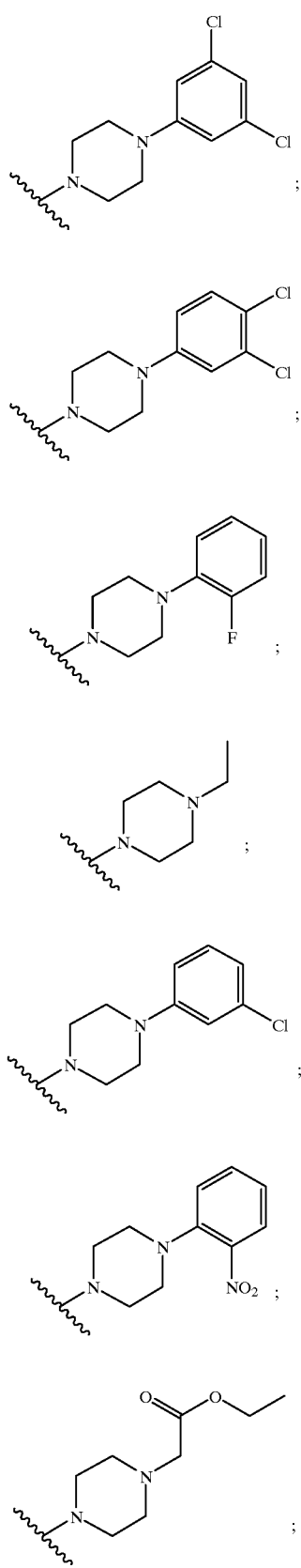
-continued
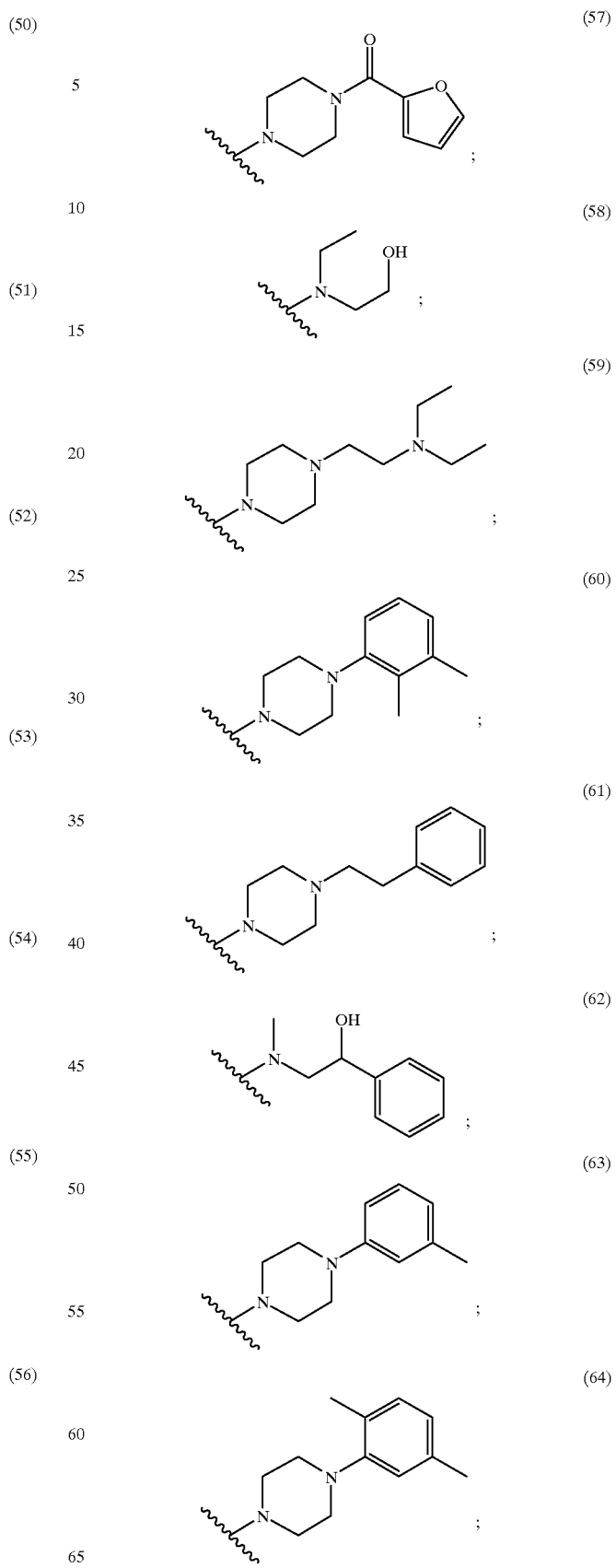

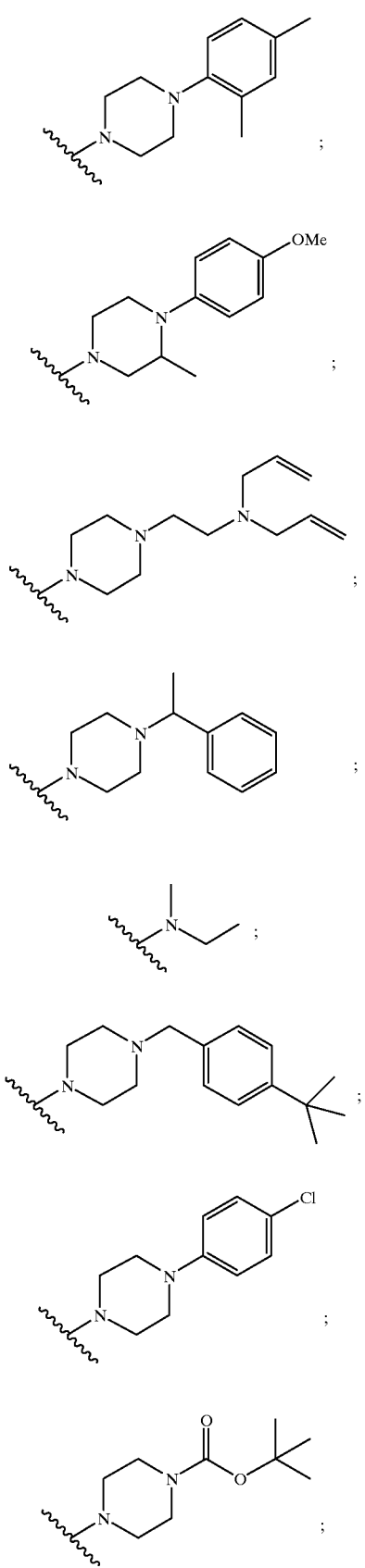
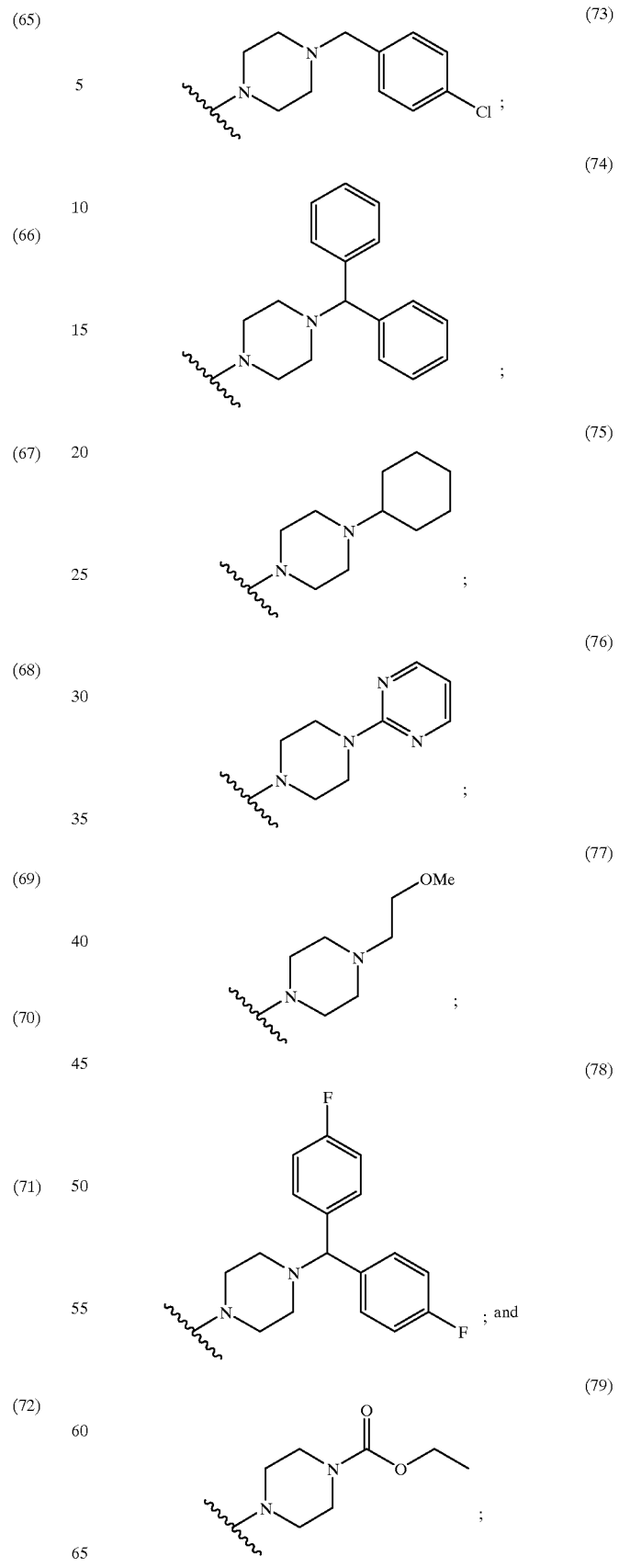

(C) a compound wherein X is O, R is CH$_2$—CH$_2$—R$^w$, and R$^w$ is selected from the group consisting of:
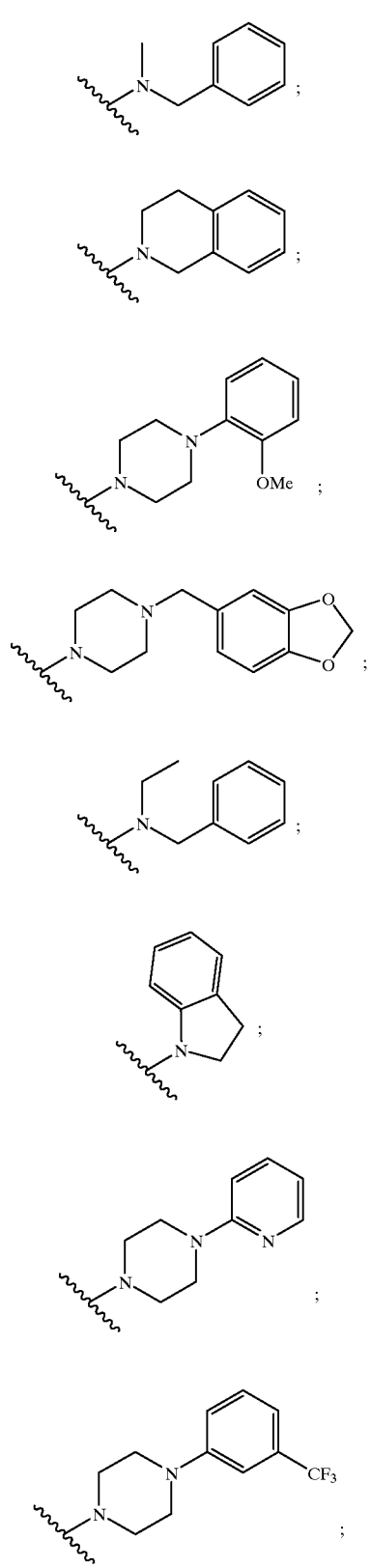
-continued
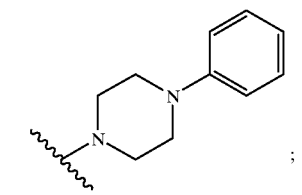
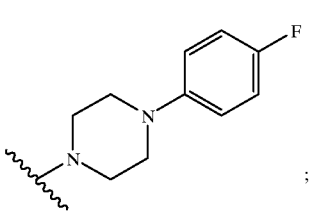
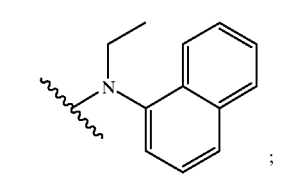
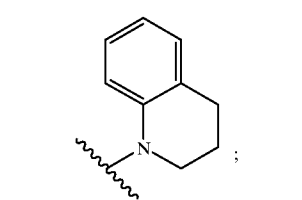
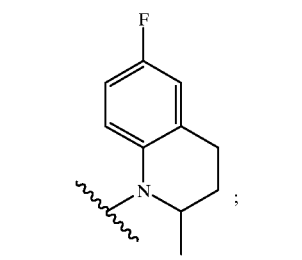
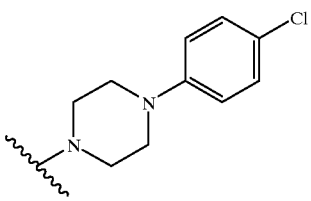
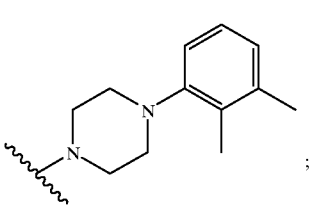

-continued
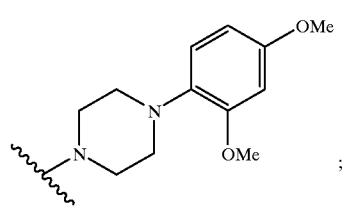 (16)
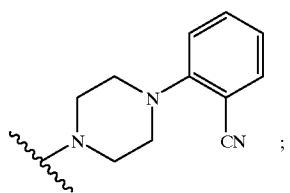 (17)
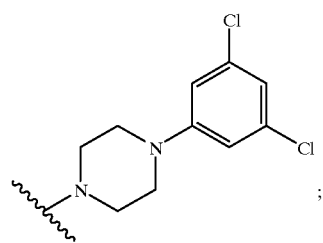 (18)
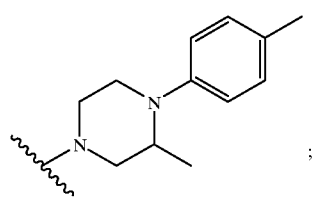 (19)
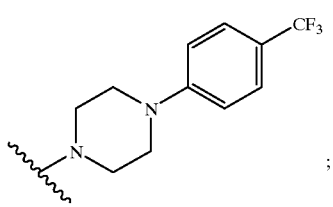 (20)
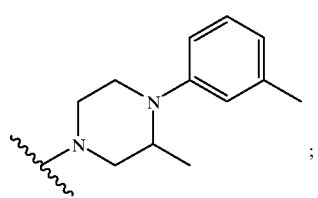 (21)
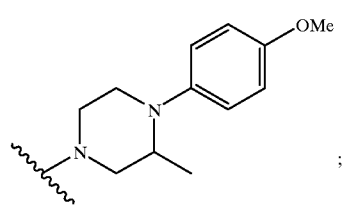 (22)
-continued
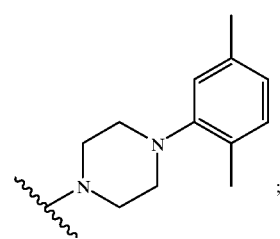 (23)
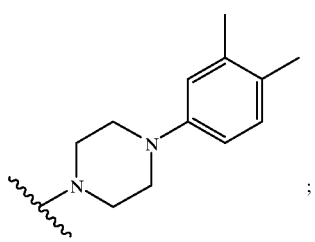 (24)
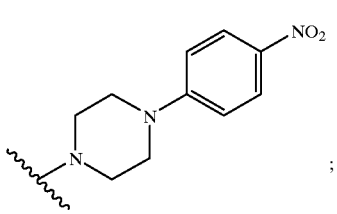 (25)
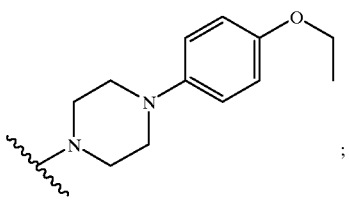 (26)
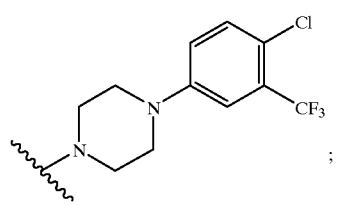 (27)
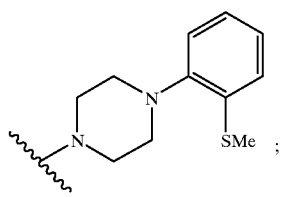 (28)
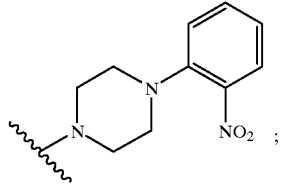 (29)

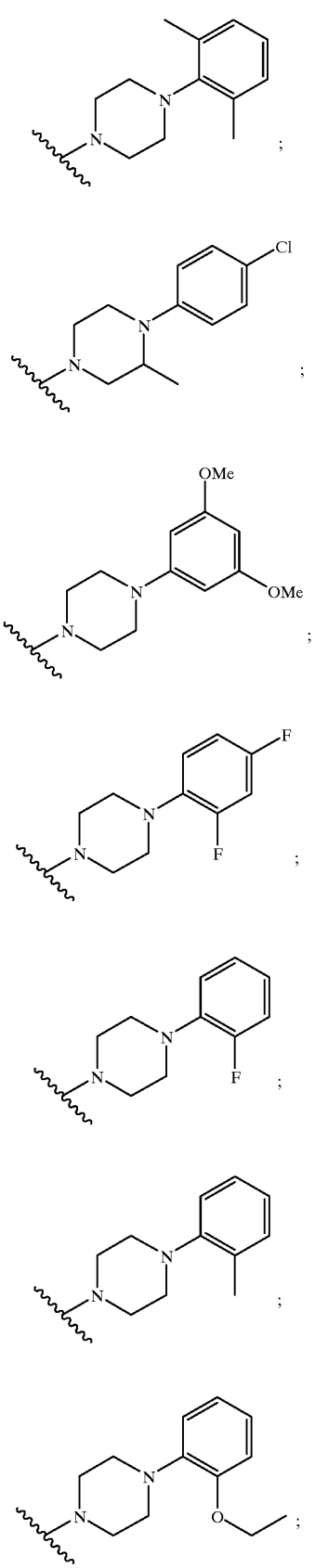
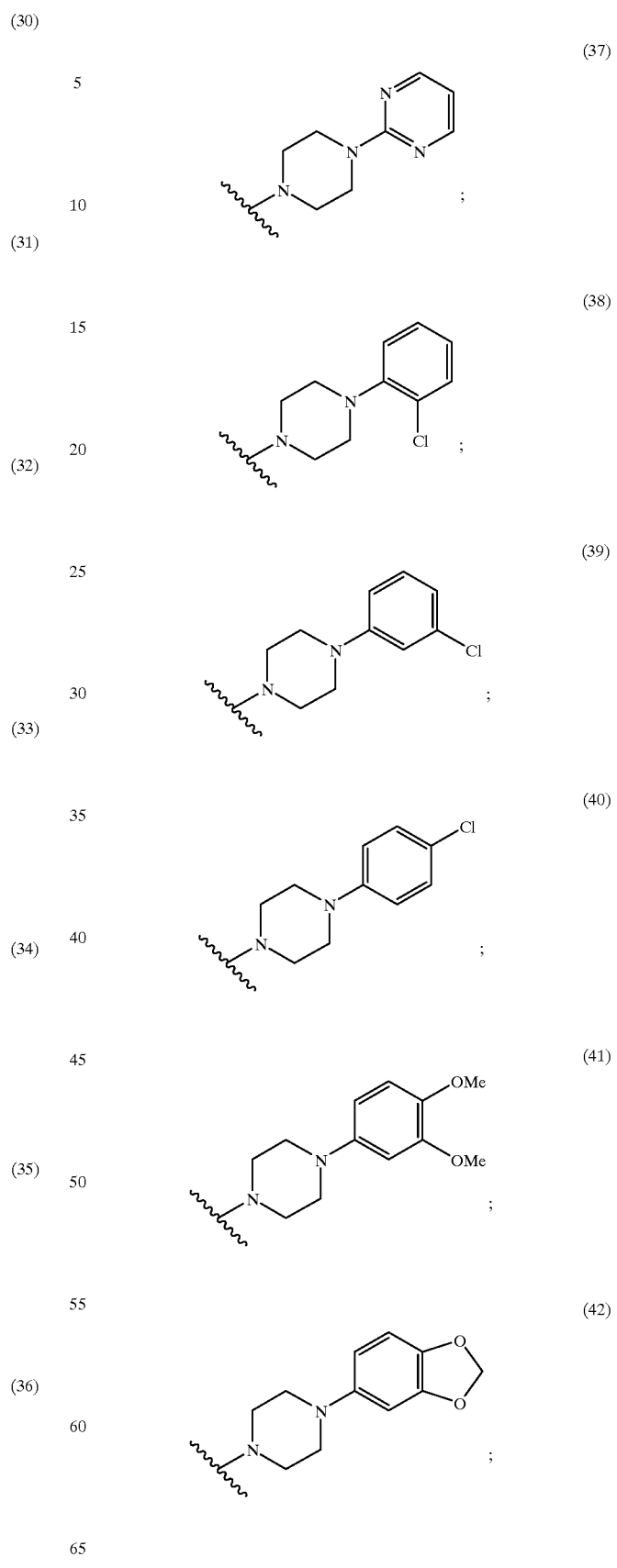

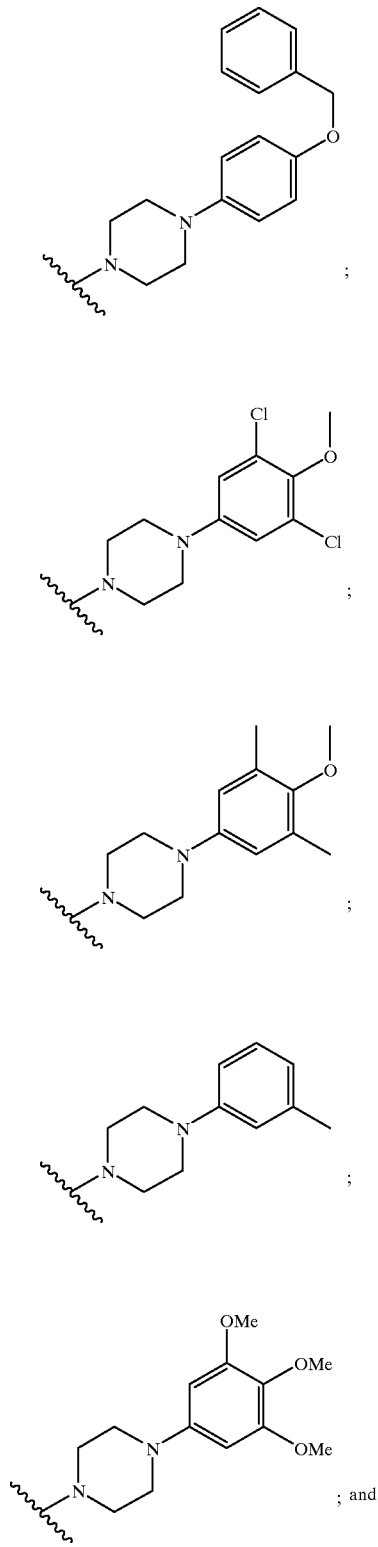
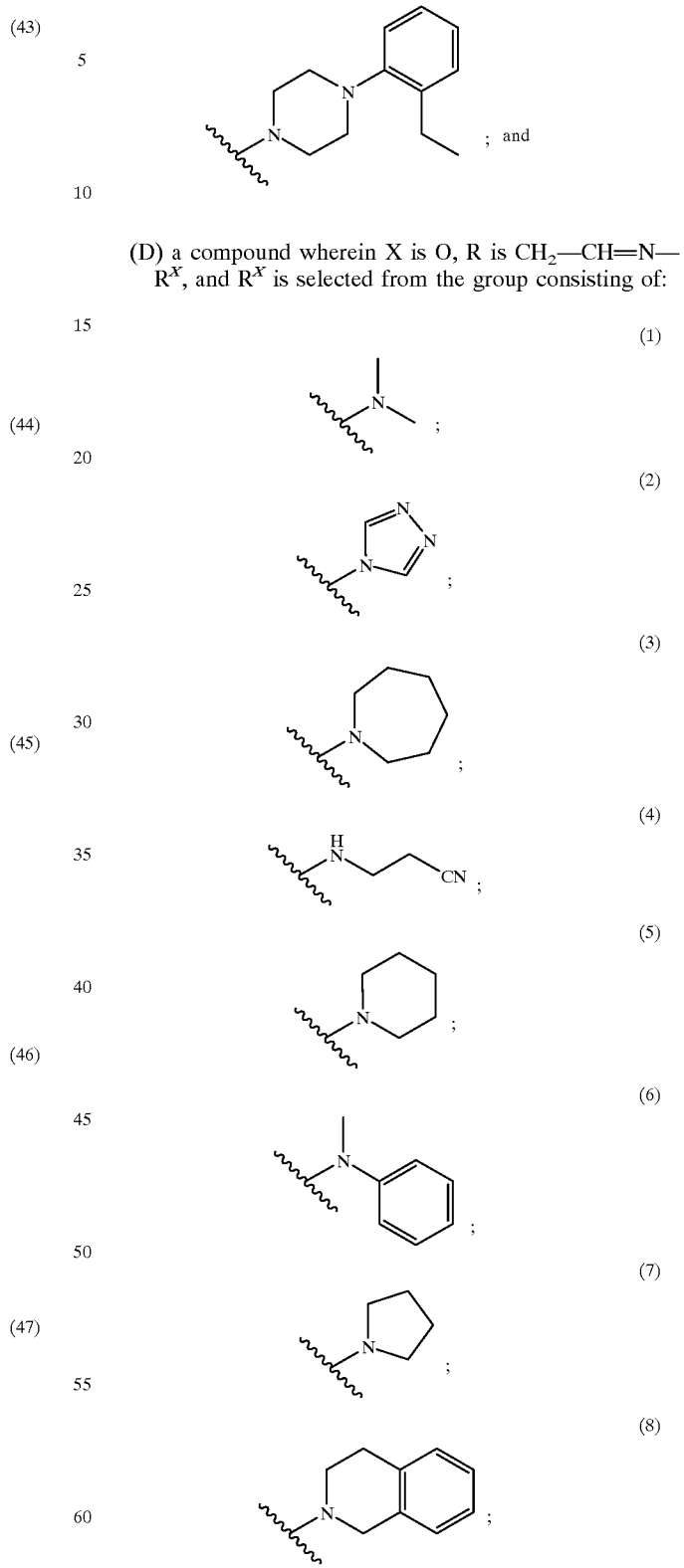
(D) a compound wherein X is O, R is $CH_2$—CH=N—$R^x$, and $R^x$ is selected from the group consisting of:

(9)

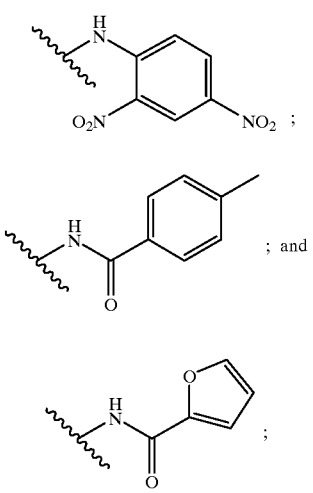

(10)

; and (11)

;

or a pharmaceutically acceptable salt, ester, or prodrug thereof.

14. A compound according to claim 13 wherein $R^a$ is OH; $R^b$ is H; $R^c$ is H; $R^d$ is OH; $R^e$ is methoxy; $R^f$ is H; selected from the group consisting of compounds wherein:

X is =O, R is —CH$_2$—CH=CH$_2$-(3-quinolinyl);
X is =O, R is allyl;
X is =O, R is 2-hydroxy-3-(benzylamino)propyl;
X is =O, R is 2-oxopropyl;
X is =O, R is —CH$_2$—C≡CH;
X is =O, R is —CH$_2$—CH=N—OH;
X is =O, R is —CH$_2$—CH$_2$OH;
X is =O, R is —CH$_2$—CH$_2$NH$_2$; and
X is =O, R is —CH$_2$—CN.

15. A pharmaceutical composition comprising a therapeutically effective amount of a compound of claim 1 in combination with a pharmaceutically acceptable carrier.

16. A method for controlling a bacterial infection in a mammal comprising administering to the mammal a therapeutically-effective pharmaceutical composition containing a compound according to claim 1.

17. A pharmaceutical composition comprising a therapeutically effective amount of a compound of claim 12 in combination with a pharmaceutically acceptable carrier.

18. A method for controlling a bacterial infection in a mammal comprising administering to the mammal a therapeutically-effective pharmaceutical composition containing a compound according to claim 12.

19. A pharmaceutical composition comprising a therapeutically effective amount of a compound of claim 13 in combination with a pharmaceutically acceptable carrier.

20. A method for controlling a bacterial infection in a mammal comprising administering to the mammal a therapeutically-effective pharmaceutical composition containing a compound according to claim 13.

21. A pharmaceutical composition comprising a therapeutically effective amount of a compound of claim 14 in combination with a pharmaceutically acceptable carrier.

22. A method for controlling a bacterial infection in a mammal comprising administering to the mammal a therapeuticaily-effective pharmaceutical composition containing a compound according to claim 14.

23. A process for preparing a compound having the formulae (II) or (III) as defined in claim 1, comprising:

(a.) treating a compound having a formula:

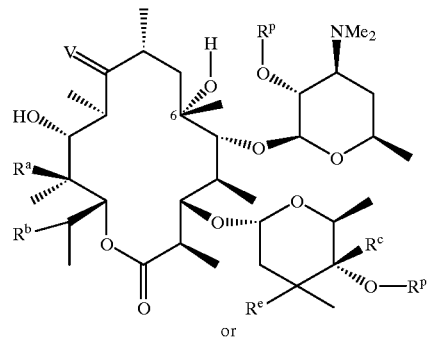

or

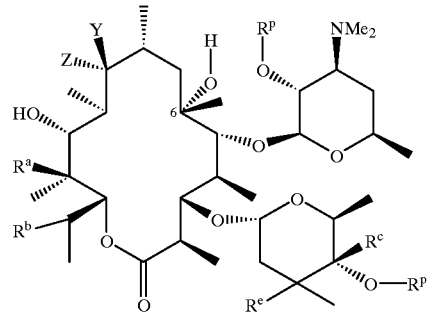

wherein $R^a$, $R^b$, $R^c$, $R^e$, RP, Y, and Z are defined in claim 1, wherein V is =N—O—$R^1$ or =N—O—C($R^5$)($R^6$)—O—R, wherein $R^1$, $R^5$, and $R^6$ are defined as in claim 1, with an alkylating agent to form a compound having a formula:

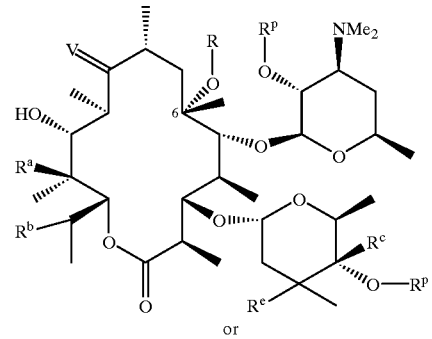

or

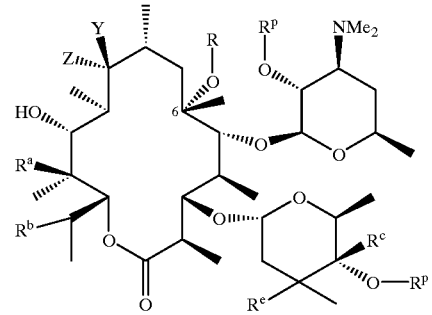

(b.) deprotecting the 2'- and 4"-hydroxyl groups of the compound as obtained in step (a.) to form a compound having a formula:

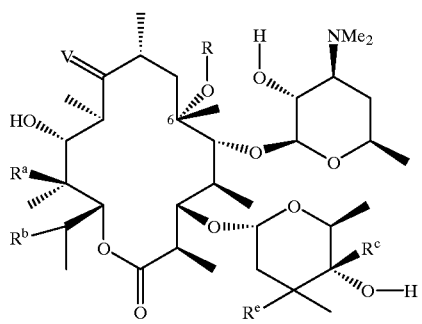

or

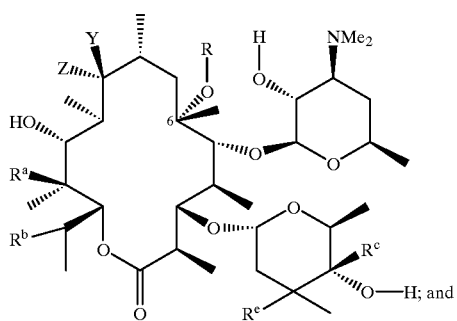

(c.) optionally deoximating the compounds obtained in step (b.) with an inorganic sulfur oxide salt or an inorganic nitrite salt in the presence of acid.

24. A process for preparing a compound of formula (IV) as defined in claim 1, comprising:

(a.) treating a compound having a formula:

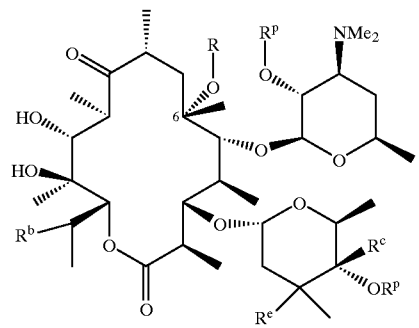

wherein RP is H or a hydroxy protecting group and R, $R^b$, $R^c$, and $R^e$ are defined as in claim 1, with formaldehyde in the presence of an acid or chloroiodomethane in the presence of a base to give a 11,12-methylenedioxy compound having a formula:

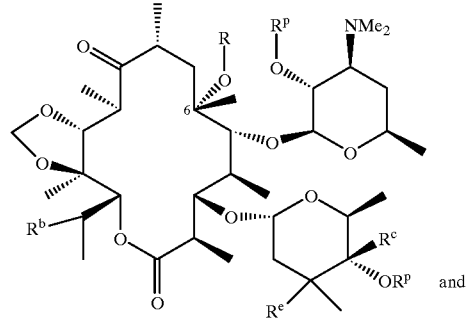

(b.) deprotecting the 2'- and 4"-hydroxy protecting groups of the compound obtained in step (a.).

25. A process for preparing a compound of formula (V) as defined in claim 1, comprising:

(a.) treating a compound having a formula:

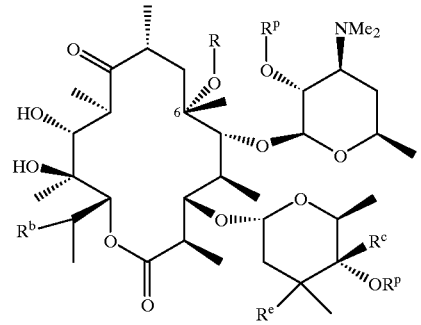

wherein RP is H or a hydroxy protecting group, and R, $R^b$, $R^c$, and $R^e$ are defined as in claim 1, with a base followed by reaction with a reagent selected from the group consisting of phosgene, diphosgene, triphosgene and benzyl chloroformate, to give a compound having a formula:

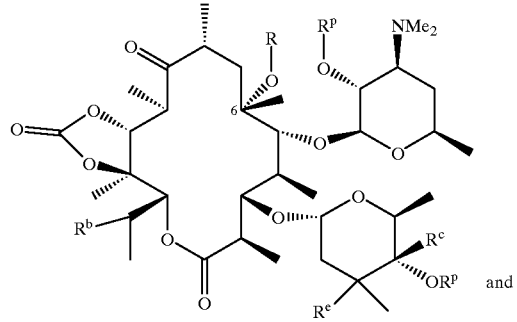

(b.) deprotecting the 2'- and 4"-hydroxy protecting groups.

26. A process for preparing a compound of formula (VI) as defined in claim 1, comprising:

(a.) treating a compound having a formula:

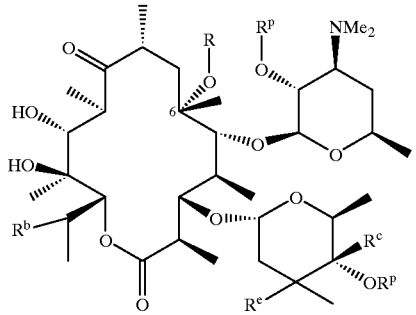

or

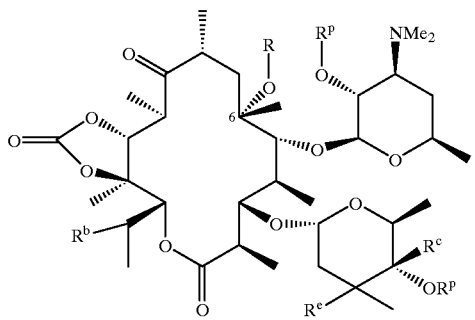

wherein RP is H or a hydroxy protecting group, and R, $R^b$, $R^c$, and $R^e$ are defined in claim 1, with a base and carbonyldiimidazole in an aprotic solvent to form a compound having a formula:

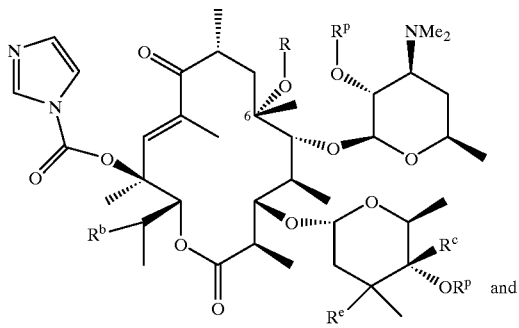

(b.) hydrolizing to afford the compound of formula (VI).

27. A process for preparing a compound having the formula (VII) as defined in claim 1, comprising:

(a.) treating a compound having a formula:

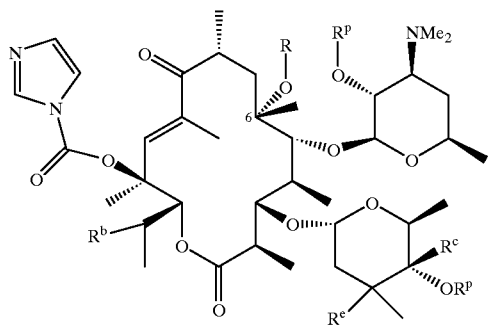

wherein RP is H or a hydroxy protecting group and R, $R^b$, $R^c$, and $R^e$, are defined as in claim 1, with a reagent selected from the group consisting of an $R^g NH_2$, hydrazine, $R^g R^4 NNH_2$, hydroxylamine, $O-C_1-C_6$-alkylated hydroxylamine, and $R^g CHO$, wherein $R^g$ and $R^4$ are defined as in claim 1, to form a compound having a formula:

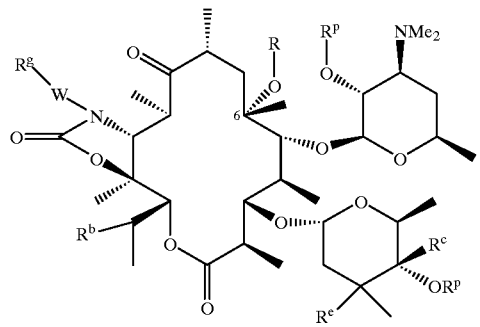

wherein RP is H or a hydroxy protecting group and R, $R^b$, $R^c$, $R^e$, $R^g$, and W are defined as in claim 1; and (b.) deprotecting the 2'- and 4''-hydroxy protecting groups.

28. A process for preparing a compound having a formula (VIII) as defined in claim 1, comprising:

(a.) treating a compound having the formula:

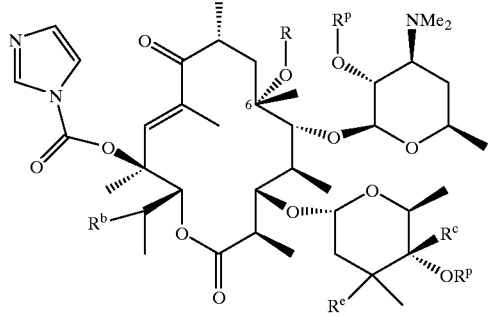

wherein RP is hydrogen or a hydroxy protecting group, and R, $R^b$, $R^c$, and $R^e$ are defined in claim 1, with a 1,2 diamine compound having a formula:

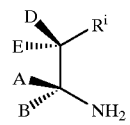

wherein $R^i$ is OH or $NH_2$, and A, B, D, and E are defined as in claim 1, to form a compound of the formula:

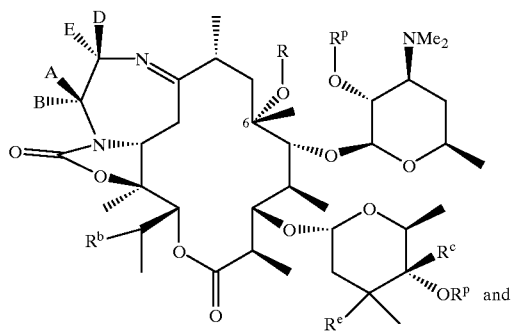

(b.) deprotecting the 2'- and 4"-hydroxy protecting groups.

29. A process for preparing a compound having a formula (IX) as defined in claim 1, comprising:

(a.) treating a compound having the formula:

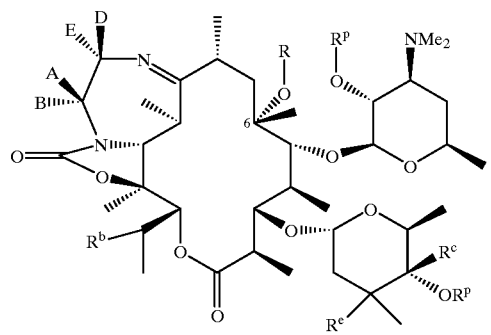

wherein RP is hydrogen or a hydroxy protecting group, and A, B, D, E, R, $R^b$, $R^c$, and $R^e$, are defined in claim 1, with a reducing agent to form a product having the formula:

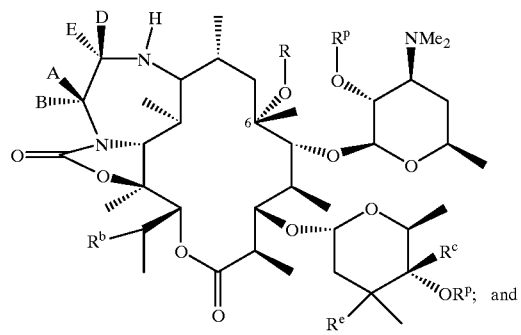

(b.) deprotecting the 2'- and 4"-hydroxy protecting groups.

* * * * *

UNITED STATES PATENT AND TRADEMARK OFFICE
CERTIFICATE OF CORRECTION

PATENT NO. : 6,075,011
DATED : June 13, 2000
INVENTOR(S) : Yat Sun Or et al.

It is certified that error appears in the above-identified patent and that said Letters Patent is hereby corrected as shown below:

Column 201,
Lines 15-16, replace "$R^a$ is OH; $R^b$ is OH; $R^c$ is H; $R^d$ is H;" with -- $R^a$ is OH; $R^b$ is H; $R^c$ is H; $R^d$ is OH; --

Column 202,
Lines 12-15, replace " 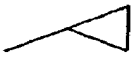 ; " with --  ; --.

Column 205,
Lines 21-22, replace "$R^b$ is OH; $R^c$ is H; $R^d$ is H;" with -- $R^b$ is H; $R^c$ is H; $R^d$ is OH; --

Column 206,
Lines 40-41, replace "$R^a$ is OH; $R^b$ is OH; $R^c$ is H; $R^d$ is H;" with -- $R^a$ is OH; $R^b$ is H; $R^c$ is H; $R^d$ is OH; --

Column 225,
Lines 37-38, replace "OH; $R^b$ is OH; $R^c$ is H; $R^d$ is H:" with -- OH; $R^b$ is H; $R^c$ is H; $R^d$ is OH; --

Column 226,
Line 56, replace "$R^b$ is OH; $R^c$ is H; $R^d$ is H;" with -- $R^b$ is H; $R^c$ is H; $R^d$ is OH; --

UNITED STATES PATENT AND TRADEMARK OFFICE
CERTIFICATE OF CORRECTION

PATENT NO.   : 6,075,011  
DATED        : June 13, 2000  
INVENTOR(S)  : Yat Sun Or et al.

It is certified that error appears in the above-identified patent and that said Letters Patent is hereby corrected as shown below:

Column 242,  
Lines 38-41,

Replace " 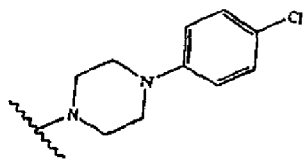 "

with -- 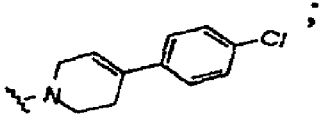 ; --

Signed and Sealed this

Third Day of September, 2002

Attest:

Attesting Officer

JAMES E. ROGAN  
Director of the United States Patent and Trademark Office